(12) United States Patent
Kawamura et al.

(10) Patent No.: US 11,020,381 B2
(45) Date of Patent: Jun. 1, 2021

(54) BIARYLOXY DERIVATIVES AS TTX-S BLOCKERS

(71) Applicants: RaQualia Pharma Inc., Aichi (JP); XuanZhu Pharma Co., Ltd., Jinan (CN)

(72) Inventors: Kiyoshi Kawamura, Aichi (JP); Tatsuya Yamagishi, Aichi (JP); Yuji Shishido, Aichi (JP); Mikio Morita, Aichi (JP); Ryuichi Yamaguchi, Aichi (JP); Masashi Ohmi, Aichi (JP)

(73) Assignees: RaQualia Pharma Inc., Aichi (JP); XuanZhu Pharma Co., Ltd., Jinan (CN)

( * ) Notice: Subject to any disclaimer, the term of this patent is extended or adjusted under 35 U.S.C. 154(b) by 0 days.

(21) Appl. No.: 16/642,706

(22) PCT Filed: Aug. 31, 2018

(86) PCT No.: PCT/JP2018/032312
§ 371 (c)(1),
(2) Date: Feb. 27, 2020

(87) PCT Pub. No.: WO2019/045035
PCT Pub. Date: Mar. 7, 2019

(65) Prior Publication Data
US 2020/0230123 A1    Jul. 23, 2020

Related U.S. Application Data
(60) Provisional application No. 62/552,507, filed on Aug. 31, 2017.

(51) Int. Cl.
| | |
|---|---|
| A61K 31/4433 | (2006.01) |
| A61P 29/00 | (2006.01) |
| A61K 31/18 | (2006.01) |
| A61K 31/415 | (2006.01) |
| A61K 31/42 | (2006.01) |
| A61K 31/4418 | (2006.01) |
| A61K 31/4545 | (2006.01) |
| A61K 31/4965 | (2006.01) |
| A61K 31/505 | (2006.01) |
| C07D 213/64 | (2006.01) |
| C07D 213/647 | (2006.01) |
| C07D 231/12 | (2006.01) |
| C07D 239/34 | (2006.01) |
| C07D 241/18 | (2006.01) |
| C07D 261/08 | (2006.01) |
| C07D 401/04 | (2006.01) |
| C07D 401/10 | (2006.01) |
| C07D 401/12 | (2006.01) |
| C07D 405/12 | (2006.01) |
| C07C 311/51 | (2006.01) |

(52) U.S. Cl.
CPC .......... *A61K 31/4433* (2013.01); *A61K 31/18* (2013.01); *A61K 31/415* (2013.01); *A61K 31/42* (2013.01); *A61K 31/4418* (2013.01); *A61K 31/4545* (2013.01); *A61K 31/4965* (2013.01); *A61K 31/505* (2013.01); *A61P 29/00* (2018.01); *C07C 311/51* (2013.01); *C07D 213/64* (2013.01); *C07D 213/647* (2013.01); *C07D 231/12* (2013.01); *C07D 239/34* (2013.01); *C07D 241/18* (2013.01); *C07D 261/08* (2013.01); *C07D 401/04* (2013.01); *C07D 401/10* (2013.01); *C07D 401/12* (2013.01); *C07D 405/12* (2013.01)

(58) Field of Classification Search
None
See application file for complete search history.

(56) References Cited

FOREIGN PATENT DOCUMENTS

| WO | 2010/079443 | 7/2010 |
|---|---|---|
| WO | 2010/137351 | 12/2010 |
| WO | 2012/007868 | 1/2012 |

(Continued)

OTHER PUBLICATIONS

Wu et al., Toxicology, 236, pp. 1-6, Apr. (Year: 2007).*

(Continued)

*Primary Examiner* — Zinna Northington Davis
(74) *Attorney, Agent, or Firm* — Wenderoth, Lind & Ponack, L.L.P.

(57) ABSTRACT

The present invention relates to biaryloxy derivatives which have blocking activities of voltage gated sodium channels as the TTX-S channels, and which are useful in the treatment or prevention of disorders and diseases in which voltage gated sodium channel is involved. The invention also relates to pharmaceutical compositions comprising these compounds and the use of these compounds and compositions in the prevention or treatment of such diseases in which voltage gated sodium channels are involved.

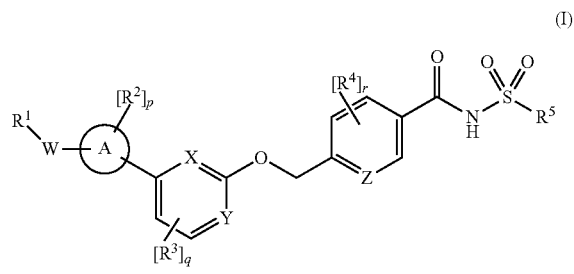

15 Claims, No Drawings

(56) References Cited

FOREIGN PATENT DOCUMENTS

| WO | 2012/007869 | 1/2012 |
|----|-------------|--------|
| WO | 2012/053186 | 4/2012 |
| WO | 2013/088315 | 6/2013 |
| WO | 2013/102826 | 7/2013 |
| WO | 2013/161308 | 10/2013 |
| WO | 2013/177224 | 11/2013 |
| WO | 2014/008458 | 1/2014 |

OTHER PUBLICATIONS

International Preliminary Report on Patentability dated Mar. 12, 2020 in International (PCT) Application No. PCT/JP2018/032312.
International Search Report and Written Opinion of the International Searching Authority dated Nov. 13, 2018 in corresponding International Patent Application No. PCT/JP2018/032312.
Cox et al., "An SCN9A channelopathy causes congenital inability to experience pain", Nature, vol. 444, pp. 894-898 (Dec. 14, 2006).
Baker et al., "Involvement of $Na^+$ channels in pain pathways", Trends in Pharmacological Sciences, vol. 22, No. 1, pp. 27-31 (Jan. 2001).
Lyu et al., "Low dose of tetrodotoxin reduces neuropathic pain behaviors in an animal model", Brain Research, vol. 871, pp. 98-103 (2000).
Extended European Search Report dated Mar. 12, 2021 in corresponding European Patent Application No. 18852154.6.

\* cited by examiner

BIARYLOXY DERIVATIVES AS TTX-S BLOCKERS

TECHNICAL FIELD

The present invention relates to the biaryloxy derivatives which are sodium channel blockers and have a number of therapeutic applications, particularly in the treatment of pain.

BACKGROUND ART

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders including epilepsy, arrhythmia, myotonia, and pain.

There are currently at least nine known members of the family of voltage-gated sodium channel (VGSC) alpha subunits ($Nav_{1.1}$-$Nav_{1.9}$). The VGSC subfamily can be functionally subdivided into two groups, those which are sensitive to blocking by tetrodotoxin (TTX-sensitive or TTX-S) and those which are resistant to blocking by tetrodotoxin (TTX-resistant or TTX-R).

The biaryloxy derivatives of the present invention are sodium channel blockers and have a number of therapeutic applications, particularly in the treatment of pain. More particularly, the biaryloxy derivatives of the invention are selective TTX-S blockers. In the discussion that follows, the invention is exemplified by reference to the inhibition of $Na_{V1.7}$ channel as the TTX-S channel. They show the affinity for $Na_{V1.7}$ channel which is significantly greater than their affinity for $Na_{V1.5}$ channel as TTX-R sodium channels. The biaryloxy derivatives of the invention show good selectivity for the $Na_{V1.7}$ channel as compared with $Na_{V1.5}$ channel.

The $Na_{v1.7}$ channel appears to be the best 'validated' pain target. The most exciting findings with respect to $Na_{v1.7}$ have come from human genetic studies. Cox et al. (NPL 1) discovered SCN9A mutations that cause a loss of $Na_{v1.7}$ function in three families from Pakistan. Their observations link loss of $Na_{v1.7}$ function with a congenital inability to experience pain, adding to the evidence indicating $Na_{v1.7}$ channel as an essential participant in human nociception.

By contrast, Gain-of-function mutations have also been described that lead to enhanced pain, for example, Primary Erythermalgia in one case and Paroxysmal Extreme Pain Disorder in another. These gain-of-function mutations in patients led to different types of gating changes in $Na_{v1.7}$ sodium currents and, interestingly, different degrees of effectiveness of specific sodium channel blocking drugs. The implication from these findings is that a selective $Na_{v1.7}$ blocker may be an effective treatment for pain in man.

A local anaesthetic lidocaine and a volatile anaesthetic halothane are known to act on both TTX-R and TTX-S sodium channels with poor selectivity and low potency ($IC_{50}$ values range from 50 microM to 10 mM). These anaesthetics at high systemic concentrations could cause devastating side effects, e.g., paralysis and cardiac arrest. However, systemic administration of lidocaine at low concentrations is effective to treat chronic pain (NPL 2). In rats, application of a very low dose of TTX to the DRG of the injured segment of the L5 spinal nerve significantly reduces mechanical allodynic behavior (NPL 3). This suggests that TTX-S subtypes of sodium channels play an important role in maintaining allodynic behaviors in an animal model of neuropathic pain.

The $Na_{V1.5}$ channel is also a member of TTX-resistant sodium channels. The $Na_{V1.5}$ channel is almost exclusively expressed in cardiac tissue and has been shown to underlie a variety of cardiac arrhythmias and conduction disorders.

CITATION LIST

Non Patent Literature

{NPL 1} Nature 444, 894-898, 2006, Cox et al.
{NPL 2} Trends in Pharm. Sci. 22, 27-31, 2001, Baker, M. D. et al.
{NPL 3} Brain Res. 871, 98-103, 2000, Lyu, Y. S. et al.

SUMMARY OF INVENTION

Technical Problem

It is an objective of the invention to provide new TTX-S blockers that are good drug candidates. Preferred compounds should bind potently to the TTX-S($Na_{V1.7}$) channel whilst showing little affinity for other sodium channels, particularly the $Na_{V1.5}$ channel. They should be well-absorbed from the gastrointestinal tract, be metabolically stable and possess favorable pharmacokinetic properties. They are non-toxic and demonstrate few side-effects. Furthermore, the ideal drug candidate will exist in a physical form that is stable, non-hygroscopic and easily formulated.

In particular, the biaryloxy derivatives of the present invention are selective for the TTX-S channels over the $Na_{V1.5}$ channel, leading to improvements in the side-effect profile.

The biaryloxy derivatives of the present invention are therefore useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS (central nervous system), including cancer pain, back pain, orofacial pain and chemo-induced pain.

Other conditions that may be treated with the biaryloxy derivatives of the present invention include multiple sclerosis, pruritus, neurodegenerative disorders, irritable bowel syndrome, osteoarthritis, rheumatoid arthritis, neuropathological disorders, functional bowel disorders, inflammatory bowel diseases pain, pain associated with dysmenorrhea, pelvic pain, cystitis pain, pancreatitis pain, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders including anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, back pain, head or neck pain, severe or intractable pain, breakthrough pain, postsurgical pain, stroke pain, cancer pain, seizure disorder and causalgia.

The compounds showed activities against $Na_{V1.7}$ channel. In addition they showed selectivity for the $Na_{V1.7}$ channel as compared with $Na_{V1.5}$ channel.

Solution to Problem

With respect to other compounds disclosed in the art, the compounds of the present invention may show less toxicity, good absorption and distribution, good solubility, less plasma protein binding, less drug-drug interaction, good metabolic stability, reduced inhibitory activity at HERG channel, and/or reduced QT prolongation.

[1] This invention provides a compound of the following formula (I):

[Chem. 1]

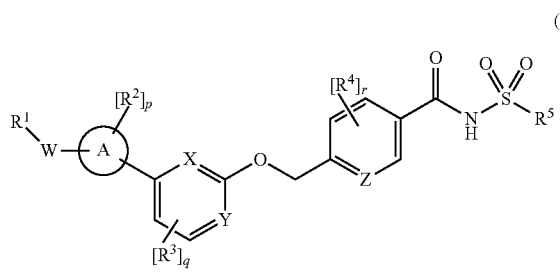

(I)

Wherein:

A is aryl or heteroaryl; preferable aryl or heteroaryl is phenyl or a 5-6 membered heteroaryl; more preferable aryl or heteroaryl is phenyl or 5-6 membered N-containing heteroaryl; further preferable aryl or heteroaryl is phenyl, pyridyl, pyrazyl, pyrimidyl, pyrazolyl, or isoxazolyl; the most preferable aryl or heteroaryl is phenyl, pyridyl, pyrazyl, or pyrimidyl; the most preferable aryl or heteroaryl is pyridyl or pyrazyl;

W is selected from the group consisting of a chemical bond, —NR$^a$—, —O—, and —S—; preferable W is selected from the group consisting of a chemical bond, —NR$^a$—, or —O—; more preferable W is —O—; further preferable W is substituted at para- or meta-position with respect to the 6 membered ring including X and Y; the most preferable W is substituted at para-position with respect to the 6 membered ring including X and Y;

R$^a$ is hydrogen or C$_{1-6}$ alkyl; preferable R$^a$ is hydrogen or C$_{1-4}$ alkyl;

R$^1$ is independently selected from the group consisting of: (1) C$_{3-7}$ cycloalkyl, (2) heterocyclyl, (3) C$_{3-7}$ cycloalkylC$_{1-6}$ alkyl, and (4) heterocyclylC$_{1-6}$ alkyl; wherein the C$_{3-7}$ cycloalkyl, the heterocyclyl, the C$_{3-7}$ cycloalkylC$_{1-6}$ alkyl, or the heterocyclylC$_{1-6}$ alkyl is unsubstituted or substituted with one or more substituents independently selected from the group consisting of: halogen, hydroxyl, C$_{1-6}$ alkyl, —O—C$_{1-6}$ alkyl, hydroxylC$_{1-6}$ alkyl, hydroxylC$_{1-6}$ alkoxy, —NR$^6$R$^7$, —(C=O)—R$^6$, —(C=O)—OR$^6$, —(C=O)—NR$^6$R$^7$, and —NR$^6$—(C=O)—R$^7$;

preferable R$^1$ is independently selected from the group consisting of:

(1) C$_{3-7}$ cycloalkyl, (2) heterocyclyl, (3) C$_{3-7}$ cycloalkylC$_{1-6}$ alkyl, and (4) heterocyclylC$_{1-6}$ alkyl; wherein the C$_{3-7}$ cycloalkyl or the C$_{3-7}$ cycloalkylC$_{1-6}$ alkyl is unsubstituted or substituted with one or more substituents independently selected from the group consisting of: halogen, hydroxyl, and C$_{1-6}$ alkyl; wherein the heterocyclyl or the heterocyclylC$_{1-6}$ alkyl is unsubstituted or substituted with one or more substituents independently selected from the group consisting of halogen, hydroxyl, C$_{1-6}$ alkyl, —(C=O)—R$^6$, —(C=O)—OR$^6$, —(C=O)—NR$^6$R$^7$, and —NR$^6$—(C=O)—R$^7$; more preferable R$^1$ is independently selected from the group consisting of: (1) C$_{3-7}$ cycloalkyl, (2) 3-7 membered heterocyclyl, (3) C$_{3-7}$ cycloalkylC$_{1-4}$ alkyl, and (4) 3-7 membered heterocyclylC$_{1-4}$ alkyl; wherein the C$_{3-7}$ cycloalkyl or the C$_{3-7}$ cycloalkylC$_{1-4}$ alkyl is unsubstituted or substituted with one or more substituents independently selected from the group consisting of: halogen, hydroxyl, and C$_{1-4}$ alkyl; wherein the 3-7 membered heterocyclyl or the 3-7 membered heterocyclylC$_{1-4}$ alkyl is unsubstituted or substituted with one or more substituents independently selected from the group consisting of halogen, hydroxyl, C$_{1-4}$ alkyl, —(C=O)—R$^6$, —(C=O)—OR$^6$, —(C=O)—NR$^6$R$^7$, and —NR$^6$—(C=O)—R$^7$; further preferable R$^1$ is independently selected from the group consisting of: (1) C$_{3-7}$ cycloalkyl and (3) C$_{3-7}$ cycloalkylC$_{1-6}$ alkyl, wherein the C$_{3-7}$ cycloalkyl or the C$_{3-7}$ cycloalkylC$_{1-6}$ alkyl is unsubstituted or substituted with one or more halogens; the most preferable R$^1$ is independently selected from the group consisting of: (1) C$_{3-6}$ cycloalkyl and (3) C$_{3-6}$ cycloalkylC$_{1-4}$ alkyl, wherein the C$_{3-6}$ cycloalkyl or the C$_{3-6}$ cycloalkylC$_{1-4}$ alkyl is unsubstituted or substituted with one or more halogens;

R$^2$ is independently selected from the group consisting of:

(1) hydrogen, (2) halogen, (3) hydroxyl, (4) C$_{1-6}$ alkyl, (5) —O—C$_{1-6}$ alkyl, (6) C$_{3-7}$ cycloalkyl, (7) —O—C$_{3-7}$ cycloalkyl, (8) —(C=O)—NR$^6$R$^7$, (9) —NR$^6$(C=O)R$^7$, (10) —NR$^6$(C=O)NR$^7$R$^8$, (11) —NR$^6$R$^7$, (12) —CN, and (13) —NO$_2$; wherein the C$_{1-6}$ alkyl, the —O—C$_{1-6}$ alkyl, the C$_{3-7}$ cycloalkyl, or the —O—C$_{3-7}$ cycloalkyl is unsubstituted or substituted with one or more substituents independently selected from the group consisting of: halogen, hydroxyl, C$_{1-6}$ alkoxyl, —NR$^6$R$^7$, —(C=O)—NR$^6$R$^7$, —NR$^6$—(C=O)—R$^7$ and —NR$^6$CH$_2$—(C=O)—NH$_2$;

preferable R$^2$ is independently selected from the group consisting of:

(1) hydrogen, (2) halogen, (4) C$_{1-6}$ alkyl, (5) —O—C$_{1-6}$ alkyl, (6) C$_{3-7}$ cycloalkyl, (7) —O—C$_{3-7}$ cycloalkyl, (8) —(C=O)—NR$^6$R$^7$, and (9) —NR$^6$(C=O)R$^7$, wherein the C$_{1-6}$ alkyl, the —O—C$_{1-6}$ alkyl, the C$_{3-7}$ cycloalkyl, or the —O—C$_{3-7}$ cycloalkyl is unsubstituted or substituted with one or more substituents independently selected from the group consisting of: halogen, hydroxyl, C$_{1-6}$ alkoxyl, —NR$^6$R$^7$, —(C=O)—NR$^6$R$^7$, —NR$^6$—(C=O)—R$^7$ and —NR$^6$CH$_2$—(C=O)—NH$_2$;

more preferable R$^2$ is independently selected from the group consisting of:

(1) hydrogen, (2) halogen, (4) C$_{1-4}$ alkyl, (5) —O—C$_{1-4}$ alkyl, (6) C$_{3-7}$ cycloalkyl, (7) —O—C$_{3-7}$ cycloalkyl, (8) —(C=O)—NR$^6$R$^7$, and (9) —NR$^6$(C=O)R$^7$, wherein the C$_{1-4}$ alkyl, the —O—C$_{1-4}$ alkyl, the C$_{3-7}$ cycloalkyl, or the —O—C$_{3-7}$ cycloalkyl is unsubstituted or substituted with one or more substituents independently selected from the group consisting of: halogen, hydroxyl, C$_{1-4}$ alkoxyl, —NR$^6$R$^7$, —(C=O)—NR$^6$R$^7$, —NR$^6$—(C=O)—R$^7$ and —NR$^6$CH$_2$—(C=O)—NH$_2$; further preferable R$^2$ is independently selected from the group consisting of: (2) halogen and (4) C$_{1-6}$ alkyl; the most preferable R$^2$ is independently selected from the group consisting of: (2) halogen and (4) C$_{1-4}$ alkyl;

p is 0, 1, 2, 3, or 4; when p is two or more, each R$^2$ is the same or different; preferable p is 0, 1, or 2; when p is two or more, each R$^2$ is the same or different; more preferable p is 0 or 1;

R$^3$ is independently selected from the group consisting of:

(1) hydrogen, (2) halogen, (3) hydroxyl, (4) C$_{1-6}$ alkyl, (5) —O—C$_{1-6}$ alkyl, wherein the C$_{1-6}$ alkyl or the —O—C$_{1-6}$ alkyl is unsubstituted or substituted with one or more substituents independently selected form the group consisting of: halogen, hydroxyl, $C_{1-6}$ alkoxyl, and $C_{3-7}$ cycloalkyl, (6) $C_{3-7}$ cycloalkyl, (7) —O—$C_{3-7}$ cycloalkyl, (8) aryl, (9) heteroaryl, (10) heterocyclyl, (11) —$NR^6R^7$, and (12) —CN; wherein the $C_{3-7}$ cycloalkyl, the —O—$C_{3-7}$ cycloalkyl, the aryl, the heteroaryl, or the heterocyclyl is unsubstituted or substituted with one or more substituents independently selected form the group consisting of: halogen, hydroxyl, and $C_{1-6}$ alkyl;

preferable $R^3$ is independently selected from the group consisting of:

(1) hydrogen, (2) halogen, (4) $C_{1-6}$ alkyl, (5) —O—$C_{1-6}$ alkyl, wherein the $C_{1-6}$ alkyl or the —O—$C_{1-6}$ alkyl is unsubstituted or substituted with one or more substituents independently selected form the group consisting of: halogen, hydroxyl, $C_{1-6}$ alkoxyl, and $C_{3-7}$ cycloalkyl, (6) $C_{3-7}$ cycloalkyl, (7) —O—$C_{3-7}$ cycloalkyl, (8) aryl, (9) heteroaryl, (11) —$NR^6R^7$, and (12) —CN; wherein the $C_{3-7}$ cycloalkyl, the —O—$C_{3-7}$ cycloalkyl, the aryl, or the heteroaryl is unsubstituted or substituted with one or more substituents independently selected form the group consisting of: halogen, hydroxyl, and $C_{1-6}$ alkyl;

more preferable $R^3$ is independently selected from the group consisting of: (1) hydrogen, (2) halogen, (4) $C_{1-4}$ alkyl, (5) —O—$C_{1-4}$ alkyl, wherein the $C_{1-4}$ alkyl or the —O—$C_{1-4}$ alkyl is unsubstituted or substituted with one or more substituents independently selected form the group consisting of: halogen, hydroxyl, $C_{1-4}$ alkoxyl, and $C_{3-7}$ cycloalkyl, (6) $C_{3-7}$ cycloalkyl, (7) —O—$C_{3-7}$ cycloalkyl, (8) aryl, (9) 5-6 membered heteroaryl, (11) —$NR^6R^7$, and (12) —CN; wherein the $C_{3-7}$ cycloalkyl, the —O—$C_{3-7}$ cycloalkyl, the aryl, or the 5-6 membered heteroaryl is unsubstituted or substituted with one or more substituents independently selected form the group consisting of: halogen, hydroxyl, and $C_{1-4}$ alkyl; further preferable $R^3$ is independently selected from the group consisting of: (1) hydrogen, (2) halogen, and (4) $C_{1-6}$ alkyl; the most preferable $R^2$ is independently selected from the group consisting of: (2) halogen and (4) $C_{1-4}$ alkyl;

q is 0, 1, 2, 3, or 4; when q is two or more, each $R^3$ is the same or different; preferable q is 0, 1, or 2; when q is two or more, each $R^3$ is the same or different; more preferable q is 0 or 1;

X is $CR^3$ or N;
preferable X is $CR^3$;
Y is $CR^3$ or N;
preferable Y is $CR^3$;
$R^4$ is independently selected from the group consisting of:

(1) hydrogen, (2) halogen, (3) hydroxyl, (4) $C_{1-6}$ alkyl, (5) —O—$C_{1-6}$ alkyl, (6) $C_{3-7}$ cycloalkyl, (7) —O—$C_{3-7}$ cycloalkyl, and (8) —CN; wherein the $C_{1-6}$ alkyl, the —O—$C_{1-6}$ alkyl, the $C_{3-7}$ cycloalkyl, or the —O—$C_{3-7}$ cycloalkyl is unsubstituted or substituted with one or more substituents independently selected form the group consisting of: halogen or hydroxyl;

preferable $R^4$ is independently selected from the group consisting of:

(1) hydrogen, (2) halogen, (4) $C_{1-6}$ alkyl, (5) —O—$C_{1-6}$ alkyl, (6) $C_{3-7}$ cycloalkyl, (7) —O—$C_{3-7}$ cycloalkyl, and (8) —CN; wherein the $C_{1-6}$ alkyl, the —O—$C_{1-6}$ alkyl, the $C_{3-7}$ cycloalkyl, or the —O—$C_{3-7}$ cycloalkyl is unsubstituted or substituted with one or more substituents independently selected form the group consisting of: halogen or hydroxyl;
more preferable
$R^4$ is independently selected from the group consisting of:
(1) hydrogen, (2) halogen, (4) $C_{1-4}$ alkyl, (5) —O—$C_{1-4}$ alkyl, (6) $C_{3-7}$ cycloalkyl, (7) —O—$C_{3-7}$ cycloalkyl, and (8) —CN; wherein the $C_{1-4}$ alkyl, the —O—$C_{1-4}$ alkyl, the $C_{3-7}$ cycloalkyl, or the —O—$C_{3-7}$ cycloalkyl is unsubstituted or substituted with one or more substituents independently selected form the group consisting of: halogen or hydroxyl; further preferable $R^4$ is independently selected from the group consisting of: (1) hydrogen, (2) halogen, and (4) $C_{1-6}$ alkyl; the most preferable $R^4$ is independently selected from the group consisting of: (1) hydrogen, (2) halogen, and (4) $C_{1-4}$ alkyl;

r is 0, 1, 2, 3, or 4; when r is two or more, each $R^4$ is the same or different; preferable r is 0, 1, 2, or 3; when r is two or more, each $R^4$ is the same or different; more preferable r is 0 or 1;

Z is $CR^4$ or N;
preferable Z is $CR^4$;
$R^5$ is selected from the group consisting of:

(1) $C_{1-6}$ alkyl, (2) —O—$C_{1-6}$ alkyl, (3) $C_{3-7}$ cycloalkyl, (4) $C_{3-7}$ cycloalkyl$C_{1-6}$ alkyl, wherein the $C_{1-6}$ alkyl, the —O—$C_{1-6}$ alkyl, the $C_{3-7}$ cycloalkyl, or the $C_{3-7}$ cycloalkyl$C_{1-6}$ alkyl is unsubstituted or substituted with one or more substituents independently selected form the group consisting of: halogen, hydroxyl, and $C_{1-6}$ alkoxyl, (5) aryl, (6) heteroaryl, wherein the aryl or the heteroaryl is unsubstituted or substituted with one or more substituents independently selected form the group consisting of: halogen, hydroxyl, $C_{1-6}$ alkyl and $C_{1-6}$ alkoxyl, and (7) —$NR^6R^7$;

preferable $R^5$ is selected from the group consisting of:
(1) $C_{1-6}$ alkyl, (3) $C_{3-7}$ cycloalkyl, (4) $C_{3-7}$ cycloalkyl$C_{1-6}$ alkyl, wherein the $C_{1-6}$ alkyl, the $C_{3-7}$ cycloalkyl, or the $C_{3-7}$ cycloalkyl$C_{1-6}$ alkyl is unsubstituted or substituted with one or more substituents independently selected form the group consisting of: halogen, hydroxyl, and $C_{1-6}$ alkoxyl, (5) aryl, and (6) heteroaryl, wherein the aryl or the heteroaryl is unsubstituted or substituted with one or more substituents independently selected form the group consisting of: halogen, hydroxyl, $C_{1-6}$ alkyl and $C_{1-6}$ alkoxyl:

more preferable $R^5$ is selected from the group consisting of:

(1) $C_{1-4}$ alkyl, (3) $C_{3-7}$ cycloalkyl, (4) $C_{3-7}$ cycloalkyl$C_{1-4}$ alkyl, wherein the $C_{1-4}$ alkyl, the $C_{3-7}$ cycloalkyl, or the $C_{3-7}$ cycloalkyl$C_{1-4}$ alkyl is unsubstituted or substituted with one or more substituents independently selected form the group consisting of: halogen, hydroxyl, and $C_{1-4}$ alkoxyl, (5) aryl, and (6) 5-6 membered heteroaryl, wherein the aryl or the 5-6 membered heteroaryl is unsubstituted or substituted with one or more substituents independently selected form the group consisting of: halogen, hydroxyl, $C_{1-4}$ alkyl, and $C_{1-4}$ alkoxyl; further preferable $R^5$ is selected from the group consisting of: (1) $C_{1-6}$ alkyl, wherein the $C_{1-6}$ alkyl is unsubstituted or substituted with one or more halogens; the most preferable $R^5$ is selected from the group consisting of:

(1) $C_{1-4}$ alkyl, (3) $C_{3-7}$ cycloalkyl, (4) $C_{3-7}$ cycloalkyl$C_{1-4}$ alkyl, wherein the $C_{1-4}$ alkyl, the $C_{3-7}$ cycloalkyl, or the $C_{3-7}$ cycloalkyl$C_{1-4}$ alkyl is unsubstituted or substituted with one or more halogens;

$R^6$ and $R^7$ are independently selected from the group consisting of:

(1) hydrogen, (2) $C_{1-6}$ alkyl, and (3) $C_{1-6}$ alkoxy$C_{1-6}$ alkyl, wherein the $C_{1-6}$ alkyl or the $C_{1-6}$ alkoxy$C_{1-6}$ alkyl is unsubstituted or substituted with one or more substituents independently selected from the group consisting of: halogen and hydroxyl; $R^6$ may form a 4 to 7 membered ring with $R^7$ which may contain a nitrogen atom, an oxygen atom, a sulfur atom, carbonyl, or a double bond; wherein the 4 to 7 membered ring is unsubstituted or substituted with one or more substituents independently selected from the group consisting of: halogen, hydroxyl, and $C_{1-6}$ alkoxyl; preferable $R^6$ and $R^7$ are independently selected from the group consisting of: (1) hydrogen, (2) $C_{1-4}$ alkyl, and (3) $C_{1-4}$ alkoxy$C_{1-4}$ alkyl, wherein the $C_{1-4}$ alkyl or the $C_{1-4}$ alkoxy$C_{1-4}$ alkyl is unsubstituted or substituted with one or more substituents independently selected from the group consisting of: halogen and hydroxyl; $R^6$ may form a 4 to 7 membered ring with $R^7$ which may contain a nitrogen atom, an oxygen atom, a sulfur atom, carbonyl, or a double bond; wherein the 4 to 7 membered ring is unsubstituted or substituted with one or more substituents independently selected from the group consisting of: halogen, hydroxyl, and $C_{1-4}$ alkoxyl;

or a prodrug thereof or a pharmaceutically acceptable salt thereof.

[2] This invention provides the compound represented by above formula (I) according to [1]
wherein:
A is phenyl or 5-6 membered heteroaryl;
W is a chemical bond, —$NR^a$—, or —O—;
$R^a$ is hydrogen or $C_{1-6}$ alkyl;
or a prodrug thereof or a pharmaceutically acceptable salt thereof.

[3] This invention provides the compound described in [1] or [2] wherein:
A is phenyl or 5-6 membered N-containing heteroaryl;
or a prodrug thereof or a pharmaceutically acceptable salt thereof.

[4] This invention provides the compound described in any one of [1] to [3] wherein:
A is phenyl, pyridyl, pyrazyl, pyrimidyl, pyrazolyl, or isoxazolyl;
or a prodrug thereof or a pharmaceutically acceptable salt thereof.

[5] This invention provides the compound described in any one of [1] to [4] wherein:
A is phenyl, pyridyl, pyrazyl, or pyrimidyl;
W is selected from the group consisting of —$NR^a$— and —O—;
$R^a$ is hydrogen or $C_{1-6}$ alkyl;
W is substituted at para- or meta-position with respect to the 6 membered ring including X and Y;
$R^1$ is independently selected from the group consisting of:
(1) $C_{3-7}$ cycloalkyl, (2) heterocyclyl, (3) $C_{3-7}$ cycloalkyl$C_{1-6}$ alkyl, and (4) heterocyclyl$C_{1-6}$ alkyl; wherein the $C_{3-7}$ cycloalkyl or the $C_{3-7}$ cycloalkyl$C_{1-6}$ alkyl is unsubstituted or substituted with one or more substituents independently selected from the group consisting of: halogen, hydroxyl, and $C_{1-6}$ alkyl; wherein the heterocyclyl or the heterocyclyl$C_{1-6}$ alkyl is unsubstituted or substituted with one or more substituents independently selected from the group consisting of halogen, hydroxyl, $C_{1-6}$ alkyl, —(C=O)—$R^6$, —(C=O)—$OR^6$, —(C=O)—$NR^6R^7$, and —$NR^6$—(C=O)—$R^7$;
$R^2$ is independently selected from the group consisting of:
(1) hydrogen, (2) halogen, (4) $C_{1-6}$ alkyl, (5) —O—$C_{1-6}$ alkyl, (6) $C_{3-7}$ cycloalkyl, (7) —O—$C_{3-7}$ cycloalkyl, (8) —(C=O)—$NR^6R^7$, and (9) —$NR^6$(C=O)$R^7$, wherein the $C_{1-6}$ alkyl, the —O—$C_{1-6}$ alkyl, the $C_{3-7}$ cycloalkyl, or the —O—$C_{3-7}$ cycloalkyl is unsubstituted or substituted with one or more substituents independently selected from the group consisting of: halogen, hydroxyl, $C_{1-6}$ alkoxyl, —$NR^6R^7$, —(C=O)—$NR^6R^7$, —$NR^6$—(C=O)—$R^7$ and —$NR^6CH_2$—(C=O)—$NH_2$;
p is 0, 1, or 2; when p is two or more, each $R^2$ is the same or different;
$R^3$ is independently selected from the group consisting of:
(1) hydrogen, (2) halogen, (4) $C_{1-6}$ alkyl, (5) —O—$C_{1-6}$ alkyl, wherein the $C_{1-6}$ alkyl or the —O—$C_{1-6}$ alkyl is unsubstituted or substituted with one or more substituents independently selected form the group consisting of: halogen, hydroxyl, $C_{1-6}$ alkoxyl, and $C_{3-7}$ cycloalkyl, (6) $C_{3-7}$ cycloalkyl, (7) —O—$C_{3-7}$ cycloalkyl, (8) aryl, (9) heteroaryl, (11) —$NR^6R^7$, and (12) —CN; wherein the $C_{3-7}$ cycloalkyl, the —O—$C_{3-7}$ cycloalkyl, the aryl, or the heteroaryl is unsubstituted or substituted with one or more substituents independently selected form the group consisting of: halogen, hydroxyl, and $C_{1-6}$ alkyl;
q is 0, 1, or 2; when q is two or more, each $R^3$ is the same or different;
X is $CR^3$ or N;
Y is $CR^3$ or N;
$R^4$ is independently selected from the group consisting of:
(1) hydrogen, (2) halogen, (4) $C_{1-6}$ alkyl, (5) —O—$C_{1-6}$ alkyl, (6) $C_{3-7}$ cycloalkyl, (7) —O—$C_{3-7}$ cycloalkyl, and (8) —CN; wherein the $C_{1-6}$ alkyl, the —O—$C_{1-6}$ alkyl, the $C_{3-7}$ cycloalkyl, or the —O—$C_{3-7}$ cycloalkyl is unsubstituted or substituted with one or more substituents independently selected form the group consisting of: halogen or hydroxyl;
r is 0, 1, 2, or 3; when r is two or more, each $R^4$ is the same or different;
Z is $CR^4$ or N;
$R^5$ is selected from the group consisting of:
(1) $C_{1-6}$ alkyl, (3) $C_{3-7}$ cycloalkyl, (4) $C_{3-7}$ cycloalkyl$C_{1-6}$ alkyl, wherein the $C_{1-6}$ alkyl, the $C_{3-7}$ cycloalkyl, or the $C_{3-7}$ cycloalkyl$C_{1-6}$ alkyl is unsubstituted or substituted with one or more substituents independently selected form the group consisting of: halogen, hydroxyl, and $C_{1-6}$ alkoxyl, (5) aryl, and (6) heteroaryl, wherein the aryl or the heteroaryl is unsubstituted or substituted with one or more substituents independently selected form the group consisting of: halogen, hydroxyl, $C_{1-6}$ alkyl, and $C_{1-6}$ alkoxyl $R^6$ and $R^7$ are independently selected from the group consisting of:
(1) hydrogen, (2) $C_{1-6}$ alkyl, and (3) $C_{1-6}$ alkoxy$C_{1-6}$ alkyl, wherein the $C_{1-6}$ alkyl or the $C_{1-6}$ alkoxy$C_{1-6}$ alkyl is unsubstituted or substituted with one or more substituents independently selected from the group consisting of: halogen and hydroxyl; $R^6$ may form a 4 to 7 membered ring with $R^7$ which may contain a nitrogen atom, an oxygen atom, a sulfur atom, carbonyl, or a double bond; wherein the 4 to 7 membered ring is unsubstituted or substituted with one or more substituents independently selected from the group consisting of: halogen, hydroxyl, and $C_{1-6}$ alkoxyl;

or a prodrug thereof or a pharmaceutically acceptable salt thereof.

[6] This invention provides the compound described in any one of [1] to [5] wherein:
A is phenyl, pyridyl, pyrazyl, or pyrimidyl;
W is selected from the group consisting of —$NR^a$— and —O—;
$R^a$ is hydrogen or $C_{1-4}$ alkyl;
W is substituted at para- or meta-position with respect to the 6 membered ring including X and Y;
$R^1$ is independently selected from the group consisting of:
(1) $C_{3-7}$ cycloalkyl, (2) 3-7 membered heterocyclyl, (3) $C_{3-7}$ cycloalkyl$C_{1-4}$ alkyl, and (4) 3-7 membered heterocyclyl$C_{1-4}$ alkyl; wherein the $C_{3-7}$ cycloalkyl or the $C_{3-7}$ cycloalkyl$C_{1-4}$ alkyl is unsubstituted or substituted with one or more substituents independently selected from the group consisting of: halogen, hydroxyl, and $C_{1-4}$ alkyl; wherein the 3-7 membered heterocyclyl or the 3-7 membered heterocyclyl$C_{1-4}$ alkyl is unsubstituted or substituted with one or more substituents independently selected from the group consisting of halogen, hydroxyl, $C_{1-4}$ alkyl, —(C=O)—$R^6$, —(C=O)—$OR^6$, —(C=O)—$NR^6R^7$, and —$NR^6$—(C=O)—$R^7$;

$R^2$ is independently selected from the group consisting of:
(1) hydrogen, (2) halogen, (4) $C_{1-4}$ alkyl, (5) —O—$C_{1-4}$ alkyl, (6) $C_{3-7}$ cycloalkyl, (7) —O—$C_{3-7}$ cycloalkyl, (8) —(C=O)—$NR^6R^7$, and (9) —$NR^6$(C=O)$R^7$, wherein the $C_{1-4}$ alkyl, the —O—$C_{1-4}$ alkyl, the $C_{3-7}$ cycloalkyl, or the —O—$C_{3-7}$ cycloalkyl is unsubstituted or substituted with one or more substituents independently selected from the group consisting of: halogen, hydroxyl, $C_{1-4}$ alkoxyl, —$NR^6R^7$, —(C=O)—$NR^6R^7$, —$NR^6$—(C=O)—$R^7$ and —$NR^6CH_2$—(C=O)—$NH_2$;

p is 0, 1, or 2; when p is two or more, each $R^2$ is the same or different;

$R^3$ is independently selected from the group consisting of:
(1) hydrogen, (2) halogen, (4) $C_{1-4}$ alkyl, (5) —O—$C_{1-4}$ alkyl, wherein the $C_{1-4}$ alkyl or the —O—$C_{1-4}$ alkyl is unsubstituted or substituted with one or more substituents independently selected form the group consisting of: halogen, hydroxyl, $C_{1-4}$ alkoxyl, and $C_{3-7}$ cycloalkyl, (6) $C_{3-7}$ cycloalkyl, (7) —O—$C_{3-7}$ cycloalkyl, (8) aryl, (9) 5-6 membered heteroaryl, (11) —$NR^6R^7$, and (12) —CN; wherein the $C_{3-7}$ cycloalkyl, the —O—$C_{3-7}$ cycloalkyl, the aryl, or the 5-6 membered heteroaryl is unsubstituted or substituted with one or more substituents independently selected form the group consisting of: halogen, hydroxyl, and $C_{1-4}$ alkyl;

q is 0, 1, or 2; when q is two or more, each $R^3$ is the same or different;

X is $CR^3$ or N;
Y is $CR^3$ or N;

$R^4$ is independently selected from the group consisting of:
(1) hydrogen, (2) halogen, (4) $C_{1-4}$ alkyl, (5) —O—$C_{1-4}$ alkyl, (6) $C_{3-7}$ cycloalkyl, (7) —O—$C_{3-7}$ cycloalkyl, and (8) —CN; wherein the $C_{1-4}$ alkyl, the —O—$C_{1-4}$ alkyl, the $C_{3-7}$ cycloalkyl, or the —O—$C_{3-7}$ cycloalkyl is unsubstituted or substituted with one or more substituents independently selected form the group consisting of: halogen or hydroxyl;

r is 0, 1, 2, or 3; when r is two or more, each $R^4$ is the same or different;

Z is $CR^4$ or N;

$R^5$ is selected from the group consisting of:
(1) $C_{1-4}$ alkyl, (3) $C_{3-7}$ cycloalkyl, (4) $C_{3-7}$ cycloalkyl$C_{1-4}$ alkyl, wherein the $C_{1-4}$ alkyl, the $C_{3-7}$ cycloalkyl, or the $C_{3-7}$ cycloalkyl$C_{1-4}$ alkyl is unsubstituted or substituted with one or more substituents independently selected form the group consisting of: halogen, hydroxyl, and $C_{1-4}$ alkoxyl, (5) aryl, and (6) 5-6 membered heteroaryl, wherein the aryl or the 5-6 membered heteroaryl is unsubstituted or substituted with one or more substituents independently selected form the group consisting of: halogen, hydroxyl, $C_{1-4}$ alkyl, and $C_{1-4}$ alkoxyl $R^6$ and $R^7$ are independently selected from the group consisting of:
(1) hydrogen, (2) $C_{1-4}$ alkyl, and (3) $C_{1-4}$ alkoxy$C_{1-4}$ alkyl, wherein the $C_{1-4}$ alkyl or the $C_{1-4}$ alkoxy$C_{1-4}$ alkyl is unsubstituted or substituted with one or more substituents independently selected from the group consisting of: halogen and hydroxyl; $R^6$ may form a 4 to 7 membered ring with $R^7$ which may contain a nitrogen atom, an oxygen atom, a sulfur atom, carbonyl, or a double bond; wherein the 4 to 7 membered ring is unsubstituted or substituted with one or more substituents independently selected from the group consisting of: halogen, hydroxyl, and $C_{1-4}$ alkoxyl;

or a prodrug thereof or a pharmaceutically acceptable salt thereof.

[7] This invention provides the compound described in any one of [1] to [6] wherein:
A is pyridyl or pyrazyl;
W is —O—;
W is substituted at para-position with respect to the 6 membered ring including X and Y;

$R^1$ is independently selected from the group consisting of:
(1) $C_{3-7}$ cycloalkyl and (3) $C_{3-7}$ cycloalkyl$C_{1-6}$ alkyl, wherein the $C_{3-7}$ cycloalkyl or the $C_{3-7}$ cycloalkyl$C_{1-6}$ alkyl is unsubstituted or substituted with one or more halogens;

$R^2$ is independently selected from the group consisting of:
(2) halogen and (4) $C_{1-6}$ alkyl;

p is 0 or 1;

$R^3$ is independently selected from the group consisting of:
(1) hydrogen, (2) halogen, and (4) $C_{1-6}$ alkyl;

q is 0 or 1;
X is $CR^3$;
Y is $CR^3$;

$R^4$ is independently selected from the group consisting of:
(1) hydrogen, (2) halogen, and (4) $C_{1-6}$ alkyl;

r is 0 or 1;
Z is $CR^4$;

$R^5$ is selected from the group consisting of: (1) $C_{1-4}$ alkyl, (3) $C_{3-7}$ cycloalkyl, (4) $C_{3-7}$ cycloalkyl$C_{1-4}$ alkyl, wherein the $C_{1-4}$ alkyl, the $C_{3-7}$ cycloalkyl, or the $C_{3-7}$ cycloalkyl$C_{1-4}$ alkyl is unsubstituted or substituted with one or more halogens;

or a prodrug thereof or a pharmaceutically acceptable salt thereof.

[8] This invention provides the compound described in any one of [1] to [7] wherein:
A is pyridyl or pyrazyl;
W is —O—;
W is substituted at para-position with respect to the 6 membered ring including X and Y;

$R^1$ is independently selected from the group consisting of:
(1) $C_{3-6}$ cycloalkyl and (3) $C_{3-6}$ cycloalkyl$C_{1-4}$ alkyl, wherein the $C_{3-6}$ cycloalkyl or the $C_{3-6}$ cycloalkyl$C_{1-4}$ alkyl is unsubstituted or substituted with one or more halogens;

$R^2$ is independently selected from the group consisting of:
(2) halogen and (4) $C_{1-4}$ alkyl;

p is 0 or 1;

$R^3$ is independently selected from the group consisting of:
(1) hydrogen, (2) halogen, and (4) $C_{1-4}$ alkyl;

q is 0 or 1;
X is $CR^3$;
Y is $CR^3$;

$R^4$ is independently selected from the group consisting of:
(1) hydrogen, (2) halogen, and (4) $C_{1-4}$ alkyl;

r is 0 or 1;
Z is $CR^4$;

$R^5$ is selected from the group consisting of: (1) $C_{1-4}$ alkyl, (3) $C_{3-7}$ cycloalkyl, (4) $C_{3-7}$ cycloalkyl$C_{1-4}$ alkyl, wherein the $C_{1-4}$ alkyl, the $C_{3-7}$ cycloalkyl, or the $C_{3-7}$ cycloalkyl$C_{1-4}$ alkyl is unsubstituted or substituted with one or more halogens;

or a prodrug thereof or a pharmaceutically acceptable salt thereof.

[9] Suitable individual compounds of the invention are:
N-(methylsulfonyl)-4-((3-(6-((tetrahydro-2H-pyran-4-yl)methoxy)pyridin-3-yl)phenoxy)methyl)benzamide;
4-((3-(6-(cyclopropylmethoxy)pyridin-3-yl)phenoxy)methyl)-N-(methylsulfonyl)benzamide;
4-((3-(6-(cyclopropylmethoxy)pyridin-3-yl)phenoxy)methyl)-N-((trifluoromethyl)sulfonyl)benzamide;
4-((3-(6-(cyclopropylmethoxy)pyridin-3-yl)phenoxy)methyl)-N-(cyclopropylsulfonyl)benzamide;
4-((3-(6-(cyclopropylmethoxy)pyridin-3-yl)phenoxy)methyl)-N-(isopropylsulfonyl)benzamide;
4-((3-(6-((3,3-difluorocyclobutyl)methoxy)pyridin-3-yl)phenoxy)methyl)-N-(methylsulfonyl)benzamide;

4-((3-(6-((4,4-difluorocyclohexyl)methoxy)pyridin-3-yl)phenoxy)methyl)-N-(methylsulfonyl)benzamide;
4-((3-(6-(cyclopropylmethoxy)-4-methylpyridin-3-yl)phenoxy)methyl)-N-(methylsulfonyl)benzamide;
4-((3-(6-(cyclopentylmethoxy)pyridin-3-yl)phenoxy)methyl)-N-(methylsulfonyl)benzamide;
4-((3-(6-(cyclopropylmethoxy)-5-methylpyridin-3-yl)phenoxy)methyl)-N-(methylsulfonyl)benzamide;
tert-butyl 4-(((5-(3-((4-((methylsulfonyl)carbamoyl)benzyl)oxy)phenyl)pyridin-2-yl)oxy)methyl)piperidine-1-carboxylate;
4-((2-chloro-5-(6-(cyclopropylmethoxy)pyridin-3-yl)phenoxy)methyl)-N-(methylsulfonyl)benzamide;
3-chloro-4-((3-(6-(cyclopropylmethoxy)pyridin-3-yl)phenoxy)methyl)-N-(methylsulfonyl)benzamide;
4-((3-(6-(cyclopropylmethoxy)pyridin-3-yl)phenoxy)methyl)-3-fluoro-N-(methylsulfonyl)benzamide;
4-((3-(6-(cyclobutylmethoxy)pyridin-3-yl)phenoxy)methyl)-N-(methylsulfonyl)benzamide;
5-chloro-4-((3-(6-(cyclopropylmethoxy)pyridin-3-yl)phenoxy)methyl)-2-fluoro-N-(methylsulfonyl)benzamide;
5-chloro-4-((3-(6-(cyclopropylmethoxy)pyridin-3-yl)phenoxy)methyl)-N-(cyclopropylsulfonyl)-2-fluorobenzamide;
4-((3-(6-(cyclopropylmethoxy)pyridin-3-yl)phenoxy)methyl)-N-(thiophen-2-ylsulfonyl)benzamide;
4-((3-(6-(cyclopropylmethoxy)pyridin-3-yl)phenoxy)methyl)-N-(thiazol-2-ylsulfonyl)benzamide;
5-chloro-4-((3-(6-(cyclopropylmethoxy)pyridin-3-yl)phenoxy)methyl)-2-fluoro-N-(thiophen-2-ylsulfonyl)benzamide;
4-((3-chloro-5-(6-(cyclopropylmethoxy)pyridin-3-yl)phenoxy)methyl)-N-(methylsulfonyl)benzamide;
4-((4-chloro-3-(6-(cyclopropylmethoxy)pyridin-3-yl)phenoxy)methyl)-N-(methylsulfonyl)benzamide;
5-cyclopropyl-4-((3-(6-(cyclopropylmethoxy)pyridin-3-yl)phenoxy)methyl)-2-fluoro-N-(methylsulfonyl)benzamide;
4-((3-(6-(cyclopropylmethoxy)pyridin-3-yl)phenoxy)methyl)-2,5-difluoro-N-(methylsulfonyl)benzamide;
3-fluoro-N-(methylsulfonyl)-4-((3-(6-((tetrahydro-2H-pyran-4-yl)methoxy)pyridin-3-yl)phenoxy)methyl)benzamide;
4-((3-(6-(cyclopropylmethoxy)pyridin-3-yl)phenoxy)methyl)-5-(difluoromethoxy)-2-fluoro-N-(methylsulfonyl)benzamide;
4-((3-(6-(cyclopropylmethoxy)pyridin-3-yl)phenoxy)methyl)-2-fluoro-N-(methylsulfonyl)benzamide;
4-((3-(6-(cyclopropylmethoxy)pyridin-3-yl)phenoxy)methyl)-3,5-difluoro-N-(methylsulfonyl)benzamide;
N-(cyclopropylsulfonyl)-4-((3-(6-((tetrahydro-2H-pyran-4-yl)methoxy)pyridin-3-yl)phenoxy)methyl)benzamide;
4-((3-(6-(cyclopropylmethoxy)pyridin-3-yl)-5-fluorophenoxy)methyl)-N-(methylsulfonyl)benzamide;
4-((3-(6-(cyclopropylmethoxy)pyridin-3-yl)-5-fluorophenoxy)methyl)-2,5-difluoro-N-(methylsulfonyl)benzamide;
4-((3-(6-(cyclopropylmethoxy)pyridin-3-yl)-5-fluorophenoxy)methyl)-3-fluoro-N-(methylsulfonyl)benzamide;
4-((3-(6-(cyclopropylmethoxy)pyridin-3-yl)-5-fluorophenoxy)methyl)-N-(cyclopropylsulfonyl)-3-fluorobenzamide;
4-((3-cyclopropyl-5-(6-(cyclopropylmethoxy)pyridin-3-yl)phenoxy)methyl)-N-(methylsulfonyl)benzamide;
4-((3-(6-(cyclopropylmethoxy)pyridin-3-yl)-5-methylphenoxy)methyl)-3-fluoro-N-(methylsulfonyl)benzamide;
4-((3-(6-(cyclopropylmethoxy)pyridin-3-yl)-5-methylphenoxy)methyl)-N-(cyclopropylsulfonyl)-3-fluorobenzamide;
4-((3-(6-(cyclopropylmethoxy)pyridin-3-yl)-5-(trifluoromethyl)phenoxy)methyl)-N-(methylsulfonyl)benzamide;
4-((3-(6-(cyclopropylmethoxy)pyridin-3-yl)phenoxy)methyl)-N-((2-methoxyethyl)sulfonyl)benzamide;
4-((3-(6-(cyclopropylmethoxy)pyridin-3-yl)-2-fluorophenoxy)methyl)-N-(methylsulfonyl)benzamide;
3-cyano-4-((3-(6-(cyclopropylmethoxy)pyridin-3-yl)phenoxy)methyl)-N-(methylsulfonyl)benzamide;
3-cyano-4-((3-(6-(cyclopropylmethoxy)pyridin-3-yl)phenoxy)methyl)-N-(cyclopropylsulfonyl)benzamide;
4-((3-(6-(cyclopropylmethoxy)pyridin-3-yl)-4-fluorophenoxy)methyl)-N-(methylsulfonyl)benzamide;
4-((3-(6-(cyclopropylmethoxy)pyridin-3-yl)-4-fluorophenoxy)methyl)-N-(cyclopropylsulfonyl)benzamide;
4-((5-(6-(cyclopropylmethoxy)pyridin-3-yl)-2-fluorophenoxy)methyl)-N-(methylsulfonyl)benzamide;
4-((3-bromo-5-(6-(cyclopropylmethoxy)pyridin-3-yl)phenoxy)methyl)-N-(methylsulfonyl)benzamide;
4-((3-(6-(cyclopropylmethoxy)pyridin-3-yl)-4-fluorophenoxy)methyl)-3-fluoro-N-(methylsulfonyl)benzamide;
4-((3-(6-(cyclopropylmethoxy)pyridin-3-yl)-4-fluorophenoxy)methyl)-N-(cyclopropylsulfonyl)-3-fluorobenzamide;
4-((3-(6-(cyclopropylmethoxy)pyridin-3-yl)-4-methylphenoxy)methyl)-3-fluoro-N-(methylsulfonyl)benzamide;
4-((3-(6-(cyclopropylmethoxy)pyridin-3-yl)-4-methylphenoxy)methyl)-N-(cyclopropylsulfonyl)-3-fluorobenzamide;
4-((4-chloro-3-(6-(cyclopropylmethoxy)pyridin-3-yl)phenoxy)methyl)-3-fluoro-N-(methylsulfonyl)benzamide;
4-((3-(6-(cyclobutylmethoxy)pyridin-3-yl)phenoxy)methyl)-3-fluoro-N-(methylsulfonyl)benzamide;
4-((3-(6-(cyclopropylmethoxy)pyridin-3-yl)phenoxy)methyl)-N-(ethylsulfonyl)-3-fluorobenzamide;
4-((3-(6-(cyclopropylmethoxy)pyridin-3-yl)phenoxy)methyl)-3-fluoro-N-(isopropylsulfonyl)benzamide;
4-((3-(6-(cyclopropylmethoxy)pyridin-3-yl)phenoxy)methyl)-N-(cyclopropylsulfonyl)-3-fluorobenzamide;
4-((3-(6-(cyclopropylmethoxy)pyridin-3-yl)phenoxy)methyl)-N-((cyclopropylmethyl)sulfonyl)-3-fluorobenzamide;
4-((3-(6-(cyclopropylmethoxy)pyridin-3-yl)phenoxy)methyl)-3-fluoro-N-(thiophen-2-ylsulfonyl)benzamide;
4-((3-(6-(cyclopropylmethoxy)pyridin-3-yl)phenoxy)methyl)-3-fluoro-N-(thiazol-2-ylsulfonyl)benzamide;
4-((3-(6-(cyclopropylmethoxy)pyridin-3-yl)phenoxy)methyl)-3-fluoro-N-((trifluoromethyl)sulfonyl)benzamide;
4-((3-(6-(cyclopropylmethoxy)pyridin-3-yl)phenoxy)methyl)-3-methoxy-N-(methylsulfonyl)benzamide;
4-((3-(2-(cyclopropylmethoxy)pyridin-3-yl)phenoxy)methyl)-N-(methylsulfonyl)benzamide;
4-((3-(5-(cyclopropylmethoxy)pyridin-3-yl)phenoxy)methyl)-N-(methylsulfonyl)benzamide;
5-cyclopropyl-6-((3-(6-(cyclopropylmethoxy)pyridin-3-yl)phenoxy)methyl)-N-(methylsulfonyl)nicotinamide;
6-((3-(6-(cyclopropylmethoxy)pyridin-3-yl)phenoxy)methyl)-N-(methylsulfonyl)nicotinamide;
6-((3-(6-(cyclopropylmethoxy)pyridin-3-yl)-5-fluorophenoxy)methyl)-N-(methylsulfonyl)nicotinamide;
4-(((6-(cyclopropylmethoxy)-[3,4'-bipyridin]-2'-yl)oxy)methyl)-N-(cyclopropylsulfonyl)benzamide;
4-(((6'-(cyclopropylmethoxy)-[2,3'-bipyridin]-6-yl)oxy)methyl)-N-(methylsulfonyl)benzamide;

4-((3-(5-(cyclopropylmethoxy)pyridin-2-yl)phenoxy)
methyl)-N-(methylsulfonyl)benzamide;
4-((3-(6-(cyclopropylmethoxy)pyridin-2-yl)phenoxy)
methyl)-N-(methylsulfonyl)benzamide;
4-((3-(3-chloro-5-(cyclopropylmethoxy)pyridin-2-yl)phenoxy)methyl)-N-(methylsulfonyl)benzamide;
4-((3-(5-(cyclopropylmethoxy)-3-fluoropyridin-2-yl)phenoxy)methyl)-N-(methylsulfonyl)benzamide;
4-((3-(5-(cyclopropylmethoxy)-3-methylpyridin-2-yl)phenoxy)methyl)-N-(methylsulfonyl)benzamide;
4-((3-(2-(cyclopropylmethoxy)pyridin-4-yl)phenoxy)
methyl)-N-(methylsulfonyl)benzamide;
4-((3-(5-(cyclopropylmethoxy)pyrazin-2-yl)phenoxy)
methyl)-N-(methylsulfonyl)benzamide;
4-((3-(5-(cyclopropylmethoxy)pyrazin-2-yl)phenoxy)
methyl)-3-fluoro-N-(methylsulfonyl)benzamide;
4-((3-(5-(cyclopropylmethoxy)pyrazin-2-yl)phenoxy)
methyl)-N-(cyclopropylsulfonyl)benzamide;
4-((3-(6-(cyclopropylmethoxy)pyrazin-2-yl)phenoxy)
methyl)-3-fluoro-N-(methylsulfonyl)benzamide;
4-((3-(5-(cyclopropylmethoxy)pyrimidin-2-yl)phenoxy)
methyl)-N-(methylsulfonyl)benzamide;
4-((3-(5-(cyclopropylmethoxy)pyrimidin-2-yl)phenoxy)
methyl)-3-fluoro-N-(methylsulfonyl)benzamide;
4-((3-(5-(cyclopropylmethoxy)pyrimidin-2-yl)phenoxy)
methyl)-N-(cyclopropylsulfonyl)benzamide;
4-(((4'-(cyclopropylmethoxy)-[1,1'-biphenyl]-3-yl)oxy)
methyl)-N-(methylsulfonyl)benzamide;
4-cyclopropylmethoxy-3'-((2-fluoro-4-((methylsulfonyl)
carbamoyl)benzyl)oxy)-N-methyl-[1,1'-biphenyl]-3-carboxamide;
4-cyclopropylmethoxy-3'-((2-fluoro-4-((methylsulfonyl)
carbamoyl)benzyl)oxy)-N,N-dimethyl-[1,1'-biphenyl]-3-carboxamide;
4-((3-(1-(cyclopropylmethyl)-1H-pyrazol-3-yl)phenoxy)
methyl)-3-fluoro-N-(methylsulfonyl)benzamide;
4-((3-(5-(cyclopropylmethyl)isoxazol-3-yl)phenoxy)
methyl)-3-fluoro-N-(methylsulfonyl)benzamide;
4-((3-(6-(cyclopropylmethoxy)-2-methylpyridin-3-yl)phenoxy)methyl)-N-(methylsulfonyl)benzamide;
4-((3-(6-(cyclopropylmethoxy)-2-methylpyridin-3-yl)phenoxy)methyl)-3-fluoro-N-(methylsulfonyl)benzamide;
3-fluoro-N-(methylsulfonyl)-4-((3-(6-((tetrahydrofuran-3-yl)methoxy)pyridin-3-yl)phenoxy)methyl)benzamide;
4-((3-fluoro-5-(6-((tetrahydrofuran-3-yl)methoxy)pyridin-3-yl)phenoxy)methyl)-N-(methylsulfonyl)benzamide;
4-((3-cyano-5-(6-(cyclopropylmethoxy)pyridin-3-yl)phenoxy)methyl)-N-(methylsulfonyl)benzamide;
4-((3-(6-(cyclobutylmethoxy)-2-methylpyridin-3-yl)-5-fluorophenoxy)methyl)-N-(methylsulfonyl)benzamide;
4-((3-(6-(cyclopropylmethoxy)-5-methylpyridin-3-yl)phenoxy)methyl)-3-fluoro-N-(methylsulfonyl)benzamide;
4-((3-(6-(cyclopropylmethoxy)-5-methylpyridin-3-yl)-5-fluorophenoxy)methyl)-N-(methylsulfonyl)benzamide;
4-((3-(6-(cyclopropylmethoxy)-2-methylpyridin-3-yl)-5-fluorophenoxy)methyl)-N-(methylsulfonyl)benzamide;
4-((3-(6-(cyclopropylmethoxy)-4-methylpyridin-3-yl)phenoxy)methyl)-3-fluoro-N-(methylsulfonyl)benzamide;
4-((3-(6-(cyclopropylmethoxy)-4-methylpyridin-3-yl)-5-fluorophenoxy)methyl)-N-(methylsulfonyl)benzamide;
4-((3-(5-chloro-6-(cyclopropylmethoxy)pyridin-3-yl)phenoxy)methyl)-N-(methylsulfonyl)benzamide;
tert-butyl 3-(((5-(3-((2-fluoro-4-((methylsulfonyl)carbamoyl)benzyl)oxy)phenyl)pyridin-2-yl)oxy)methyl)azetidine-1-carboxylate;
4-((3-(5-chloro-6-(cyclopropylmethoxy)pyridin-3-yl)-5-fluorophenoxy)methyl)-3-fluoro-N-(methylsulfonyl)benzamide;
4-((3-(5-chloro-6-(cyclopropylmethoxy)pyridin-3-yl)-4-fluorophenoxy)methyl)-3-fluoro-N-(methylsulfonyl)benzamide;
4-((3-(6-(cyclopropylmethoxy)-2-methylpyridin-3-yl)-4-fluorophenoxy)methyl)-3-fluoro-N-(methylsulfonyl)benzamide;
4-((3-(6-(cyclobutylmethoxy)-5-(hydroxymethyl)pyridin-3-yl)phenoxy)methyl)-3-fluoro-N-(methylsulfonyl)benzamide;
4-((3-(6-(cyclobutylmethoxy)-5-(hydroxymethyl)pyridin-3-yl)-5-fluorophenoxy)methyl)-3-fluoro-N-(methylsulfonyl)benzamide;
4-((3-(6-(cyclobutylmethoxy)-5-(hydroxymethyl)pyridin-3-yl)phenoxy)methyl)-N-(methylsulfonyl)benzamide;
4-((3-(6-(cyclobutylmethoxy)-5-(hydroxymethyl)pyridin-3-yl)-5-fluorophenoxy)methyl)-N-(methylsulfonyl)benzamide;
4-((3-(6-(cyclobutylmethoxy)-2-(hydroxymethyl)pyridin-3-yl)phenoxy)methyl)-3-fluoro-N-(methylsulfonyl)benzamide;
4-((3-(6-(cyclobutylmethoxy)-2-(hydroxymethyl)pyridin-3-yl)phenoxy)methyl)-N-(methylsulfonyl)benzamide;
4-(((5-(6-(cyclopropylmethoxy)pyridin-3-yl)-[1,1'-biphenyl]-3-yl)oxy)methyl)-N-(methylsulfonyl)benzamide;
4-((3-(6-(cyclopropylmethoxy)pyridin-3-yl)-5-(pyrimidin-5-yl)phenoxy)methyl)-N-(methylsulfonyl)benzamide;
4-((3-(6-(cyclopropylmethoxy)pyridin-3-yl)-5-(1-methyl-1H-pyrazol-4-yl)phenoxy)methyl)-N-(methylsulfonyl)benzamide;
4-((3-(6-(cyclopropylmethoxy)pyridin-3-yl)-5-(pyridin-3-yl)phenoxy)methyl)-N-(methylsulfonyl)benzamide;
4-((3-(5-(cyclopropylmethoxy)pyridin-3-yl)phenoxy)
methyl)-3-fluoro-N-(methylsulfonyl)benzamide;
4-((3-(5-(cyclopropylmethoxy)pyridin-3-yl)-5-fluorophenoxy)methyl)-N-(methylsulfonyl)benzamide;
6-((3-(6-(cyclobutylmethoxy)pyridin-3-yl)phenoxy)
methyl)-N-(methylsulfonyl)nicotinamide;
4-((3-(6-(cyclopropylmethoxy)pyridin-2-yl)phenoxy)
methyl)-3-fluoro-N-(methylsulfonyl)benzamide;
4-((3-(6-(cyclopropylmethoxy)pyridin-2-yl)-5-fluorophenoxy)methyl)-N-(methylsulfonyl)benzamide;
4-((3-(6-(cyclopropylmethoxy)pyridin-2-yl)-4-fluorophenoxy)methyl)-3-fluoro-N-(methylsulfonyl)benzamide;
4-((3-(5-(cyclopropylmethoxy)-3-fluoropyridin-2-yl)phenoxy)methyl)-3-fluoro-N-(methylsulfonyl)benzamide;
4-((3-(5-(cyclopropylmethoxy)-3-fluoropyridin-2-yl)-5-fluorophenoxy)methyl)-N-(methylsulfonyl)benzamide;
4-((3-(5-(cyclopropylmethoxy)-3-methylpyridin-2-yl)-5-fluorophenoxy)methyl)-N-(methylsulfonyl)benzamide;
4-((3-(5-(cyclopropylmethoxy)-3-methylpyridin-2-yl)phenoxy)methyl)-3-fluoro-N-(methylsulfonyl)benzamide;
4-((3-(5-(cyclobutylmethoxy)-3-methylpyridin-2-yl)-5-fluorophenoxy)methyl)-N-(methylsulfonyl)benzamide;
4-((3-(5-(cyclobutylmethoxy)-3-methylpyridin-2-yl)phenoxy)methyl)-3-fluoro-N-(methylsulfonyl)benzamide;
4-((3-(5-(cyclobutylmethoxy)-3-methylpyridin-2-yl)phenoxy)methyl)-N-(methylsulfonyl)benzamide;
4-((3-(5-(cyclopropylmethoxy)pyridin-2-yl)phenoxy)
methyl)-3-fluoro-N-(methylsulfonyl)benzamide;
4-((3-(5-(cyclopropylmethoxy)pyridin-2-yl)-5-fluorophenoxy)methyl)-N-(methylsulfonyl)benzamide;
4-((3-(4-(cyclopropylmethoxy)-3-methylpyridin-2-yl)phenoxy)methyl)-3-fluoro-N-(methylsulfonyl)benzamide;

4-((3-(4-(cyclopropylmethoxy)-3-methylpyridin-2-yl)-5-fluorophenoxy)methyl)-N-(methylsulfonyl)benzamide;
4-((3-(4-(cyclopropylmethoxy)pyridin-2-yl)-5-fluorophenoxy)methyl)-N-(methylsulfonyl)benzamide;
4-((3-(4-(cyclopropylmethoxy)pyridin-2-yl)phenoxy)methyl)-N-(methylsulfonyl)benzamide;
4-((3-(4-(cyclopropylmethoxy)pyridin-2-yl)phenoxy)methyl)-3-fluoro-N-(methylsulfonyl)benzamide;
4-((3-(2-(cyclopropylmethoxy)pyridin-4-yl)phenoxy)methyl)-3-fluoro-N-(methylsulfonyl)benzamide
4-((3-(2-(cyclopropylmethoxy)pyridin-4-yl)-5-fluorophenoxy)methyl)-N-(methylsulfonyl)benzamide;
4-((3-(2-(cyclopropylmethoxy)-3-methylpyridin-4-yl)phenoxy)methyl)-3-fluoro-N-(methylsulfonyl)benzamide;
4-((3-(2-(cyclopropylmethoxy)-3-methylpyridin-4-yl)-5-fluorophenoxy)methyl)-N-(methylsulfonyl)benzamide;
4-((3-(2-(cyclopropylmethoxy)-3-methylpyridin-4-yl)-4-fluorophenoxy)methyl)-3-fluoro-N-(methylsulfonyl)benzamide;
4-((3-(2-((cyclopropylmethyl)(methyl)amino)pyridin-4-yl)phenoxy)methyl)-3-fluoro-N-(methylsulfonyl)benzamide;
4-((3-(5-(cyclobutylmethoxy)pyrazin-2-yl)phenoxy)methyl)-N-(methylsulfonyl)benzamide;
4-((3-(5-(cyclopropylmethoxy)pyrazin-2-yl)-5-fluorophenoxy)methyl)-N-(methylsulfonyl)benzamide;
4-((3-(5-(cyclopropylmethoxy)pyrazin-2-yl)-4-fluorophenoxy)methyl)-3-fluoro-N-(methylsulfonyl)benzamide;
4-((3-(5-(cyclobutylmethoxy)pyrazin-2-yl)phenoxy)methyl)-3-fluoro-N-(methylsulfonyl)benzamide;
4-((3-(6-(cyclopropylmethoxy)pyrazin-2-yl)-5-fluorophenoxy)methyl)-N-(methylsulfonyl)benzamide;
4-((3-(6-(cyclopropylmethoxy)pyrazin-2-yl)phenoxy)methyl)-N-(methylsulfonyl)benzamide;
4-((3-(5-(cyclopropylmethoxy)pyrimidin-2-yl)-5-fluorophenoxy)methyl)-N-(methylsulfonyl)benzamide;
4-((3-(5-(cyclobutylmethoxy)pyrimidin-2-yl)-5-fluorophenoxy)methyl)-N-(methylsulfonyl)benzamide;
4-((3-(5-(cyclopropylmethoxy)pyrimidin-2-yl)-4-fluorophenoxy)methyl)-3-fluoro-N-(methylsulfonyl)benzamide;
4-((3-(6-(cyclopropylmethoxy)pyrimidin-4-yl)phenoxy)methyl)-N-(methylsulfonyl)benzamide;
4-((3-(6-(cyclopropylmethoxy)pyrimidin-4-yl)-5-fluorophenoxy)methyl)-N-(methylsulfonyl)benzamide;
4-((3-(6-(cyclopropylmethoxy)pyrimidin-4-yl)phenoxy)methyl)-3-fluoro-N-(methylsulfonyl)benzamide;
4-((3-(6-(cyclopropylmethoxy)-5-methylpyrimidin-4-yl)phenoxy)methyl)-3-fluoro-N-(methylsulfonyl)benzamide;
4-((3-(6-(cyclopropylmethoxy)-5-methylpyrimidin-4-yl)-5-fluorophenoxy)methyl)-N-(methylsulfonyl)benzamide;
4-((3-(6-(cyclopropylmethoxy)-5-methylpyrimidin-4-yl)phenoxy)methyl)-N-(methylsulfonyl)benzamide;
4-((3-(2-(cyclopropylmethoxy)pyrimidin-5-yl)phenoxy)methyl)-3-fluoro-N-(methylsulfonyl)benzamide;
4-((3-(2-(cyclopropylmethoxy)pyrimidin-5-yl)-5-fluorophenoxy)methyl)-N-(methylsulfonyl)benzamide;
4-((3-(2-(cyclopropylmethoxy)-4-methylpyrimidin-5-yl)phenoxy)methyl)-3-fluoro-N-(methylsulfonyl)benzamide;
4-((3-(2-(cyclopropylmethoxy)-4-methylpyrimidin-5-yl)-5-fluorophenoxy)methyl)-N-(methylsulfonyl)benzamide;
4-((3-(2-((cyclopropylmethyl)(methyl)amino)pyrimidin-5-yl)phenoxy)methyl)-3-fluoro-N-(methylsulfonyl)benzamide;
4-(((3'-(2-aminoethoxy)-5'-(cyclopropylmethoxy)-5-fluoro-[1,1'-biphenyl]-3-yl)oxy)methyl)-3-fluoro-N-(methylsulfonyl)benzamide;
4-(((3'-(2-amino-2-oxoethoxy)-5'-(cyclopropylmethoxy)-5-fluoro-[1,1'-biphenyl]-3-yl)oxy)methyl)-3-fluoro-N-(methylsulfonyl)benzamide;
4-(((3'-(cyclopropylmethoxy)-5-fluoro-5'-(2-methoxyethoxy)-[1,1'-biphenyl]-3-yl)oxy)methyl)-3-fluoro-N-(methylsulfonyl)benzamide;
4-(((3'-(cyclopropylmethoxy)-5-fluoro-5'-(2-hydroxyethoxy)-[1,1'-biphenyl]-3-yl)oxy)methyl)-3-fluoro-N-(methylsulfonyl)benzamide;
4-(((3'-(cyclopropylmethoxy)-5-fluoro-5'-(morpholine-4-carbonyl)-[1,1'-biphenyl]-3-yl)oxy)methyl)-3-fluoro-N-(methylsulfonyl)benzamide;
5-(cyclopropylmethoxy)-3'-fluoro-5'-((2-fluoro-4-((methylsulfonyl)carbamoyl)benzyl)oxy)-N-methyl-[1,1'-biphenyl]-3-carboxamide;
5-(cyclopropylmethoxy)-3'-fluoro-5'-((2-fluoro-4-((methylsulfonyl)carbamoyl)benzyl)oxy)-N,N-dimethyl-[1,1'-biphenyl]-3-carboxamide;
4-(((3'-(cyclopropylmethoxy)-5'-(2-(dimethylamino)-2-oxoethoxy)-5-fluoro-[1,1'-biphenyl]-3-yl)oxy)methyl)-3-fluoro-N-(methylsulfonyl)benzamide;
4-(((3'-(cyclopropylmethoxy)-5-fluoro-5'-(3-methoxyazetidine-1-carbonyl)-[1,1'-biphenyl]-3-yl)oxy)methyl)-3-fluoro-N-(methylsulfonyl)benzamide;
4-(((3'-(cyclopropylmethoxy)-5-fluoro-5'-(((2-hydroxyethyl)(methyl)amino)methyl)-[1,1'-biphenyl]-3-yl)oxy)methyl)-3-fluoro-N-(methylsulfonyl)benzamide;
4-(((3'-(((2-amino-2-oxoethyl)(methyl)amino)methyl)-5'-(cyclopropylmethoxy)-5-fluoro-[1,1'-biphenyl]-3-yl)oxy)methyl)-3-fluoro-N-(methylsulfonyl)benzamide;
N-(methylsulfonyl)-4-((3-(6-((1-(3,3,3-trifluoropropanoyl)piperidin-4-yl)methoxy)pyridin-3-yl)phenoxy)methyl)benzamide;
N,N-dimethyl-4-(((5-(3-((4-((methylsulfonyl)carbamoyl)benzyl)oxy)phenyl)pyridin-2-yl)oxy)methyl)piperidine-1-carboxamide;
ethyl 4-(((5-(3-((4-((methylsulfonyl)carbamoyl)benzyl)oxy)phenyl)pyridin-2-yl)oxy)methyl)piperidine-1-carboxylate;
4-(((3'-(2-acetamidoethoxy)-5'-(cyclopropylmethoxy)-5-fluoro-[1,1'-biphenyl]-3-yl)oxy)methyl)-3-fluoro-N-(methylsulfonyl)benzamide;
4-((3-(6-(cyclopropylmethoxy)pyridin-3-yl)-5-fluorophenoxy)methyl)-N-(ethylsulfonyl)benzamide;
4-((3-(6-(cyclopropylmethoxy)pyridin-3-yl)-5-fluorophenoxy)methyl)-N-(isopropylsulfonyl)benzamide;
4-((3-(6-(cyclopropylmethoxy)pyridin-3-yl)-5-fluorophenoxy)methy)-N-(cyclopropylsulfonyl)benzamide;
4-((3-(6-(cyclopropylmethoxy)pyridin-3-yl)-5-fluorophenoxy)methy)-N-((cyclopropylmethyl)sulfonyl)benzamide;
4-((3-(6-(cyclopropylmethoxy)pyridin-3-yl)-5-fluorophenoxy)methyl)-N-(thiophen-2-ylsulfonyl)benzamide; and
4-((3-(6-(cyclopropylmethoxy)pyridin-3-yl)-5-fluorophenoxy)methyl)-N-((trifluoromethyl)sulfonyl)benzamide
or a prodrug thereof or a pharmaceutically acceptable salt thereof.

[10] More suitable individual compounds of the invention are:
4-((3-(6-(cyclopropylmethoxy)pyridin-3-yl)phenoxy)methyl)-N-((trifluoromethyl)sulfonyl)benzamide;
4-((3-(6-(cyclopropylmethoxy)pyridin-3-yl)-5-fluorophenoxy)methyl)-3-fluoro-N-(methylsulfonyl)benzamide;

4-((3-(6-(cyclopropylmethoxy)pyridin-3-yl)-5-methylphenoxy)methyl)-3-fluoro-N-(methylsulfonyl)benzamide;
4-((3-bromo-5-(6-(cyclopropylmethoxy)pyridin-3-yl)phenoxy)methyl)-N-(methylsulfonyl)benzamide;
4-((3-(6-(cyclopropylmethoxy)pyridin-3-yl)-4-fluorophenoxy)methyl)-3-fluoro-N-(methylsulfonyl)benzamide;
4-((3-(6-(cyclopropylmethoxy)pyridin-3-yl)-4-methylphenoxy)methyl)-3-fluoro-N-(methylsulfonyl)benzamide;
4-((4-chloro-3-(6-(cyclopropylmethoxy)pyridin-3-yl)phenoxy)methyl)-3-fluoro-N-(methylsulfonyl)benzamide;
4-((3-(6-(cyclopropylmethoxy)pyridin-2-yl)phenoxy)methyl)-N-(methylsulfonyl)benzamide;
4-((3-(6-(cyclopropylmethoxy)-2-methylpyridin-3-yl)phenoxy)methyl)-3-fluoro-N-(methylsulfonyl)benzamide;
4-((3-(5-chloro-6-(cyclopropylmethoxy)pyridin-3-yl)phenoxy)methyl)-3-fluoro-N-(methylsulfonyl)benzamide;
4-((3-(5-chloro-6-(cyclopropylmethoxy)pyridin-3-yl)-5-fluorophenoxy)methyl)-3-fluoro-N-(methylsulfonyl)benzamide;
4-((3-(5-chloro-6-(cyclopropylmethoxy)pyridin-3-yl)-4-fluorophenoxy)methyl)-3-fluoro-N-(methylsulfonyl)benzamide;
4-((3-(6-(cyclopropylmethoxy)-2-methylpyridin-3-yl)-4-fluorophenoxy)methyl)-3-fluoro-N-(methylsulfonyl)benzamide;
4-((3-(6-(cyclobutylmethoxy)-5-(hydroxymethyl)pyridin-3-yl)phenoxy)methyl)-3-fluoro-N-(methylsulfonyl)benzamide;
4-((3-(6-(cyclobutylmethoxy)-5-(hydroxymethyl)pyridin-3-yl)-5-fluorophenoxy)methyl)-3-fluoro-N-(methylsulfonyl)benzamide;
4-((3-(6-(cyclobutylmethoxy)-5-(hydroxymethyl)pyridin-3-yl)-5-fluorophenoxy)methyl)-N-(methylsulfonyl)benzamide;
4-((3-(6-(cyclopropylmethoxy)pyridin-2-yl)-4-fluorophenoxy)methyl)-3-fluoro-N-(methylsulfonyl)benzamide;
4-((3-(2-(cyclopropylmethoxy)-3-methylpyridin-4-yl)-4-fluorophenoxy)methyl)-3-fluoro-N-(methylsulfonyl)benzamide;
4-((3-(2-((cyclopropylmethyl)(methyl)amino)pyridin-4-yl)phenoxy)methyl)-3-fluoro-N-(methylsulfonyl)benzamide;
4-((3-(5-(cyclopropylmethoxy)pyrazin-2-yl)-4-fluorophenoxy)methyl)-3-fluoro-N-(methylsulfonyl)benzamide;
4-((3-(5-(cyclobutylmethoxy)pyrazin-2-yl)phenoxy)methyl)-3-fluoro-N-(methylsulfonyl)benzamide;
4-(((3'-(cyclopropylmethoxy)-5-fluoro-5'-(2-methoxyethoxy)-[1,1'-biphenyl]-3-yl)oxy)methyl)-3-fluoro-N-(methylsulfonyl)benzamide;
4-((3-(6-(cyclopropylmethoxy)pyridin-3-yl)phenoxy)methyl)-N-(methylsulfonyl)benzamide;
4-((3-(6-(cyclopropylmethoxy)pyridin-3-yl)phenoxy)methyl)-3-fluoro-N-(methylsulfonyl)benzamide;
4-((3-(6-(cyclopropylmethoxy)pyridin-3-yl)-5-fluorophenoxy)methyl)-N-(methylsulfonyl)benzamide;
4-((3-(6-(cyclopropylmethoxy)pyridin-3-yl)phenoxy)methyl)-N-(cyclopropylsulfonyl)-3-fluorobenzamide;
4-((3-(6-(cyclopropylmethoxy)pyridin-3-yl)-5-fluorophenoxy)methyl)-N-(ethylsulfonyl)benzamide;
4-((3-(6-(cyclopropylmethoxy)pyridin-3-yl)-5-fluorophenoxy)methyl)-N-(cyclopropylsulfonyl)benzamide;
4-((3-(6-(cyclopropylmethoxy)pyridin-3-yl)-5-fluorophenoxy)methyl)-N-((cyclopropylmethyl)sulfonyl)benzamide; and
4-((3-(6-(cyclopropylmethoxy)pyridin-3-yl)-5-fluorophenoxy)methyl)-N-(thiophen-2-ylsulfonyl)benzamide or a prodrug thereof or a pharmaceutically acceptable salt thereof.

[11] The present invention provides a pharmaceutical composition comprising a compound or a prodrug thereof or a pharmaceutically acceptable salt thereof, as described in any one of [1] to [10], and a pharmaceutically acceptable carrier.

[12] The present invention provides the pharmaceutical composition as described in [11], further comprising another pharmacologically active agent.

[13] The present invention provides a method for the treatment of a condition or disorder in which TTX-S channel blockers are involved, in an animal, including a human, which comprises administering to the animal in need of such treatment a therapeutically effective amount of a compound or a prodrug thereof or a pharmaceutically acceptable salt thereof, as described in any one of [1] to [10].

[14] The present invention provides the method as described in [13], wherein said condition or disorder is selected from the group consisting of: pain, acute pain, chronic pain, neuropathic pain, inflammatory pain, visceral pain, nociceptive pain, pruritus, multiple sclerosis, neurodegenerative disorder, irritable bowel syndrome, osteoarthritis, rheumatoid arthritis, neuropathological disorders, functional bowel disorders, inflammatory bowel diseases pain, pain associated with dysmenorrhea, pelvic pain, cystitis pain, pancreatitis pain, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders including anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, back pain, head or neck pain, severe or intractable pain, breakthrough pain, postsurgical pain, stroke pain, cancer pain, seizure disorder, causalgia, and chemo-induced pain; and combinations thereof.

[15] The present invention provides a use of a compound described in any one of [1] to [10] or a pharmaceutically acceptable salt, prodrug, solvate or composition thereof for the manufacture of a medicament for the treatment of a condition or disorder in which TTX-S channel blockers are involved.

[16] The present invention provides the use as described in [15], wherein said condition or disorder is selected from the group consisting of: pain, acute pain, chronic pain, neuropathic pain, inflammatory pain, visceral pain, nociceptive pain, pruritus, multiple sclerosis, neurodegenerative disorder, irritable bowel syndrome, osteoarthritis, rheumatoid arthritis, neuropathological disorders, functional bowel disorders, inflammatory bowel diseases pain, pain associated with dysmenorrhea, pelvic pain, cystitis pain, pancreatitis pain, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders including anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, back pain, head or neck pain, severe or intractable pain, breakthrough pain, postsurgical pain, stroke pain, cancer pain, seizure disorder, causalgia, and chemo-induced pain;

and combinations thereof.

[17] The present invention provides a compound described in any one of [1] to [10] or a prodrug thereof or a pharmaceutically acceptable salt thereof for use in the treatment of a condition or disorder in which TTX-S channel blockers are involved.

[18] The present invention provides a process for preparing a pharmaceutical composition comprising mixing a compound or a prodrug thereof or a pharmaceutically acceptable salt thereof, as described in any one of [1] to [10], and a pharmaceutically acceptable carrier or excipient.

Advantageous Effects of Invention

The biaryloxy derivatives of the present invention are sodium channel blockers and have a number of therapeutic applications, particularly in the treatment of pain.

More particularly, the biaryloxy derivatives of the invention are selective tetrodotoxin-sensitive (TTX-S) blockers. In the discussion that follows, the invention is exemplified by reference to the inhibition of $Na_{V1.7}$ channel as the TTX-S channel.

They show the affinity for $Na_{V1.7}$ channel which is significantly greater than their affinity for $Na_{V1.5}$ channel as the tetrodotoxin-resistant (TTX-R) sodium channels.

The biaryloxy derivatives of the invention show good selectivity for the $Na_{V1.7}$ channel as compared with $Na_{V1.5}$ channel.

In particular, the biaryloxy derivatives of the present invention are selective for the TTX-S channels over the $Na_{V1.5}$ channel, leading to improvements in the side-effect profile.

The biaryloxy derivatives of the present invention are therefore useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back pain, orofacial pain and chemo-induced pain.

Other conditions that may be treated with the biaryloxy derivatives of the present invention include multiple sclerosis, pruritus, neurodegenerative disorders, irritable bowel syndrome, osteoarthritis, rheumatoid arthritis, neuropathological disorders, functional bowel disorders, inflammatory bowel diseases pain, pain associated with dysmenorrhea, pelvic pain, cystitis pain, pancreatitis pain, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders including anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, back pain, head or neck pain, severe or intractable pain, breakthrough pain, postsurgical pain, stroke pain, cancer pain, seizure disorder and causalgia.

Pfizer discloses structurally close arts in WO2012/007868, WO2012/007869 and WO2013/088315. Xenon discloses structurally close arts in WO2013/177224, WO2014/008458 and WO2015/078374. The compounds of present invention show much better activities than those of the close arts. As summarized in the Table 1, the compounds of the present invention show excellent activities by introducing cyclopropylmethyl or cyclopropylmethyloxy substituent as $R^1$—W-substituent to the A ring in the above formula (I), comparing with the comparative compound in WO2012/007868. The compound of Example 84 and the compound of Example 24 in the present invention, which are introduced cyclopropylmethyl group on the oxazole ring and cyclopropylmethyloxy group on the pyridine ring as $R^1$—W-group on the A ring respectively in the above formula (I), show the $IC_{50}$ against $Na_{v1.7}$ channel with both 0.05 microM. Whereas, according to data cited from the table at page 103 in WO2012/007868, the compounds of Example 35, Example 102, Example 106, and Example 166 to be thought as the close compounds, which have piperidine, pyrazole, N-methylpiperidine, and oxadiazole, respectively, corresponding to the A ring of formula (I) in the present invention, show the $IC_{50}$ against $Na_{v1.7}$ channel with >3 microM, >3 microM, 9.2 microM, and 1.3 microM, respectively.

TABLE 1

| Literature/Present invention | Chemical structure | $Na_{V1.7}$ activity ($IC_{50}$) |
|---|---|---|
| WO2012/007868 | 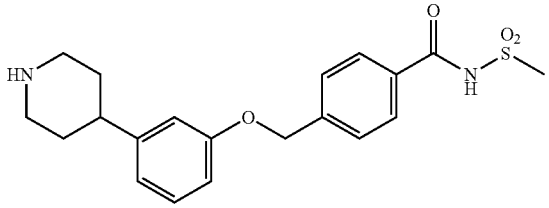<br>comparative compound Example 35 | >3 microM |
| WO2012/007868 | 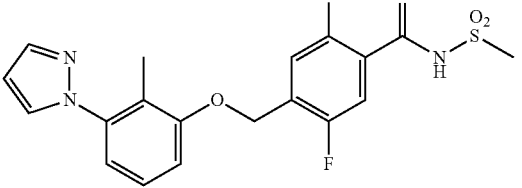<br>comparative compound Example 102 | >3 microM |

TABLE 1-continued

| Literature/Present invention | Chemical structure | Na$_{V1.7}$ activity (IC$_{50}$) |
|---|---|---|
| WO2012/007868 | comparative compound Example 106 | 9.2 microM |
| WO2012/007868 | comparative compound Example 166 | 1.3 microM |
| Present invention | Example 84 | 0.05 microM |
| Present invention | Example 24 | 0.05 microM |

Namely the present invention is characterized by R$^1$—W-substituent on the A ring in the above formula (I). The structurally closest compounds are synthesized and are described as reference compounds in the present application. The difference between the present invention and the structurally closest art is further well brought out as follows.

The Na$_{v1.7}$ activities of the representative chemical structures in the present invention and the structurally close arts are summarized in the following Table 2. The reference compound (A) of the structurally close arts shows the inhibitory activity against Na$_{v1.7}$ channel with >3 microM, whereas Example 2 of the present invention has inhibitory activities against Na$_{v1.7}$ channel with 0.08 microM. The reference compound (B) of the structurally close arts shows the inhibitory activity against Na$_{v1.7}$ channel with 1.3 microM, whereas Example 14 of the present invention has inhibitory activities against Na$_{v1.7}$ channel with 0.05 microM. The reference compound (C) of the structurally close arts shows the inhibitory activity against Na$_{v1.7}$ channel with 0.6 microM, whereas Example 24 of the present invention has inhibitory activities against Na$_{v1.7}$ channel with 0.05 microM. Therefore the compound of the present invention, which has R$^1$—W-substituent on the A ring in the above formula (I) shows excellent activity against Na$_{v1.7}$ channel comparing with the corresponding compound of the structurally close arts.

TABLE 2
| Literature/Present invention | Chemical structure | Na$_{V1.7}$ activity (IC$_{50}$) |
|---|---|---|
| WO2012/007868 | 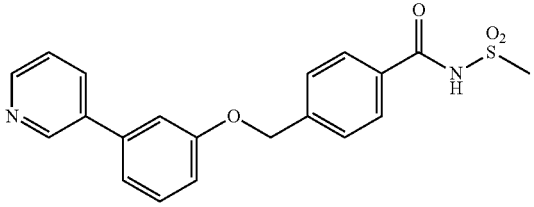<br>Reference compound (A) | >3 microM |
| Present invention | 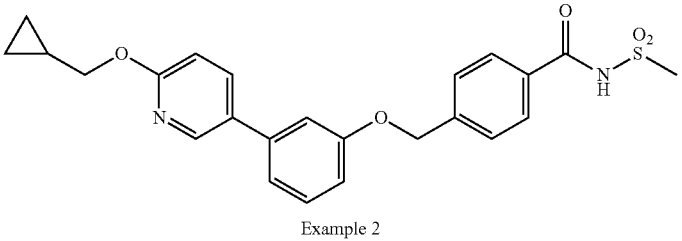 [SMILES: CS(=O)(=O)NC(=O)c1ccc(COc2cccc(-c3ccc(OCC4CC4)nc3)c2)cc1]<br>Example 2 | 0.08 microM |
| WO2012/007868 | 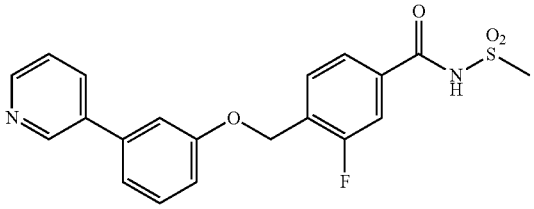<br>Reference compound (B) | 1.3 microM |
| Present invention | 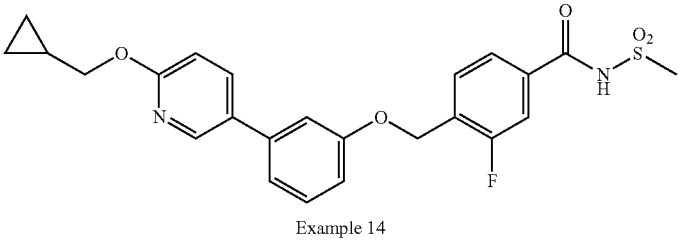 [SMILES: CS(=O)(=O)NC(=O)c1ccc(COc2cccc(-c3ccc(OCC4CC4)nc3)c2)c(F)c1]<br>Example 14 | 0.05 microM |
| WO2012/007868 | 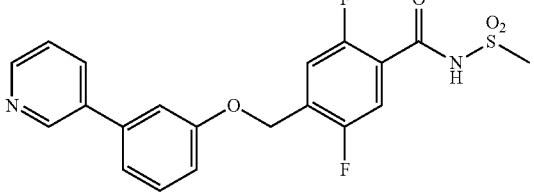<br>Reference compound (C) | 0.6 microM |
| Present invention | 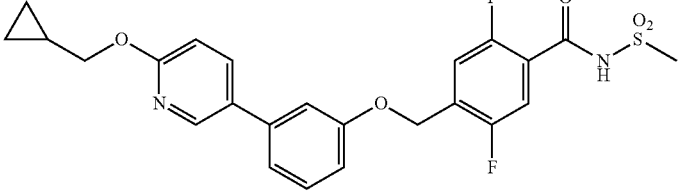<br>Example 24 | 0.05 microM |

Examples of conditions or disorders mediated by TTX-S channels include, but are not limited to, TTX-S channels related diseases. The compounds of the present invention show the TTX-S channels blocking activity. The compounds of the present invention may show less toxicity, good absorption and distribution, good solubility, less protein binding affinity other than TTX-S channels, less drug-drug interaction, good metabolic stability, reduced inhibitory activity at HERG channel, and/or reduced QT prolongation.

DESCRIPTION OF EMBODIMENTS

As appreciated by those of skill in the art, "halogen" as used herein is intended to include fluoro, chloro, bromo and iodo. Similarly, 1-6, as in $C_{1-6}$ is defined to identify the number as having 1, 2, 3, 4, 5 or 6. According to the definition, for example, $C_{1-6}$, as in $C_{1-6}$ alkyl is defined to identify the alkyl group as having 1, 2, 3, 4, 5 or 6 carbons. Similarly, $C_{2-6}$ alkenyl is defined to identify the alkenyl group as having 2, 3, 4, 5 or 6 carbons. A group which is designated as being independently substituted with substituents may be independently substituted with multiple numbers of such substituents.

The term "alkyl", as used herein, means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

The term "alkoxy", as used herein, means an —O-alkyl such as, but not limited to, methoxy, ethoxy, propoxy, or 2-propoxy, butoxy (including all isomeric forms), and the like.

The term "cycloalkyl", as used herein, means a mono- or bicyclic ring such as, but not limited to, cyclopropyl, cyclobutyl, cyclopentyl, cyclohexyl, cycloheptyl, norbornyl, adamantyl groups, and the like. In this specification, preferable cycloalkyl is $C_{3-7}$ mono cycloalkyl, more preferable cycloalkyl is $C_{3-6}$ mono cycloalkyl, and further preferable cycloalkyl is $C_{3-5}$ mono cycloalkyl.

The term "aryl", as used herein, means unsaturated or partially saturated mono- or bicyclic 5-15 membered ring which consists of carbon atoms. Examples of such aryl include, but are not limited to, phenyl, naphthyl, indanyl, indenyl, 1,2,3,4-tetrahydronaphthyl, 1,2-dihydronaphthyl, 2,3-dihydro-1H-indenyl, cyclohexenyl, cyclopentenyl, (1S, 4S)-bicyclo[2.2.2]oct-2-enyl, and (1R,4S)-bicyclo[2.2.1]hept-2-enyl and the like. In this specification, preferable aryl is 6-10 membered unsaturated aryl, more preferable aryl is 6-8 membered unsaturated aryl.

The term "heteroaryl" as used herein, means unsaturated and partially saturated mono- or bicyclic 5-15 membered ring, preferably 5-10 membered ring, which may contain 1-4 heteroatoms selected from O, N and S.

Examples of such heteroaryl include, but are not limited to, thiophenyl, thiazolyl, isoxazolyl, pyrazolyl, pyrazyl, tetrazolyl, furanyl, pyrrolyl, imidazolyl, oxazolyl, isothiazolyl, triazolyl, thiadiazolyl, pyridyl, pyrimidyl, pyridazinyl, pyrazinyl, triazinyl, benzofuranyl, benzothiophenyl, benzotriazolyl, indolyl, indazolyl, benzoimidazolyl, pyrrolopyridyl, pyrrolopyrimidinyl, pyrazolopyridyl, pyrazolopyrimidinyl, imidazopyridinyl, furopyridyl, benzoisoxazolyl, imidazopyrazinyl, imidazopyridazinyl, imidazopyrimidinyl, quinolyl, isoquinolyl, quinoxalyl, quinazolinyl, phthalazinyl, quinoxalinyl, naphthyridinyl, pyridopyrimidinyl, and N-oxides thereof and S-oxides thereof and the like. In this specification, preferable heteroaryl is 5-6 membered mono heteroaryl, more preferable heteroaryl is 5-6 membered N-containing mono heteroaryl.

The term "heterocyclyl" as used herein includes both unsaturated and saturated heterocyclic moieties, wherein the unsaturated heterocyclic moieties (i.e. "heteroaryl") include, but not limited to, benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, carbazolyl, carbolinyl, chromanyl, cinnolinyl, 2,3-dioxoindolyl, furanyl, furazanyl, furopyridyl, furopyrrolyl, imidazolyl, imidazopyrazinyl, imidazopyridinyl, imidazopyrimidinyl, imidazothiazolyl, indazolyl, indolazinyl, indolinyl, indolyl, isobenzofuranyl, isochromanyl, isoindolyl, isoquinolyl, isoxazolopyridyl, isoxazolinyl, isoxazolyl, isothiazolyl, naphthyridinyl, oxazolinyl, oxadiazolyl, oxazolyl, oxetanyl, 2-oxoindolyl, oxoisoindolyl, phthalazyl, pyrazolyl, pyrazolopyridyl, pyrazolopyrimidinyl, pyrazinyl, pyridyl, pyrimidyl, pyridazinyl, pyridopyrimidinyl, pyrrolopyridyl, pyrrolyl, quinazolinyl, quinolyl, quinoxalinyl, tetrazolopyridyl, tetrazolyl, thiadiazolyl, thiazolyl, thiophenyl, thienopyrazinyl, thienopyrazolyl, thienopyridyl, thienopyrrolyl, triazolopyrimidinyl, triazolyl, 4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 4-oxo-1,4-dihydro-1,8-naphthyridyl, and N-oxides thereof, and wherein the saturated heterocyclic moieties include, but not limited to, azetidinyl, 1,4-dioxanyl, hexahydroazepinyl, piperazinyl, piperidinyl, pyridin-2-onyl, pyrrolidinyl, morpholinyl, tetrahydrofuranyl, tetrahydropyranyl, thiomorpholinyl, triazolopyrimidyl, tetrahydrothienyl, pyrrolidinonyl, 3,4-dihydro-2H-pyrido[3,2-b][1,4]oxazinyl, 2-oxo-2,5,6,7-tetrahydro-1H-cyclopentapyridyl, 4,5,6,7-tetrahydro-indazolyl, 5,6,7,8-tetrahydro-1,6-naphthyridyl, and N-oxides thereof and S-oxides thereof. In this specification, preferable heterocyclyl is 3-6 membered saturated mono heterocyclyl, which may contain 1-4 heteroatoms selected from O, N and S, more preferable heterocyclyl is 5-6 membered saturated mono heterocyclyl The term "protecting group", as used herein, means a hydroxy or amino protecting group which is selected from typical hydroxy or amino protecting groups described in Protective Groups in Organic Synthesis edited by T. W. Greene et al. (John Wiley and Sons, 2007).

The term "treating" or "treatment", as used herein, includes prohibiting, restraining, slowing, stopping, or reversing the progression or severity of an existing symptom or disorder. As used herein, the term "preventing" or "to prevent" includes prohibiting, restraining, or inhibiting the incidence or occurrence of a symptom or disorder.

As used herein, the article "a" or "an" refers to both the singular and plural form of the object to which it refers unless indicated otherwise.

Included within the scope of the "compounds of the invention" are all salts, solvates, hydrates, complexes, polymorphs, prodrugs, radiolabeled derivatives, stereoisomers and optical isomers of the compounds of formula (I).

Compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci, 1977, 66, 1-19, such as acid addition salts formed with inorganic acids e.g., but not limited to, hydrochloric, hydrobromic, sulfuric, nitric or phosphoric acid; and organic acids e.g., but not limited to, succinic, maleic, formic, acetic, trifluoroacetic, propionic, fumaric, citric, tartaric, benzoic, p-toluenesulfonic, methanesulfonic or naphthalene-sulfonic acid. Certain of the compounds of formula (I) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases such as choline, arginine, benzathine, diethylamine, glycine, lysine, meglumine, olamine, 2-amino-2-methylpropan-1-ol, benethamine, tert-butylamine, epolamine, ethylenediamine, hydrabamine, morpholine, piperazine, procaine, triethanolamine, diethanolamine, monoethanolamine, triisopropanolamine, and tromethamine.

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

The term "animal," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese. The preferred mammalian subject is a human.

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H Bundgaard (Elsevier, 1985). Some examples of prodrugs in accordance with the invention include:

(i) where the compound of formula (I) contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxyl group by e.g. hydrolysis and/or by an enzyme, e.g. an esterase. Examples of said moiety include, but are not limited to, ester and ether groups which may be hydrolyzed easily in vivo. Preferred the moieties are replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl; and (ii) where the compound of the formula (I) contains an amino group, a biaryloxy derivative prepared by reacting with a suitable acid halide or a suitable acid anhydride is exemplified as a prodrug. A particularly preferred biaryloxy derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

Salts and solvates having non-pharmaceutically acceptable counter-ions or associated solvents are within the scope of the present invention, for example, for use as intermediates in the preparation of other compounds of formula (I) and their pharmaceutically acceptable salts.

Compounds of formula (I) may have polymorphs in crystalline form, which are within the scope of the present invention.

Additionally, compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I), there may be one or more chiral carbon atoms. In such cases, compounds of formula (I) exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^2$H, $^3$H, $^{11}$C, $^{13}$C, $^{14}$C, $^{18}$F, $^{123}$I and $^{125}$I. Compounds of the invention that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{123}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the invention can generally be prepared by carrying out the procedures disclosed in the Scheme and/or in the Examples below, then substituting a readily available isotopically labeled reagent for a non-isotopically labeled reagent.

With respect to other compounds disclosed in the art, certain compounds exhibit unexpected properties, such as with respect to duration of action and/or metabolism, such as increased metabolic stability, enhanced oral bioavailability or absorption, and/or decreased drug-drug interactions.

The compounds of formula (I), being $Na_{v1.7}$ channel blocker, are potentially useful in the treatment of a range of disorders. The treatment of pain, particularly chronic, inflammatory, neuropathic, nociceptive and visceral pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, or postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf and Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any types of surgical procedure), posttraumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf and Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan and Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge and Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:

(i) pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

(ii) heart and vascular pain, including pain caused by angina, myocardial infarction, mitral stenosis, pericarditis, Raynaud's phenomenon, scleredema and skeletal muscle ischemia;

(iii) head pain, such as migraine (including migraine with aura and migraine without aura), cluster headache, tension-type headache mixed headache and headache associated with vascular disorders; and (iv) orofacial pain, including dental pain, otic pain, burning mouth syndrome and temporomandibular myofascial pain.

Compounds of formula (I) are also expected to be useful in the treatment of multiple sclerosis.

The invention also relates to therapeutic use of compounds of formula (I) as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, and hypotension as well as similar injuries seen during procedures from embole, hypoperfusion, and hypoxia. The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

TTX-S sodium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with TTX-S sodium channels, including one or more of the following conditions or diseases: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, back pain, head or neck pain, severe or intractable pain, breakthrough pain, post-surgical pain, stroke, cancer pain, seizure disorder, causalgia, and chemo-induced pain.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy.

The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

For administration to human patients, the total daily dose of the compounds of the invention is typically in the range of 0.1 mg to 1000 mg depending, of course, on the mode of administration. For example, oral administration may require a total daily dose of from 1 mg to 1000 mg, while an intravenous dose may only require from 0.1 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

A TTX-S sodium channels blocker may be usefully combined with another pharmacologically active compound, or with two or more other pharmacologically active compounds, particularly in the treatment of inflammatory, pain and urological diseases or disorders. For example, a TTX-S sodium channels blocker, particularly a compound of formula (I), or a prodrug thereof or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal anti-inflammatory drug (NSAID), e.g. aspirin, diclofenac, diflunisal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butalbital, mephobarbital, metharbital, methohexital, pentobarbital, phenobarbital, secobarbital, talbutal, thiamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine; —a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphenadrine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinone, cis-4-(phosphonomethyl)-2-piperidinecarboxylic acid, budipine, EN-3231 (MorphiDex (registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2 (1H)-quinolinone;

an alpha-adrenergic, e.g. doxazosin, tamsulosin, clonidine, guanfacine, dexmedetomidine, modafinil, or 4-amino-6,7-dimethoxy-2-(5-methane-s ulfonamido-1, 2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiramate or valproate;

a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6,13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, trospium chloride, darifenacin, solifenacin, temiverine, oripratropium;

a COX-2 selective inhibitor, e.g. celecoxib, rofecoxib, parecoxib, valdecoxib, deracoxib, etoricoxib, or lumiracoxib;

a coal-tar analgesic, e.g. paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion (registered trademark) or sarizotan;

a vanilloid receptor agonist (e.g. resiniferatoxin) or antagonist (e.g. capsazepine);

a transient receptor potential cation channel subtype (V1, V2, V3, V4, M8, M2, A1) agonist or antagonist;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594), or nicotine;

Tramadol (registered trademark);

a PDEV inhibitor, such as 5-[2-ethoxy-5-(4-methyl-1-piperazinylsulphonyl)phenyl]-1-methyl-3-n-propyl-1, 6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)pyrazino[2',1':6,1] pyrido[3,4-b]indole-1,4-dione (IC-351 or tadalafil), 2-[2-ethoxy-5-(4-ethyl-piperazin-1-yl-sulphonyl)phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl) pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, or 3-(1-methyl-7-oxo-3-propyl-6,7-dihydro-H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (3-(aminomethyl)bicyclo[3.2.0] hept-3-yl)acetic acid, (3S,5R)-3-(aminomethyl)-5-methylheptanoic acid, (3S,5R)-3-amino-5-methylheptanoic acid, (3S,5R)-3-amino-5-methyloctanoic acid, (2S,4S)-4-(3-chlorophenoxy)proline, (2S,4S)-4-(3-fluorobenzyl)proline, [(1R,5R,6S)-6-(aminomethyl)bicyclo[3.2.0]hept-6-yl]acetic acid, 3-((1-(aminomethyl) cyclohexyl)methyl)-4H-[1,2,4]oxadiazol-5-one, C-[1-((1H-tetrazol-5-yl)methyl)cycloheptyl]methylamine, (3S,4S)-(1-(aminomethyl)-3,4-dimethylcyclopentyl) acetic acid, (3S,5R)-3-(aminomethyl)-5-methyloctanoic acid, (3S,5R)-3-amino-5-methylnonanoic acid, (3S,5R)-3-amino-5-methyloctanoic acid, (3R,4R,5R)-3-amino-4,5-dimethylheptanoic acid, or (3R,4R,5R)-3-amino-4,5-dimethyloctanoic acid;

a cannabinoid;

a metabotropic glutamate receptors (mGluRs) antagonist such as mGluR1, mGluR2, mGluR3, mGluR5, or mGluR7;

a serotonin reuptake inhibitor such as sertraline, sertraline metabolite desmethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, ortrazodone;

a noradrenaline (norepinephrine) reuptake inhibitor, such as maprotiline, lofepramine, mirtazapine, oxaprotiline, fezolamine, tomoxetine, mianserin, bupropion, bupropion metabolite hydroxybupropion, nomifensine and viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran, orimipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl] thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c] pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);

a sodium channel blocker, such as lidocaine;

a calcium channel blocker, such as ziconotide, zonisamide, mibefradil;

a 5-HT3 antagonist, such as ondansetron;

a chemotherapy drug such as oxaliplatin, 5-fluorouracil, leucovorin, paclitaxel;

a calcitonin gene related peptide (CGRP) antagonist;

a bradykinin (BK1 and BK2) antagonist;

a voltage gated sodium dependent channel blocker ($Na_{v1.7}$, $Na_{v1.8}$, $Na_{v1.9}$);

a voltage dependent calcium channel blocker (N-type, T-type);

a P2X (ion channel type ATP receptor) antagonist;

an acid-sensing ion channel (ASIC1a, ASIC3) antagonist;

an Angiotensin AT2 antagonist;

a Chemokine CCR2B receptor antagonist;

a Cathepsin (B, S, K) inhibitor;

a sigmal receptor agonist or antagonist;

a nerve growth factor (NGF) binder or inhibitor such as tanezumab;

a tropomyosin receptor kinase A (TrkA) inhibitor;

a fatty acid amide hydrolase (FAAH) inhibitor;

a monoacylglycerol lipase (MAGL) inhibitor;

a microsomal prostaglandin E synthase type-1 (mPGES-1) inhibitor;

a $GABA_A$ modulator;

a GlyR3 agonist or positive modulator;

an AMPA receptor antagonist such as perampanel;

a potassium channel KCNQ/Kv7 opener or positive modulator such as retigabine or flupirtine;

a G protein-coupled inwardly-rectifying potassium channel (GIRK) opener or positive modulator;

a calcium-activated potassium channel (Kca) opener or positive modulator;

a potassium channel opener or positive modulator of a potassium voltage-gated channel such as a member of subfamily A (e.g. Kv1.1), subfamily B (e.g. Kv2.2) or subfamily K (e.g. TASK, TREK or TRESK);

or the pharmaceutically acceptable salts, or the solvates thereof.

Such combinations offer significant advantages, including synergistic activity, in therapy.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrated compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formula (I) or pharmaceutically acceptable salt thereof and a sterile vehicle. Formulations for injection may be presented in unit dosage form e.g. in ampoules or in multi-dose, utilising a compound of formula (I) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

Compounds of formula (I) or pharmaceutically acceptable salts thereof may also be formulated in rectal compositions such as suppositories or retention enemas, e.g. containing conventional suppository bases such as cocoa butter or other glycerides.

Compounds of formula (I) or pharmaceutically acceptable salts may also be formulated as depot preparations. Such long acting formulations may be administered by implantation (for example subcutaneously or intramuscularly) or by intramuscular injection. Thus, for example, the compounds of formula (I) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, compounds formula (I) or pharmaceutically acceptable salts thereof may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, and topical (including ophthalmic and nasal), depot or rectal administration or in a form suitable for administration by inhalation or insufflation (either through the mouth or nose). The compounds of formula (I) and pharmaceutically acceptable salts thereof may be formulated for topical administration in the form of ointments, creams, gels, lotions, pack, tape, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

General Synthesis

Throughout the instant application, the following abbreviations are used with the following meanings:
DCM Dichloromethane
DMF N,N-Dimethylformamide
DMA N,N-Dimethylacetamide
DMAP N,N-dimethyl-4-aminopyridine
DME 1,2-Dimethoxyethane DMSO Dimethyl sulfoxide
EDC 1-Ethyl-3-(3-dimethylaminopropyl)carbodiimide Hydrochloride
ESI Electrospray Ionization
EtOAc Ethyl acetate
EtOH Ethanol
Ex Example
HOBT 1-Hydroxybenztriazole
HATU O-(7-Azabenzotriazol-1-yl)-N,N,N',N'-tetramethyluronium Hexafluorophosphate
HBTU O-(Benzotriazol-1-yl)-N,N,N',N'-tetramethyluronium Hexafluorophosphate
HPLC High-Performance Liquid Chromatography
LC Liquid Chromatography
LG Leaving Group
tR Retention Time
MeCN Acetonitrile
MeOH Methanol
MHz Megahertz
MS Mass Spectrometry
NMP N-methylpyrrolidone
NMR Nuclear Magnetic Resonance
rt Room Temperature
TBAF Tetrabutylammonium fluoride
TBS tert-butyldimethylsilyl
T3P Propylphosphonic Acid Anhydride (Cyclic Trimer, registered trademark)
TFA Trifluoroacetic Acid
THF Tetrahydrofuran
TLC Thin Layer Chromatography
UV Ultraviolet The term of "base" is likewise no particular restriction on the nature of the bases used, and any base commonly used in reactions of this type may equally be used here.

Examples of such bases include, but not limited to: alkali metal hydroxides, such as lithium hydroxide, sodium hydroxide, potassium hydroxide, potassium phosphate, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogen-carbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, N,N-dimethyl-4-aminopyridine (DMAP), 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DMAP, DBU, DBN, DABCO, pyridine, lutidine, colidine, sodium carbonate, sodium hydrogencarbonate, sodium hydroxide, potassium carbonate, potassium hydrogencarbonate, potassium hydroxide, potassium phosphate, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as DCM, chloroform, carbon tetrachloride, and dichloroethane; ethers, such as diethyl ether, diisopropyl ether, THF, and dioxane; aromatic hydrocarbons, such as benzene, toluene and nitrobenzene; amides, such as, DMF, DMA, and hexamethylphosphoric triamide;

amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMA, DMSO, THF, diethylether, diisopropylether, dimethoxyethane, acetonitrile, DCM, dichloroethane and chloroform are preferred.

EXAMPLES

The invention is illustrated in the following non-limiting examples in which, unless stated otherwise: all reagents are commercially available, all operations are carried out at room or ambient temperature, that is, in the range of about 18-25° C.; microwave reactions are carried out using Biotage Initiator or Biotage Initiator+; evaporation of solvent is carried out using a rotary evaporator under reduced pressure with a bath temperature of up to about 60° C.; reactions are monitored by thin layer chromatography (TLC) and reaction times are given for illustration only; the structure and purity of all isolated compounds are assured by at least one of the following techniques: TLC (Merck silica gel 60 $F_{254}$ precoated TLC plates or Merck $NH_2$ $F_{254}$ precoated HPTLC plates), mass spectrometry or NMR. Yields are given for illustrative purposes only. Flash column chromatography is carried out using Biotage SNAP KP-Sil, Biotage SNAP Isolute NH2, Merck silica gel 60 (230-400 mesh ASTM), Fuji Silysia Chromatorex (registered trade mark) NH-DM1020 and NH-DM2035, Wako Wakogel C300-HG, Yamazen Hi-FLASH column, or YMC DispoPack-SIL. Ion-exchange chromatography is carried out using a strong cation exchange cartridge (ISOLUTE (registered trademark) SCX, 1 g/6 mL, Biotage), or strong anion exchange cartridge (ISOLUTE (registered trademark) PE-AX, 1 g/6 mL, Biotage). The purification of compounds using HPLC (preparative LC-MS) is performed by the following apparatus and conditions.

Apparatus; Waters MS-trigger AutoPurification (registered trademark) system

Column; Waters XTerra C18, 19×50 mm, 5 micrometer particle

Condition A: Methanol or acetonitrile/0.01% (v/v) ammonia aqueous solution

Condition B: Methanol or acetonitrile/0.05% (v/v) formic acid aqueous solution

Low-resolution mass spectral data (ESI) are obtained by the following apparatus and conditions: Apparatus; Waters Alliance HPLC system on ZQ or ZMD mass spectrometer and UV detector. NMR data are determined at 270 MHz (JEOL JNM-LA 270 spectrometer), 300 MHz (JEOL JNM-LA300), or 400 MHz (JEOL JNM-ECZ400S) using deuterated chloroform (99.8% D) or dimethyl sulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; M (mol(s) per liter), L (liter(s)), mL (milliliter(s)), g (gram(s)), mg (milligram(s)), mol (moles), mmol (millimoles).

Each prepared compound is generally named by Chem-BioDraw (Ultra, version 12.0, CambridgeSoft).

Conditions for determining HPLC retention time:

HPLC-method A:

Apparatus: Waters Acquity Ultra Performance LC on PDA Detector and ZQ mass spectrometer Column: Waters ACQUITY C18, 2.1×100 mm, 1.7 um particle Column Temperature: 60° C.

PDA detection: 200-400 nm scan

MS detection: ESI positive/negative mode

Solvents:

A1: 10 mM ammonium acetate aqueous solution

B1: acetonitrile

| Time(min) | A1(%) | B1(%) |
|---|---|---|
| 0 | 95 | 5 |
| 0.1 | 95 | 5 |
| 1.8 | 5 | 95 |
| 2.3 | 95 | 5 |
| run time | 3 min | |
| Flow rate | 0.7 mL/min | |

HPLC-method B:

Apparatus: Waters Acquity Ultra Performance LC on PDA Detector and ZQ mass spectrometer Column: YMC Meteoric core C18, 2.1×100 mm, s-2.1 microm particle Column Temperature: 60° C.

PDA detection: 200-400 nm scan

MS detection: ESI positive/negative mode

Solvents:

A1: 10 mM ammonium acetate aqueous solution

B1: acetonitrile

| Time(min) | A1(%) | B1(%) |
|---|---|---|
| 0 | 95 | 5 |
| 0.1 | 95 | 5 |
| 1.8 | 5 | 95 |
| 2.3 | 5 | 95 |
| 2.31 | 95 | 5 |
| run time | 3 min | |
| Flow rate | 0.7 mL/min | |

HPLC-method C:

Apparatus: Waters Acquity Ultra Performance LC on PDA Detector and ZQ mass spectrometer Column: Waters ACQUITY C18, 2.1×100 mm, 1.7 um particle Column Temperature: 60° C.

PDA detection: 200-400 nm scan

MS detection: ESI positive/negative mode

Solvents:

A1: 10 mM ammonium acetate aqueous solution

B1: acetonitrile

| Time(min) | A1(%) | B1(%) |
|---|---|---|
| 0 | 95 | 5 |
| 0.1 | 95 | 5 |
| 1.8 | 5 | 95 |
| 2.3 | 5 | 95 |
| 2.31 | 95 | 5 |
| run time | 3 min | |
| Flow rate | 0.7 mL/min | |

HPLC-method D:
Apparatus: Waters Acquity Ultra Performance LC on PDA Detector and ZQ mass spectrometer
Column: YMC Triart C18, 2.1×100 mm, 1.9 um particle
Column Temperature: 60° C.
PDA detection: 200-400 nm scan
MS detection: ESI positive/negative mode
Solvents:
A1: 10 mM ammonium acetate aqueous solution
B1: acetonitrile

| Time(min) | A1(%) | B1(%) |
|---|---|---|
| 0 | 90 | 10 |
| 0.05 | 90 | 10 |
| 1.9 | 5 | 95 |
| 2.5 | 5 | 95 |
| 2.51 | 90 | 10 |
| run time | 3 min | |
| Flow rate | 0.75 mL/min | |

All of the biaryloxy derivatives of the formula (I) can be prepared by the procedures described in the general methods presented below or by the specific methods described in the Example synthesis part and Intermediate synthesis part, or by routine modifications thereof. The present invention also encompasses any one or more of these processes for preparing the biaryloxy derivatives of formula (I), in addition to any novel intermediates used therein.

In the following general methods, descriptors are as previously defined for the biaryloxy derivatives of the formula (I) unless otherwise stated. All starting materials in the following general syntheses may be commercially available or obtained by the conventional methods known to those skilled in the art, otherwise noted in the intermediate synthesis part.

<Scheme A>

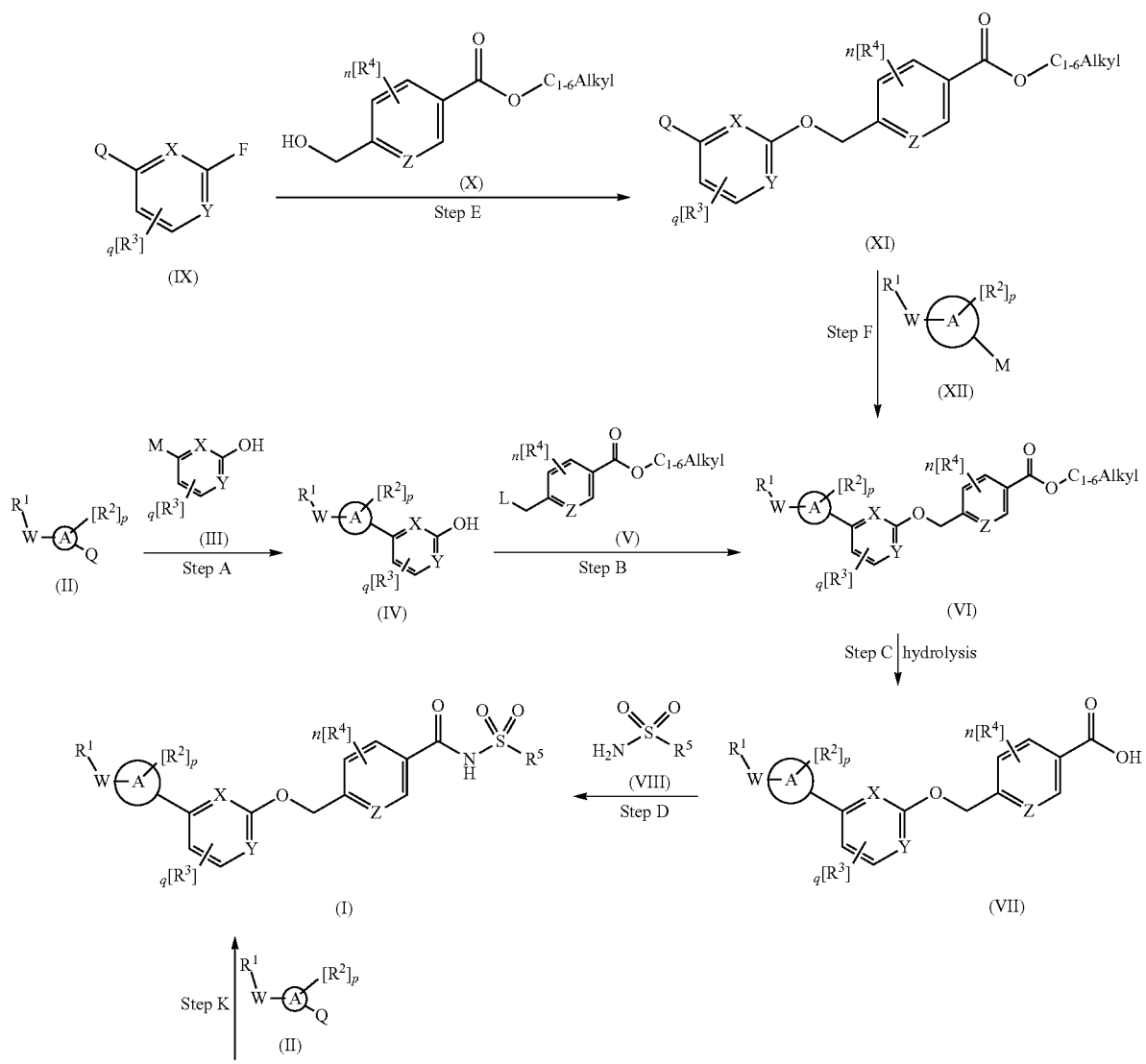

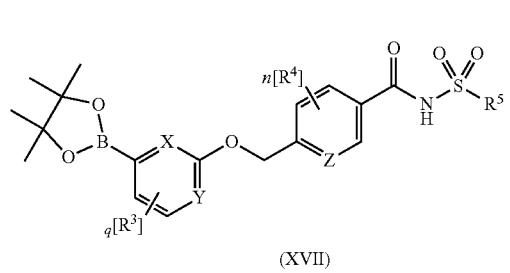
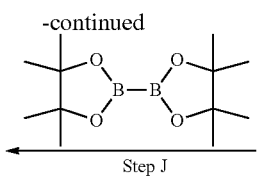
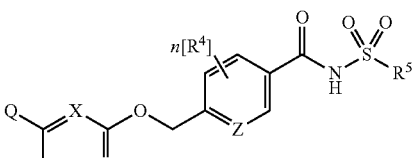
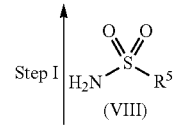
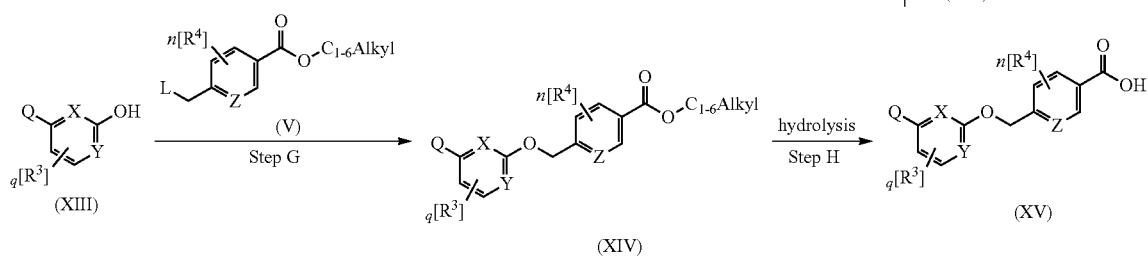
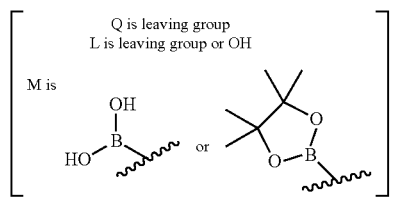

In Step A, when Q of formula (II) is a suitable leaving group such as O-trifluoromethanesulfonate, O-tosylate, O-mesylate, iodide, bromide, or chloride, a compound of formula (IV) can be prepared by cross coupling of a compound of formula (II) with a suitable boronic acid or borate of formula (III) under coupling conditions in suitable organic solvents in the presence of a suitable transition metal catalyst and in the presence or absence of a base. Examples of suitable transition metal catalysts include: tetrakis(triphenylphosphine)palladium(0), bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, palladium(II) acetate, palladium(II) chloride, bis(acetonitrile)dichloropalladium(II), bis(dibenzylideneacetone)palladium(0), tris(dibenzylideneacetone)dipalladium(0), [1,1'-bis(diphenylphosphino)ferrocene]palladium(II) dichloride, and bis(di-tert-butyl(4-dimethylaminophenyl)phosphine)dichloropalladium(II). Preferred catalysts are tetrakis(triphenylphosphine)palladium(0), bis(triphenylphosphine)palladium(II) chloride, palladium(II) acetate, palladium(II) chloride, bis(acetonitrile)dichloropalladium(0), bis(dibenzylideneacetone)palladium(0), tris(dibenzylideneacetone)dipalladium(0), [1,1-bis(diphenylphosphino)ferrocene]palladium(II) dichloride, and bis(di-tert-butyl(4-dimethylaminophenyl)phosphine)dichloropalladium(II). Examples of suitable organic solvent include: THF; 1,4-dioxane; DMF; MeCN; alcohols, such as methanol or ethanol; halogenated hydrocarbons, such as DCM, 1,2-dichloroethane, chloroform, or carbon tetrachloride; and diethylether. Example of suitable base include: tripotassium phosphate, sodium bicarbonate, sodium carbonate, and potassium carbonate. This reaction can be carried out in the presence of a suitable additive agent. Examples of such additive agents include: 4,5-Bis(diphenylphosphino)-9,9-dimethylxanthene, triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, and triphenylarsine. The reaction can be carried out at a temperature of about 50 to 200° C., more preferably from about 80 to 150° C. Reaction times are, in general, from about 5 minutes to 48 hours, more preferably from about 30 minutes to 24 hours. In an alternative case, the reaction can be carried out with microwave system. The reaction can be carried out at a temperature in the range of about 100 to 200° C., preferably in the range of about 120 to 160° C. Reaction times are, in general, from about 10 minutes to 3 hours, preferably from about 15 minutes to 1 hour.

In Step B, when L of formula (V) is a suitable leaving group such as O-trifluoromethanesulfonate, O-tosylate, O-mesylate, iodide, bromide, or chloride, a compound of formula (VI) can be prepared by O-alkylation of a compound of formula (IV) with a compound of formula (V) in the presence of a suitable base in an inert solvent. Examples of a suitable base include, but not limited to, such as sodium hydride, potassium carbonate, cesium carbonate, potassium tert-butoxide, triethylamine, pyridine, and N,N-diisopropylethylamine. Examples of suitable organic solvent include such as THF, 1,4-dioxane, DMF, MeCN, DMA, and toluene. The reaction can be carried out at a temperature of about −20 to 150° C., more preferably from about 0 to 100° C. Reaction times are, in general, from about 30 minutes to 48 hours, more preferably from about 1 hour to 24 hours. Alternatively, when L of formula (V) is a hydroxyl group, a compound of formula (VI) can be prepared by Mitsunobu reaction condition of a compound of formula (IV) with a compound of formula (V) in organic solvent in the presence of azo-dicarboxylate include, but not limited to, such as diethyl azodicarboxylate, diisopropyl azodicarboxylate, di-tert-butyl azodicarboxylate, and di-2-methoxyethyl azodicarboxylate as a coupling reagent. Examples of suitable organic solvent include such as THF, 1,4-dioxane, DMF, MeCN, and toluene. The reaction can be carried out at a temperature of about −20 to 180° C., more preferably from about 0 to 150° C. Reaction times are, in general, from about 30 minutes to 48 hours, more preferably from about 30 minutes to 24 hours.

In Step C, a compound of formula (VII) can be prepared by hydrolysis of the ester compound of formula (V). The hydrolysis can be carried out by the conventional procedures. In a typical procedure, the hydrolysis is carried out under basic conditions, e.g. in the presence of sodium hydroxide, potassium hydroxide, or lithium hydroxide. Suitable solvents include, for example: alcohols such as water, methanol, ethanol, propanol, butanol, 2-methoxyethanol, and ethylene glycol; ethers such as THF, DME, and 1,4-dioxane; amides such as DMF and hexamethylphosphorictriamide; and sulfoxides such as DMSO. Preferred solvents are water, methanol, ethanol, propanol, THF, DME, 1,4-dioxane, DMF, and DMSO. This reaction can be carried out at a temperature in the range of about 20 to 100° C. for from about 30 minutes to 24 hours.

In Step D, a compound of formula (I) can be prepared from a compound of formula (VII) by condensation with a compound of formula (VIII) using a suitable condensation reagent such as HBTU, HATU, T3P (registered trademark), EDC, and EDC-HOBT, preferably under the presence of a base such as triethylamine, N,N-diisopropylethylamine, DMAP, DABCO, and DBU in a suitable solvent such as THF, DME, 1,4-dioxane, DMF, DMA, and DCM. This reaction can be carried out at a temperature in the range of about 5 to 60° C. for from about 1 hour to 48 hours.

In Step E, a compound of formula (XI) can be prepared from a compound of formula (IX) and a compound of formula (X) in the presence of a suitable base in an inert solvent. Examples of a suitable base include, but not limited to, such as sodium hydride, potassium carbonate, cesium carbonate, potassium tert-butoxide, triethylamine, pyridine, and N,N-diisopropylethylamine. Examples of suitable organic solvent include such as THF, 1,4-dioxane, DMF, MeCN, DMA, and toluene. The reaction can be carried out at a temperature of about −20 to 150° C., more preferably from about 0 to 100° C. Reaction times are, in general, from about 30 minutes to 48 hours, more preferably from about 1 hour to 24 hours.

In Step F, when Q of formula (XI) is a suitable leaving group such as O-trifluoromethanesulfonate, O-tosylate, O-mesylate, iodide, bromide, or chloride, a compound of formula (VI) can be prepared from a compound of formula (XI) and a compound of formula (XII) by cross coupling reaction by the similar general protocol in Step A.

In Step G, when L of formula (V) is a suitable leaving group such as O-trifluoromethanesulfonate, O-tosylate, O-mesylate, iodide, bromide, or chloride, a compound of formula (XIV) can be prepared by O-alkylation with a compound of formula (XIII) by the similar general protocol in Step B.

In Step H, a compound of formula (XV) can be prepared by hydrolysis of the ester compound of formula (XIV) by the similar general protocol in Step C.

In Step I, a compound of formula (XVI) can be prepared from a compound of formula (XV) by condensation with a compound of formula (VIII) by the similar general protocol in Step D.

In Step J, when Q of formula (XVI) is a suitable leaving group such as O-trifluoromethanesulfonate, O-tosylate, O-mesylate, iodide, bromide, or chloride, a compound of formula (XVII) can be prepared from a compound of formula (XVI) by borylation reaction with bis(pinacolato)diboron in the presence of suitable organic solvents in the presence of a suitable transition metal catalyst and in the presence or absence of a base by the similar general protocol in Step A.

In Step K, when Q of formula (II) is a suitable leaving group such as O-trifluoromethanesulfonate, O-tosylate, O-mesylate, iodide, bromide, or chloride, a compound of formula (I) can be prepared from a compound of formula (XVII) by cross coupling reaction with a compound of formula (II) in the presence of suitable organic solvents in the presence of a suitable transition metal catalyst and in the presence or absence of a base by the similar general protocol in Step A.

Intermediate Synthesis Part

Intermediate compounds (Acid-1 to Acid-57, Borate-1 to Borate-6, Aryl halide-1 to Aryl halide-32, Amine-1) are prepared as follows. Lists of the intermediate compounds are shown in the Table 3, Table 4, and Table 5. All starting materials in the intermediate syntheses may be commercially available or obtained by conventional methods known to those skilled in the art, unless otherwise stated in the synthesis part.

<Acid Part>

Acid-1: 4-((3-(6-(cyclopropylmethoxy)-5-methylpyridin-3-yl)phenoxy)methyl)benzoic acid <Step-1>:
5-bromo-2-(cyclopropylmethoxy)-3-methylpyridine To a stirred solution of cyclopropylmethanol (0.86 g, 12 mmol) in DMF (25 mL) is added sodium hydride (60%, 0.48 g, 12 mmol) at 0° C., and the mixture is stirred for 20 min at room temperature. 2,5-dibromo-3-methylpyridine (2 g, 8 mmol) is added portion-wise to the reaction mixture. The reaction mixture is stirred for 20 min at room temperature, then at 60° C. overnight. The reaction mixture is added saturated aqueous $NH_4Cl$ (50 mL) and water (50 mL), then, extracted with EtOAc/n-hexane (1:1, 100 mL). Organic layer is washed with water (50 mL×2), and dried over sodium sulfate. Insoluble materials are separated by filtration and the filtrate is concentrated. The residue is purified by column chromatography on silica-gel eluting with n-hexane/EtOAc (9:1) to give 1.7 g (89% yield) of the title compound as a colorless liquid.

$^1$H-NMR (400 MHz, $CDCl_3$) delta 7.99 (1H, d, J=2.7 Hz), 7.48 (1H, dd, J=2.7, 0.9 Hz), 4.12 (2H, d, J=6.9 Hz), 2.19 (3H, s), 1.33-1.21 (1H, m), 0.63-0.54 (2H, m), 0.37-0.30 (2H, m), MS (ESI) m/z: 242.0 (M+H)$^+$.

<Step-2>: 3-(6-(cyclopropylmethoxy)-5-methylpyridin-3-yl)phenol

To a stirred solution of 5-bromo-2-(cyclopropylmethoxy)-3-methylpyridine (Step-1 in Acid-1, 1.0 g, 4.1 mmol), (3-hydroxyphenyl)boronic acid (0.68 g, 5.0 mmol) in dioxane/water (20 mL/7 mL) is added tetrakis(triphenylphosphine)palladium(0) (0.24 g, 0.21 mmol), potassium carbonate (2.3 g, 16.5 mmol), and the reaction mixture is stirred at 100° C. for 1 hour. The reaction mixture is cooled to room temperature and diluted with EtOAc (50 mL), washed with water (50 mL×1), and dried over sodium sulfate. Insoluble materials are separated by filtration and the filtrate is concentrated. The residue is purified by column chromatography on silica-gel eluting with n-hexane/EtOAc (5:1 to 4:1) to give 945 mg (90% yield) of the title compound as a colorless oil.

$^1$H-NMR (400 MHz, CDCl$_3$) delta 8.17 (1H, d, J=2.7 Hz), 7.62-7.57 (1H, m), 7.34-7.25 (1H, m), 7.12-7.05 (1H, m), 7.02-6.97 (1H, m), 6.83-6.78 (1H, m), 4.95 (1H, br.s), 4.20 (2H, d, J=7.3 Hz), 2.27 (3H, s), 1.38-1.25 (1H, m), 0.64-0.56 (2H, m), 0.40-0.34 (2H, m), MS (ESI) m/z: 256.0 (M+H)$^+$.

<Step-3>: methyl 4-((3-(6-(cyclopropylmethoxy)-5-methylpyridin-3-yl)phenoxy)methyl)benzoate To a stirred solution of 3-(6-(cyclopropylmethoxy)-5-methylpyridin-3-yl)phenol (Step-2 in Acid-1, 200 mg, 0.78 mmol), methyl 4-(bromomethyl)benzoate (215 mg, 0.94 mmol) in DMF (5 mL) is added potassium carbonate (325 mg, 2.4 mmol), and stirred at 60° C. for 1 hour. The reaction mixture is cooled to room temperature and diluted with EtOAc (30 mL), washed with water (20 mL×3), and dried over sodium sulfate. Insoluble materials are separated by filtration and the filtrate is concentrated. The residue is purified by column chromatography on silica-gel eluting with n-hexane/EtOAc (6:1 to 3:1) to give 260 mg (82% yield) of the title compound as a colorless oil.

$^1$H-NMR (400 MHz, CDCl$_3$) delta 8.16 (1H, d, J=3.2 Hz), 8.07 (2H, d, J=8.7 Hz), 7.60-7.52 (1H, m), 7.53 (2H, d, J=8.7 Hz), 7.48-7.31 (1H, m), 7.15-7.10 (2H, m), 6.96-6.90 (1H, m), 5.18 (2H, s), 4.20 (2H, d, J=7.3 Hz), 3.93 (3H, s), 2.27 (3H, s), 1.38-1.26 (1H, m), 0.64-0.57 (2H, m), 0.40-0.34 (2H, m), MS (ESI) m/z: 404.0 (M+H)$^+$.

<Step-4>: 4-((3-(6-(cyclopropylmethoxy)-5-methylpyridin-3-yl)phenoxy)methyl)benzoic acid To a stirred solution of methyl 4-((3-(6-(cyclopropylmethoxy)-5-methylpyridin-3-yl)phenoxy)methyl)benzoate (Step-3 in Acid-1, 260 mg, 0.64 mmol) in THF/MeOH (2 mL/4 mL) is added 2M aqueous sodium hydroxide solution (1 mL), and stirred at 60° C. for 1 hour. The reaction mixture is cooled to room temperature, and 2M hydrochloric acid (1 mL) is added. The mixture is extracted with DCM (20 mL×3) and dried over sodium sulfate. Insoluble materials are separated by filtration and the filtrate is concentrated to give 188 mg (75% yield) of the title compound as a white solid.

Alternatively, precipitates which are formed after the addition of 2M hydrochloric acid are collected by filtration, washed with water, then, dried in vacuo at 50° C. to give the title compound as a white solid.

$^1$H-NMR (400 MHz, DMSO-d$_6$) delta 8.27 (1H, d, J=2.7 Hz), 7.98 (2H, d, J=8.7 Hz), 7.90-7.85 (1H, m), 7.59 (2H, d, J=8.7 Hz), 7.40-7.33 (1H, m), 7.31-7.27 (1H, m), 7.25-7.21 (1H, m), 7.03-6.97 (1H, m), 5.28 (2H, s), 4.17 (2H, d, J=6.9 Hz), 2.22 (3H, s), 1.35-1.27 (1H, m), 0.60-0.52 (2H, m), 0.38-0.31 (2H, m), COOH is not observed, MS (ESI) m/z: 390.0 (M+H)$^+$.

Acid-2: 4-((3-(6-(cyclopropylmethoxy)pyridin-3-yl)phenoxy)methyl)benzoic acid

<Step-1>: 3-(6-(cyclopropylmethoxy)pyridin-3-yl)phenol

The title compound is prepared in 96% yield (1.0 g, a colorless oil) by the similar manner to Step-2 of Acid-1 using 5-bromo-2-(cyclopropylmethoxy)pyridine (1 g, 4.4 mmol).

$^1$H-NMR (400 MHz, CDCl$_3$) delta 8.34 (1H, d, J=2.7 Hz), 7.78 (1H, dd, J=8.7, 2.7 Hz), 7.31 (1H, t, J=7.8 Hz), 7.12-7.07 (1H, m), 7.02-6.98 (1H, m), 6.82-6.79 (2H, m), 4.99 (1H, br.s), 4.17 (2H, d, J=7.3 Hz), 1.37-1.26 (1H, m), 0.67-0.60 (2H, m), 0.40-0.34 (2H, m), MS (ESI) m/z: 242.0 (M+H)$^+$.

<Step-2>: methyl 4-((3-(6-(cyclopropylmethoxy)pyridin-3-yl)phenoxy)methyl)benzoate The title compound is prepared in quantitative yield (340 mg, a white solid) by the similar manner to Step-3 of Acid-1 using 3-(6-(cyclopropylmethoxy)pyridin-3-yl)phenol (Step-1 of Acid-2, 200 mg, 0.83 mmol).

$^1$H-NMR (400 MHz, CDCl$_3$) delta 8.33 (1H, d, J=3.2 Hz), 8.07 (2H, d, J=8.3 Hz), 7.76 (1H, dd, J=8.7, 2.7 Hz), 7.53 (2H, d, J=8.2 Hz), 7.38-7.32 (1H, m), 7.15-7.11 (2H, m), 6.97-6.92 (1H, m), 6.84 (1H, d, J=6.8 Hz), 5.18 (2H, s), 4.17 (2H, d, J=6.9 Hz), 3.93 (3H, s), 1.37-1.24 (1H, m), 0.67-0.60 (2H, m), 0.40-0.34 (2H, m), MS (ESI) m/z: 390.0 (M+H)$^+$.

<Step-3>: 4-((3-(6-(cyclopropylmethoxy)pyridin-3-yl)phenoxy)methyl)benzoic acid

The title compound is prepared in 85% yield (280 mg, a white solid) by the similar manner to Step-4 of Acid-1 using methyl 4-((3-(6-(cyclopropylmethoxy)pyridin-3-yl)phenoxy)methyl)benzoate (Step-2 of Acid-2, 340 mg, 0.88 mmol).

$^1$H-NMR (400 MHz, DMSO-d$_6$) delta 8.45 (1H, d, J=2.7 Hz), 8.01 (1H, dd, J=8.7, 2.7 Hz), 7.96 (2H, d, J=8.2 Hz), 7.56 (2H, d, J=8.2 Hz), 7.41-7.34 (1H, m), 7.32-7.27 (1H, m), 7.23 (1H, d, J=7.8 Hz), 7.14-6.97 (1H, m), 6.90 (1H, d, J=8.2 Hz), 5.27 (2H, s), 4.12 (2H, d, J=7.3 Hz), 1.31-1.19 (1H, m), 0.60-0.50 (2H, m), 0.37-0.25 (2H, m), COOH is not observed, MS (ESI) m/z: 376.0 (M+H)$^+$.

Acid-3: 4-((3-(6-((3,3-difluorocyclobutyl)methoxy)pyridin-3-yl)phenoxy)methyl)benzoic acid <Step-1>: 5-bromo-2-((3,3-difluorocyclobutyl)methoxy)pyridine The title compound is prepared in 41% yield (1.0 g, a colorless oil) by the similar manner to Step-1 of Acid-1 using 5-bromo-2-fluoropyridine (720 mg, 4.1 mmol) and (3,3-difluorocyclobutyl)methanol (500 mg, 4.1 mmol).

$^1$H-NMR (400 MHz, CDCl$_3$) delta 8.17 (1H, d, J=2.1 Hz), 7.65 (1H, dd, J=8.9, 2.1 Hz), 6.67 (1H, d, J=8.9 Hz), 4.31 (2H, d, J=5.5 Hz), 2.78-2.54 (3H, m), 2.52-2.37 (2H, m), MS (ESI) m/z: 278 (M+H)$^+$.

<Step-2>: 3-(6-((3,3-difluorocyclobutyl)methoxy)pyridin-3-yl)phenol

The title compound is prepared in quantitative yield (490 mg, a white solid) by the similar manner to Step-2 of Acid-1 using 5-bromo-2-((3,3-difluorocyclobutyl)methoxy)pyridine (Step-1 of Acid-3, 470 mg, 1.7 mmol).
$^1$H-NMR (400 MHz, CDCl$_3$) delta 8.37-8.33 (1H, m), 7.79 (1H, dd, J=8.9, 2.7 Hz), 7.31 (1H, t, J=7.6 Hz), 7.13-7.06 (1H, m), 7.03-6.99 (1H, m), 6.86-6.80 (2H, m), 5.70 (1H, br.s), 4.39 (2H, d, J=6.1 Hz), 2.80-2.57 (3H, m), 2.56-2.41 (2H, m), MS (ESI) m/z: 292 (M+H)$^+$.

<Step-3>: methyl 4-((3-(6-((3,3-difluorocyclobutyl)methoxy)pyridin-3-yl)phenoxy)methyl)benzoate The title compound is prepared in 54% yield (410 mg, a white solid) by the similar manner to Step-3 of Acid-1 using 3-(6-((3,3-difluorocyclobutyl)methoxy)pyridin-3-yl)phenol (Step-2 of Acid-3, 500 mg, 1.7 mmol).
$^1$H-NMR (400 MHz, CDCl$_3$) delta 8.33 (1H, d, J=1.8 Hz), 8.07 (2H, d, J=8.0 Hz), 7.78 (1H, dd, J=8.6, 2.4 Hz), 7.53 (2H, d, J=8.0 Hz), 7.36 (1H, t, J=7.6 Hz), 7.17-7.10 (2H, m), 6.97-6.92 (1H, m), 6.81 (1H, d, J=8.6 Hz), 5.19 (2H, s), 4.39 (2H, d, J=6.8 Hz), 3.93 (3H, s), 2.81-2.57 (3H, m), 2.56-2.41 (2H, m), MS (ESI) m/z: 440 (M+H)$^+$.

<Step-4>: 4-((3-(6-((3,3-difluorocyclobutyl)methoxy)pyridin-3-yl)phenoxy)methyl)benzoic acid The title compound is prepared in quantitative yield (394 mg, a white solid) by the similar manner to Step-4 of Acid-1 using methyl 4-((3-(6-((3,3-difluorocyclobutyl)methoxy)pyridin-3-yl)phenoxy)methyl)benzoate (Step-3 of Acid-3, 410 mg, 0.93 mmol).
$^1$H-NMR (400 MHz, DMSO-d$_6$) delta 12.97 (1H, br.s), 8.47 (1H, d, J=2.4 Hz), 8.03 (1H, dd, J=8.6, 2.4 Hz), 7.97 (2H, d, J=7.9 Hz), 7.59 (2H, d, J=8.6 Hz), 7.38 (1H, t, J=8.0 Hz), 7.33-7.28 (1H, m), 7.25 (1H, d, J=7.3 Hz), 7.02 (1H, dd, J=8.0, 2.4 Hz), 6.91 (1H, d, J=8.6 Hz), 5.29 (2H, s), 4.37 (2H, d, J=6.7 Hz), 2.82-2.56 (3H, m), 2.54-2.38 (2H, m).

Acid-4: 4-((3-(6-((4,4-difluorocyclohexyl)methoxy)pyridin-3-yl)phenoxy)methyl)benzoic acid <Step-1>: 5-bromo-2-((4,4-difluorocyclohexyl)methoxy)pyridine The title compound is prepared in 70% yield (710 mg, a white solid) by the similar manner to Step-1 of Acid-1 using 5-bromo-2-fluoropyridine (590 mg, 3.3 mmol) and (4,4-difluorocyclohexyl)methanol (500 mg, 3.3 mmol).
$^1$H-NMR (400 MHz, CDCl$_3$) delta 8.17 (1H, d, J=2.4 Hz), 7.64 (1H, dd, J=8.6, 2.4 Hz), 6.65 (1H, d, J=8.6 Hz), 4.13 (2H, d, J=6.1 Hz), 2.21-2.08 (2H, m), 1.97-1.65 (5H, m), 1.48-1.35 (2H, m), MS (ESI) m/z: 306 (M+H)$^+$.

<Step-2>: 3-(6-((4,4-difluorocyclohexyl)methoxy)pyridin-3-yl)phenol

The title compound is prepared in 70% yield (520 mg, a white solid) by the similar manner to Step-2 of Acid-1 using 5-bromo-2-((4,4-difluorocyclohexyl)methoxy)pyridine (Step-1 of Acid-4, 710 mg, 2.3 mmol).
$^1$H-NMR (400 MHz, CDCl$_3$) delta 8.36 (1H, d, J=2.4 Hz), 7.78 (1H, dd, J=8.6, 3.0 Hz), 7.31 (1H, t, J=8.0 Hz), 7.08 (1H, d, J=8.0 Hz), 7.05-6.97 (1H, m), 6.90-6.75 (2H, m), 5.53 (1H, s), 4.20 (2H, d, J=6.1 Hz), 2.25-2.09 (2H, m), 2.02-1.85 (3H, m), 1.85-1.64 (2H, m), 1.55-1.38 (2H, m), MS (ESI) m/z: 320 (M+H)$^+$.

<Step-3>: methyl 4-((3-(6-((4,4-difluorocyclohexyl)methoxy)pyridin-3-yl)phenoxy)methyl)benzoate The title compound is prepared in 44% yield (330 mg, a white solid) by the similar manner to Step-3 of Acid-1 using 3-(6-((4,4-difluorocyclohexyl)methoxy)pyridin-3-yl)phenol (Step-2 of Acid-4, 520 mg, 1.6 mmol).
$^1$H-NMR (400 MHz, CDCl$_3$) delta 8.33 (1H, d, J=1.8 Hz), 8.07 (2H, d, J=8.6 Hz), 7.77 (1H, dd, J=8.6, 2.4 Hz), 7.53 (2H, d, J=8.6 Hz), 7.36 (1H, t, J=8.0 Hz), 7.17-7.10 (2H, m), 6.98-6.92 (1H, m), 6.80 (1H, d, J=8.6 Hz), 5.19 (2H, s), 4.21 (2H, d, J=6.1 Hz), 3.93 (3H, s), 2.21-2.09 (2H, m), 2.01-1.85 (3H, m), 1.85-1.67 (2H, m), 1.53-1.39 (2H, m), MS (ESI) m/z: 468 (M+H)$^+$.

<Step-4>: 4-((3-(6-((4,4-difluorocyclohexyl)methoxy)pyridin-3-yl)phenoxy)methyl)benzoic acid The title compound is prepared in 98% yield (397 mg, a white solid) by the similar manner to Step-4 of Acid-1 using methyl 4-((3-(6-((4,4-difluorocyclohexyl)methoxy)pyridin-3-yl)phenoxy)methyl)benzoate (Step-3 of Acid-4, 333 mg, 0.71 mmol).
$^1$H-NMR (400 MHz, DMSO-d$_6$) delta 13.02 (1H, br.s), 8.46 (1H, d, J=2.4 Hz), 8.02 (1H, dd, J=8.6, 2.4 Hz), 7.97 (2H, d, J=8.6 Hz), 7.59 (2H, d, J=8.6 Hz), 7.38 (1H, t, J=8.0 Hz), 7.32-7.27 (1H, m), 7.24 (1H, d, J=8.0 Hz), 7.05-6.99 (1H, m), 6.90 (1H, d, J=8.6 Hz), 5.28 (2H, s), 4.19 (2H, d, J=6.1 Hz), 2.11-1.74 (7H, m), 1.40-1.22 (2H, m), MS (ESI) m/z: 454 (M+H)$^+$.

Acid-5: 4-((3-(6-(cyclopropylmethoxy)-4-methylpyridin-3-yl)phenoxy)methyl)benzoic acid <Step-1>: 5-bromo-2-(cyclopropylmethoxy)-4-methylpyridine The title compound is prepared in quantitative yield (500 mg, a pale yellow solid) by the similar manner to Step-1 of Acid-1 using 2,5-dibromo-4-methylpyridine (500 mg, 2.0 mmol).
MS (ESI) m/z: 242 (M+H)$^+$.

<Step-2>: 3-(6-(cyclopropylmethoxy)-4-methylpyridin-3-yl)phenol

The title compound is prepared in quantitative yield (540 mg, a white solid) by the similar manner to Step-2 of Acid-1 using 5-bromo-2-(cyclopropylmethoxy)-4-methylpyridine (Step-1 of Acid-5, 500 mg, 2.1 mmol).
$^1$H-NMR (400 MHz, CDCl$_3$) delta 8.64 (1H, br.s), 8.01 (1H, s), 7.25 (1H, t, J=8.6 Hz), 6.89 (1H, dd, J=9.2, 2.4 Hz), 6.79 (2H, dd, J=6.7, 1.2 Hz), 6.70 (1H, s), 4.13 (2H, d, J=7.3 Hz), 2.23 (3H, s), 1.35-1.20 (1H, m), 0.65-0.55 (2H, m), 0.39-0.30 (2H, m), MS (ESI) m/z: 256 (M+H)$^+$.

<Step-3>: methyl 4-((3-(6-(cyclopropylmethoxy)-4-methylpyridin-3-yl)phenoxy)methyl)benzoate The title compound is prepared in quantitative yield (950 mg, a white solid) by the similar manner to Step-3 of Acid-1 using 3-(6-(cyclopropylmethoxy)-4-methylpyridin-3-yl)phenol (Step-2 of Acid-5, 520 mg, 2.0 mmol).
$^1$H-NMR (400 MHz, CDCl$_3$) delta 8.06 (2H, d, J=8.6 Hz), 7.94 (1H, s), 7.51 (2H, d, J=8.6 Hz), 7.33 (1H, t, J=7.9 Hz), 7.00-6.95 (1H, m), 6.91-6.86 (2H, m), 6.67 (1H, s), 5.16

(2H, s), 4.14 (2H, d, J=6.7 Hz), 3.92 (3H, s), 2.19 (3H, s), 1.35-1.25 (1H, m), 0.65-0.59 (2H, m), 0.40-0.32 (2H, m), MS (ESI) m/z: 404 (M+H)⁺.

<Step-4>: 4-((3-(6-(cyclopropylmethoxy)-4-methylpyridin-3-yl)phenoxy)methyl)benzoic acid The title compound is prepared in 76% yield (700 mg, a white solid) by the similar manner to Step-4 of Acid-1 using methyl 4-((3-(6-(cyclopropylmethoxy)-4-methylpyridin-3-yl)phenoxy)methyl)benzoate (Step-3 of Acid-5, 950 mg, 2.4 mmol).
MS (ESI) m/z: 390 (M+H)⁺.

Acid-6: 4-((3-(6-(cyclopentylmethoxy)pyridin-3-yl)phenoxy)methyl)benzoic acid

<Step-1>: 3-(6-(cyclopentylmethoxy)pyridin-3-yl)phenol

The title compound is prepared in 95% yield (1.0 g, a yellow oil) by the similar manner to Step-2 of Acid-1 using 5-bromo-2-(cyclopentylmethoxy)pyridine (1.0 g, 3.9 mmol).
¹H-NMR (400 MHz, CDCl₃) delta 8.36 (1H, d, J=2.4 Hz), 7.77 (1H, dd, J=8.6, 3.1 Hz), 7.30 (1H, t, J=7.9 Hz), 7.08 (1H, d, J=8.0 Hz), 7.01 (1H, d, J=2.4 Hz), 6.84-6.80 (2H, m), 5.38 (1H, s), 4.20 (2H, d, J=7.3 Hz), 2.45-2.35 (1H, m), 1.89-1.80 (2H, m), 1.70-1.54 (4H, m), 1.44-1.34 (2H, m), MS (ESI) m/z: 270 (M+H)⁺.

<Step-2>: methyl 4-((3-(6-(cyclopentylmethoxy)pyridin-3-yl)phenoxy)methyl)benzoate The title compound is prepared in 83% yield (320 mg, a white solid) by the similar manner to Step-3 of Acid-1 using 3-(6-(cyclopentylmethoxy)pyridin-3-yl)phenol (Step-1 of Acid-6, 250 mg, 0.93 mmol).
¹H-NMR (400 MHz, CDCl₃) delta 8.33 (1H, d, J=1.8 Hz), 8.07 (2H, d, J=8.6 Hz), 7.76 (1H, dd, J=8.6, 2.4 Hz), 7.53 (2H, d, J=7.9 Hz), 7.36 (1H, t, J=7.7 Hz), 7.14-7.12 (1H, m), 6.95-6.92 (1H, m), 6.80 (1H, d, J=8.6 Hz), 5.19 (2H, s), 4.19 (2H, d, J=7.3 Hz), 3.93 (3H, s), 2.44-2.34 (1H, m), 1.90-1.80 (2H, m), 1.70-1.55 (4H, m), 1.44-1.34 (2H, m), MS (ESI) m/z: 418 (M+H)⁺.

<Step-3>: 4-((3-(6-(cyclopentylmethoxy)pyridin-3-yl)phenoxy)methyl)benzoic acid

The title compound is prepared in 97% yield (300 mg, a white solid) by the similar manner to Step-4 of Acid-1 using methyl 4-((3-(6-(cyclopentylmethoxy)pyridin-3-yl)phenoxy)methyl)benzoate (Step-2 of Acid-6, 320 mg, 0.75 mmol).
¹H-NMR (400 MHz, DMSO-d₆) delta 8.45 (1H, d, J=2.4 Hz), 8.05-7.95 (3H, m), 7.60 (2H, d, J=6.9 Hz), 7.38 (1H, t, J=7.9 Hz), 7.32-7.28 (1H, m), 7.26-7.22 (1H, m), 7.04-6.98 (1H, m), 6.88 (1H, d, J=8.6 Hz), 5.29 (2H, s), 4.17 (2H, d, J=6.7 Hz), 2.40-2.27 (1H, m), 1.82-1.70 (2H, m), 1.66-1.48 (4H, m), 1.38-1.26 (2H, m), COOH is not observed, MS (ESI) m/z: 404 (M+H)⁺.

Acid-7: 4-((3-(6-((tetrahydro-2H-pyran-4-yl)methoxy)pyridin-3-yl)phenoxy)methyl)benzoic acid <Step-1>: 5-bromo-2-((tetrahydro-2H-pyran-4-yl)methoxy)pyridine The title compound is prepared in 53% yield (560 mg, a white solid) by the similar manner to Step-1 of Acid-1 using 2,5-dibromo-pyridine (500 mg, 4.3 mmol). and (tetrahydro-2H-pyran-4-yl)methanol (920 mg, 3.9 mmol).
¹H-NMR (400 MHz, CDCl₃) delta 8.17 (1H, d, J=2.8 Hz), 7.64 (1H, dd, J=8.9, 2.8 Hz), 6.65 (1H, d, J=8.9 Hz), 4.12 (2H, d, J=6.8 Hz), 4.05-3.98 (2H, m), 3.43 (2H, td, J=11.8, 2.0 Hz), 2.12-1.99 (1H, m), 1.75-1.69 (2H, m), 1.49-1.38 (2H, m), MS (ESI) m/z: 272 (M+H)⁺.

<Step-2>: 3-(6-((tetrahydro-2H-pyran-4-yl)methoxy)pyridin-3-yl)phenol

The title compound is prepared in 75% yield (440 mg, a white solid) by the similar manner to Step-2 of Acid-1 using 5-bromo-2-((tetrahydro-2H-pyran-4-yl)methoxy)pyridine (Step-1 of Acid-7, 560 mg, 2.1 mmol).
¹H-NMR (400 MHz, CDCl₃) delta 8.36 (1H, dd, J=2.6, 0.6 Hz), 7.78 (1H, dd, J=8.6, 2.6 Hz), 7.31 (1H, t, J=7.8 Hz), 7.11-7.07 (1H, m), 7.02-6.98 (1H, m), 6.86-6.78 (2H, m), 5.32 (1H, br.s), 4.20 (2H, d, J=6.7 Hz), 4.07-3.98 (2H, m), 3.46 (2H, td, J=11.8, 2.1 Hz), 2.17-2.04 (1H, m), 1.81-1.73 (2H, m), 1.57-1.43 (2H, m), MS (ESI) m/z: 286 (M+H)⁺.

<Step-3>: methyl 4-((3-(6-((tetrahydro-2H-pyran-4-yl)methoxy)pyridin-3-yl)phenoxy)methyl)benzoate The title compound is prepared in 90% yield (270 mg, a white solid) by the similar manner to Step-3 of Acid-1 using 3-(6-((tetrahydro-2H-pyran-4-yl)methoxy)pyridin-3-yl)phenol (Step-2 of Acid-7, 200 mg, 0.70 mmol).
¹H-NMR (400 MHz, CDCl₃) delta 8.35-8.33 (1H, m), 8.09-8.05 (2H, m), 7.77 (1H, dd, J=8.6, 2.4 Hz), 7.55-7.52 (2H, m), 7.36 (1H, t, J=8.0 Hz), 7.16-7.11 (2H, m), 6.97-6.93 (1H, m), 6.81-6.78 (1H, m), 5.19 (2H, s), 4.19 (2H, d, J=6.4 Hz), 4.05-4.00 (2H, m), 3.93 (3H, s), 3.45 (2H, td, J=11.9, 2.1 Hz), 2.16-2.05 (1H, m), 1.81-1.74 (2H, m), 1.55-1.42 (2H, m), MS (ESI) m/z: 434 (M+H)⁺.

<Step-4>: 4-((3-(6-((tetrahydro-2H-pyran-4-yl)methoxy)pyridin-3-yl)phenoxy)methyl)benzoic acid The title compound is prepared in quantitative yield (270 mg, a white solid) by the similar manner to Step-4 of Acid-1 using methyl 4-((3-(6-((tetrahydro-2H-pyran-4-yl)methoxy)pyridin-3-yl)phenoxy)methyl)benzoate (Step-3 of Acid-7, 270 mg, 0.63 mmol).
¹H-NMR (400 MHz, DMSO-d₆) delta 8.44 (1H, d, J=2.5 Hz), 8.03-7.94 (3H, m), 7.63-7.57 (2H, m), 7.37 (1H, t, J=7.8 Hz), 7.31-7.27 (1H, m), 7.25-7.21 (1H, m), 7.02-6.98 (1H, m), 6.88 (1H, d, J=8.6 Hz), 5.27 (2H, s), 4.14 (2H, d, J=6.4 Hz), 3.91-3.83 (2H, m), 3.40-3.27 (2H, m), 2.08-1.96 (1H, m), 1.68-1.61 (2H, m), 1.38-1.25 (2H, m), COOH is not observed, MS (ESI) m/z: 420 (M+H)⁺.

Acid-8: 4-((3-(6-((1-(tert-butoxycarbonyl)piperidin-4-yl)methoxy)pyridin-3-yl)phenoxy)methyl)benzoic acid <Step-1>: tert-butyl 4-(((5-(3-hydroxyphenyl)pyridin-2-yl)oxy)methyl)piperidine-1-carboxylate The title compound is prepared in 45% yield (830 mg, a white solid) by the similar manner to Step-2 of Acid-1 using tert-butyl 4-(((5-bromopyridin-2-yl)oxy)methyl)piperidine-1-carboxylate (1.8 g, 4.8 mmol).
¹H-NMR (400 MHz, CDCl₃) delta 8.34 (1H, d, J=2.2 Hz), 7.77 (1H, dd, J=8.6, 2.7 Hz), 7.31 (1H, t, J=8.0 Hz), 7.13-7.06 (1H, m), 7.03-6.98 (1H, m), 6.87-6.75 (2H, m), 5.33 (1H, br.s), 4.28-4.03 (2H, m), 4.19 (2H, d, J=6.4 Hz), 2.85-2.67 (2H, m), 2.04-1.92 (1H, m), 1.90-1.78 (2H, m), 1.47 (9H, s), 1.37-1.21 (2H, m), MS (ESI) m/z: 385 (M+H)$^+$.

<Step-2>: tert-butyl 4-(((5-(3-((4-(methoxycarbonyl)benzyl)oxy)phenyl)pyridin-2-yl)oxy)methyl)piperidine-1-carboxylate The title compound is prepared in 85% yield (740 mg, a white solid) by the similar manner to Step-3 of Acid-1 using tert-butyl 4-(((5-(3-hydroxyphenyl)pyridin-2-yl)oxy)methyl)piperidine-1-carboxylate (Step-1 of Acid-8, 630 mg, 1.6 mmol).
$^1$H-NMR (400 MHz, CDCl$_3$) delta 8.33 (1H, d, J=1.8 Hz), 8.07 (2H, d, J=7.9 Hz), 7.76 (1H, dd, J=8.6, 2.4 Hz), 7.53 (2H, d, J=8.0 Hz), 7.36 (1H, t, J=8.0 Hz), 7.17-7.06 (2H, m), 6.98-6.92 (1H, m), 6.79 (1H, d, J=8.6 Hz), 5.18 (2H, s), 4.24-4.08 (2H, m), 4.19 (2H, d, J=6.1 Hz), 3.93 (3H, s), 2.85-2.65 (2H, m), 2.06-1.92 (1H, m), 1.90-1.77 (2H, m), 1.47 (9H, s), 1.35-1.18 (2H, m), MS (ESI) m/z: 533 (M+H)$^+$.

<Step-3>: 4-((3-(6-((1-(tert-butoxycarbonyl)piperidin-4-yl)methoxy)pyridin-3-yl)phenoxy)methyl)benzoic acid The title compound is prepared in quantitative yield (210 mg, a white solid) by the similar manner to Step-4 of Acid-1 using tert-butyl 4-(((5-(3-((4-(methoxycarbonyl)benzyl)oxy)phenyl)pyridin-2-yl)oxy)methyl)piperidine-1-carboxylate (Step-2 of Acid-8, 210 mg, 0.40 mmol).
MS (ESI) m/z: 519 (M+H)$^+$.

Acid-9: 4-((2-chloro-5-(6-(cyclopropylmethoxy)pyridin-3-yl)phenoxy)methyl)benzoic acid <Step-1>: 2-chloro-5-(6-(cyclopropylmethoxy)pyridin-3-yl)phenol To a stirred solution of 2-(cyclopropylmethoxy)-5-(4,4,5,5-tetramethyl-1,3,2-dioxaborolan-2-yl)pyridine (330 mg, 1.2 mmol), 5-bromo-2-chlorophenol (270 mg, 1.3 mmol) in dioxane/water (30 mL/10 mL) is added tetrakis(triphenylphosphine)palladium(0) (69 mg, 0.060 mmol), potassium carbonate (660 mg, 4.8 mmol), and the reaction mixture is stirred at 100° C. for 4 hours. The reaction mixture is cooled to room temperature and diluted with EtOAc (50 mL), washed with water (50 mL×1), and dried over sodium sulfate. Insoluble materials are separated by filtration and the filtrate is concentrated. The residue is used in the next step without further purification.
$^1$H-NMR (400 MHz, CDCl$_3$) delta 8.31 (1H, d, J=1.8 Hz), 7.74 (1H, dd, J=8.6, 2.4 Hz), 7.36 (1H, d, J=8.0 Hz), 7.17 (1H, d, J=2.4 Hz), 7.01 (1H, dd, J=8.6, 2.4 Hz), 6.83 (1H, d, J=8.6 Hz), 6.07 (1H, s), 4.17 (2H, d, J=7.3 Hz), 1.35-1.25 (1H, m), 0.65-0.59 (2H, m), 0.40-0.35 (2H, m), MS (ESI) m/z: 276 (M+H)$^+$.

<Step-2>: methyl 4-((2-chloro-5-(6-(cyclopropylmethoxy)pyridin-3-yl)phenoxy)methyl)benzoate The title compound is prepared in 85% yield (110 mg, a white solid) by the similar manner to Step-3 of Acid-1 using 2-chloro-5-(6-(cyclopropylmethoxy)pyridin-3-yl)phenol (Step-1 of Acid-9, 83 mg, 0.30 mmol).
$^1$H-NMR (400 MHz, CDCl$_3$) delta 8.25 (1H, d, J=1.8 Hz), 8.07 (2H, d, J=8.0 Hz), 7.69 (1H, dd, J=8.6, 2.4 Hz), 7.56 (2H, d, J=8.6 Hz), 7.44 (1H, dd, J=7.4, 1.2 Hz), 7.07 (1H, d, J=1.8 Hz), 7.05 (1H, s), 6.82 (1H, d, J=8.6 Hz), 5.26 (2H, s), 4.17 (2H, d, J=7.4 Hz), 3.92 (3H, s), 1.35-1.25 (1H, m), 0.76-0.60 (2H, m), 0.40-0.34 (2H, m), MS (ESI) m/z: 424 (M+H)$^+$.

<Step-3>: 4-((2-chloro-5-(6-(cyclopropylmethoxy)pyridin-3-yl)phenoxy)methyl)benzoic acid The title compound is prepared in 79% yield (82 mg, a white solid) by the similar manner to Step-4 of Acid-1 using methyl 4-((2-chloro-5-(6-(cyclopropylmethoxy)pyridin-3-yl)phenoxy)methyl)benzoate (Step-2 of Acid-9, 110 mg, 0.26 mmol).
MS (ESI) m/z: 410 (M+H)$^+$.

Acid-10: 3-chloro-4-((3-(6-(cyclopropylmethoxy)pyridin-3-yl)phenoxy)methyl)benzoic acid <Step-1>: methyl 3-chloro-4-((3-(6-(cyclopropylmethoxy)pyridin-3-yl)phenoxy)methyl)benzoate The title compound is prepared in 85% yield (108 mg, a white solid) by the similar manner to Step-3 of Acid-1 using 3-(6-(cyclopropylmethoxy)pyridin-3-yl)phenol (Step-1 of Acid-2, 72 mg, 0.30 mmol) and methyl 4-(bromomethyl)-3-chlorobenzoate (87 mg, 0.33 mmol).
$^1$H-NMR (400 MHz, CDCl$_3$) delta 8.34 (1H, d, J=2.5 Hz), 8.07 (1H, d, J=1.2 Hz), 7.95 (1H, dd, J=8.0, 1.8 Hz), 7.77 (1H, dd, J=8.6, 2.4 Hz), 7.69 (1H, d, J=7.9 Hz), 7.36 (1H, t, J=8.0 Hz), 7.15 (2H, d, J=7.3 Hz), 6.94 (1H, dd, J=7.3, 1.8 Hz), 6.84 (1H, d, J=8.6 Hz), 5.24 (2H, s), 4.17 (2H, d, J=7.3 Hz), 3.92 (3H, s), 1.38-1.22 (1H, m), 0.68-0.59 (2H, m), 0.42-0.35 (2H, m), MS (ESI) m/z: 424 (M+H)$^+$.

<Step-2>: 3-chloro-4-((3-(6-(cyclopropylmethoxy)pyridin-3-yl)phenoxy)methyl)benzoic acid The title compound is prepared in quantitative yield (88 mg, a white solid) by the similar manner to Step-4 of Acid-1 using methyl 3-chloro-4-((3-(6-(cyclopropylmethoxy)pyridin-3-yl)phenoxy)methyl)benzoate (Step-1 of Acid-10, 85 mg, 0.20 mmol).
MS (ESI) m/z: 410 (M+H)$^+$.

Acid 11: 4-((3-(6-(cyclopropylmethoxy)pyridin-3-yl)phenoxy)methyl)-3-fluorobenzoic acid <Step-1>: methyl 4-((3-(6-(cyclopropylmethoxy)pyridin-3-yl)phenoxy)methyl)-3-fluorobenzoate The title compound is prepared in 86% yield (105 mg, a white solid) by the similar manner to Step-3 of Acid-1 using 3-(6-(cyclopropylmethoxy)pyridin-3-yl)phenol (Step-1 of Acid-2, 72 mg, 0.30 mmol) and methyl 4-(bromomethyl)-3-fluorobenzoate (82 mg, 0.33 mmol).
$^1$H-NMR (400 MHz, CDCl$_3$) delta 8.34 (1H, d, J=3.2 Hz), 7.87 (1H, dd, J=7.8, 1.4 Hz), 7.79-7.74 (2H, m), 7.64 (1H, t, J=7.8 Hz), 7.37 (1H, t, J=7.8 Hz), 7.16-7.13 (2H, m), 6.98-6.94 (1H, m), 6.84 (1H, d, J=7.8 Hz), 5.24 (2H, s), 4.17 (2H, d, J=7.3 Hz), 3.93 (3H, s), 1.34-1.25 (1H, m), 0.66-0.61 (2H, m), 0.40-0.35 (2H, m), MS (ESI) m/z: 408 (M+H)$^+$.

<Step-2>: 4-((3-(6-(cyclopropylmethoxy)pyridin-3-yl)phenoxy)methyl)-3-fluorobenzoic acid The title compound is prepared in quantitative yield (82 mg, a white solid) by the similar manner to Step-4 of Acid-1 using methyl 4-((3-(6-(cyclopropylmethoxy)pyridin-3-yl)phenoxy)methyl)-3-fluorobenzoate (Step-1 of Acid-11, 81 mg, 0.20 mmol).

$^1$H-NMR (400 MHz, DMSO-d$_6$) delta 8.47 (1H, d, J=2.3 Hz), 8.03 (1H, dd, J=8.7, 2.3 Hz), 7.82 (1H, dd, J=7.8, 1.8 Hz), 7.74-7.69 (2H, m), 7.40 (1H, t, J=7.8 Hz), 7.34-7.32 (1H, m), 7.26 (1H, d, J=7.8 Hz), 7.04 (1H, dd, J=7.8, 1.8 Hz), 6.90 (1H, d, J=8.7 Hz), 5.31 (2H, s), 4.13 (2H, d, J=7.3 Hz), 1.31-1.22 (1H, m), 0.59-0.53 (2H, m), 0.36-0.31 (2H, m), COOH is not observed, MS (ESI) m/z: 394 (M+H)$^+$.

Acid-12: 4-((3-(6-(cyclobutylmethoxy)pyridin-3-yl)phenoxy)methyl)benzoic acid

<Step-1>: 5-bromo-2-(cyclobutylmethoxy)pyridine

The title compound is prepared in 77% yield (1.1 g, a colorless oil) by the similar manner to Step-1 of Acid-1 using 2,5-dibromopyridine (0.73 g, 8.5 mmol) and cyclobutylmethanol (1.0 g, 5.7 mmol).

$^1$H-NMR (400 MHz, CDCl$_3$) delta 8.17 (1H, d, J=2.4 Hz), 7.62 (1H, dd, J=8.6, 2.4 Hz), 6.65 (1H, d, J=8.6 Hz), 4.22 (2H, d, J=7.3 Hz), 2.81-2.69 (1H, m), 2.17-2.07 (2H, m), 2.03-1.78 (4H, m).

<Step-2>: 3-(6-(cyclobutylmethoxy)pyridin-3-yl)phenol

The title compound is prepared in 57% yield (300 mg, a colorless oil) by the similar manner to Step-2 of Acid-1 using 5-bromo-2-(cyclobutylmethoxy)pyridine (Step-1 of Acid-12, 500 mg, 2.1 mmol).

$^1$H-NMR (400 MHz, CDCl$_3$) delta 8.36 (1H, d, J=2.4 Hz), 7.77 (1H, dd, J=8.6, 2.4 Hz), 7.31 (1H, t, J=7.9 Hz), 7.12-7.07 (1H, m), 7.03-6.98 (1H, m), 6.85-6.80 (1H, m), 6.81 (1H, d, J=8.6 Hz), 5.17 (1H, s), 4.31 (2H, d, J=7.3 Hz), 2.85-2.74 (1H, m), 2.20-2.10 (2H, m), 2.03-1.80 (4H, m), MS (ESI) m/z: 254 (M+H)$^+$.

<Step-3>: methyl 4-((3-(6-(cyclobutylmethoxy)pyridin-3-yl)phenoxy)methyl)benzoate The title compound is prepared in 92% yield (290 mg, a white solid) by the similar manner to Step-3 of Acid-1 using 3-(6-(cyclobutylmethoxy)pyridin-3-yl)phenol (Step-2 of Acid-12, 200 mg, 0.78 mmol).

$^1$H-NMR (400 MHz, CDCl$_3$) delta 8.34 (1H, dd, J=2.8, 0.6 Hz), 8.09-8.05 (2H, m), 7.76 (1H, dd, J=8.9, 2.8 Hz), 7.55-7.52 (2H, m), 7.36 (1H, t, J=8.3 Hz), 7.15-7.12 (2H, m), 6.97-6.92 (1H, m), 6.82-6.78 (1H, m), 5.19 (2H, s), 4.31 (2H, d, J=7.0 Hz), 3.93 (3H, s), 2.84-2.73 (1H, m), 2.20-2.11 (2H, m), 2.01-1.82 (4H, m), MS (ESI) m/z: 404 (M+H)$^+$.

<Step-4>: 4-((3-(6-(cyclopropylmethoxy)pyridin-3-yl)phenoxy)methyl)-3-fluorobenzoic acid The title compound is prepared in 89% yield (250 mg, a white solid) by the similar manner to Step-4 of Acid-1 using methyl 4-((3-(6-(cyclobutylmethoxy)pyridin-3-yl)phenoxy)methyl)benzoate (Step-3 of Acid-12, 290 mg, 0.72 mmol).

$^1$H-NMR (400 MHz, DMSO-d$_6$) delta 12.98 (1H, br.s), 8.46 (1H, dd, J=2.8, 0.6 Hz), 8.04-7.96 (3H, m), 7.65-7.57 (2H, m), 7.38 (1H, t, J=7.9 Hz), 7.32-7.29 (1H, m), 7.27-7.23 (1H, m), 7.05-6.99 (1H, m), 6.92-6.86 (1H, m), 5.29 (2H, s), 4.28 (2H, d, J=7.0 Hz), 2.80-2.68 (1H, m), 2.12-2.03 (2H, m), 1.96-1.77 (4H, m), MS (ESI) m/z: 390 (M+H)$^+$.

Acid-13: 5-chloro-4-((3-(6-(cyclopropylmethoxy)pyridin-3-yl)phenoxy)methyl)-2-fluorobenzoic acid <Step-1>: methyl 4-(bromomethyl)-5-chloro-2-fluorobenzoate A mixture of methyl 5-chloro-2-fluoro-4-methylbenzoate (1.0 g, 4.9 mmol), N-bromosuccinimide (970 mg, 5.4 mmol), and azobisisobutyronitrile (41 mg, 0.25 mmol) in CCl$_4$ is stirred at reflux temperature overnight. The reaction mixture is cooled to room temperature and diluted with DCM (150 mL), and washed with saturated aqueous NaHCO$_3$ (50 mL), water (50 mL), brine (50 mL), and dried over sodium sulfate. Insoluble materials are separated by filtration and the filtrate is concentrated. The residue is purified by column chromatography on silica-gel eluting with n-hexane/EtOAc (95:5) to give 0.71 g (51% yield) of the title compound as a white solid.

$^1$H-NMR (400 MHz, CDCl$_3$) delta 7.97 (1H, d, J=6.7 Hz), 7.27 (1H, d, J=10.4 Hz), 4.52 (2H, s), 3.94 (3H, s).

<Step-2>: methyl 5-chloro-4-((3-(6-(cyclopropylmethoxy)pyridin-3-yl)phenoxy)methyl)-2-fluorobenzoate The title compound is prepared in 96% yield (260 mg, a white solid) by the similar manner to Step-3 of Acid-1 using 3-(6-(cyclopropylmethoxy)pyridin-3-yl)phenol (Step-1 of Acid-2, 150 mg, 0.62 mmol) and methyl 4-(bromomethyl)-5-chloro-2-fluorobenzoate (Step-1 of Acid-13, 190 mg, 1.1 mmol).

$^1$H-NMR (400 MHz, CDCl$_3$) delta 8.35 (1H, d, J=2.4 Hz), 7.98 (1H, d, J=6.1 Hz), 7.79 (1H, dd, J=8.6, 2.4 Hz), 7.47 (1H, d, J=11.0 Hz), 7.39 (1H, t, J=7.9 Hz), 7.20-7.12 (2H, m), 6.98-6.93 (1H, m), 6.85 (1H, d, J=8.6 Hz), 5.20 (2H, s), 4.18 (2H, d, J=7.3 Hz), 3.94 (3H, s), 1.38-1.24 (1H, m), 0.67-0.60 (2H, m), 0.41-0.34 (2H, m).

<Step-3>: 5-chloro-4-((3-(6-(cyclopropylmethoxy)pyridin-3-yl)phenoxy)methyl)-2-fluorobenzoic acid The title compound is prepared in quantitative yield (258 mg, a white solid) by the similar manner to Step-4 of Acid-1 using methyl 5-chloro-4-((3-(6-(cyclopropylmethoxy)pyridin-3-yl)phenoxy)methyl)-2-fluorobenzoate (Step-2 of Acid-13, 260 mg, 0.59 mmol).

$^1$H-NMR (400 MHz, DMSO-d$_6$) delta 13.64 (1H, br.s), 8.49 (1H, d, J=1.8 Hz), 8.06 (1H, dd, J=8.6, 2.4 Hz), 7.93 (1H, d, J=6.7 Hz), 7.62 (1H, d, J=11.0 Hz), 7.42 (1H, t, J=7.9 Hz), 7.39-7.36 (1H, m), 7.30 (1H, d, J=7.9 Hz), 7.10-7.04 (1H, m), 6.92 (1H, d, J=7.9 Hz), 5.29 (2H, s), 4.15 (2H, d, J=6.7 Hz), 1.33-1.21 (1H, m), 0.60-0.52 (2H, m), 0.38-0.31 (2H, m), MS (ESI) m/z: 428 (M+H)$^+$.

Acid-14: 4-((3-chloro-5-(6-(cyclopropylmethoxy)pyridin-3-yl)phenoxy)methyl)benzoic acid <Step-1>: 3-chloro-5-(6-(cyclopropylmethoxy)pyridin-3-yl)phenol The title compound is prepared in quantitative yield (402 mg, a white solid) by the similar manner to Step-1 of Acid-9 using 3-bromo-5-chlorophenol (342 mg, 1.66 mmol).

$^1$H-NMR (400, MHz, CDCl$_3$) delta 8.31 (1H, d, J=1.8 Hz), 7.85 (1H, br.s), 7.75 (1H, dd, J=8.6, 2.5 Hz), 7.02 (1H, s), 6.89 (2H, d, J=7.4 Hz), 6.84 (1H, d, J=8.6 Hz), 4.13 (2H, d, J=7.4 Hz), 1.35-1.21 (1H, m), 0.72-0.53 (2H, m), 0.45-0.26 (2H, m), MS (ESI) m/z: 276 (M+H)$^+$.

<Step-2>: methyl 4-((3-chloro-5-(6-(cyclopropyl-methoxy)pyridin-3-yl)phenoxy)methyl)benzoate The title compound is prepared in 71% yield (426 mg, a white solid) by the similar manner to Step-3 of Acid-1 using 3-chloro-5-(6-(cyclopropylmethoxy)pyridin-3-yl)phenol (Step-1 of Acid-14, 386 mg, 1.4 mmol).
$^1$H-NMR (400 MHz, CDCl$_3$) delta 8.29 (1H, d, J=1.8 Hz), 8.07 (2H, d, J=8.6 Hz), 7.71 (1H, dd, J=8.6, 2.5 Hz), 7.50 (2H, d, J=8.0 Hz), 7.11 (1H, t, J=1.2 Hz), 6.99 (1H, t, J=1.8 Hz), 6.93 (1H, t, J=2.4 Hz), 6.82 (1H, d, J=8.6 Hz), 5.15 (2H, s), 4.17 (2H, d, J=7.4 Hz), 3.92 (3H, s), 1.38-1.24 (1H, m), 0.70-0.59 (2H, m), 0.41-0.32 (2H, m), MS (ESI) m/z: 424 (M+H)$^+$.

<Step-3>: 4-((3-chloro-5-(6-(cyclopropylmethoxy)pyridin-3-yl)phenoxy)methyl)benzoic acid The title compound is prepared in 93% yield (380 mg, a white solid) by the similar manner to Step-4 of Acid-1 using methyl 4-((3-chloro-5-(6-(cyclopropylmethoxy)pyridin-3-yl)phenoxy)methyl)benzoate (Step-2 of Acid-14, 424 mg, 1.0 mmol).
MS (ESI) m/z: 410 (M+H)$^+$.

Acid 15: 4-((4-chloro-3-(6-(cyclopropylmethoxy)pyridin-3-yl)phenoxy)methyl)benzoic acid <Step-1>: 4-chloro-3-(6-(cyclopropylmethoxy)pyridin-3-yl)phenol The title compound is prepared in 97% yield (400 mg, a white solid) by the similar manner to Step-1 of Acid-9 using 3-bromo-4-chlorophenol (342 mg, 1.66 mmol).
$^1$H-NMR (400 MHz, CDCl$_3$) delta 8.19 (1H, d, J=2.4 Hz), 7.76 (1H, dd, J=9.2, 2.4 Hz), 7.32 (1H, d, J=9.2 Hz), 7.07 (1H, br.s), 6.88-6.80 (3H, m), 4.16 (2H, d, J=7.3 Hz), 1.36-1.24 (1H, m), 0.67-0.60 (2H, m), 0.40-0.34 (2H, m), MS (ESI) m/z: 276 (M+H)$^+$.

<Step-2>: methyl 4-((4-chloro-3-(6-(cyclopropyl-methoxy)pyridin-3-yl)phenoxy)methyl)benzoate The title compound is prepared in 75% yield (444 mg, a white solid) by the similar manner to Step-3 of Acid-1 using 4-chloro-3-(6-(cyclopropylmethoxy)pyridin-3-yl)phenol (Step-1 of Acid-15, 386 mg, 1.4 mmol).
$^1$H-NMR (400 MHz, CDCl$_3$) delta 8.17 (1H, d, J=2.4 Hz), 8.06 (2H, d, J=8.6 Hz), 7.68 (1H, dd, J=8.6, 2.4 Hz), 7.48 (2H, d, J=8.6 Hz), 7.36 (1H, d, J=8.6 Hz), 6.92 (1H, d, J=3.0 Hz), 6.89 (1H, dd, J=8.6, 3.0 Hz), 6.82 (1H, d, J=8.6 Hz), 5.12 (2H, s), 4.18 (2H, d, J=7.3 Hz), 3.92 (3H, s), 1.37-1.22 (1H, m), 0.67-0.59 (2H, m), 0.40-0.34 (2H, m), MS (ESI) m/z: 424 (M+H)$^+$.

<Step-3>: 4-((4-chloro-3-(6-(cyclopropylmethoxy)pyridin-3-yl)phenoxy)methyl)benzoic acid The title compound is prepared in 89% yield (366 mg, a white solid) by the similar manner to Step-4 of Acid-1 using methyl 4-((4-chloro-3-(6-(cyclopropylmethoxy)pyridin-3-yl)phenoxy)methyl)benzoate (Step-2 of Acid-15, 424 mg, 1.0 mmol).
MS (ESI) m/z: 428 (M+H)$^+$.

Acid-16: 5-cyclopropyl-4-((3-(6-(cyclopropyl-methoxy)pyridin-3-yl)phenoxy)methyl)-2-fluorobenzoic acid <Step-1>: methyl 5-cyclopropyl-4-((3-(6-(cyclopropylmethoxy)pyridin-3-yl)phenoxy)methyl)-2-fluorobenzoate A mixture of methyl 5-chloro-4-((3-(6-(cyclopropylmethoxy)pyridin-3-yl)phenoxy)methyl)-2-fluorobenzoate (Step-2 of Acid-13, 50 mg, 0.11 mmol), cyclopropylboronic acid (49 mg, 0.57 mmol), tricyclohexylphosphine tetrafluoroborate (25 mg, 0.068 mmol), palladium (II) acetate trimer (23 mg, 0.034 mmol) and potassium phosphatetribasic (72 mg, 0.34 mmol) in toluene (2 mL) and water (0.2 mL) is heated at reflux temperature for 2.5 hours. The reaction mixture is cooled to room temperature and diluted with EtOAc (20 mL), washed with water (20 mL), and dried over sodium sulfate. Insoluble materials are separated by filtration and the filtrate is concentrated. The residue is purified by column chromatography on silica-gel eluting with n-hexane/EtOAc (95:5 to 4:1) to give 35 mg (69% yield) of the title compound as a pale yellow oil.
$^1$H-NMR (400 MHz, CDCl$_3$) delta 8.34 (1H, d, J=2.4 Hz), 7.78 (1H, dd, J=8.6, 2.4 Hz), 7.66 (1H, d, J=6.7 Hz), 7.38 (1H, t, J=7.9 Hz), 7.34 (1H, d, J=11.6 Hz), 7.18-7.12 (2H, m), 6.98-6.94 (1H, m), 6.85 (1H, d, J=8.6 Hz), 5.31 (2H, s), 4.17 (2H, d, J=7.3 Hz), 3.93 (3H, s), 1.92-1.83 (1H, m), 1.37-1.26 (1H, m), 1.03-0.96 (2H, m), 0.76-0.70 (2H, m), 0.67-0.60 (2H, m), 0.40-0.35 (2H, m), MS (ESI) m/z: 448 (M+H)$^+$.

<Step-2>: 5-cyclopropyl-4-((3-(6-(cyclopropyl-methoxy)pyridin-3-yl)phenoxy)methyl)-2-fluorobenzoic acid The title compound is prepared in 98% yield (33 mg, a pale yellow oil) by the similar manner to Step-4 of Acid-1 using methyl 5-chloro-4-((3-(6-(cyclopropylmethoxy)pyridin-3-yl)phenoxy)methyl)-2-fluorobenzoate (Step-1 of Acid-16, 35 mg, 0.078 mmol).
MS (ESI) m/z: 434 (M+H)$^+$.

Acid-17: 4-((3-(6-(cyclopropylmethoxy)pyridin-3-yl)phenoxy)methyl)-2,5-difluorobenzoic acid <Step-1>: methyl 4-((3-(6-(cyclopropylmethoxy)pyridin-3-yl)phenoxy)methyl)-2,5-difluorobenzoate The title compound is prepared in 89% yield (157 mg, a white solid) by the similar manner to Step-3 of Acid-1 using 3-(6-(cyclopropylmethoxy)pyridin-3-yl)phenol (Step-1 of Acid-2, 100 mg, 0.41 mmol) and methyl 4-(bromomethyl)-2,5-difluorobenzoate (121 mg, 0.46 mmol).
$^1$H-NMR (400 MHz, CDCl$_3$) delta 8.34 (1H, d, J=2.4 Hz), 7.78 (1H, dd, J=8.6, 2.4 Hz), 7.70-7.64 (1H, m), 7.40-7.35 (2H, m), 7.19-7.11 (2H, m), 6.97-6.93 (1H, m), 6.85 (1H, d, J=8.6 Hz), 5.21 (2H, s), 4.18 (2H, d, J=6.7 Hz), 3.95 (3H, s), 1.38-1.25 (1H, m), 0.67-0.60 (2H, m), 0.41-0.35 (2H, m).

<Step-2>: 4-((3-(6-(cyclopropylmethoxy)pyridin-3-yl)phenoxy)methyl)-2,5-difluorobenzoic acid The title compound is prepared in 75% yield (110 mg, a white solid) by the similar manner to Step-4 of Acid-1 using methyl 4-((3-(6-(cyclopropylmethoxy)pyridin-3-yl)phenoxy)methyl)-2,5-difluorobenzoate (Step-1 of Acid-17, 152 mg, 0.36 mmol).

$^1$H-NMR (400 MHz, DMSO-d$_6$) delta 13.60 (1H, br.s), 8.48 (1H, d, J=2.4 Hz), 8.04 (1H, dd, J=8.6, 2.4 Hz), 7.69 (1H, dd, J=9.8, 6.1 Hz), 7.58 (1H, dd, J=10.4, 5.5 Hz), 7.41 (1H, t, J=7.9 Hz), 7.38-7.34 (1H, m), 7.28 (1H, d, J=8.6 Hz), 7.10-7.03 (1H, m), 6.91 (1H, d, J=8.6 Hz), 5.29 (2H, s), 4.15 (2H, d, J=7.3 Hz), 1.33-1.21 (1H, m), 0.60-0.53 (2H, m), 0.38-0.30 (2H, m), MS (ESI) m/z: 412 (M+H)$^+$.

Acid-18: 3-fluoro-4-((3-(6-((tetrahydro-2H-pyran-4-yl)methoxy)pyridin-3-yl)phenoxy)methyl)benzoic acid <Step-1>: methyl 3-fluoro-4-((3-(6-((tetrahydro-2H-pyran-4-yl)methoxy)pyridin-3-yl)phenoxy)methyl)benzoate The title compound is prepared in 72% yield (170 mg, a white solid) by the similar manner to Step-3 of Acid-1 using 3-(6-((tetrahydro-2H-pyran-4-yl)methoxy)pyridin-3-yl)phenol (Step-2 of Acid-7, 150 mg, 0.53 mmol) and methyl 4-(bromomethyl)-3-fluorobenzoate (130 mg, 0.53 mmol).

$^1$H-NMR (400 MHz, CDCl$_3$) delta 8.34 (1H, d, J=2.4 Hz), 7.88-7.86 (1H, m), 7.79-7.75 (2H, m), 7.64 (1H, t, J=8.4 Hz), 7.38 (1H, t, J=8.0 Hz), 7.16-7.12 (2H, m), 6.98-6.95 (1H, m), 6.80 (1H, d, J=8.6 Hz), 5.24 (2H, s), 4.19 (2H, d, J=6.7 Hz), 4.04-4.01 (2H, m), 3.93 (3H, s), 3.48-3.42 (2H, m), 2.15-2.04 (1H, m), 1.79-1.75 (2H, m), 1.55-1.43 (2H, m), MS (ESI) m/z: 452 (M+H)$^+$.

<Step-2>: 3-fluoro-4-((3-(6-((tetrahydro-2H-pyran-4-yl)methoxy)pyridin-3-yl)phenoxy)methyl)benzoic acid The title compound is prepared in 91% yield (150 mg, a white solid) by the similar manner to Step-4 of Acid-1 using methyl 3-fluoro-4-((3-(6-((tetrahydro-2H-pyran-4-yl)methoxy)pyridin-3-yl)phenoxy)methyl)benzoate (Step-1 of Acid-18, 152 mg, 0.36 mmol).

$^1$H-NMR (400 MHz, CDCl$_3$) delta 8.35 (1H, d, J=1.8 Hz), 7.94-7.92 (1H, m), 7.83-7.77 (2H, m), 7.69 (1H, t, J=7.3 Hz), 7.38 (1H, t, J=7.9 Hz), 7.17-7.14 (2H, m), 6.99-6.97 (1H, m), 6.80 (1H, d, J=8.6 Hz), 5.26 (2H, s), 4.20 (2H, d, J=6.8 Hz), 4.05-4.01 (2H, m), 3.48-3.42 (2H, m), 2.16-2.04 (1H, m), 1.79-1.75 (2H, m), 1.54-1.43 (2H, m), COOH is not observed, MS (ESI) m/z: 438 (M+H)$^+$.

Acid-19: 4-((3-(6-(cyclopropylmethoxy)pyridin-3-yl)phenoxy)methyl)-5-(difluoromethoxy)-2-fluorobenzoic acid <Step-1>: methyl 4-bromo-2-fluoro-5-hydroxybenzoate To a stirred solution of 4-bromo-2-fluoro-5-hydroxybenzoic acid (4.9 g, 21 mmol) in methanol (60 mL) is added thionyl chloride (4.5 mL, 62 mmol) at 0° C., then, the reaction mixture is stirred at reflux temperature for 3 hours. After cooled to room temperature, 2M hydrochloric acid (20 mL) and water (50 mL) is added, and extracted with DCM (80 mL×3), dried over sodium sulfate. Insoluble materials are separated by filtration and the filtrate is concentrated. The residue is purified by column chromatography on silica-gel eluting with n-hexane/EtOAc (3:1) to give 2.8 g (55% yield) of the title compound as a white solid.

$^1$H-NMR (400 MHz, CDCl$_3$) delta 7.58 (1H, d, J=6.7 Hz), 7.32 (1H, d, J=9.8 Hz), 5.49 (1H, s), 3.93 (3H, s).

<Step-2>: methyl 4-bromo-5-(difluoromethoxy)-2-fluorobenzoate

A mixture of methyl 4-bromo-2-fluoro-5-hydroxybenzoate (Step-1 of Acid-19, 600 mg, 2.4 mmol), sodium difluorochloroacetate (550 mg, 3.6 mmol), and potassium carbonate (999 mg, 7.2 mmol) in DMF (10 mL) is heated at 70° C. for 15 hours. The mixture is added water (30 mL) and extracted with EtOAc/toluene (9:1, 30 mL×3). The combined organic layer is washed with water (50 mL×3), brine (30 mL), dried over sodium sulfate. Insoluble materials are separated by filtration and the filtrate is concentrated. The residue is purified by column chromatography on silica-gel eluting with n-hexane/EtOAc (92:8) to give 460 mg (64% yield) of the title compound as a white solid.

$^1$H-NMR (400 MHz, CDCl$_3$) delta 7.80 (1H, d, J=6.1 Hz), 7.46 (1H, d, J=9.2 Hz), 6.54 (1H, t, J=72.2 Hz), 3.95 (3H, s).

<Step-3>: methyl 5-(difluoromethoxy)-2-fluoro-4-methylbenzoate

A mixture of methyl 4-bromo-5-(difluoromethoxy)-2-fluorobenzoate (Step-2 of Acid-19, 455 mg, 1.5 mmol), 2,4,6-trimethyl-1,3,5,2,4,6-trioxatriborinane (0.32 mL, 2.3 mmol), potassium carbonate (421 mg, 3.0 mmol) and tetrakis(triphenylphosphine)palladium(0) (176 mg, 0.15 mmol) in DMF (5 mL) is stirred at 100° C. for 15 hours. The reaction mixture is diluted with EtOAc (50 mL) and washed with water (20 mL×3), dried over magnesium sulfate. Insoluble materials are separated by filtration and the filtrate is concentrated. The residue is purified by column chromatography on silica-gel eluting with n-hexane/EtOAc (9:1) to give 322 mg (90% yield) of the title compound as a colorless oil.

$^1$H-NMR (400 MHz, CDCl$_3$) delta 7.66 (1H, d, J=6.1 Hz), 7.02 (1H, d, J=11.0 Hz), 6.51 (1H, t, J=73.4 Hz), 3.93 (3H, s), 2.33 (3H, s).

<Step-4>: methyl 4-(bromomethyl)-5-(difluoromethoxy)-2-fluorobenzoate

The title compound is prepared in 37% yield (150 mg, a pale yellow oil) by the similar manner to Step-1 of Acid-13 using methyl 5-(difluoromethoxy)-2-fluoro-4-methylbenzoate (Step-3 of Acid-19, 315 mg, 1.3 mmol).

$^1$H-NMR (400 MHz, CDCl$_3$) delta 7.73 (1H, d, J=5.5 Hz), 7.26 (1H, d, J=10.4 Hz), 6.58 (1H, t, J=72.7 Hz), 4.47 (2H, s), 3.95 (3H, s).

<Step-5>: methyl 4-((3-(6-(cyclopropylmethoxy)pyridin-3-yl)phenoxy)methyl)-5-(difluoromethoxy)-2-fluorobenzoate The title compound is prepared in 91% yield (193 mg, a white solid) by the similar manner to Step-3 of Acid-1 using 3-(6-(cyclopropylmethoxy)pyridin-3-yl)phenol (Step-1 of Acid-2, 110 mg, 0.45 mmol) and methyl 4-(bromomethyl)-5-(difluoromethoxy)-2-fluorobenzoate (Step-4 of Acid-19, 154 mg, 0.49 mmol).

$^1$H-NMR (400 MHz, CDCl$_3$) delta 8.34 (1H, d, J=2.4 Hz), 7.80-7.73 (2H, m), 7.46 (1H, d, J=11.0 Hz), 7.38 (1H, t, J=7.9 Hz), 7.19-7.10 (2H, m), 6.97-6.92 (1H, m), 6.85 (1H, d, J=8.6 Hz), 6.60 (1H, t, J=73.1 Hz), 5.20 (2H, s), 4.18 (2H, d, J=7.3 Hz), 3.95 (3H, s), 1.38-1.24 (1H, m), 0.67-0.60 (2H, m), 0.40-0.35 (2H, m), MS (ESI) m/z: 474 (M+H)⁺.

<Step-6>: 4-((3-(6-(cyclopropylmethoxy)pyridin-3-yl)phenoxy)methyl)-5-(difluoromethoxy)-2-fluorobenzoic acid The title compound is prepared in quantitative yield (189 mg, a white solid) by the similar manner to Step-4 of Acid-1 using methyl 4-((3-(6-(cyclopropylmethoxy)pyridin-3-yl)phenoxy)methyl)-5-(difluoromethoxy)-2-fluorobenzoate (Step-5 of Acid-19, 188 mg, 0.40 mmol).
¹H-NMR (400 MHz, CDCl₃) delta 8.46 (1H, d, J=2.4 Hz), 8.02 (1H, dd, J=8.6, 2.4 Hz), 7.65 (1H, d, J=6.1 Hz), 7.40 (1H, t, J=7.9 Hz), 7.35-7.25 (3H, m), 7.30 (1H, t, J=73.4 Hz), 7.06-7.01 (1H, m), 6.90 (1H, d, J=8.6 Hz), 5.22 (2H, s), 4.14 (2H, d, J=7.3 Hz), 1.33-1.20 (1H, m), 0.60-0.52 (2H, m), 0.37-0.30 (2H, m), COOH is not observed, MS (ESI) m/z: 460 (M+H)⁺.

Acid-20: 4-((3-(6-(cyclopropylmethoxy)pyridin-3-yl)phenoxy)methyl)-2-fluorobenzoic acid <Step-1>: ethyl 4-(bromomethyl)-2-fluorobenzoate The title compound is prepared in 89% yield (455 mg, a pale yellow oil) by the similar manner to Step-1 of Acid-13 using ethyl 2-fluoro-4-methylbenzoate (355 mg, 1.9 mmol). MS (ESI) m/z: 261 (M+H)⁺.

<Step-2>: ethyl 4-((3-(6-(cyclopropylmethoxy)pyridin-3-yl)phenoxy)methyl)-2-fluorobenzoate The title compound is prepared in 69% yield (121 mg, a white solid) by the similar manner to Step-3 of Acid-1 using 3-(6-(cyclopropylmethoxy)pyridin-3-yl)phenol (Step-1 of Acid-2, 100 mg, 0.41 mmol) and ethyl 4-(bromomethyl)-2-fluorobenzoate (Step-1 of Acid-20, 130 mg, 0.50 mmol).
¹H-NMR (400 MHz, CDCl₃) delta 8.33 (1H, d, J=2.4 Hz), 7.98-7.92 (1H, m), 7.77 (1H, dd, J=8.6, 2.4 Hz), 7.36 (1H, t, J=7.9 Hz), 7.29-7.22 (2H, m), 7.17-7.08 (2H, m), 6.95-6.90 (1H, m), 6.84 (1H, d, J=8.6 Hz), 5.16 (2H, s), 4.40 (2H, q, J=7.3 Hz), 4.17 (2H, d, J=7.3 Hz), 1.40 (3H, t, J=7.3 Hz), 1.36-1.25 (1H, m), 0.67-0.60 (2H, m), 0.40-0.35 (2H, m), MS (ESI) m/z: 422 (M+H)⁺.

<Step-3>: 4-((3-(6-(cyclopropylmethoxy)pyridin-3-yl)phenoxy)methyl)-2-fluorobenzoic acid The title compound is prepared in 95% yield (103 mg, a white solid) by the similar manner to Step-4 of Acid-1 using ethyl 4-((3-(6-(cyclopropylmethoxy)pyridin-3-yl)phenoxy)methyl)-2-fluorobenzoate (Step-2 of Acid-20, 116 mg, 0.28 mmol).
MS (ESI) m/z: 394 (M+H)⁺.

Acid-21: 4-((3-(6-(cyclopropylmethoxy)pyridin-3-yl)phenoxy)methyl)-3,5-difluorobenzoic acid <Step-1>: methyl 4-((3-(6-(cyclopropylmethoxy)pyridin-3-yl)phenoxy)methyl)-3,5-difluorobenzoate The title compound is prepared in 95% yield (134 mg, a colorless oil) by the similar manner to Step-3 of Acid-1 using 3-(6-(cyclopropylmethoxy)pyridin-3-yl)phenol (Step-1 of Acid-2, 80 mg, 0.33 mmol) and methyl 4-(chloromethyl)-3,5-difluorobenzoate (88 mg, 0.40 mmol).
¹H-NMR (400 MHz, CDCl₃) delta 8.34 (1H, d, J=2.4 Hz), 7.78 (1H, dd, J=8.6, 2.4 Hz), 7.65-7.57 (2H, m), 7.41-7.33 (1H, m), 7.18-7.12 (2H, m), 7.02-6.95 (1H, m), 6.83 (1H, d, J=8.6 Hz), 5.21 (2H, s), 4.17 (2H, d, J=7.3 Hz), 3.94 (3H, s), 1.38-1.25 (1H, m), 0.67-0.60 (2H, m), 0.40-0.33 (2H, m), MS (ESI) m/z: 426 (M+H)⁺.

<Step-2>: 4-((3-(6-(cyclopropylmethoxy)pyridin-3-yl)phenoxy)methyl)-3,5-difluorobenzoic acid The title compound is prepared in 97% yield (120 mg, a pale yellow solid) by the similar manner to Step-4 of Acid-1 using methyl 4-((3-(6-(cyclopropylmethoxy)pyridin-3-yl)phenoxy)methyl)-3,5-difluorobenzoate (Step-1 of Acid-21, 129 mg, 0.30 mmol).
MS (ESI) m/z: 412 (M+H)⁺.

Acid-22: 4-((3-(6-(cyclopropylmethoxy)pyridin-3-yl)-5-fluorophenoxy)methyl)benzoic acid <Step-1>: 3-(6-(cyclopropylmethoxy)pyridin-3-yl)-5-fluorophenol The title compound is prepared in 81% yield (370 mg, a yellow oil) by the similar manner to Step-2 of Acid-1 using 5-bromo-2-(cyclopropylmethoxy)pyridine (400 mg, 1.8 mmol) and (3-fluoro-5-hydroxyphenyl)boronic acid (273 mg, 1.8 mmol).
¹H-NMR (400 MHz, CDCl₃) delta 8.33 (1H, d, J=2.4 Hz), 7.55 (1H, dd, J=8.6, 2.4 Hz), 6.85 (1H, d, J=8.6 Hz), 6.82-6.76 (2H, m), 6.60-6.54 (1H, m), 6.07 (1H, br.s), 4.17 (2H, d, J=7.3 Hz), 1.37-1.23 (1H, m), 0.68-0.60 (2H, m), 0.40-0.33 (2H, m), MS (ESI) m/z: 260 (M+H)⁺.

<Step-2>: methyl 4-((3-(6-(cyclopropylmethoxy)pyridin-3-yl)-5-fluorophenoxy)methyl)benzoate The title compound is prepared in 81% yield (96 mg, a white solid) by the similar manner to Step-3 of Acid-1 using 3-(6-(cyclopropylmethoxy)pyridin-3-yl)-5-fluorophenol (Step-1 of Acid-22, 75 mg, 0.29 mmol).
¹H-NMR (400 MHz, CDCl₃) delta 8.30 (1H, d, J=2.4 Hz), 8.10-8.05 (2H, m), 7.73 (1H, dd, J=8.6, 2.4 Hz), 7.51 (2H, d, J=8.6 Hz), 6.93-6.80 (3H, m), 6.69-6.62 (1H, m), 5.16 (2H, s), 4.17 (2H, d, J=7.3 Hz), 3.93 (3H, s), 1.36-1.24 (1H, m), 0.67-0.60 (2H, m), 0.40-0.34 (2H, m).

<Step-3>: 4-((3-(6-(cyclopropylmethoxy)pyridin-3-yl)-5-fluorophenoxy)methyl)benzoic acid The title compound is prepared in quantitative yield (89 mg, a pale yellow solid) by the similar manner to Step-4 of Acid-1 using methyl 4-((3-(6-(cyclopropylmethoxy)pyridin-3-yl)-5-fluorophenoxy)methyl)benzoate (Step-2 of Acid-22, 92 mg, 0.23 mmol).
MS (ESI) m/z: 394 (M+H)⁺.

Acid-23: 4-((3-(6-(cyclopropylmethoxy)pyridin-3-yl)-5-fluorophenoxy)methyl)-2,5-difluorobenzoic acid <Step-1>: methyl 4-((3-(6-(cyclopropylmethoxy)pyridin-3-yl)-5-fluorophenoxy)methyl)-2,5-difluorobenzoate The title compound is prepared in 85% yield (95 mg, a white solid) by the similar manner to Step-3 of Acid-1 using 3-(6-(cyclopropylmethoxy)pyridin-3-yl)-5-fluorophenol (Step-1 of Acid-22, 65 mg, 0.25 mmol) and methyl 4-(bromomethyl)-2,5-difluorobenzoate (80 mg, 0.30 mmol).

$^1$H-NMR (400 MHz, CDCl$_3$) delta 8.32 (1H, d, J=2.4 Hz), 7.75 (1H, dd, J=8.6, 2.4 Hz), 7.71-7.65 (1H, m), 7.36 (1H, dd, J=10.4, 5.5 Hz), 6.93-6.82 (3H, m), 6.70-6.63 (1H, m), 5.18 (2H, s), 4.18 (2H, d, J=7.3 Hz), 3.95 (3H, s), 1.36-1.26 (1H, m), 0.67-0.60 (2H, m), 0.40-0.34 (2H, m), MS (ESI) m/z: 444 (M+H)$^+$.

<Step-2>: 4-((3-(6-(cyclopropylmethoxy)pyridin-3-yl)-5-fluorophenoxy)methyl)-2,5-difluorobenzoic acid The title compound is prepared in quantitative yield (91 mg, a pale brown solid) by the similar manner to Step-4 of Acid-1 using methyl 4-((3-(6-(cyclopropylmethoxy)pyridin-3-yl)-5-fluorophenoxy)methyl)-2,5-difluorobenzoate (Step-1 of Acid-23, 90 mg, 0.20 mmol).

MS (ESI) m/z: 430 (M+H)$^+$.

Acid-24: 4-((3-(6-(cyclopropylmethoxy)pyridin-3-yl)-5-fluorophenoxy)methyl)-3-fluorobenzoic acid <Step-1>: methyl 4-((3-(6-(cyclopropylmethoxy)pyridin-3-yl)-5-fluorophenoxy)methyl)-3-fluorobenzoate The title compound is prepared in 89% yield (100 mg, a white solid) by the similar manner to Step-3 of Acid-1 using 3-(6-(cyclopropylmethoxy)pyridin-3-yl)-5-fluorophenol (Step-1 of Acid-22, 68 mg, 0.26 mmol) and methyl 4-(bromomethyl)-3-fluorobenzoate (82 mg, 0.32 mmol).

$^1$H-NMR (400 MHz, CDCl$_3$) delta 8.31 (1H, d, J=2.4 Hz), 7.90-7.85 (1H, m), 7.80-7.72 (2H, m), 7.65-7.58 (1H, m), 6.95-6.80 (3H, m), 6.71-6.65 (1H, m), 5.21 (2H, s), 4.18 (2H, d, J=7.3 Hz), 3.94 (3H, s), 1.36-1.24 (1H, m), 0.67-0.60 (2H, m), 0.40-0.34 (2H, m), MS (ESI) m/z: 426 (M+H)$^+$.

<Step-2>: 4-((3-(6-(cyclopropylmethoxy)pyridin-3-yl)-5-fluorophenoxy)methyl)-3-fluorobenzoic acid The title compound is prepared in quantitative yield (109 mg, a pale brown solid) by the similar manner to Step-4 of Acid-1 using methyl 4-((3-(6-(cyclopropylmethoxy)pyridin-3-yl)-5-fluorophenoxy)methyl)-3-fluorobenzoate (Step-1 of Acid-24, 95 mg, 0.22 mmol).

$^1$H-NMR (400 MHz, DMSO-d$_6$) delta 8.51 (1H, d, J=1.8 Hz), 8.07 (1H, dd, J=8.6, 2.8 Hz), 7.78-7.72 (1H, m), 7.67-7.61 (1H, m), 7.58 (1H, t, J=7.6 Hz), 7.23-7.12 (2H, m), 6.98-6.92 (1H, m), 6.90 (1H, d, J=8.6 Hz), 5.26 (2H, s), 4.14 (2H, d, J=7.0 Hz), 1.32-1.20 (1H, m), 0.67-0.52 (2H, m), 0.37-0.30 (2H, m), COOH is not observed, MS (ESI) m/z: 412 (M+H)$^+$.

Acid-25: 4-((3-cyclopropyl-5-(6-(cyclopropylmethoxy)pyridin-3-yl)phenoxy)methyl)benzoic acid <Step-1>: methyl 4-((3-cyclopropyl-5-(6-(cyclopropylmethoxy)pyridin-3-yl)phenoxy)methyl)benzoate The title compound is prepared in 31% yield (36 mg, a yellow oil) by the similar manner to Step-1 of Acid-16 using methyl 4-((3-chloro-5-(6-(cyclopropylmethoxy)pyridin-3-yl)phenoxy)methyl)benzoate (Step-2 of Acid-14, 113 mg, 0.27 mmol).

$^1$H-NMR (400 MHz, CDCl$_3$) delta 8.30 (1H, d, J=2.4 Hz), 8.06 (2H, d, J=7.9 Hz), 7.74 (1H, dd, J=8.6, 2.4 Hz), 7.52 (2H, d, J=7.9 Hz), 6.92-6.80 (3H, m), 6.68-6.63 (1H, m), 5.16 (2H, s), 4.16 (2H, d, J=7.3 Hz), 3.93 (3H, s), 1.97-1.87 (1H, m), 1.38-1.24 (1H, m), 1.03-0.95 (2H, m), 0.76-0.70 (2H, m), 0.67-0.60 (2H, m), 0.40-0.34 (2H, m), MS (ESI) m/z: 430 (M+H)$^+$.

<Step-2>: 4-((3-cyclopropyl-5-(6-(cyclopropylmethoxy)pyridin-3-yl)phenoxy)methyl)benzoic acid The title compound is prepared in quantitative yield (38 mg, a white solid) by the similar manner to Step-4 of Acid-1 using methyl 4-((3-cyclopropyl-5-(6-(cyclopropylmethoxy)pyridin-3-yl)phenoxy)methyl)benzoate (Step-1 of Acid-25, 36 mg, 0.083 mmol).

MS (ESI) m/z: 416 (M+H)$^+$.

Acid-26: 4-((3-(6-(cyclopropylmethoxy)pyridin-3-yl)-5-methylphenoxy)methyl)-3-fluorobenzoic acid <Step-1>: 3-(6-(cyclopropylmethoxy)pyridin-3-yl)-5-methylphenol The title compound is prepared in 83% yield (203 mg, a colorless oil) by the similar manner to Step-2 of Acid-1 using 5-bromo-2-(cyclopropylmethoxy)pyridine (230 mg, 0.95 mmol) and 3-methyl-5-(4,4,5,5-tetramethyl-1,3,2-dioxaborolan-2-yl)phenol (235 mg, 0.95 mmol).

$^1$H-NMR (400 MHz, CDCl$_3$) delta 8.33 (1H, d, J=2.4 Hz), 7.76 (1H, dd, J=8.6, 2.4 Hz), 6.89 (1H, br.s), 6.83 (1H, d, J=8.6 Hz), 6.81 (1H, br.s), 6.66 (1H, br.s), 5.55 (1H, br.s), 4.17 (2H, d, J=7.3 Hz), 2.36 (3H, s), 1.36-1.24 (1H, m), 0.67-0.60 (2H, m), 0.40-0.34 (2H, m), MS (ESI) m/z: 256 (M+H)$^+$.

<Step-2>: methyl 4-((3-(6-(cyclopropylmethoxy)pyridin-3-yl)-5-methylphenoxy)methyl)-3-fluorobenzoate The title compound is prepared in quantitative yield (310 mg, a pale yellow oil) by the similar manner to Step-3 of Acid-1 using 3-(6-(cyclopropylmethoxy)pyridin-3-yl)-5-methylphenol (Step-1 of Acid-26, 198 mg, 0.74 mmol) and methyl 4-(bromomethyl)-3-fluorobenzoate (223 mg, 0.88 mmol).

$^1$H-NMR (400 MHz, CDCl$_3$) delta 8.32 (1H, d, J=2.4 Hz), 7.88-7.83 (1H, m), 7.78-7.72 (2H, m), 7.67-7.60 (1H, m), 6.96 (1H, br.s), 6.93 (1H, br.s), 6.82 (1H, d, J=8.6 Hz), 6.80 (1H, br.s), 5.22 (2H, s), 4.17 (2H, d, J=7.3 Hz), 3.93 (3H, s), 2.39 (3H, s), 1.37-1.26 (1H, m), 0.67-0.60 (2H, m), 0.40-0.34 (2H, m), MS (ESI) m/z: 422 (M+H)$^+$.

<Step-3>: 4-((3-(6-(cyclopropylmethoxy)pyridin-3-yl)-5-methylphenoxy)methyl)-3-fluorobenzoic acid The title compound is prepared in 99% yield (292 mg, a pale yellow solid) by the similar manner to Step-4 of Acid-1 using methyl 4-((3-(6-(cyclopropylmethoxy)pyridin-3-yl)-5-methylphenoxy)methyl)-3-fluorobenzoate (Step-2 of Acid-26, 305 mg, 0.72 mmol).

MS (ESI) m/z: 408 (M+H)$^+$.

Acid-27: 4-((3-(6-(cyclopropylmethoxy)pyridin-3-yl)-5-(trifluoromethyl)phenoxy)methyl)benzoic acid <Step-1>: 3-(6-(cyclopropylmethoxy)pyridin-3-yl)-5-(trifluoromethyl)phenol The title compound is prepared in 76% yield (344 mg, a white solid) by the similar manner to Step-2 of Acid-1 using 5-bromo-2-(cyclopropylmethoxy)pyridine (350 mg, 1.5 mmol) and (3-hydroxy-5-(trifluoromethyl)phenyl)boronic acid (273 mg, 1.8 mmol).
$^1$H-NMR (400 MHz, CDCl$_3$) delta 8.36 (1H, d, J=2.4 Hz), 7.80 (1H, dd, J=8.6, 2.4 Hz), 7.31 (1H, br.s), 7.18 (1H, br.s), 7.09 (1H, br.s), 6.88 (1H, d, J=8.6 Hz), 6.31 (1H, br.s), 4.18 (2H, d, J=7.3 Hz), 1.36-1.26 (1H, m), 0.67-0.60 (2H, m), 0.40-0.34 (2H, m), MS (ESI) m/z: 310 (M+H)$^+$.

<Step-2>: methyl 4-((3-(6-(cyclopropylmethoxy)pyridin-3-yl)-5-(trifluoromethyl)phenoxy)methyl)benzoate The title compound is prepared in quantitative yield (224 mg, a colorless oil) by the similar manner to Step-3 of Acid-1 using 3-(6-(cyclopropylmethoxy)pyridin-3-yl)-5-(trifluoromethyl)phenol (Step-1 of Acid-27, 150 mg, 0.49 mmol).
$^1$H-NMR (400 MHz, CDCl$_3$) delta 8.32 (1H, d, J=2.4 Hz), 8.00 (2H, d, J=8.6 Hz), 7.77 (1H, dd, J=8.6, 2.4 Hz), 7.53 (2H, d, J=8.6 Hz), 7.47 (1H, br.s), 7.26 (1H, br.s), 7.18 (1H, br.s), 6.86 (1H, d, J=8.6 Hz), 5.21 (2H, s), 4.18 (2H, d, J=6.7 Hz), 3.93 (3H, s), 1.37-1.26 (1H, m), 0.67-0.60 (2H, m), 0.40-0.34 (2H, m), MS (ESI) m/z: 458 (M+H)$^+$.

<Step-3>: 4-((3-(6-(cyclopropylmethoxy)pyridin-3-yl)-5-(trifluoromethyl)phenoxy)methyl)benzoic acid The title compound is prepared in 92% yield (195 mg, a white solid) by the similar manner to Step-4 of Acid-1 using methyl 4-((3-(6-(cyclopropylmethoxy)pyridin-3-yl)-5-(trifluoromethyl)phenoxy)methyl)benzoate (Step-2 of Acid-27, 218 mg, 0.48 mmol).
MS (ESI) m/z: 444 (M+H)$^+$.

Acid-28: 3-cyano-4-((3-(6-(cyclopropylmethoxy)pyridin-3-yl)phenoxy)methyl)benzoic acid <Step-1>: methyl 3-cyano-4-methylbenzoate A mixture of methyl 3-iodo-4-methylbenzoate (1.0 g, 3.6 mmol) and CuCN (389 mg, 4.3 mmol) in NMP (10 mL) is stirred at 200° C. for 1 hour with microwave irradiation. The mixture is diluted with EtOAc/toluene (10:1, 50 mL) to afford precipitate, which is separated by filtration through a pad of Celite. The filtrate is washed with water (30 mL×3), brine (20 mL×1), dried over sodium sulfate. The insoluble materials are separated by filtration and the filtrate is concentrated. The residue is purified by column chromatography on silica-gel eluting with n-hexane/EtOAc (7:1 to 6:1) to give 511 g (81% yield) of the title compound as a white solid.
$^1$H-NMR (400 MHz, CDCl$_3$) delta 8.27 (1H, d, J=1.8 Hz), 8.13 (1H, dd, J=8.6, 1.8 Hz), 7.42 (1H, d, J=8.6 Hz), 3.94 (3H, s), 2.61 (3H, s).

<Step-2>: methyl 4-(bromomethyl)-3-cyanobenzoate

The title compound is prepared in 60% yield (443 mg, a white solid) by the similar manner to Step-1 of Acid-13 using methyl 3-cyano-4-methylbenzoate (Step-1 of Acid-28, 506 mg, 2.9 mmol).
$^1$H-NMR (400 MHz, CDCl$_3$) delta 8.33 (1H, d, J=1.8 Hz), 8.23 (1H, dd, J=8.6, 1.8 Hz), 7.65 (1H, d, J=8.6 Hz), 4.66 (2H, s), 3.97 (3H, s).

<Step-3>: methyl 3-cyano-4-((3-(6-(cyclopropylmethoxy)pyridin-3-yl)phenoxy)methyl)benzoate The title compound is prepared in 91% yield (389 mg, a white solid) by the similar manner to Step-3 of Acid-1 using 3-(6-(cyclopropylmethoxy)pyridin-3-yl)phenol (Step-1 of Acid-2, 250 mg, 1.0 mmol) and methyl 4-(bromomethyl)-3-cyanobenzoate (Step-2 of Acid-28, 290 mg, 1.1 mmol).
$^1$H-NMR (400 MHz, CDCl$_3$) delta 8.37 (1H, d, J=1.8 Hz), 8.34 (1H, d, J=1.8 Hz), 8.29 (1H, dd, J=8.6, 1.8 Hz), 7.84 (1H, d, J=8.6 Hz), 7.78 (1H, dd, J=8.6, 2.4 Hz), 7.39 (1H, t, J=7.9 Hz), 7.20-7.13 (2H, m), 7.00-6.95 (1H, m), 6.84 (1H, d, J=8.6 Hz), 5.37 (2H, s), 4.18 (2H, d, J=6.7 Hz), 3.96 (3H, s), 1.36-1.24 (1H, m), 0.67-0.60 (2H, m), 0.40-0.34 (2H, m), MS (ESI) m/z: 415 (M+H)$^+$.

<Step-4>: 3-cyano-4-((3-(6-(cyclopropylmethoxy)pyridin-3-yl)phenoxy)methyl)benzoic acid The title compound is prepared in quantitative yield (379 mg, a pale tan colored solid) by the similar manner to Step-4 of Acid-1 using methyl 3-cyano-4-((3-(6-(cyclopropylmethoxy)pyridin-3-yl)phenoxy)methyl)benzoate (Step-3 of Acid-28, 376 mg, 0.91 mmol).
MS (ESI) m/z: 401 (M+H)$^+$.

Acid-29: 4-((3-(6-(cyclopropylmethoxy)pyridin-3-yl)-4-fluorophenoxy)methyl)benzoic acid <Step-1>: 3-(6-(cyclopropylmethoxy)pyridin-3-yl)-4-fluorophenol The title compound is prepared in 98% yield (335 mg, a colorless oil) by the similar manner to Step-2 of Acid-1 using 5-bromo-2-(cyclopropylmethoxy)pyridine (300 mg, 1.3 mmol) and (2-fluoro-5-hydroxyphenyl)boronic acid (215 mg, 1.4 mmol).
$^1$H-NMR (400 MHz, CDCl$_3$) delta 8.30 (1H, br.s), 7.82-7.76 (1H, m), 7.06-6.98 (1H, m), 6.90-6.75 (3H, m), 6.02 (1H, br.s), 4.17 (2H, d, J=6.7 Hz), 1.36-1.24 (1H, m), 0.67-0.60 (2H, m), 0.40-0.34 (2H, m), MS (ESI) m/z: 260 (M+H)$^+$.

<Step-2>: methyl 4-((3-(6-(cyclopropylmethoxy)pyridin-3-yl)-4-fluorophenoxy)methyl)benzoate The title compound is prepared in 88% yield (300 mg, a white solid) by the similar manner to Step-3 of Acid-1 using 3-(6-(cyclopropylmethoxy)pyridin-3-yl)-4-fluorophenol (Step-1 of Acid-29, 216 mg, 0.83 mmol).
$^1$H-NMR (400 MHz, CDCl$_3$) delta 8.28 (1H, br.s), 8.08-8.04 (2H, m), 7.78-7.72 (1H, m), 7.53-7.47 (2H, m), 7.10-7.04 (1H, m), 6.99-6.95 (1H, m), 6.91-6.85 (1H, m), 6.84 (1H, d, J=8.6 Hz), 5.13 (2H, s), 4.17 (2H, d, J=7.3 Hz), 3.93

(3H, s), 1.36-1.25 (1H, m), 0.67-0.60 (2H, m), 0.40-0.34 (2H, m), MS (ESI) m/z: 408 (M+H)⁺.

<Step-3>: 4-((3-(6-(cyclopropylmethoxy)pyridin-3-yl)-4-fluorophenoxy)methyl)benzoic acid The title compound is prepared in 90% yield (256 mg, a white solid) by the similar manner to Step-4 of Acid-1 using methyl 4-((3-(6-(cyclopropylmethoxy)pyridin-3-yl)-4-fluorophenoxy)methyl)benzoate (Step-2 of Acid-29, 293 mg, 0.72 mmol).
MS (ESI) m/z: 394 (M+H)⁺.

Acid-30: 4-((5-(6-(cyclopropylmethoxy)pyridin-3-yl)-2-fluorophenoxy)methyl)benzoic acid <Step-1>: 5-(6-(cyclopropylmethoxy)pyridin-3-yl)-2-fluorophenol The title compound is prepared in 79% yield (289 mg, a colorless oil) by the similar manner to Step-2 of Acid-1 using 5-bromo-2-(cyclopropylmethoxy)pyridine (323 mg, 1.4 mmol) and (4-fluoro-3-hydroxyphenyl)boronic acid (221 mg, 1.4 mmol).
$^1$H-NMR (400 MHz, CDCl$_3$) delta 8.29 (1H, d, J=1.8 Hz), 7.73 (1H, dd, J=8.6, 3.1 Hz), 7.18-7.10 (2H, m), 7.02-6.95 (1H, m), 6.83 (1H, d, J=9.2 Hz), 5.51 (1H, br.s), 4.17 (2H, d, J=7.3 Hz), 1.36-1.24 (1H, m), 0.67-0.60 (2H, m), 0.40-0.34 (2H, m), MS (ESI) m/z: 260 (M+H)⁺.

<Step-2>: methyl 4-((5-(6-(cyclopropylmethoxy)pyridin-3-yl)-2-fluorophenoxy)methyl)benzoate The title compound is prepared in 95% yield (330 mg, a white solid) by the similar manner to Step-3 of Acid-1 using 5-(6-(cyclopropylmethoxy)pyridin-3-yl)-2-fluorophenol (Step-1 of Acid-30, 221 mg, 0.85 mmol).
$^1$H-NMR (400 MHz, CDCl$_3$) delta 8.23 (1H, d, J=2.4 Hz), 8.07 (2H, d, J=7.9 Hz), 7.67 (1H, dd, J=8.6, 3.1 Hz), 7.54 (2H, d, J=7.9 Hz), 7.20-7.02 (3H, m), 6.82 (1H, d, J=8.6 Hz), 5.26 (2H, s), 4.16 (2H, d, J=7.3 Hz), 3.93 (3H, s), 1.36-1.24 (1H, m), 0.67-0.60 (2H, m), 0.40-0.34 (2H, m), MS (ESI) m/z: 408 (M+H)⁺.

<Step-3>: 4-((5-(6-(cyclopropylmethoxy)pyridin-3-yl)-2-fluorophenoxy)methyl)benzoic acid The title compound is prepared in 97% yield (304 mg, a white solid) by the similar manner to Step-4 of Acid-1 using methyl 4-((5-(6-(cyclopropylmethoxy)pyridin-3-yl)-2-fluorophenoxy)methyl)benzoate (Step-2 of Acid-30, 323 mg, 0.79 mmol).
MS (ESI) m/z: 394 (M+H)⁺.

Acid-31: 4-((3-bromo-5-(6-(cyclopropylmethoxy)pyridin-3-yl)phenoxy)methyl)benzoic acid <Step-1>: 3-bromo-5-(6-(cyclopropylmethoxy)pyridin-3-yl)phenol The title compound is prepared in 59% yield (567 mg, a white solid) by the similar manner to Step-1 of Acid-9 using 3-bromo-5-iodophenol (905 mg, 3.0 mmol).
$^1$H-NMR (400 MHz, CDCl$_3$) delta 8.31 (1H, d, J=2.4 Hz), 7.75 (1H, dd, J=8.6, 2.4 Hz), 7.23-7.20 (1H, m), 7.03-7.00 (1H, m), 6.94-6.92 (1H, m), 6.85 (1H, d, J=8.6 Hz), 6.10 (1H, br.s), 4.16 (2H, d, J=7.3 Hz), 1.36-1.24 (1H, m), 0.67-0.60 (2H, m), 0.40-0.34 (2H, m), MS (ESI) m/z: 320 (M+H)⁺.

<Step-2>: methyl 4-((3-bromo-5-(6-(cyclopropylmethoxy)pyridin-3-yl)phenoxy)methyl)benzoate The title compound is prepared in 98% yield (904 mg, a pale yellow solid) by the similar manner to Step-3 of Acid-1 using 3-bromo-5-(6-(cyclopropylmethoxy)pyridin-3-yl)phenol (Step-1 of Acid-31, 630 mg, 2.0 mmol).
$^1$H-NMR (400 MHz, CDCl$_3$) delta 8.28 (1H, d, J=2.4 Hz), 8.08 (2H, d, J=8.6 Hz), 7.72 (1H, dd, J=8.6, 3.1 Hz), 7.51 (2H, d, J=7.9 Hz), 7.28-7.25 (1H, m), 7.12-7.09 (1H, m), 7.05-7.02 (1H, m), 6.83 (1H, d, J=8.6 Hz), 5.16 (2H, s), 4.17 (2H, d, J=7.3 Hz), 3.93 (3H, s), 1.36-1.24 (1H, m), 0.67-0.60 (2H, m), 0.40-0.34 (2H, m), MS (ESI) m/z: 468 (M+H)⁺.

<Step-3>: 4-((3-bromo-5-(6-(cyclopropylmethoxy)pyridin-3-yl)phenoxy)methyl)benzoic acid The title compound is prepared in 98% yield (853 mg, a pale brown solid) by the similar manner to Step-4 of Acid-1 using methyl 4-((3-bromo-5-(6-(cyclopropylmethoxy)pyridin-3-yl)phenoxy)methyl)benzoate (Step-2 of Acid-31, 898 mg, 1.9 mmol).
MS (ESI) m/z: 454 (M+H)⁺.

Acid-32: 4-((3-(6-(cyclopropylmethoxy)pyridin-3-yl)-4-fluorophenoxy)methyl)-3-fluorobenzoic acid <Step-1>: methyl 4-((3-(6-(cyclopropylmethoxy)pyridin-3-yl)-4-fluorophenoxy)methyl)-3-fluorobenzoate The title compound is prepared in 92% yield (156 mg, a white solid) by the similar manner to Step-3 of Acid-1 using 3-(6-(cyclopropylmethoxy)pyridin-3-yl)-4-fluorophenol (Step-1 of Acid-29, 103 mg, 0.40 mmol) and methyl 4-(bromomethyl)-3-fluorobenzoate (108 mg, 0.44 mmol).
$^1$H-NMR (400 MHz, CDCl$_3$) delta 8.29 (1H, br.s), 7.89-7.84 (1H, m), 7.78-7.73 (2H, m), 7.64-7.58 (1H, m), 7.13-7.05 (1H, m), 7.02-6.97 (1H, m), 6.94-6.87 (1H, m), 6.84 (1H, d, J=8.6 Hz), 5.19 (2H, s), 4.18 (2H, d, J=6.7 Hz), 3.93 (3H, s), 1.36-1.24 (1H, m), 0.67-0.60 (2H, m), 0.40-0.34 (2H, m), MS (ESI) m/z: 426 (M+H)⁺.

<Step-2>: 4-((3-(6-(cyclopropylmethoxy)pyridin-3-yl)-4-fluorophenoxy)methyl)-3-fluorobenzoic acid The title compound is prepared in quantitative yield (146 mg, a pale yellow solid) by the similar manner to Step-4 of Acid-1 using methyl 4-((3-(6-(cyclopropylmethoxy)pyridin-3-yl)-4-fluorophenoxy)methyl)-3-fluorobenzoate (Step-1 of Acid-32, 150 mg, 0.35 mmol).
MS (ESI) m/z: 412.4 (M+H)⁺.

Acid-33: 4-((3-(6-(cyclopropylmethoxy)pyridin-3-yl)-4-methylphenoxy)methyl)-3-fluorobenzoic acid <Step-1>: 3-(6-(cyclopropylmethoxy)pyridin-3-yl)-4-methylphenol The title compound is prepared in 86% yield (288 mg, a colorless oil) by the similar manner to Step-2 of Acid-1 using 5-bromo-2-(cyclopropylmethoxy)pyridine (300 mg, 1.3 mmol) and 4-methyl-3-(4,4,5,5-tetramethyl-1,3,2-dioxaborolan-2-yl)phenol (323 mg, 1.4 mmol).
$^1$H-NMR (400 MHz, CDCl$_3$) delta 8.11 (1H, d, J=2.4 Hz), 7.57 (1H, dd, J=8.6, 2.4 Hz), 7.13 (1H, d, J=8.6 Hz), 6.83 (1H, d, J=8.6 Hz), 6.78 (1H, dd, J=8.6, 2.4 Hz), 6.71 (1H, d, J=2.4 Hz), 6.03 (1H, br.s), 4.16 (2H, d, J=6.7 Hz), 2.18 (3H, s), 1.37-1.24 (1H, m), 0.67-0.60 (2H, m), 0.40-0.34 (2H, m), MS (ESI) m/z: 256 (M+H)$^+$.

<Step-2>: methyl 4-((3-(6-(cyclopropylmethoxy)pyridin-3-yl)-4-methylphenoxy)methyl)-3-fluorobenzoate The title compound is prepared in 90% yield (420 mg, a colorless oil) by the similar manner to Step-3 of Acid-1 using 3-(6-(cyclopropylmethoxy)pyridin-3-yl)-4-methylphenol (Step-1 of Acid-33, 283 mg, 1.1 mmol) and methyl 4-(bromomethyl)-3-fluorobenzoate (300 mg, 1.2 mmol).
$^1$H-NMR (400 MHz, CDCl$_3$) delta 8.08 (1H, d, J=2.4 Hz), 7.85 (1H, dd, J=7.9, 1.8 Hz), 7.74 (1H, dd, J=10.4, 1.8 Hz), 7.65-7.59 (1H, m), 7.54 (1H, dd, J=8.6, 2.4 Hz), 7.19 (1H, d, J=8.6 Hz), 6.90 (1H, dd, J=8.6, 2.4 Hz), 6.87-6.80 (2H, m), 5.18 (2H, s), 4.17 (2H, d, J=7.3 Hz), 3.93 (3H, s), 2.20 (3H, s), 1.37-1.24 (1H, m), 0.67-0.60 (2H, m), 0.40-0.34 (2H, m), MS (ESI) m/z: 422 (M+H)$^+$.

<Step-3>: 4-((3-(6-(cyclopropylmethoxy)pyridin-3-yl)-4-methylphenoxy)methyl)-3-fluorobenzoic acid The title compound is prepared in 93% yield (374 mg, a white solid) by the similar manner to Step-4 of Acid-1 using methyl 4-((3-(6-(cyclopropylmethoxy)pyridin-3-yl)-4-methylphenoxy)methyl)-3-fluorobenzoate (Step-2 of Acid-33, 415 mg, 0.99 mmol).
MS (ESI) m/z: 408 (M+H)$^+$.

Acid-34: 4-((4-chloro-3-(6-(cyclopropylmethoxy)pyridin-3-yl)phenoxy)methyl)-3-fluorobenzoic acid <Step-1>: 4-chloro-3-(6-(cyclopropylmethoxy)pyridin-3-yl)phenol The title compound is prepared in 75% yield (559 mg, a colorless oil) by the similar manner to Step-2 of Acid-1 using 5-bromo-2-(cyclopropylmethoxy)pyridine (620 mg, 2.7 mmol) and (2-chloro-5-hydroxyphenyl)boronic acid (492 mg, 2.9 mmol).
MS (ESI) m/z: 276 (M+H)$^+$.

<Step-2>: methyl 4-((4-chloro-3-(6-(cyclopropylmethoxy)pyridin-3-yl)phenoxy)methyl)-3-fluorobenzoate The title compound is prepared in 98% yield (235 mg, a colorless oil) by the similar manner to Step-3 of Acid-1 using 4-chloro-3-(6-(cyclopropylmethoxy)pyridin-3-yl)phenol (Step-1 of Acid-34, 150 mg, 0.54 mmol) and methyl 4-(bromomethyl)-3-fluorobenzoate (150 mg, 0.60 mmol).
MS (ESI) m/z: 442 (M+H)$^+$.

<Step-3>: 4-((4-chloro-3-(6-(cyclopropylmethoxy)pyridin-3-yl)phenoxy)methyl)-3-fluorobenzoic acid The title compound is prepared in 94% yield (210 mg, a pale yellow solid) by the similar manner to Step-4 of Acid-1 using methyl 4-((4-chloro-3-(6-(cyclopropylmethoxy)pyridin-3-yl)phenoxy)methyl)-3-fluorobenzoate (Step-2 of Acid-34, 230 mg, 0.52 mmol).
MS (ESI) m/z: 428 (M+H)$^+$.

Acid-35: 4-((3-(6-(cyclobutylmethoxy)pyridin-3-yl)phenoxy)methyl)-3-fluorobenzoic acid <Step-1>: methyl 4-((3-(6-(cyclobutylmethoxy)pyridin-3-yl)phenoxy)methyl)-3-fluorobenzoate The title compound is prepared in 98% yield (162 mg, a colorless oil) by the similar manner to Step-1 of Acid-1 using 3-(6-(cyclobutylmethoxy)pyridin-3-yl)phenol (Step-2 of Acid-12, 100 mg, 0.39 mmol) and methyl 4-(bromomethyl)-3-fluorobenzoate (106 mg, 0.43 mmol).
$^1$H-NMR (400 MHz, CDCl$_3$) delta 8.35 (1H, d, J=2.4 Hz), 7.89-7.84 (1H, m), 7.79-7.73 (2H, m), 7.68-7.61 (1H, m), 7.37 (1H, t, J=7.9 Hz), 7.18-7.12 (2H, m), 6.98-6.93 (1H, m), 6.80 (1H, d, J=8.6 Hz), 5.24 (2H, s), 4.31 (2H, d, J=7.3 Hz), 3.93 (3H, s), 2.87-2.73 (1H, m), 2.20-2.10 (2H, m), 2.03-1.80 (4H, m), MS (ESI) m/z: 422 (M+H)$^+$.

<Step-2>: 4-((3-(6-(cyclobutylmethoxy)pyridin-3-yl)phenoxy)methyl)-3-fluorobenzoic acid The title compound is prepared in 96% yield (146 mg, a white solid) by the similar manner to Step-4 of Acid-1 using methyl 4-((3-(6-(cyclobutylmethoxy)pyridin-3-yl)phenoxy)methyl)-3-fluorobenzoate (Step-1 of Acid-35, 157 mg, 0.37 mmol).
MS (ESI) m/z: 408 (M+H)$^+$.

Acid-36: 4-((3-(6-(cyclopropylmethoxy)pyridin-3-yl)phenoxy)methyl)-3-methoxybenzoic acid <Step-1>: methyl 4-((3-(6-(cyclopropylmethoxy)pyridin-3-yl)phenoxy)methyl)-3-methoxybenzoate The title compound is prepared in 95% yield (247 mg, a colorless oil) by the similar manner to Step-1 of Acid-1 using 3-(6-(cyclopropylmethoxy)pyridin-3-yl)phenol (Step-1 of Acid-2, 150 mg, 0.62 mmol) and methyl 4-(bromomethyl)-3-methoxybenzoate (177 mg, 0.68 mmol).
$^1$H-NMR (400 MHz, CDCl$_3$) delta 8.34 (1H, d, J=3.1 Hz), 7.78 (1H, dd, J=8.6, 3.1 Hz), 7.70-7.66 (1H, m), 7.60-7.55 (2H, m), 7.35 (1H, t, J=7.9 Hz), 7.17-7.10 (2H, m), 7.00-6.94 (1H, m), 6.84 (1H, d, J=8.6 Hz), 5.20 (2H, s), 4.17 (2H, d, J=7.3 Hz), 3.94 (3H, s), 3.93 (3H, s), 1.37-1.24 (1H, m), 0.67-0.60 (2H, m), 0.40-0.34 (2H, m), MS (ESI) m/z: 420 (M+H)$^+$.

<Step-2>: 4-((3-(6-(cyclopropylmethoxy)pyridin-3-yl)phenoxy)methyl)-3-methoxybenzoic acid The title compound is prepared in quantitative yield (243 mg, a pale yellow solid) by the similar manner to Step-4 of Acid-1 using methyl 4-((3-(6-(cyclopropylmethoxy)pyridin-3-yl)phenoxy)methyl)-3-methoxybenzoate (Step-1 of Acid-36, 242 mg, 0.58 mmol).
MS (ESI) m/z: 406 (M+H)$^+$.

Acid-37: 4-((3-(2-(cyclopropylmethoxy)pyridin-3-yl)phenoxy)methyl)benzoic acid

<Step-1>: methyl 4-((3-(2-(cyclopropylmethoxy)pyridin-3-yl)phenoxy)methyl)benzoate The title compound is prepared in 93% yield (340 mg, a colorless oil) by the similar manner to Step-2 of Acid-1 using methyl 4-((3-bromophenoxy)methyl)benzoate (Step-1 of Borate-1, 300 mg, 0.93 mmol) and 2-(cyclopropylmethoxy)-3-(4,4,5,5-tetramethyl-1,3,2-dioxaborolan-2-yl)pyridine (283 mg, 1.0 mmol).

$^1$H-NMR (400 MHz, CDCl$_3$) delta 8.12 (1H, dd, J=1.8, 4.9 Hz), 8.07 (2H, d, J=8.6 Hz), 7.63 (1H, dd, J=7.3, 1.8 Hz), 7.53 (2H, d, J=8.0 Hz), 7.35-7.30 (2H, m), 7.23-7.21 (1H, m), 7.00-6.92 (2H, m), 5.18 (2H, s), 4.21 (2H, d, J=6.7 Hz), 3.93 (3H, s), 1.32-1.22 (1H, m), 0.57-0.54 (2H, m), 0.35-0.33 (2H, m), MS (ESI) m/z: 390 (M+H)$^+$.

<Step-2>: 4-((3-(2-(cyclopropylmethoxy)pyridin-3-yl)phenoxy)methyl)benzoic acid

The title compound is prepared in 92% yield (300 mg, a white solid) by the similar manner to Step-4 of Acid-1 using methyl 4-((3-(2-(cyclopropylmethoxy)pyridin-3-yl)phenoxy)methyl)benzoate (Step-1 of Acid-37, 340 mg, 0.37 mmol).

$^1$H-NMR (400 MHz, CDCl$_3$) delta 8.15-8.11 (3H, m), 7.63 (1H, dd, J=1.8, 7.4 Hz), 7.57 (2H, d, J=8.6 Hz), 7.36 (1H, t, J=8.0 Hz), 7.32-7.31 (1H, m), 7.24-7.22 (1H, m), 6.99-6.93 (2H, m), 5.21 (2H, s), 4.21 (2H, d, J=6.7 Hz), 1.33-1.24 (1H, m), 0.59-0.54 (2H, m), 0.37-0.33 (2H, m), COOH is not observed, MS (ESI) m/z: 376 (M+H)$^+$.

Acid-38: 4-4-((3-(5-(cyclopropylmethoxy)pyridin-3-yl)phenoxy)methyl)benzoic acid <Step-1>:
3-(5-(cyclopropylmethoxy)pyridin-3-yl)phenol The title compound is prepared in 94% yield (903 mg, a white solid) by the similar manner to Step-2 of Acid-1 using 3-bromo-5-(cyclopropylmethoxy)pyridine (907 mg, 4.0 mmol).

$^1$H-NMR (400 MHz, CDCl$_3$) delta 8.56 (1H, d, J=1.5 Hz), 8.28 (1H, d, J=2.8 Hz), 7.80 (1H, br.s), 7.44-7.41 (1H, m), 7.36 (1H, t, J=7.8 Hz), 7.21-7.18 (1H, m), 7.13-7.09 (1H, m), 6.95-6.92 (1H, m), 3.92 (2H, d, J=7.0 Hz), 1.38-1.26 (1H, m), 0.72-0.66 (2H, m), 0.42-0.36 (2H, m), MS (ESI) m/z: 242 (M+H)$^+$.

<Step-2>: methyl 4-((3-(5-(cyclopropylmethoxy)pyridin-3-yl)phenoxy)methyl)benzoate The title compound is prepared in 63% yield (203 mg, a yellow oil) by the similar manner to Step-3 of Acid-1 using 3-(5-(cyclopropylmethoxy)pyridin-3-yl)phenol (Step-1 of Acid-38, 200 mg, 0.83 mmol).

$^1$H-NMR (400 MHz, CDCl$_3$) delta 8.42 (1H, d, J=1.8 Hz), 8.29 (1H, d, J=2.7 Hz), 8.10-8.06 (2H, m), 7.57-7.52 (2H, m), 7.39 (1H, t, J=8.0 Hz), 7.36-7.32 (1H, m), 7.21-7.16 (2H, m), 7.02-6.97 (1H, m), 5.20 (2H, s), 3.93 (3H, s), 3.91 (2H, d, J=7.0 Hz), 1.37-1.25 (1H, m), 0.72-0.66 (2H, m), 0.43-0.36 (2H, m), MS (ESI) m/z: 390 (M+H)$^+$.

<Step-3>: 4-((3-(5-(cyclopropylmethoxy)pyridin-3-yl)phenoxy)methyl)benzoic acid

The title compound is prepared in 95% yield (186 mg, a pale yellow solid) by the similar manner to Step-4 of Acid-1 using methyl 4-((3-(5-(cyclopropylmethoxy)pyridin-3-yl)phenoxy)methyl)benzoate (Step-2 of Acid-38, 203 mg, 0.52 mmol).

$^1$H-NMR (400 MHz, DMSO-d$_6$) delta 8.46 (1H, d, J=1.8 Hz), 8.27 (1H, d, J=2.8 Hz), 7.98-7.93 (2H, m), 7.61-7.54 (3H, m), 7.45-7.30 (3H, m), 7.10-7.05 (1H, m), 5.28 (2H, s), 3.98 (2H, d, J=7.0 Hz), 1.32-1.17 (1H, m), 0.65-0.52 (2H, m), 0.42-0.30 (2H, m), COOH is not observed, MS (ESI) m/z: 376 (M+H)$^+$.

Acid-39: 5-cyclopropyl-6-((3-(6-(cyclopropylmethoxy)pyridin-3-yl)phenoxy)methyl)nicotinic acid <Step-1>: ethyl 5-chloro-6-((3-(6-(cyclopropylmethoxy)pyridin-3-yl)phenoxy)methyl)nicotinate The title compound is prepared in 75% yield (291 mg, a pale yellow oil) by the similar manner to Step-3 of Acid-1 using 3-(6-(cyclopropylmethoxy)pyridin-3-yl)phenol (Step-1 of Acid-2, 193 mg, 0.80 mmol) and ethyl 5-chloro-6-(chloromethyl)nicotinate hydrochloride (238 mg, 0.88 mmol).

$^1$H-NMR (400 MHz, CDCl$_3$) delta 9.12 (1H, d, J=1.8 Hz), 8.35-8.31 (2H, m), 7.77 (1H, dd, J=8.6, 3.1 Hz), 7.35 (1H, t, J=7.9 Hz), 7.21-7.18 (1H, m), 7.17-7.12 (1H, m), 7.03-6.97 (1H, m), 6.84 (1H, d, J=8.6 Hz), 5.40 (2H, s), 4.43 (2H, q, J=7.3 Hz), 4.17 (2H, d, J=6.7 Hz), 1.42 (3H, t, J=7.3 Hz), 1.37-1.24 (1H, m), 0.67-0.60 (2H, m), 0.40-0.34 (2H, m), MS (ESI) m/z: 439 (M+H)$^+$.

<Step-2>: ethyl 5-cyclopropyl-6-((3-(6-(cyclopropylmethoxy)pyridin-3-yl)phenoxy)methyl)nicotinate The title compound is prepared in 79% yield (40 mg, a pale yellow oil) by the similar manner to Step-1 of Acid-16 using ethyl 5-chloro-6-((3-(6-(cyclopropylmethoxy)pyridin-3-yl)phenoxy)methyl)nicotinate (Step-1 of Acid-39, 50 mg, 0.11 mmol).

$^1$H-NMR (400 MHz, CDCl$_3$) delta 9.02 (1H, d, J=1.8 Hz), 8.33 (1H, d, J=1.8 Hz), 7.91 (1H, d, J=1.8 Hz), 7.77 (1H, dd, J=8.6, 2.4 Hz), 7.35 (1H, t, J=7.9 Hz), 7.22-7.18 (1H, m), 7.15-7.10 (1H, m), 7.04-6.99 (1H, m), 6.83 (1H, d, J=7.9 Hz), 5.46 (2H, s), 4.41 (2H, q, J=7.3 Hz), 4.17 (2H, d, J=7.3 Hz), 2.25-2.15 (1H, m), 1.41 (3H, t, J=7.3 Hz), 1.37-1.24 (1H, m), 1.12-1.04 (2H, m), 0.81-0.75 (2H, m), 0.66-0.60 (2H, m), 0.40-0.34 (2H, m), MS (ESI) m/z: 445 (M+H)$^+$.

<Step-3>: 5-cyclopropyl-6-((3-(6-(cyclopropylmethoxy)pyridin-3-yl)phenoxy)methyl)nicotinic acid The title compound is prepared in 93% yield (35 mg, a pale green solid) by the similar manner to Step-4 of Acid-1 using ethyl 5-cyclopropyl-6-((3-(6-(cyclopropylmethoxy)pyridin-3-yl)phenoxy)methyl)nicotinate (Step-2 of Acid-39, 40 mg, 0.89 mmol).

MS (ESI) m/z: 417 (M+H)$^+$.

Acid-40: 6-((3-(6-(cyclopropylmethoxy)pyridin-3-yl)phenoxy)methyl)nicotinic acid <Step-1>: methyl 6-((3-(6-(cyclopropylmethoxy)pyridin-3-yl)phenoxy)methyl)nicotinate To a stirred solution of 3-(6-(cyclopropylmethoxy)pyridin-3-yl)phenol (Step-1 of Acid-2, 2.5 g, 15.0 mmol), methyl 6-(hydroxymethyl)nicotinate (2.9 g, 16.5 mmol), and triphenylphosphine (3.9 g, 18.0 mmol) in THF (50 mL) is dropwise added a solution of 2-methoxyethyl 2-(3-methoxypropanoyl)diazenecarboxylate in THF (10 mL) at 0° C. The reaction mixture is stirred at room temperature for 3 hours and the solvent is removed under reduced pressure. The residue is diluted with EtOAc (100 mL) and washed with water (50 mL×3), brine (50 mL×1), and dried over sodium sulfate. Insoluble materials are separated by filtration and the filtrate is concentrated. The residue is purified by column chromatography on silica-gel eluting with n-hexane/EtOAc (4:1) to give 3.6 g (75% yield) of the title compound as a white solid.

$^1$H-NMR (400 MHz, CDCl$_3$) delta 9.20 (1H, d, J=3.1 Hz), 8.35-8.30 (2H, m), 7.76 (1H, dd, J=8.6, 2.5 Hz), 7.66 (1H, d, J=8.0 Hz), 7.36 (1H, t, J=8.0 Hz), 7.16-7.12 (2H, m), 6.95 (1H, dd, J=9.2, 2.5 Hz), 6.84 (1H, d, J=8.6 Hz), 5.32 (2H, s), 4.17 (2H, d, J=7.3 Hz), 3.96 (3H, s), 1.38-1.24 (1H, m), 0.66-0.60 (2H, m), 0.40-0.35 (2H, m), MS (ESI) m/z: 391 (M+H)$^+$.

<Step-2>: 6-((3-(6-(cyclopropylmethoxy)pyridin-3-yl)phenoxy)methyl)nicotinic acid The title compound is prepared in 96% yield (300 mg, a white solid) by the similar manner to Step-4 of Acid-1 using methyl 6-((3-(6-(cyclopropylmethoxy)pyridin-3-yl)phenoxy)methyl)nicotinate (Step-1 of Acid-40, 325 mg, 0.83 mmol).
MS (ESI) m/z: 377 (M+H)$^+$.

Acid-41: 6-((3-(6-(cyclopropylmethoxy)pyridin-3-yl)-5-fluorophenoxy)methyl)nicotinic acid <Step-1>: methyl 6-((3-(6-(cyclopropylmethoxy)pyridin-3-yl)-5-fluorophenoxy)methyl)nicotinate The title compound is prepared in 51% yield (82 mg, a white solid) by the similar manner to Step-1 of Acid-40 using 3-(6-(cyclopropylmethoxy)pyridin-3-yl)-5-fluorophenol (Step-1 of Acid-22, 100 mg, 0.39 mmol).
$^1$H-NMR (400 MHz, CDCl$_3$) delta 9.21 (1H, br.s), 8.40-8.28 (2H, m), 7.77-7.70 (1H, m), 7.66-7.60 (1H, m), 6.97-6.80 (3H, m), 6.73-6.64 (1H, m), 5.30 (2H, s), 4.17 (2H, d, J=7.3 Hz), 3.97 (3H, s), 1.37-1.24 (1H, m), 0.68-0.58 (2H, m), 0.43-0.34 (2H, m), MS (ESI) m/z: 409 (M+H)$^+$.

<Step-2>: 6-((3-(6-(cyclopropylmethoxy)pyridin-3-yl)-5-fluorophenoxy)methyl)nicotinic acid The title compound is prepared in quantitative yield (79 mg, a white solid) by the similar manner to Step-4 of Acid-1 using methyl 6-((3-(6-(cyclopropylmethoxy)pyridin-3-yl)-5-fluorophenoxy)methyl)nicotinate (Step-1 of Acid-41, 78 mg, 0.19 mmol).
MS (ESI) m/z: 395 (M+H)$^+$.

Acid-42: 4-(((6-(cyclopropylmethoxy)-[3,4'-bipyridin]-2'-yl)oxy)methyl)benzoic acid <Step-1>: methyl 4-(((4-bromopyridin-2-yl)oxy)methyl)benzoate To a stirred solution of methyl 4-(hydroxymethyl)benzoate (50 mg, 0.30 mmol), 4-bromo-2-fluoropyridine (69 mg, 0.39 mmol) in THF (2 mL) is added sodium tert-butoxide at 0° C., and the reaction mixture is stirred for 1 hour at 0° C. The mixture is added saturated aqueous NH$_4$Cl (2 mL) and extracted with EtOAc (10 mL×2), and dried over sodium sulfate. Insoluble materials are separated by filtration and the filtrate is concentrated. The residue is purified by column chromatography on silica-gel eluting with n-hexane/EtOAc (85:15) to give 66 mg (68% yield) of the title compound as a pale yellow solid.
$^1$H-NMR (400 MHz, CDCl$_3$) delta 8.04 (2H, d, J=6.4 Hz), 7.99 (1H, d, J=6.4 Hz), 7.49 (2H, d, J=7.8 Hz), 7.08-7.04 (2H, m), 5.43 (2H, s), 3.92 (3H, s), MS (ESI) m/z: 322, 324 (M+H)$^+$.

<Step-2>: 4-(((6-(cyclopropylmethoxy)-[3,4'-bipyridin]-2'-yl)oxy)methyl)benzoic acid A mixture of 2-(cyclopropylmethoxy)-5-(4,4,5,5-tetramethyl-1,3,2-dioxaborolan-2-yl)pyridine (30 mg, 0.11 mmol), methyl 4-(((4-bromopyridin-2-yl)oxy)methyl)benzoate (Step-1 of Acid-42, 29 mg, 0.091 mmol) in dioxane/saturated aqueous NaHCO$_3$ (1 mL/0.5 mL) is added bis(di-tert-butyl(4-dimethylaminophenyl)phosphine)dichloropalladium(II) (6 mg, 0.009 mmol), and the reaction mixture is stirred at 120° C. for 20 min with microwave irradiation. Then, the reaction mixture is added MeOH (1 mL) and 2M aqueous sodium hydroxide solution (1 mL), and stirred at 60° C. for 1 hour. The reaction mixture is diluted with 10% aqueous citric acid (1 mL) and extracted with DCM (3 mL×2), and dried over sodium sulfate. Insoluble materials are separated by filtration and the filtrate is concentrated. The residue is purified by strong anion exchange cartridge (ISOLUTE (registered trademark) PE-AX, 1 g/6 mL, Biotage) to give 34 mg (99% yield) of the title compound as a pale yellow solid.
MS (ESI) m/z: 377 (M+H)$^+$.

Acid-43: 4-(((6'-(cyclopropylmethoxy)-[2,3'-bipyridin]-6-yl)oxy)methyl)benzoic acid <Step-1>: methyl 4-(((6-bromopyridin-2-yl)oxy)methyl)benzoate The title compound is prepared in 89% yield (172 mg, a pale yellow solid) by the similar manner to Step-1 of Acid-42 using 2-bromo-6-fluoropyridine (138 mg, 0.78 mmol).
MS (ESI) m/z: 322 (M+H)$^+$.

<Step-2>: methyl 4-(((6'-(cyclopropylmethoxy)-[2,3'-bipyridin]-6-yl)oxy)methyl)benzoate The title compound is prepared in 34% yield (28 mg, a pale yellow gum) by the similar manner to Step-2 of Acid-42 using 2-(cyclopropylmethoxy)-5-(4,4,5,5-tetramethyl-1,3,2-dioxaborolan-2-yl)pyridine (60 mg, 0.21 mmol) and methyl 4-(((6-bromopyridin-2-yl)oxy)methyl)benzoate (Step-1 of Acid-42, 88 mg, 0.27 mmol).
$^1$H-NMR (400 MHz, CDCl$_3$) delta 8.77 (1H, d, J=2.7 Hz), 8.17 (1H, dd, J=8.7, 2.7 Hz), 8.05 (2H, d, J=8.2), 7.65 (1H, dd, J=8.7, 8.2 Hz), 7.55 (2H, d, J=8.2 Hz), 7.31-7.25 (1H, m), 6.84 (1H, d, J=8.7 Hz), 6.77 (1H, d, J=8.2 Hz), 5.55 (2H, s), 4.19 (2H, d, J=7.3 Hz), 3.92 (3H, s), 1.38-1.23 (1H, m), 0.71-0.57 (2H, m), 0.45-0.32 (2H, m), MS (ESI) m/z: 391 (M+H)$^+$.

<Step-3>: 4-(((6'-(cyclopropylmethoxy)-[2,3'-bipyridin]-6-yl)oxy)methyl)benzoic acid The title compound is prepared in 94% yield (28 mg, a pale yellow gum) by the similar manner to Step-4 of Acid-1 using methyl 4-(((6'-(cyclopropylmethoxy)-[2,3'-bipyridin]-6-yl)oxy)methyl)benzoate (Step-2 of Acid-43, 31 mg, 0.079 mmol).
MS (ESI) m/z: 377 (M+H)+.

Acid-44: 4-((3-(5-(cyclopropylmethoxy)pyridin-2-yl)phenoxy)methyl)benzoic acid

<Step-1>: 3-(5-(cyclopropylmethoxy)pyridin-2-yl)phenol

The title compound is prepared in 90% yield (951 mg, a yellow oil) by the similar manner to Step-2 of Acid-1 using 2-bromo-5-(cyclopropylmethoxy)pyridine (1.0 g, 4.4 mmol).
$^1$H-NMR (400 MHz, CDCl$_3$) delta 8.37 (1H, d, J=2.7 Hz), 7.63 (1H, d, J=8.7 Hz), 7.51-7.46 (1H, m), 7.44-7.39 (1H, m), 7.38-7.24 (2H, m), 6.88-6.82 (1H, m), 5.67 (1H, br.s), 3.90 (2H, d, J=7.3 Hz), 1.37-1.24 (1H, m), 0.67-0.60 (2H, m), 0.42-0.36 (2H, m), MS (ESI) m/z: 242 (M+H)+.

<Step-2>: methyl 4-((3-(5-(cyclopropylmethoxy)pyridin-2-yl)phenoxy)methyl)benzoate The title compound is prepared in 73% yield (236 mg, a white solid) by the similar manner to Step-3 of Acid-1 using 3-(5-(cyclopropylmethoxy)pyridin-2-yl)phenol (Step-1 of Acid-44, 200 mg, 0.83 mmol).
$^1$H-NMR (400 MHz, CDCl$_3$) delta 8.39 (1H, d, J=3.2 Hz), 8.10-8.03 (2H, m), 7.67-7.60 (2H, m), 7.57-7.46 (3H, m), 7.36 (1H, t, J=7.8 Hz), 7.28-7.23 (1H, m), 7.00-6.95 (1H, m), 5.22 (2H, s), 3.93 (3H, s), 3.90 (2H, d, J=6.9 Hz), 1.37-1.24 (1H, m), 0.73-0.65 (2H, m), 0.43-0.36 (2H, m), MS (ESI) m/z: 390 (M+H)+.

<Step-3>: 4-((3-(5-(cyclopropylmethoxy)pyridin-2-yl)phenoxy)methyl)benzoic acid

The title compound is prepared in 89% yield (202 mg, a white solid) by the similar manner to Step-4 of Acid-1 using methyl 4-((3-(5-(cyclopropylmethoxy)pyridin-2-yl)phenoxy)methyl)benzoate (Step-2 of Acid-44, 236 mg, 0.61 mmol).
$^1$H-NMR (400 MHz, DMSO-d$_6$) delta 8.36 (1H, d, J=2.7 Hz), 8.00-7.95 (2H, m), 7.91 (1H, d, J=8.2 Hz), 7.69-7.65 (1H, m), 7.63-7.58 (3H, m), 7.45 (1H, dd, J=8.7, 3.2 Hz), 7.37 (1H, t, J=7.8 Hz), 7.05-7.00 (1H, m), 5.28 (2H, s), 3.95 (2H, d, J=6.9 Hz), 1.32-1.20 (1H, m), 0.64-0.56 (2H, m), 0.39-0.32 (2H, m), COOH is not observed, MS (ESI) m/z: 376 (M+H)+.

Acid-45: 4-((3-(6-(cyclopropylmethoxy)pyridin-2-yl)phenoxy)methyl)benzoic acid

<Step-1>: 3-(6-(cyclopropylmethoxy)pyridin-2-yl)phenol

The title compound is prepared in 97% yield (1.0 g, a pale orange colored oil) by the similar manner to Step-2 of Acid-1 using 2-bromo-6-(cyclopropylmethoxy)pyridine (1.0 g, 4.4 mmol).
$^1$H-NMR (400 MHz, CDCl$_3$) delta 7.65-7.59 (1H, m), 7.58-7.53 (2H, m), 7.35-7.28 (2H, m), 6.89-6.84 (1H, m), 6.72 (1H, d, J=7.9 Hz), 4.87 (1H, br.s), 4.26 (2H, d, J=7.3 Hz), 1.40-1.29 (1H, m), 0.67-0.60 (2H, m), 0.41-0.36 (2H, m), MS (ESI) m/z: 242 (M+H)+.

<Step-2>: methyl 4-((3-(6-(cyclopropylmethoxy)pyridin-2-yl)phenoxy)methyl)benzoate The title compound is prepared in 85% yield (276 mg, a white solid) by the similar manner to Step-3 of Acid-1 using 3-(6-(cyclopropylmethoxy)pyridin-2-yl)phenol (Step-1 of Acid-45, 200 mg, 0.83 mmol).
$^1$H-NMR (400 MHz, CDCl$_3$) delta 8.07 (2H, d, J=7.9 Hz), 7.68-7.65 (1H, m), 7.64-7.58 (2H, m), 7.54 (2H, d, J=8.6 Hz), 7.36 (1H, t, J=7.9 Hz), 7.29 (1H, d, J=7.9 Hz), 7.01-6.96 (1H, m), 6.71 (1H, d, J=7.9 Hz), 5.21 (2H, s), 4.23 (2H, d, J=6.7 Hz), 3.92 (3H, s), 1.40-1.28 (1H, m), 0.67-0.60 (2H, m), 0.41-0.35 (2H, m), MS (ESI) m/z: 390 (M+H)+.

<Step-3>: 4-((3-(6-(cyclopropylmethoxy)pyridin-2-yl)phenoxy)methyl)benzoic acid

The title compound is prepared in 91% yield (243 mg, a white solid) by the similar manner to Step-4 of Acid-1 using methyl 4-((3-(6-(cyclopropylmethoxy)pyridin-2-yl)phenoxy)methyl)benzoate (Step-2 of Acid-45, 276 mg, 0.71 mmol).
$^1$H-NMR (400 MHz, DMSO-d$_6$) delta 12.99 (1H, br.s), 7.98 (2H, d, J=8.6 Hz), 7.80-7.73 (1H, m), 7.70-7.62 (2H, m), 7.60 (2H, d, J=8.6 Hz), 7.54 (1H, d, J=7.3 Hz), 7.40 (1H, t, J=7.9 Hz), 7.11-7.05 (1H, m), 6.78 (1H, d, J=7.9 Hz), 5.30 (2H, s), 4.18 (2H, d, J=7.3 Hz), 1.35-1.22 (1H, m), 0.60-0.53 (2H, m), 0.40-0.33 (2H, m), MS (ESI) m/z: 376 (M+H)+.

Acid-46: 4-((3-(3-chloro-5-(cyclopropylmethoxy)pyridin-2-yl)phenoxy)methyl)benzoic acid <Step-1>: 2,3-dichloro-5-(cyclopropylmethoxy)pyridine A mixture of 5,6-dichloropyridin-3-ol (1.0 g, 6.1 mmol), (bromomethyl)cyclopropane (0.99 g, 7.3 mmol) in DMF (15 mL) is added potassium carbonate (1.3 g, 9.2 mmol) and stirred at 60° C. overnight. The reaction mixture is diluted with EtOAc (60 mL) and washed with water (30 mL×2), and dried over sodium sulfate. Insoluble materials are separated by filtration and the filtrate is concentrated. The residue is purified by column chromatography on silica-gel eluting with n-hexane/EtOAc (9:1 to 8:2) to give 937 mg (71% yield) of the title compound as a colorless liquid.
$^1$H-NMR (400 MHz, CDCl$_3$) delta 8.00 (1H, d, J=2.4 Hz), 7.33 (1H, d, J=2.4 Hz), 3.84 (2H, d, J=6.7 Hz), 1.33-1.21 (1H, m), 0.72-0.65 (2H, m), 0.40-0.34 (2H, m), MS (ESI) m/z: 218 (M+H)+.

<Step-2>: 3-(3-chloro-5-(cyclopropylmethoxy)pyridin-2-yl)phenol

The title compound is prepared in 83% yield (986 mg, a yellow oil) by the similar manner to Step-2 of Acid-1 using 2,3-dichloro-5-(cyclopropylmethoxy)pyridine (Step-1 of Acid-46, 937 mg, 4.3 mmol).
$^1$H-NMR (400 MHz, CDCl$_3$) delta 8.29 (1H, d, J=2.7 Hz), 7.35-7.20 (3H, m), 7.17-7.12 (1H, m), 6.88-6.83 (1H, m), 5.64 (1H, br.s), 3.89 (2H, d, J=6.9 Hz), 1.36-1.23 (1H, m), 0.73-0.66 (2H, m), 0.43-0.35 (2H, m), MS (ESI) m/z: 276 (M+H)+.

<Step-3>: methyl 4-((3-(3-chloro-5-(cyclopropylmethoxy)pyridin-2-yl)phenoxy)methyl)benzoate The title compound is prepared in quantitative yield (1.5 g, a yellow oil) by the similar manner to Step-3 of Acid-1 using 3-(3-chloro-5-(cyclopropylmethoxy)pyridin-2-yl)phenol (Step-2 of Acid-46, 986 mg, 3.6 mmol).
¹H-NMR (400 MHz, CDCl₃) delta 8.30 (1H, d, J=2.4 Hz), 8.05 (2H, d, J=7.9 Hz), 7.52 (2H, d, J=8.6 Hz), 7.40-7.23 (4H, m), 7.03-6.97 (1H, m), 5.18 (2H, s), 3.92 (3H, s), 3.89 (2H, d, J=6.7 Hz), 1.36-1.24 (1H, m), 0.74-0.67 (2H, m), 0.43-0.36 (2H, m), MS (ESI) m/z: 424 (M+H)⁺.

<Step-4>: 4-((3-(3-chloro-5-(cyclopropylmethoxy) pyridin-2-yl)phenoxy)methyl)benzoic acid The title compound is prepared in 84% yield (1.2 g, a white solid) by the similar manner to Step-4 of Acid-1 using methyl 4-((3-(3-chloro-5-(cyclopropylmethoxy)pyridin-2-yl)phenoxy)methyl)benzoate (Step-3 of Acid-46, 1.5 g, 3.59 mmol).
¹H-NMR (400 MHz, DMSO-d₆) delta 13.0 (1H, br.s), 8.36 (1H, d, J=2.4 Hz), 7.97 (2H, d, J=7.9 Hz), 7.65 (1H, d, J=2.4 Hz), 7.58 (2H, d, J=7.9 Hz), 7.39 (1H, t, J=7.9 Hz), 7.25-7.19 (2H, m), 7.11-7.05 (1H, m), 5.25 (2H, s), 3.98 (2H, d, J=7.3 Hz), 1.30-1.20 (1H, m), 0.64-0.55 (2H, m), 0.40-0.30 (2H, m), MS (ESI) m/z: 410 (M+H)⁺.

Acid-47: 4-((3-(5-(cyclopropylmethoxy)-3-fluoropyridin-2-yl)phenoxy)methyl)benzoic acid <Step-1>: 3-(5-(cyclopropylmethoxy)-3-fluoropyridin-2-yl)phenol The title compound is prepared in quantitative yield (860 mg, a colorless oil) by the similar manner to Step-2 of Acid-1 using 2-chloro-5-(cyclopropylmethoxy)-3-fluoropyridine (640 mg, 3.2 mmol).
¹H-NMR (400 MHz, CDCl₃) delta 8.23 (1H, s), 7.45-7.41 (2H, m), 7.33-7.28 (1H, m), 7.04 (1H, dd, J=12.2, 2.4 Hz), 6.87-6.84 (1H, m), 5.98 (1H, br.s), 3.89 (2H, d, J=6.7 Hz), 1.34-1.24 (1H, m), 0.72-0.67 (2H, m), 0.41-0.36 (2H, m), MS (ESI) m/z: 260 (M+H)⁺.

<Step-2>: methyl 4-((3-(5-(cyclopropylmethoxy)-3-fluoropyridin-2-yl)phenoxy)methyl)benzoate The title compound is prepared in quantitative yield (320 mg, a white solid) by the similar manner to Step-3 of Acid-1 using 3-(5-(cyclopropylmethoxy)-3-fluoropyridin-2-yl)phenol (Step-1 of Acid-47, 200 mg, 0.77 mmol).
¹H-NMR (400 MHz, CDCl₃) delta 8.25 (1H, dd, J=1.2, 2.4 Hz), 8.06 (2H, d, J=8.6 Hz), 7.57-7.52 (4H, m), 7.37 (1H, t, J=8.6 Hz), 7.04-7.00 (2H, m), 5.20 (2H, s), 3.92 (3H, s), 3.89 (2H, d, J=7.3 Hz), 1.35-1.25 (1H, m), 0.73-0.68 (2H, m), 0.42-0.38 (2H, m), MS (ESI) m/z: 408 (M+H)⁺.

<Step-3>: 4-((3-(5-(cyclopropylmethoxy)-3-fluoropyridin-2-yl)phenoxy)methyl)benzoic acid The title compound is prepared in 97% yield (300 mg, a white solid) by the similar manner to Step-4 of Acid-1 using methyl 4-((3-(5-(cyclopropylmethoxy)-3-fluoropyridin-2-yl)phenoxy)methyl)benzoate (Step-2 of Acid-47, 320 mg, 0.79 mmol).
¹H-NMR (400 MHz, CDCl₃) delta 8.29 (1H, s), 8.12 (2H, d, J=8.0 Hz), 7.57-7.52 (4H, m), 7.38 (1H, t, J=7.9 Hz), 7.06-7.00 (2H, m), 5.22 (2H, s), 3.90 (2H, d, J=7.3 Hz), 1.36-1.24 (1H, m), 0.74-0.65 (2H, m), 0.42-0.38 (2H, m), COOH is not observed, MS (ESI) m/z: 394 (M+H)⁺.

Acid-48: 4-((3-(5-(cyclopropylmethoxy)-3-methylpyridin-2-yl)phenoxy)methyl)benzoic acid <Step-1>: 2-chloro-5-(cyclopropylmethoxy)-3-methylpyridine The title compound is prepared in 92% yield (633 mg, a colorless oil) by the similar manner to Step-1 of Acid-46 using 6-chloro-5-methylpyridin-3-ol (500 mg, 3.5 mmol).
¹H-NMR (400 MHz, CDCl₃) delta 7.90 (1H, d, J=3.0 Hz), 7.11 (1H, d, J=3.0 Hz), 3.82 (2H, d, J=7.0 Hz), 2.34 (3H, s), 1.33-1.20 (1H, m), 0.74-0.59 (2H, m), 0.44-0.31 (2H, m), MS (ESI) m/z: 198 (M+H)⁺.

<Step-2>: 3-(5-(cyclopropylmethoxy)-3-methylpyridin-2-yl)phenol

The title compound is prepared in 81% yield (661 mg, a white solid) by the similar manner to Step-2 of Acid-1 using 2-chloro-5-(cyclopropylmethoxy)-3-methylpyridine (Step-1 of Acid-48, 633 mg, 3.2 mmol).
¹H-NMR (400 MHz, CDCl₃) delta 8.19 (1H, d, J=2.8 Hz), 7.23 (1H, t, J=7.8 Hz), 7.16-7.13 (1H, m), 7.01-6.98 (1H, m), 6.97-6.92 (1H, m), 6.81-6.76 (1H, m), 3.87 (2H, d, J=7.0 Hz), 2.32 (3H, s), 1.36-1.22 (1H, m), 0.72-0.62 (2H, m), 0.44-0.32 (2H, m), OH is not observed, MS (ESI) m/z: 256 (M+H)+, 254 (M−H)⁻.

<Step-3>: methyl 4-((3-(5-(cyclopropylmethoxy)-3-methylpyridin-2-yl)phenoxy)methyl)benzoate The title compound is prepared in 78% yield (248 mg, a colorless oil) by the similar manner to Step-3 of Acid-1 using 3-(5-(cyclopropylmethoxy)-3-methylpyridin-2-yl)phenol (Step-2 of Acid-48, 200 mg, 0.78 mmol).
¹H-NMR (400 MHz, CDCl₃) delta 8.22 (1H, d, J=2.7 Hz), 8.07-8.03 (2H, m), 7.55-7.49 (2H, m), 7.37-7.32 (1H, m), 7.12-7.07 (3H, m), 7.01-6.94 (1H, m), 5.17 (2H, s), 3.92 (3H, s), 3.88 (2H, d, J=6.7 Hz), 2.30 (3H, s), 1.38-1.22 (1H, m), 0.75-0.62 (2H, m), 0.45-0.34 (2H, m), MS (ESI) m/z: 404 (M+H)⁺.

<Step-4>: 4-((3-(5-(cyclopropylmethoxy)-3-methylpyridin-2-yl)phenoxy)methyl)benzoic acid The title compound is prepared in 58% yield (139 mg, a white solid) by the similar manner to Step-4 of Acid-1 using methyl 4-((3-(5-(cyclopropylmethoxy)-3-methylpyridin-2-yl)phenoxy)methyl)benzoate (Step-3 of Acid-48, 248 mg, 0.62 mmol).
¹H-NMR (400 MHz, DMSO-d₆) delta 12.98 (1H, br.s), 8.17 (1H, d, J=2.8 Hz), 8.01-7.95 (2H, m), 7.64-7.53 (2H, m), 7.35 (1H, t, J=8.0 Hz), 7.31 (1H, d, J=2.8 Hz), 7.12-7.01 (3H, m), 5.24 (2H, s), 3.91 (2H, d, J=7.0 Hz), 2.25 (3H, s), 1.32-1.20 (1H, m), 0.66-0.52 (2H, m), 0.42-0.28 (2H, m), MS (ESI) m/z: 390 (M+H)⁺.

Acid-49: 4-((3-(2-(cyclopropylmethoxy)pyridin-4-yl)phenoxy)methyl)benzoic acid

<Step-1>: 3-(2-(cyclopropylmethoxy)pyridin-4-yl)phenol

The title compound is prepared in 67% yield (652 mg, a white solid) by the similar manner to Step-2 of Acid-1 using 4-bromo-2-(cyclopropylmethoxy)pyridine (919 mg, 4.0 mmol).

¹H-NMR (400 MHz, CDCl₃) delta 8.17 (1H, d, J=5.2 Hz), 7.33 (1H, t, J=7.9 Hz), 7.22-7.18 (1H, m), 7.10-7.06 (2H, m), 6.99-6.96 (1H, m), 6.92-6.87 (1H, m), 4.99 (1H, br.s), 4.17 (2H, d, J=7.0 Hz), 1.37-1.24 (1H, m), 0.68-0.57 (2H, m), 0.44-0.31 (2H, m), MS (ESI) m/z: 242 (M+H)⁺, 240 (M−H)⁻.

<Step-2>: methyl 4-((3-(2-(cyclopropylmethoxy)pyridin-4-yl)phenoxy)methyl)benzoate The title compound is prepared in 97% yield (312 mg, a white solid) by the similar manner to Step-3 of Acid-1 using 3-(2-(cyclopropylmethoxy)pyridin-4-yl)phenol (Step-1 of Acid-49, 200 mg, 0.83 mmol).

¹H-NMR (400 MHz, CDCl₃) delta 8.18-8.15 (1H, m), 8.11-8.06 (2H, m), 7.53 (2H, d, J=8.6 Hz), 7.41-7.36 (1H, m), 7.26-7.21 (2H, m), 7.06 (1H, dd, J=5.5, 1.5 Hz), 7.04-7.00 (1H, m), 7.00-6.97 (1H, m), 5.19 (2H, s), 4.17 (2H, d, J=7.0 Hz), 3.93 (3H, s), 1.37-1.23 (1H, m), 0.70-0.58 (2H, m), 0.45-0.31 (2H, m), MS (ESI) m/z: 390 (M+H)⁺.

<Step-4>: 4-((3-(2-(cyclopropylmethoxy)pyridin-4-yl)phenoxy)methyl)benzoic acid

The title compound is prepared in 86% yield (258 mg, a white solid) by the similar manner to Step-4 of Acid-1 using methyl 4-((3-(2-(cyclopropylmethoxy)pyridin-4-yl)phenoxy)methyl)benzoate (Step-3 of Acid-49, 312 mg, 0.80 mmol).

¹H-NMR (400 MHz, DMSO-d₆) delta 8.18 (1H, d, J=5.2 Hz), 7.95 (2H, d, J=8.2 Hz), 7.53 (2H, d, J=8.2 Hz), 7.47-7.34 (3H, m), 7.28 (1H, dd, J=5.2, 1.5 Hz), 7.17-7.08 (2H, m), 5.27 (2H, s), 4.12 (2H, d, J=7.4 Hz), 1.34-1.17 (1H, m), 0.72-0.48 (2H, m), 0.40-0.26 (2H, m), COOH is not observed, MS (ESI) m/z: 376 (M+H)⁺.

Acid-50: 4-((3-(5-(cyclopropylmethoxy)pyrazin-2-yl)phenoxy)methyl)benzoic acid

<Step-1>: 2-chloro-5-(cyclopropylmethoxy)pyrazine

The title compound is prepared in 63% yield (781 mg, a colorless oil) by the similar manner to Step-1 of Acid-1 using 2,5-dichloropyrazine (581 mg, 8.1 mmol).

¹H-NMR (400 MHz, CDCl₃) delta 8.07 (1H, d, J=1.4 Hz), 8.03 (1H, d, J=1.4 Hz), 4.14 (2H, d, J=7.0 Hz), 1.35-1.22 (1H, m), 0.72-0.52 (2H, m), 0.47-0.30 (2H, m).

<Step-2>: 3-(5-(cyclopropylmethoxy)pyrazin-2-yl)phenol

The title compound is prepared in 80% yield (818 mg, a white solid) by the similar manner to Step-2 of Acid-1 using 2-chloro-5-(cyclopropylmethoxy)pyrazine (Step-1 of Acid-50, 781 mg, 4.2 mmol).

¹H-NMR (400 MHz, CDCl₃) delta 8.46 (1H, d, J=1.4 Hz), 8.30 (1H, d, J=1.4 Hz), 7.43-7.37 (2H, m), 7.33 (1H, t, J=7.9 Hz), 6.88 (1H, ddd, J=7.9, 2.5, 0.9 Hz), 5.50 (1H, s), 4.20 (2H, d, J=7.0 Hz), 1.37-1.23 (1H, m), 0.73-0.58 (2H, m), 0.47-0.33 (2H, m), MS (ESI) m/z: 243 (M+H)⁺.

<Step-3>: methyl 4-((3-(5-(cyclopropylmethoxy)pyrazin-2-yl)phenoxy)methyl)benzoate The title compound is prepared in 94% yield (303 mg, a white solid) by the similar manner to Step-3 of Acid-1 using 3-(5-(cyclopropylmethoxy)pyrazin-2-yl)phenol (Step-2 of Acid-50, 200 mg, 0.83 mmol).

¹H-NMR (400 MHz, CDCl₃) delta 8.46 (1H, d, J=1.5 Hz), 8.30 (1H, d, J=1.5 Hz), 8.11-8.05 (2H, m), 7.60-7.48 (4H, m), 7.38 (1H, t, J=8.0 Hz), 7.03-6.98 (1H, m), 5.21 (2H, s), 4.20 (2H, d, J=7.0 Hz), 3.93 (3H, s), 1.38-1.26 (1H, m), 0.71-0.61 (2H, m), 0.44-0.31 (2H, m), MS (ESI) m/z: 391 (M+H)⁺.

<Step-4>: 4-((3-(5-(cyclopropylmethoxy)pyrazin-2-yl)phenoxy)methyl)benzoic acid

The title compound is prepared in quantitative yield (300 mg, a white solid) by the similar manner to Step-4 of Acid-1 using methyl 4-((3-(5-(cyclopropylmethoxy)pyrazin-2-yl)phenoxy)methyl)benzoate (Step-3 of Acid-50, 303 mg, 0.78 mmol).

¹H-NMR (400 MHz, DMSO-d₆) delta 8.77 (1H, d, J=1.2 Hz), 8.38 (1H, d, J=1.2 Hz), 8.00-7.95 (2H, m), 7.69-7.57 (4H, m), 7.41 (1H, t, J=7.9 Hz), 7.10-7.05 (1H, m), 5.28 (2H, s), 4.18 (2H, d, J=7.3 Hz), 1.35-1.21 (1H, m), 0.63-0.51 (2H, m), 0.43-0.29 (2H, m), COOH is not observed, MS (ESI) m/z: 377 (M+H)⁺.

Acid-51: 4-((3-(5-(cyclopropylmethoxy)pyrazin-2-yl)phenoxy)methyl)-3-fluorobenzoic acid <Step-1>: methyl 4-((3-(5-(cyclopropylmethoxy)pyrazin-2-yl)phenoxy)methyl)-3-fluorobenzoate The title compound is prepared in 81% yield (205 mg, a white solid) by the similar manner to Step-3 of Acid-1 using 3-(5-(cyclopropylmethoxy)pyrazin-2-yl)phenol (Step-1 of Acid-50, 150 mg, 0.62 mmol) and methyl 4-(bromomethyl)-3-fluorobenzoate (153 mg, 0.62 mmol).

¹H-NMR (400 MHz, CDCl₃) delta 8.47 (1H, d, J=1.2 Hz), 8.30 (1H, d, J=1.2 Hz), 7.86 (1H, dd, J=8.0, 1.8 Hz), 7.76 (1H, dd, J=10.4, 1.8 Hz), 7.68-7.63 (1H, m), 7.60 (1H, t, J=1.2 Hz), 7.52-7.50 (1H, m), 7.39 (1H, t, J=8.0 Hz), 7.03-7.00 (1H, m), 5.27 (2H, s), 4.20 (2H, d, J=7.4 Hz), 3.92 (3H, s), 1.36-1.26 (1H, m), 0.67-0.63 (2H, m), 0.41-0.38 (2H, m), MS (ESI) m/z: 409 (M+H)⁺.

<Step-2>: 4-((3-(5-(cyclopropylmethoxy)pyrazin-2-yl)phenoxy)methyl)-3-fluorobenzoic acid The title compound is prepared in 88% yield (170 mg, a white solid) by the similar manner to Step-4 of Acid-1 using methyl 4-((3-(5-(cyclopropylmethoxy)pyrazin-2-yl)phenoxy)methyl)-3-fluorobenzoate (Step-1 of Acid-51, 200 mg, 0.49 mmol).

¹H-NMR (400 MHz, CDCl₃) delta 8.48 (1H, d, J=1.2 Hz), 8.31 (1H, d, J=1.2 Hz), 7.93 (1H, dd, J=7.9, 1.8 Hz), 7.82 (1H, dd, J=10.4, 1.2 Hz), 7.71 (1H, t, J=8.6 Hz), 7.61 (1H, t, J=1.8 Hz), 7.53-7.50 (1H, m), 7.40 (1H, t, J=8.6 Hz), 7.02 (1H, dd, J=7.4, 2.5 Hz), 5.29 (2H, s), 4.20 (2H, d, J=7.4 Hz), 1.35-1.28 (1H, m), 0.68-0.63 (2H, m), 0.41-0.38 (2H, m), COOH is not observed, MS (ESI) m/z: 395 (M+H)⁺.

Acid-52: 4-((3-(5-(cyclopropylmethoxy)pyrimidin-2-yl)phenoxy)methyl)benzoic acid <Step-1>: 3-(5-(cyclopropylmethoxy)pyrimidin-2-yl)phenol The title compound is prepared in 94% yield (740 mg, a white solid) by the similar manner to Step-2 of Acid-1 using 2-chloro-5-(cyclopropylmethoxy)pyrimidine (600 mg, 3.3 mmol).

¹H-NMR (400 MHz, CDCl₃) delta 8.46 (2H, s), 7.92 (1H, d, J=7.4 Hz), 7.83-7.81 (1H, m), 7.35 (1H, t, J=7.3 Hz), 6.93 (1H, dd, J=1.8, 7.4 Hz), 5.05 (1H, br.s), 3.96 (2H, d, J=6.7 Hz), 1.35-1.24 (1H, m), 0.74-0.68 (2H, m), 0.43-0.39 (2H, m), MS (ESI) m/z: 243 (M+H)⁺.

<Step-2>: methyl 4-((3-(5-(cyclopropylmethoxy) pyrimidin-2-yl)phenoxy)methyl)benzoate The title compound is prepared in 85% yield (410 mg, a white solid) by the similar manner to Step-3 of Acid-1 using 3-(5-(cyclopropylmethoxy)pyrimidin-2-yl)phenol (Step-1 of Acid-52, 300 mg, 1.2 mmol).
¹H-NMR (400 MHz, CDCl₃) delta 8.46 (2H, s), 8.06 (2H, d, J=7.9 Hz), 8.01-7.97 (2H, m), 7.55 (2H, d, J=8.0 Hz), 7.39 (1H, t, J=8.0 Hz), 7.07-7.04 (1H, m), 5.23 (2H, s), 3.96 (2H, d, J=7.4 Hz), 3.92 (3H, s), 1.35-1.25 (1H, m), 0.74-0.68 (2H, m), 0.43-0.39 (2H, m), MS (ESI) m/z: 391 (M+H)⁺.

<Step-3>: 4-((3-(5-(cyclopropylmethoxy)pyrimidin-2-yl)phenoxy)methyl)benzoic acid The title compound is prepared in 99% yield (380 mg, a white solid) by the similar manner to Step-4 of Acid-1 using methyl 4-((3-(5-(cyclopropylmethoxy)pyrimidin-2-yl)phenoxy)methyl)benzoate (Step-2 of Acid-52, 400 mg, 1.0 mmol).
¹H-NMR (400 MHz, CDCl₃) delta 8.51 (2H, s), 8.14 (2H, d, J=8.6 Hz), 8.19-7.97 (2H, m), 7.59 (2H, d, J=8.6 Hz), 7.41 (1H, t, J=8.6 Hz), 7.07 (1H, dd, J=7.4, 1.8 Hz), 5.26 (2H, s), 3.97 (2H, d, J=6.7 Hz), 1.37-1.27 (1H, m), 0.74-0.69 (2H, m), 0.44-0.40 (2H, m), COOH is not observed, MS (ESI) m/z: 395 (M+H)⁺.

Acid-53: 4-((3-(5-(cyclopropylmethoxy)pyrimidin-2-yl)phenoxy)methyl)-3-fluorobenzoic acid <Step-1>: methyl 4-((3-(5-(cyclopropylmethoxy) pyrimidin-2-yl)phenoxy)methyl)-3-fluorobenzoate The title compound is prepared in 83% yield (210 mg, a white solid) by the similar manner to Step-3 of Acid-1 using 3-(5-(cyclopropylmethoxy)pyrimidin-2-yl)phenol (Step-1 of Acid-52, 150 mg, 0.62 mmol) and methyl 4-(bromomethyl)-3-fluorobenzoate (153 mg, 0.62 mmol).
¹H-NMR (400 MHz, CDCl₃) delta 8.47 (2H, s), 8.03-7.98 (2H, m), 7.86 (1H, dd, J=8.0, 1.8 Hz), 7.75 (1H, dd, J=10.4, 1.2 Hz), 7.68 (1H, t, J=8.0 Hz), 7.40 (1H, t, J=8.0 Hz), 7.07-7.05 (1H, m), 5.29 (2H, s), 3.96 (2H, d, J=6.7 Hz), 3.93 (3H, s), 1.36-1.26 (1H, m), 0.73-0.70 (2H, m), 0.43-0.40 (2H, m), MS (ESI) m/z: 409 (M+H)⁺.

<Step-2>: 4-((3-(5-(cyclopropylmethoxy)pyrimidin-2-yl)phenoxy)methyl)benzoic acid The title compound is prepared in 84% yield (170 mg, a white solid) by the similar manner to Step-4 of Acid-1 using methyl 4-((3-(5-(cyclopropylmethoxy)pyrimidin-2-yl)phenoxy)methyl)-3-fluorobenzoate (Step-1 of Acid-53, 210 mg, 0.51 mmol).
¹H-NMR (400 MHz, CDCl₃) delta 8.47 (2H, s), 8.02-7.97 (2H, m), 7.89-7.86 (1H, m), 7.78-7.75 (1H, m), 7.68-7.63 (1H, m), 7.42-7.37 (1H, m), 7.07-7.05 (1H, m), 5.28 (2H, s), 3.96 (2H, d, J=7.3 Hz), 1.35-1.27 (2H, m), 0.73-0.68 (2H, m), 0.43-0.38 (2H, m), COOH is not observed, MS (ESI) m/z: 395 (M+H)⁺.

Acid-54: 4-(((4'-(cyclopropylmethoxy)-[1,1'-biphenyl]-3-yl)oxy)methyl)benzoic acid <Step-1>: 4'-(cyclopropylmethoxy)-[1,1'-biphenyl]-3-ol The title compound is prepared in 63% yield (670 mg, a white solid) by the similar manner to Step-2 of Acid-1 using 1-bromo-4-(cyclopropylmethoxy)benzene (1.0 g, 4.4 mmol).
¹H-NMR (400 MHz, CDCl₃) delta 7.49 (2H, d, J=9.2 Hz), 7.29 (1H, d, J=8.0 Hz), 7.14-7.11 (1H, m), 7.02 (1H, t, J=2.4 Hz), 6.96 (2H, d, J=9.2 Hz), 4.76 (1H, s), 3.84 (2H, d, J=6.7 Hz), 1.36-1.24 (1H, m), 0.69-0.64 (2H, m), 0.39-0.35 (2H, m), OH is not observed, MS (ESI) m/z: 241 (M+H)⁺.

<Step-2>: methyl 4-(((4'-(cyclopropylmethoxy)-[1,1'-biphenyl]-3-yl)oxy)methyl)benzoate The title compound is prepared in 82% yield (400 mg, a white solid) by the similar manner to Step-3 of Acid-1 using 4'-(cyclopropylmethoxy)-[1,1'-biphenyl]-3-ol (Step-1 of Acid-54, 300 mg, 1.2 mmol).
¹H-NMR (400 MHz, CDCl₃) delta 8.06 (2H, d, J=8.0 Hz), 7.54-7.48 (4H, m), 7.33 (1H, t, J=8.0 Hz), 7.17-7.15 (2H, m), 6.96 (2H, d, J=9.2 Hz), 6.93-6.87 (1H, m), 5.18 (2H, s), 3.93 (3H, s), 3.84 (2H, d, J=6.7 Hz), 1.35-1.25 (1H, m), 0.69-0.64 (2H, m), 0.39-0.35 (2H, m).

<Step-3>: 4-(((4'-(cyclopropylmethoxy)-[1,1'-biphenyl]-3-yl)oxy)methyl)benzoic acid The title compound is prepared in 91% yield (350 mg, a white solid) by the similar manner to Step-4 of Acid-1 using methyl 4-(((4'-(cyclopropylmethoxy)-[1,1'-biphenyl]-3-yl)oxy)methyl)benzoate (Step-2 of Acid-54, 400 mg, 1.0 mmol).
¹H-NMR (400 MHz, CDCl₃) delta 8.13 (2H, d, J=7.9 Hz), 7.57 (2H, d, J=8.6 Hz), 7.49 (2H, d, J=8.6 Hz), 7.34 (1H, t, J=7.9 Hz), 7.18-7.16 (2H, m), 6.97 (2H, d, J=8.6 Hz), 6.92-6.88 (1H, m), 5.21 (2H, s), 3.84 (2H, d, J=6.7 Hz), 1.35-1.25 (1H, m), 0.68-0.64 (2H, m), 0.39-0.35 (2H, m), COOH is not observed, MS (ESI) m/z: 373 (M−H)⁻.

Acid-55: 4-((3-(1-(cyclopropylmethyl)-1H-pyrazol-3-yl)phenoxy)methyl)-3-fluorobenzoic acid <Step-1>: 1-(cyclopropylmethyl)-3-(3-methoxyphenyl)-1H-pyrazole A mixture of 3-(3-methoxyphenyl)-1H-pyrazole (1.4 g, 8.2 mmol), (bromomethyl)cyclopropane (1.3 g, 9.8 mmol), and potassium carbonate (3.4 g, 24.5 mmol) in DMF (10 mL) is stirred at 55° C. for 12 hours. The reaction mixture is diluted with ethyl acetate (80 mL) and washed with water (80 mL×2), and dried over sodium sulfate. Insoluble materials are separated by filtration and the filtrate is concentrated. The residue is purified by column chromatography on silica-gel eluting with n-hexane/EtOAc (9:1 to 5:1) to give 1.1 g (61% yield) of the title compound as a pale yellow solid. In addition, 127 mg (7% yield) of the regio isomer is obtained as a more polar product.
¹H-NMR (400 MHz, CDCl₃) delta 7.53 (1H, d, J=1.8 Hz), 7.40-7.36 (1H, m), 7.37 (1H, d, J=1.8 Hz), 7.30 (1H, t, J=7.9 Hz), 6.84 (1H, dt, J=7.9, 1.8 Hz), 6.55 (1H, d, J=1.8 Hz), 4.05 (2H, d, J=7.3 Hz), 3.87 (3H, s), 1.38-1.29 (1H, m), 0.70-0.63 (2H, m), 0.42-0.37 (2H, m), MS (ESI) m/z: 229 (M+H)$^+$.

<Step-2>: 3-(1-(cyclopropylmethyl)-1H-pyrazol-3-yl)phenol

To a stirred solution of 1-(cyclopropylmethyl)-3-(3-methoxyphenyl)-1H-pyrazole (Step-1 of Acid-55, 1.3 g, 5.7 mmol) in DCM (10 mL) is added dropwise 1M boron tribromide (14.1 mL, 14.1 mmol) at −20° C., and the reaction mixture is allowed to warm up to room temperature for 2 hours with stirring. The reaction mixture is quenched with water (100 mL) and extracted with DCM (80 mL, ×2), and the combined DCM layer is washed with water (50 mL), and dried over sodium sulfate. Insoluble materials are separated by filtration and the filtrate is concentrated. The residue is purified by column chromatography on silica-gel eluting with n-hexane/EtOAc (5:1 to 2:1) to give 511 mg (42% yield) of the title compound as a white solid.
$^1$H-NMR (400 MHz, CDCl$_3$) delta 7.53 (1H, d, J=2.5 Hz), 7.38-7.35 (1H, m), 7.32-7.28 (1H, m), 7.25-7.21 (1H, m), 6.79-6.75 (1H, m), 6.53-6.51 (1H, m), 6.1 (1H, br.s), 4.03 (1H, d, J=7.3 Hz), 1.37-1.29 (1H, m), 0.68-0.62 (2H, m), 0.42-0.37 (2H, m), OH is not observed, MS (ESI) m/z: 215 (M+H)$^+$.

<Step-3>: methyl 4-((3-(1-(cyclopropylmethyl)-1H-pyrazol-3-yl)phenoxy)methyl)-3-fluorobenzoate The title compound is prepared in quantitative yield (185 mg, a white solid) by the similar manner to Step-3 of Acid-1 using 3-(1-(cyclopropylmethyl)-1H-pyrazol-3-yl)phenol (Step-2 of Acid-55, 100 mg, 0.47 mmol) and methyl 4-(bromomethyl)-3-fluorobenzoate (138 mg, 0.56 mmol).
$^1$H-NMR (400 MHz, CDCl$_3$) delta 7.86 (1H, dd, J=7.4, 1.8 Hz), 7.74 (1H, dd, J=10.4, 1.8 Hz), 7.66 (1H, t, J=7.4 Hz), 7.53 (1H, d, J=2.4 Hz), 7.49-7.47 (1H, m), 7.44-7.40 (1H, m), 7.31 (1H, t, J=7.4 Hz), 6.93-6.89 (1H, m), 6.55 (1H, d, J=2.4 Hz), 5.25 (2H, s), 4.04 (2H, d, J=6.7 Hz), 3.93 (3H, s), 1.40-1.28 (1H, m), 0.70-0.64 (2H, m), 0.43-0.38 (2H, m), MS (ESI) m/z: 381 (M+H)$^+$.

<Step-4>: 4-((3-(1-(cyclopropylmethyl)-1H-pyrazol-3-yl)phenoxy)methyl)-3-fluorobenzoic acid The title compound is prepared in 87% yield (150 mg, a white solid) by the similar manner to Step-4 of Acid-1 using methyl 4-((3-(1-(cyclopropylmethyl)-1H-pyrazol-3-yl)phenoxy)methyl)-3-fluorobenzoate (Step-3 of Acid-55, 178 mg, 0.47 mmol).
$^1$H-NMR (400 MHz, DMSO-d$_6$) delta 7.83-7.78 (1H, m), 7.80 (1H, s), 7.74-7.68 (2H, m), 7.46-7.39 (2H, m), 7.32 (1H, t, J=8.0 Hz), 6.98-6.94 (1H, m), 6.72 (1H, d, J=2.4 Hz), 5.27 (2H, s), 4.00 (2H, d, J=7.4 Hz), 1.32-1.23 (1H, m), 0.56-0.51 (2H, m), 0.41-0.35 (2H, m), COOH is not observed, MS (ESI) m/z: 367 (M+H)$^+$.

Acid-56: 4-((3-(5-(cyclopropylmethyl)isoxazol-3-yl)phenoxy)methyl)-3-fluorobenzoic acid <Step-1>:
4-cyclopropyl-1-(3-methoxyphenyl)butane-1,3-dione To a stirred solution of 1-(3-methoxyphenyl)ethanone (1.0 g, 6.6 mmol) in THF (15 mL) is added dropwise a solution of lithium bis(trimethylsilyl)amide in THF (1.3 M, 7.7 mL, 10.0 mmol) at −78° C., and the reaction mixture is stirred at 78° C. for 1 hour. Then, a solution of 2-cyclopropylacetyl chloride in THF (5 mL) is added to the reaction mixture and the resulting mixture is allowed to warm up to room temperature. After stirring at room temperature for 24 hours, saturated aqueous NH$_4$Cl (100 mL) is added and extracted with EtOAc (100 mL×2). The combined organic layer is dried over sodium sulfate. Insoluble materials are separated by filtration and the filtrate is concentrated. The residue is purified by column chromatography on silica-gel eluting with n-hexane/EtOAc (10:1 to 3:1) to give 438 mg (28% yield) of the title compound as a colorless oil.
MS (ESI) m/z: 233 (M+H)$^+$.

<Step-2>:5-(cyclopropylmethyl)-3-(3-methoxyphenyl)isoxazole

A mixture of hydroxylamine hydrochloride (119 mg, 1.7 mmol) and Et$_3$N (0.24 mL, 1.7 mmol) in isopropyl alcohol (5 mL) is stirred for 10 min. Then, TFA (0.27 mL, 3.5 mmol) and 4-cyclopropyl-1-(3-methoxyphenyl)butane-1,3-dione are added successively to the reaction mixture, and stirred at 60° C. for 12 hours. The reaction mixture is concentrated and the residue is diluted with EtOAc (50 mL), washed with saturated aqueous NaHCO$_3$ (50 mL), and dried over sodium sulfate. Insoluble materials are separated by filtration and the filtrate is concentrated. The residue is purified by column chromatography on silica-gel eluting with n-hexane/EtOAc (10:1) to give 337 mg (90% yield) of the title compound as a colorless oil.
$^1$H-NMR (400 MHz, CDCl$_3$) delta 7.39-7.29 (3H, m), 6.99-6.94 (1H, m), 6.47 (1H, s), 3.87 (3H, s), 2.62 (2H, d, J=6.7 Hz), 1.10-1.00 (1H, m), 0.63-0.57 (2H, m), 0.31-0.25 (2H, m), MS (ESI) m/z: 230 (M+H)$^+$.

<Step-3>:
3-(5-(cyclopropylmethyl)isoxazol-3-yl)phenol

The title compound is prepared in 69% yield (215 mg, a white solid) by the similar manner to Step-2 of Acid-55 using 5-(cyclopropylmethyl)-3-(3-methoxyphenyl)isoxazole (Step-2 of Acid-56, 335 mg, 1.5 mmol).
$^1$H-NMR (400 MHz, CDCl$_3$) delta 7.82 (1H, br.s), 7.36-7.24 (3H, m), 6.97 (1H, dd, J=8.0, 2.4 Hz), 6.52 (1H, s), 2.65 (1H, d, J=7.4 Hz), 1.13-1.05 (1H, m), 0.65-0.60 (2H, m), 0.31-0.26 (2H, m), OH is not observed, MS (ESI) m/z: 216 (M+H)$^+$.

<Step-4>: methyl 4-((3-(5-(cyclopropylmethyl)isoxazol-3-yl)phenoxy)methyl)-3-fluorobenzoate The title compound is prepared in quantitative yield (190 mg, a white solid) by the similar manner to Step-3 of Acid-1 using 3-(5-(cyclopropylmethyl)isoxazol-3-yl)phenol (Step-3 of Acid-56, 100 mg, 0.47 mmol) and methyl 4-(bromomethyl)-3-fluorobenzoate (138 mg, 0.56 mmol).
$^1$H-NMR (400 MHz, CDCl$_3$) delta 7.87 (1H, dd, J=8.0, 1.2 Hz), 7.76 (1H, dd, J=10.4, 1.2 Hz), 7.64 (1H, t, J=8.0 Hz), 7.43-7.36 (3H, m), 7.06-7.03 (1H, m), 6.48 (1H, s), 5.24 (2H, s), 3.94 (3H, s), 2.62 (2H, d, J=6.7 Hz), 1.10-1.00 (1H, m), 0.63-0.57 (2H, m), 0.31-0.25 (2H, m), MS (ESI) m/z: 382 (M+H)$^+$.

<Step-5>: 4-((3-(5-(cyclopropylmethyl)isoxazol-3-yl)phenoxy)methyl)-3-fluorobenzoic acid The title compound is prepared in 92% yield (168 mg, a white solid) by the similar manner to Step-4 of Acid-1 using methyl 4-((3-(5-(cyclopropylmethyl)isoxazol-3-yl)phenoxy)methyl)-3-fluorobenzoate (Step-4 of Acid-56, 190 mg, 0.50 mmol).

$^1$H-NMR (400 MHz, DMSO-d$_6$) delta 13.4 (1H, br.s), 7.83 (1H, dd, J=8.0, 1.8 Hz), 7.76-7.70 (2H, m), 7.53 (1H, br.s), 7.48-7.45 (2H, m), 7.20-7.15 (1H, m), 7.06 (1H, s), 5.32 (2H, s), 2.57 (2H, d, J=6.7 Hz), 1.06-0.98 (1H, m), 0.55-0.50 (2H, m), 0.28-0.23 (2H, m), MS (ESI) m/z: 368 (M+H)$^+$.

Acid-57: 4-(cyclopropylmethoxy)-3'-((2-fluoro-4-((methylsulfonyl)carbamoyl)benzyl)oxy)-[1,1'-biphenyl]-3-carboxylic acid <Step-1>: cyclopropylmethyl 5-bromo-2-(cyclopropylmethoxy)benzoate The title compound is prepared in 98% yield (1.5 g, a pale yellow oil) by the similar manner to Step-1 of Acid-46 using 5-bromo-2-hydroxybenzoic acid (1.0 g, 4.6 mmol).

$^1$H-NMR (400 MHz, CDCl$_3$) delta 7.89 (1H, d, J=2.7 Hz), 7.50 (1H, dd, J=8.7, 2.7 Hz), 6.82 (1H, d, J=8.7 Hz), 4.14 (2H, d, J=5.1 Hz), 3.89 (2H, d, J=6.4 Hz), 1.35-1.20 (2H, m), 0.67-0.58 (4H, m), 0.43-0.33 (4H, m), MS (ESI) m/z: 325 (M+H)$^+$.

<Step-2>: cyclopropylmethyl 4-(cyclopropylmethoxy)-3'-((2-fluoro-4-((methylsulfonyl)carbamoyl)benzyl)oxy)-[1,1'-biphenyl]-3-carboxylate A mixture of 3-fluoro-N-(methylsulfonyl)-4-((3-(4,4,5,5-tetramethyl-1,3,2-dioxaborolan-2-yl)phenoxy)methyl)benzamide (Step-4 of Borate-2, 200 mg, 0.45 mmol), cyclopropylmethyl 5-bromo-2-(cyclopropylmethoxy)benzoate (Step-1 of Acid-57, 174 mg, 0.53 mmol) in dioxane/saturated aqueous NaHCO$_3$ (10 mL/5 mL) is added bis(di-tert-butyl(4-dimethylaminophenyl)phosphine)dichloropalladium(II) (36 mg, 0.045 mmol), and the reaction mixture is stirred at 100° C. for 1 hour. Then, the reaction mixture is diluted with 10% aqueous citric acid and extracted with DCM (50 mL×2), and dried over sodium sulfate. Insoluble materials are separated by filtration, and the filtrate is concentrated to give 182 mg (72% yield) of the title compound as a brown gum.

$^1$H-NMR (400 MHz, CDCl$_3$) delta 7.87 (1H, d, J=2.3 Hz), 7.73-7.57 (4H, m), 7.34 (1H, t, J=8.2 Hz), 7.16 (1H, d, J=8.2 Hz), 7.09 (1H, dd, J=2.3, 1.8 Hz), 6.99 (1H, d, J=8.7H), 6.93 (1H, dd, J=8.7, 2.3 Hz), 5.26 (2H, s), 4.22 (2H, d, J=7.3 Hz), 3.95 (2H, d, J=6.4 Hz), 3.42 (3H, s), 1.98 (1H, br.s), 1.38-1.21 (2H, m), 0.68-0.58 (4H, m), 0.47-0.35 (4H, m), MS (ESI) m/z: 568 (M+H)$^+$.

<Step-3>: 4-(cyclopropylmethoxy)-3'-((2-fluoro-4-((methylsulfonyl)carbamoyl)benzyl)oxy)-[1,1'-biphenyl]-3-carboxylic acid The title compound is prepared in 91% yield (150 mg, a brown gum) by the similar manner to Step-4 of Acid-1 using cyclopropylmethyl 4-(cyclopropylmethoxy)-3'-((2-fluoro-4-((methylsulfonyl)carbamoyl)benzyl)oxy)-[1,1'-biphenyl]-3-carboxylate (Step-2 of Acid-57, 182 mg, 0.32 mmol).

MS (ESI) m/z: 514 (M+H)$^+$.

<Borate Part>

Borate-1: N-(methylsulfonyl)-4-((3-(4,4,5,5-tetramethyl-1,3,2-dioxaborolan-2-yl)phenoxy)methyl)benzamide <Step-1>: methyl 4-((3-bromophenoxy)methyl)benzoate The title compound is prepared in 99% yield (1.8 g, a colorless gum) by the similar manner to Step-3 of Acid-1 using 3-bromophenol (1.0 g, 5.8 mmol).

$^1$H-NMR (400 MHz, CDCl$_3$) delta 8.06 (2H, d, J=8.6 Hz), 7.49 (2H, d, J=8.6 Hz), 7.17-7.09 (3H, m), 6.91-6.88 (1H, m), 5.11 (2H, s), 3.93 (3H, s), MS (ESI) m/z: 321 (M+H)$^+$.

<Step-2>: 4-((3-bromophenoxy)methyl)benzoic acid

The title compound is prepared in quantitative yield (1.8 g, a white solid) by the similar manner to Step-4 of Acid-1 using methyl 4-((3-bromophenoxy)methyl)benzoate (Step-1 of Borate-1, 1.8 g, 5.7 mmol).

MS (ESI) m/z: 306 (M−H)$^−$.

<Step-3>: 4-((3-bromophenoxy)methyl)-N-(methylsulfonyl)benzamide

To a stirred solution of 4-((3-bromophenoxy)methyl)benzoic acid (Step-2 of Borate-1, 1.8 g, 5.7 mmol), methanesulfonamide (1.6 g, 17.2 mmol), and DMAP (1.4 g, 11.5 mmol) in DMF (40 mL) is added EDC (2.2 g, 11.5 mmol) at room temperature. The reaction mixture is stirred at 50° C. for 20 hours and diluted with EtOAc/n-hexane (4:1: 150 mL), and washed with 0.5 M hydrochloric acid (100 mL), water (50 mL), then, dried over sodium sulfate. Insoluble materials are separated by filtration and the filtrate is concentrated. The residue is purified by column chromatography on silica-gel eluting with EtOAc/MeOH (20:1), then, solidified from ethyl acetate and n-hexane mix solvent. The solid is collected by filtration to give 1.4 g (65% yield) of the title compound as a white solid.

$^1$H-NMR (400 MHz, DMSO-d$_6$) delta 12.15 (1H, br.s), 7.96 (2H, d, J=8.2 Hz), 7.56 (2H, d, J=8.2 Hz), 7.28-7.24 (2H, m), 7.16 (1H, dd, J=1.8, 0.9 Hz), 7.06-7.02 (1H, m), 5.23 (2H, s), 2.50 (3H, s), MS (ESI) m/z: 384 (M−H)$^−$.

<Step-4>: N-(methylsulfonyl)-4-((3-(4,4,5,5-tetramethyl-1,3,2-dioxaborolan-2-yl)phenoxy)methyl)benzamide To a stirred solution of 4-((3-bromophenoxy)methyl)-N-(methylsulfonyl)benzamide (Step-3 of Borate-1, 800 mg, 2.1 mmol), 4,4,4',4',5,5,5',5'-octamethyl-2,2'-bi(1,3,2-dioxaborolane) (790 mg, 3.1 mmol), and [1,1'-Bis(diphenylphosphino)ferrocene]palladium(II) dichloride dichloromethane adduct (170 mg, 0.21 mmol) in DMSO (20 mL) is added potassium acetate (613 mg, 6.3 mmol). The reaction mixture is stirred at 90° C. for 20 hours and cooled to room temperature. The reaction mixture is diluted with EtOAc/n-hexane (4:1, 60 mL), and washed with water (30 mL×3), then, dried over sodium sulfate. Insoluble materials are separated by filtration and the filtrate is concentrated. The residue is purified by column chromatography on silica-gel eluting with n-hexane/EtOAc (1:4) to give 457 mg (51% yield) of the title compound as a brown foam.

$^1$H-NMR (400 MHz, CDCl$_3$) delta 8.75 (1H, br.s), 7.86 (2H, d, J=8.2 Hz), 7.59 (2H, d, J=8.6 Hz), 7.47-7.42 (2H, m), 7.31 (1H, t, J=7.9 Hz), 7.07 (1H, ddd, J=8.2, 2.7, 1.2 Hz), 5.17 (2H, s), 3.44 (3H, s), 1.35 (12H, s), MS (ESI) m/z: 432 (M+H)⁺.

Borate-2: 3-fluoro-N-(methylsulfonyl)-4-((3-(4,4,5, 5-tetramethyl-1,3,2-dioxaborolan-2-yl)phenoxy) methyl)benzamide <Step-1>: methyl 4-((3-bromophenoxy)methyl)-3-fluorobenzoate The title compound is prepared in 99% yield (3.9 g, a white solid) by the similar manner to Step-3 of Acid-1 using 3-bromophenol (2.0 g, 11.6 mmol) and methyl 4-(bromomethyl)-3-fluorobenzoate (2.9 g, 11.6 mmol).
¹H-NMR (400 MHz, CDCl₃) delta 7.86 (1H, dd, J=7.9, 1.5 Hz), 7.75 (1H, dd, J=10.4, 1.5 Hz), 7.59 (1H, t, J=7.5 Hz), 7.19-7.11 (3H, m), 6.93-6.89 (1H, m), 5.16 (2H, s), 3.93 (3H, s).

<Step-2>: 4-((3-bromophenoxy)methyl)-3-fluorobenzoic acid

The title compound is prepared in 97% yield (2.7 g, a white solid) by the similar manner to Step-4 of Acid-1 using methyl 4-((3-bromophenoxy)methyl)-3-fluorobenzoate (Step-1 of Borate-2, 2.7 g, 8.5 mmol).
¹H-NMR (400 MHz, DMSO-d₆) delta 13.35 (1H, br.s), 7.82 (1H, dd, J=8.0, 1.5 Hz), 7.75-7.67 (2H, m), 7.34-7.24 (2H, m), 7.21-7.16 (1H, m), 7.07 (1H, ddd, J=8.6, 2.8, 0.8 Hz), 5.25 (2H, s), MS (ESI) m/z: 325 (M+H)⁺.

<Step-3>: 4-((3-bromophenoxy)methyl)-3-fluoro-N-(methylsulfonyl)benzamide

The title compound is prepared in 84% yield (2.8 g, a white solid) by the similar manner to Step-3 of Borate-1 using 4-((3-bromophenoxy)methyl)-3-fluorobenzoic acid (Step-2 of Borate-2, 2.7 g, 8.2 mmol).
¹H-NMR (400 MHz, CDCl₃) delta 7.71-7.63 (3H, m), 7.23-7.12 (3H, m), 6.95-6.88 (1H, m), 5.18 (2H, s), 3.44 (3H, s), NH is not observed, MS (ESI) m/z: 402 (M+H)⁺.

<Step-4>: 3-fluoro-N-(methylsulfonyl)-4-((3-(4,4,5, 5-tetramethyl-1,3,2-dioxaborolan-2-yl)phenoxy) methyl)benzamide The title compound is prepared in quantitative yield (3.1 g, a pale brown solid) by the similar manner to Step-4 of Borate-1 using 4-((3-bromophenoxy)methyl)-3-fluoro-N-(methylsulfonyl)benzamide (Step-3 of Borate-2, 2.8 g, 6.9 mmol).
¹H-NMR (400 MHz, CDCl₃) delta 8.95 (1H, br.s), 7.73 (1H, t, J=7.5 Hz), 7.68-7.61 (2H, m), 7.48-7.43 (2H, m), 7.32 (1H, t, J=7.7 Hz), 7.08 (1H, ddd, J=8.2, 2.8, 1.2 Hz), 5.22 (2H, s), 3.44 (3H, s), 1.35 (12H, s), MS (ESI) m/z: 450 (M+H)⁺.

Borate-3: 4-((3-fluoro-5-(4,4,5,5-tetramethyl-1,3,2-dioxaborolan-2-yl)phenoxy)methyl)-N-(methylsulfonyl)benzamide <Step-1>: methyl 4-((3-bromo-5-fluorophenoxy)methyl)benzoate The title compound is prepared in 97% yield (4.3 g, a white solid) by the similar manner to Step-3 of Acid-1 using 3-bromo-5-fluorophenol (2.5 g, 13.1 mmol).
¹H-NMR (400 MHz, CDCl₃) delta 8.10-8.04 (2H, m), 7.50-7.45 (2H, m), 6.95-6.92 (1H, m), 6.90-6.86 (1H, m), 6.65-6.60 (1H, m), 5.09 (2H, s), 3.93 (3H, s), MS (ESI) m/z: 339.1 (M+H)⁺.

<Step-2>: 4-((3-bromo-5-fluorophenoxy)methyl)benzoic acid

The title compound is prepared in 87% yield (3.6 g, a white solid) by the similar manner to Step-4 of Acid-1 using methyl 4-((3-bromo-5-fluorophenoxy)methyl)benzoate (Step-1 of Borate-3, 4.3 g, 12.7 mmol).
¹H-NMR (400 MHz, CDCl₃) delta 8.20-8.12 (2H, m), 7.56-7.48 (2H, m), 6.98-6.86 (2H, m), 6.68-6.60 (1H, m), 5.12 (2H, s), COOH is not observed, MS (ESI) m/z: 323 (M−H)⁻.

<Step-3>: 4-((3-bromo-5-fluorophenoxy)methyl)-N-(methylsulfonyl)benzamide

The title compound is prepared in 88% yield (3.9 g, a white solid) by the similar manner to Step-3 of Borate-1 using 4-((3-bromo-5-fluorophenoxy)methyl)benzoic acid (Step-2 of Borate-3, 3.6 g, 11.0 mmol).
¹H-NMR (400 MHz, CDCl₃) delta 12.17 (1H, br.s), 8.00-7.93 (2H, m), 7.62-7.55 (2H, m), 7.17-7.10 (2H, m), 7.04-6.96 (1H, m), 5.26 (2H, s), 3.38 (3H, s), MS (ESI) m/z: 402 (M+H)⁺.

<Step-4>: 4-((3-fluoro-5-(4,4,5,5-tetramethyl-1,3,2-dioxaborolan-2-yl)phenoxy)methyl)-N-(methylsulfonyl)benzamide The title compound is prepared in 93% yield (3.1 g, a pale brown solid) by the similar manner to Step-4 of Borate-1 using 4-((3-bromo-5-fluorophenoxy)methyl)-N-(methylsulfonyl)benzamide (Step-3 of Borate-3, 3.0 g, 7.5 mmol).
¹H-NMR (400 MHz, CDCl₃) delta 7.88 (2H, d, J=8.2 Hz), 7.55 (2H, d, J=7.8 Hz), 7.20 (1H, d, J=2.3 Hz), 7.13 (1H, dd, J=8.2, 2.3 Hz), 6.76 (1H, dt, J=10.5, 2.3 Hz), 5.14 (2H, s), 3.41 (3H, s), 1.34 (12H, s), MS (ESI) m/z: 448 (M−H)⁻.

Borate-4: 3-fluoro-4-((3-fluoro-5-(4,4,5,5-tetramethyl-1,3,2-dioxaborolan-2-yl)phenoxy)methyl)-N-(methylsulfonyl)benzamide <Step-1>: methyl 4-((3-bromo-5-fluorophenoxy) methyl)-3-fluorobenzoate The title compound is prepared in 86% yield (3.1 g, a white solid) by the similar manner to Step-3 of Acid-1 using 3-bromo-5-fluorophenol (1.9 g, 10.1 mmol) and methyl 4-(bromomethyl)-3-fluorobenzoate (2.5 g, 10.1 mmol).
¹H-NMR (400 MHz, CDCl₃) delta 7.87 (1H, dd, J=7.9, 1.5 Hz), 7.76 (1H, dd, J=10.4, 1.5 Hz), 7.56 (1H, t, J=7.5 Hz), 6.97-6.94 (1H, m), 6.92-6.88 (1H, m), 6.65 (1H, dt, J=10.4, 2.2 Hz), 5.14 (2H, s), 3.94 (3H, s).

<Step-2>: 4-((3-bromo-5-fluorophenoxy)methyl)-3-fluorobenzoic acid

The title compound is prepared in 97% yield (2.9 g, a white solid) by the similar manner to Step-4 of Acid-1 using methyl 4-((3-bromo-5-fluorophenoxy)methyl)-3-fluorobenzoate (Step-1 of Borate-4, 3.1 g, 8.8 mmol).

¹H-NMR (400 MHz, DMSO-d₆) delta 7.85-7.77 (1H, m), 7.72-7.65 (2H, m), 7.17-7.10 (2H, m), 7.05-6.98 (1H, m), 5.24 (2H, s), COOH is not observed, MS (ESI) m/z: 341 (M−H)⁻.

<Step-3>: 4-((3-bromo-5-fluorophenoxy)methyl)-3-fluoro-N-(methylsulfonyl)benzamide The title compound is prepared in 84% yield (3.4 g, a white solid) by the similar manner to Step-3 of Borate-1 using 4-((3-bromo-5-fluorophenoxy)methyl)-3-fluorobenzoic acid (Step-2 of Borate-4, 3.3 g, 9.5 mmol).
¹H-NMR (400 MHz, CDCl₃) delta 7.74-7.61 (3H, m), 7.00-6.94 (1H, m), 6.91 (1H, dt, J=8.0, 1.8 Hz), 6.65 (1H, dt, J=10.4, 2.3 Hz), 5.16 (2H, s), 3.45 (3H, s), NH is not observed, MS (ESI) m/z: 420 (M+H)⁺.

<Step-4>: 3-fluoro-4-((3-fluoro-5-(4,4,5,5-tetramethyl-1,3,2-dioxaborolan-2-yl)phenoxy)methyl)-N-(methylsulfonyl)benzamide The title compound is prepared in 55% yield (1.9 g, a brown solid) by the similar manner to Step-4 of Borate-1 using 4-((3-bromo-5-fluorophenoxy)methyl)-3-fluoro-N-(methylsulfonyl)benzamide (Step-3 of Borate-4, 3.1 g, 7.3 mmol).
¹H-NMR (400 MHz, CDCl₃) delta 7.72-7.62 (3H, m), 7.22 (1H, d, J=2.2 Hz), 7.15 (1H, dd, J=8.4, 2.2 Hz), 6.78 (1H, dt, J=10.4, 2.4 Hz), 5.20 (2H, s), 3.45 (3H, s), 1.35 (12H, s), NH is not observed, MS (ESI) m/z: 466 (M−H)⁻.

Borate-5: 3-fluoro-4-((4-fluoro-3-(4,4,5,5-tetramethyl-1,3,2-dioxaborolan-2-yl)phenoxy)methyl)-N-(methylsulfonyl)benzamide <Step-1>: methyl 4-((3-bromo-4-fluorophenoxy)methyl)-3-fluorobenzoate The title compound is prepared in 88% yield (1.4 g, a white solid) by the similar manner to Step-3 of Acid-1 using 3-bromo-4-fluorophenol (850 mg, 4.5 mmol) and methyl 4-(bromomethyl)-3-fluorobenzoate (1.2 g, 4.9 mmol).
¹H-NMR (400 MHz, CDCl₃) delta 7.88-7.84 (1H, m), 7.78-7.73 (1H, m), 7.60-7.54 (1H, m), 7.20-7.15 (1H, m), 7.08-7.02 (1H, m), 6.91-6.85 (1H, m), 5.13 (2H, s), 3.93 (3H, s).

<Step-2>: 4-((3-bromo-4-fluorophenoxy)methyl)-3-fluorobenzoic acid

The title compound is prepared in 96% yield (1.3 g, a white solid) by the similar manner to Step-4 of Acid-1 using methyl 4-((3-bromo-4-fluorophenoxy)methyl)-3-fluorobenzoate (Step-1 of Borate-5, 1.4 g, 3.9 mmol).
MS (ESI) m/z: 341 (M−H)⁻.

<Step-3>: 4-((3-bromo-4-fluorophenoxy)methyl)-3-fluoro-N-(methylsulfonyl)benzamide The title compound is prepared in 85% yield (1.3 g, a white solid) by the similar manner to Step-3 of Borate-1 using 4-((3-bromo-4-fluorophenoxy)methyl)-3-fluorobenzoic acid (Step-2 of Borate-5, 1.3 g, 3.7 mmol).
¹H-NMR (400 MHz, CDCl₃) delta 12.28 (1H, br.s), 7.85-7.78 (2H, m), 7.75-7.67 (1H, m), 7.47-7.42 (1H, m), 7.37-7.30 (1H, m), 7.18-7.07 (1H, m), 5.25 (2H, s), 3.39 (3H, s), MS (ESI) m/z: 420 (M+H)⁺.

<Step-4>: 3-fluoro-4-((4-fluoro-3-(4,4,5,5-tetramethyl-1,3,2-dioxaborolan-2-yl)phenoxy)methyl)-N-(methylsulfonyl)benzamide The title compound is prepared in 92% yield (514 mg, a pale brown solid) by the similar manner to Step-4 of Borate-1 using 4-((3-bromo-4-fluorophenoxy)methyl)-3-fluoro-N-(methylsulfonyl)benzamide (Step-3 of Borate-5, 500 mg, 1.2 mmol).
¹H-NMR (400 MHz, CDCl₃) delta 7.75-7.60 (3H, m), 7.35-7.30 (1H, m), 7.05-6.94 (2H, m), 5.17 (2H, s), 3.44 (3H, s), 1.37 (12H, s), NH is not observed, MS (ESI) m/z: 466 (M−H)⁻.

Borate-6: N-(methylsulfonyl)-6-((3-(4,4,5,5-tetramethyl-1,3,2-dioxaborolan-2-yl)phenoxy)methyl)nicotinamide <Step-1>: methyl 6-((3-bromophenoxy)methyl)nicotinate The title compound is prepared in 75% yield (3.6 g, a white solid) by the similar manner to Step-1 of Acid-40 using 3-bromophenol (2.9 g, 16.5 mmol).
¹H-NMR (400 MHz, CDCl₃) delta 9.19 (1H, d, J=1.2 Hz), 8.33 (1H, dd, J=8.0, 1.8 Hz), 7.60 (1H, d, J=7.3 Hz), 7.17-7.12 (3H, m), 6.92-6.88 (1H, m), 5.24 (2H, s), 3.97 (3H, s), MS (ESI) m/z: 322 (M+H)⁺.

<Step-2>: 6-((3-bromophenoxy)methyl)nicotinic acid

The title compound is prepared in quantitative yield (1.1 g, a white solid) by the similar manner to Step-4 of Acid-1 using methyl 6-((3-bromophenoxy)methyl)nicotinate (Step-1 of Borate-6, 1.2 g, 3.7 mmol).
MS (ESI) m/z: 308 (M+H)⁺.

<Step-3>: 6-((3-bromophenoxy)methyl)-N-(methylsulfonyl)nicotinamide

The title compound is prepared in 57% yield (822 mg, a white solid) by the similar manner to Step-3 of Borate-1 using 6-((3-bromophenoxy)methyl)nicotinic acid (Step-2 of Borate-6, 1.1 g, 3.7 mmol).
¹H-NMR (400 MHz, DMSO-d₆) delta 9.02 (1H, d, J=1.8 Hz), 8.27 (1H, dd, J=8.2, 2.3 Hz), 7.56 (1H, d, J=7.8 Hz), 7.27-7.21 (2H, m), 7.13 (1H, dd, J=7.8, 0.9 Hz), 7.03 (1H, dd, J=7.8, 1.8 Hz), 5.25 (2H, s), 3.14 (3H, s), NH is not observed, MS (ESI) m/z: 385, 387 (M+H)⁺.

<Step-4>: N-(methylsulfonyl)-6-((3-(4,4,5,5-tetramethyl-1,3,2-dioxaborolan-2-yl)phenoxy)methyl)nicotinamide The title compound is prepared in 86% yield (674 mg, a brown foam) by the similar manner to Step-4 of Borate-1 using 6-((3-bromophenoxy)methyl)-N-(methylsulfonyl) nicotinamide (Step-3 of Borate-6, 700 mg, 1.8 mmol).
¹H-NMR (400 MHz, CDCl₃) delta 9.06 (1H, s), 8.21-8.17 (1H, m), 7.69-7.59 (1H, m), 7.44-7.42 (2H, m), 7.30 (1H, t, J=7.8 Hz), 7.07-7.03 (1H, m), 5.24 (2H, s), 3.37 (3H, s), 1.34 (12H, s), NH is not observed, MS (ESI) m/z: 433 (M+H)⁺.

<Aryl Halide Part>

Aryl Halide-1: 4-((3-bromo-2-fluorophenoxy)methyl)-N-(methylsulfonyl)benzamide

<Step-1>: methyl 4-((3-bromo-2-fluorophenoxy)methyl)benzoate

The title compound is prepared in 69% yield (365 mg, a white solid) by the similar manner to Step-3 of Acid-1 using 3-bromo-2-fluorophenol (300 mg, 1.6 mmol).
$^1$H-NMR (400 MHz, CDCl$_3$) delta 8.06 (2H, d, J=8.6 Hz), 7.50 (2H, d, J=8.6 Hz), 7.18-7.11 (1H, m), 6.93-6.88 (2H, m), 5.20 (2H, s), 3.92 (3H, s), MS (ESI) m/z: 339 (M+H)$^+$.

<Step-2>: 4-((3-bromo-2-fluorophenoxy)methyl)benzoic acid

The title compound is prepared in 90% yield (311 mg, a white solid) by the similar manner to Step-4 of Acid-1 using methyl 4-((3-bromo-2-fluorophenoxy)methyl)benzoate (Step-1 of Aryl halide-1, 360 mg, 1.1 mmol).
MS (ESI) m/z: 323 (M−H)$^-$.

<Step-3>: 4-((3-bromo-2-fluorophenoxy)methyl)-N-(methylsulfonyl)benzamide

The title compound is prepared in 93% yield (356 mg, a white solid) by the similar manner to Step-3 of Borate-1 using 4-((3-bromo-2-fluorophenoxy)methyl)benzoic acid (Step-2 of Aryl halide-1, 311 mg, 0.96 mmol).
MS (ESI) m/z: 402 (M+H)$^+$.

Aryl Halide-2: 4-((3-bromo-5-cyanophenoxy)methyl)-N-(methylsulfonyl)benzamide

<Step-1>: methyl 4-((3-bromo-5-cyanophenoxy)methyl)benzoate

The title compound is prepared in 69% yield (365 mg, a white solid) by the similar manner to Step-3 of Acid-1 using 3-bromo-5-hydroxybenzonitrile (240 mg, 1.2 mmol).
$^1$H-NMR (400 MHz, CDCl$_3$) delta 8.08 (2H, d, J=8.6 Hz), 7.47 (2H, d, J=8.6 Hz), 7.42-7.39 (1H, m), 7.38-7.35 (1H, m), 7.16-7.14 (1H, m), 5.14 (2H, s), 3.94 (3H, s).

<Step-2>: 4-((3-bromo-5-cyanophenoxy)methyl)benzoic acid

The title compound is prepared in quantitative yield (413 mg, a pale yellow solid) by the similar manner to Step-4 of Acid-1 using methyl 4-((3-bromo-5-cyanophenoxy)methyl)benzoate (Step-1 of Aryl halide-2, 405 mg, 1.2 mmol).
MS (ESI) m/z: 330 (M+H)$^+$.

<Step-3>: 4-((3-bromo-5-cyanophenoxy)methyl)-N-(methylsulfonyl)benzamide

The title compound is prepared in 71% yield (361 mg, a white solid) by the similar manner to Step-3 of Borate-1 using 4-((3-bromo-5-cyanophenoxy)methyl)benzoic acid (Step-2 of Aryl halide-2, 412 mg, 1.2 mmol).
MS (ESI) m/z: 409 (M+H)$^+$.

Aryl Halide-3: 3-bromo-6-(cyclopropylmethoxy)-2-methylpyridine

<Step-1>: 3-bromo-6-(cyclopropylmethoxy)-2-methylpyridine

The title compound is prepared in 86% yield (0.97 g, a colorless liquid) by the similar manner to Step-1 of Acid-1 using 3,6-dibromo-2-methylpyridine (1.0 g, 4.0 mmol).
$^1$H-NMR (400 MHz, CDCl$_3$) delta 7.60 (1H, d, J=8.6 Hz), 6.48 (1H, d, J=8.6 Hz), 4.08 (2H, d, J=7.3 Hz), 2.48 (3H, s), 1.30-1.22 (1H, m), 0.63-0.57 (2H, m), 0.36-0.32 (2H, m), MS (ESI) m/z: 242 (M+H)$^+$.

Aryl Halide-4: 5-bromo-2-((tetrahydrofuran-3-yl)methoxy)pyridine

<Step-1>: 5-bromo-2-((tetrahydrofuran-3-yl)methoxy)pyridine

The title compound is prepared in 71% yield (1.0 g, a white solid) by the similar manner to Step-1 of Acid-1 using 5-bromo-2-fluoropyridine (1.0 g, 5.7 mmol) and (tetrahydrofuran-3-yl)methanol (0.64 g, 6.3 mmol).
$^1$H-NMR (400 MHz, CDCl$_3$) delta 8.17 (1H, d, J=2.4 Hz), 7.64 (1H, dd, J=9.2, 2.4 Hz), 6.65 (1H, d, J=8.6 Hz), 4.26 (1H, dd, J=10.4, 6.7 Hz), 4.17 (1H, dd, J=10.4, 8.6 Hz), 3.93-3.83 (2H, m), 3.78 (1H, dd, J=14.7, 7.4 Hz), 3.67 (1H, dd, J=8.6, 5.5 Hz), 2.77-2.69 (1H, m), 2.13-2.05 (1H, m), 1.76-1.68 (1H, m), MS (ESI) m/z: 258 (M+H)$^+$.

Aryl Halide-5: 3-bromo-6-(cyclobutylmethoxy)-2-methylpyridine

<Step-1>: 3-bromo-6-(cyclobutylmethoxy)-2-methylpyridine

The title compound is prepared in 19% yield (196 mg, a colorless liquid) by the similar manner to Step-1 of Acid-1 using 3,6-dibromo-2-methylpyridine (1.0 g, 4.0 mmol) and cyclobutylmethanol (0.38 g, 4.4 mmol).
MS (ESI) m/z: 256 (M+H)$^+$.

Aryl Halide-6: 5-bromo-2-(cyclopropylmethoxy)-3-methylpyridine

<Step-1>: 5-bromo-2-(cyclopropylmethoxy)-3-methylpyridine

The title compound is prepared in 83% yield (6.4 g, a colorless liquid) by the similar manner to Step-1 of Acid-1 using 2,5-dibromo-3-methylpyridine (8.0 g, 31.9 mmol).
$^1$H-NMR (400 MHz, CDCl$_3$) delta 7.99 (1H, d, J=2.7 Hz), 7.48 (1H, dd, J=2.7, 0.9 Hz), 4.12 (2H, d, J=6.9 Hz), 2.19 (3H, s), 1.33-1.21 (1H, m), 0.63-0.54 (2H, m), 0.37-0.30 (2H, m), MS (ESI) m/z: 242 (M+H)$^+$.

Aryl Halide-7: 5-bromo-2-(cyclopropylmethoxy)-4-methylpyridine

<Step-1>: 5-bromo-2-(cyclopropylmethoxy)-4-methylpyridine

The title compound is prepared in 73% yield (0.72 g, a pale yellow oil) by the similar manner to Step-1 of Acid-1 using 5-bromo-2-fluoro-4-methylpyridine (0.77 g, 4.1 mmol).
MS (ESI) m/z: 242 (M+H)$^+$.

Aryl Halide-8:
5-bromo-3-chloro-2-(cyclopropylmethoxy)pyridine

<Step-1>:
5-bromo-3-chloro-2-(cyclopropylmethoxy)pyridine

The title compound is prepared in 94% yield (1.8 g, a colorless oil) by the similar manner to Step-1 of Acid-1 using 5-bromo-3-chloro-2-fluoropyridine (1.5 g, 7.1 mmol).
$^1$H-NMR (400 MHz, CDCl$_3$) delta 8.05 (1H, d, J=2.4 Hz), 7.75 (1H, d, J=2.4 Hz), 4.20 (2H, d, J=7.3 Hz), 1.37-1.26 (1H, m), 0.65-0.58 (2H, m), 0.41-0.34 (2H, m).

Aryl Halide-9: tert-butyl 3-(((5-bromopyridin-2-yl)oxy)methyl)azetidine-1-carboxylate <Step-1>: tert-butyl 3-(((5-bromopyridin-2-yl)oxy)methyl)azetidine-1-carboxylate The title compound is prepared in 68% yield (1.1 g, a colorless oil) by the similar manner to Step-1 of Acid-1 using 5-bromo-2-fluoropyridine (0.86 g, 4.9 mmol) and tert-butyl 3-(hydroxymethyl)azetidine-1-carboxylate (1.1 gm 5.8 mmol).
$^1$H-NMR (400 MHz, CDCl$_3$) delta 8.17 (1H, dd, J=2.6, 0.6 Hz), 7.65 (1H, dd, J=8.9, 2.6 Hz), 6.66 (1H, dd, J=8.9, 0.6 Hz), 4.40 (2H, d, J=6.7 Hz), 4.06 (2H, t, J=8.7 Hz), 3.77 (2H, dd, J=8.7, 5.2 Hz), 2.99-2.92 (1H, m), 1.44 (9H, s), MS (ESI) m/z: 343 (M+H)$^+$.

Aryl Halide-10: (5-bromo-2-(cyclobutylmethoxy)pyridin-3-yl)methanol

<Step-1>: cyclobutylmethyl 5-bromo-2-(cyclobutylmethoxy)nicotinate

The title compound is prepared in 55% yield (195 mg, a pale yellow oil) by the similar manner to Step-1 of Acid-46 using methyl 5-bromo-2-chloronicotinate (250 mg, 1.0 mmol).
$^1$H-NMR (400 MHz, CDCl$_3$) delta 8.30 (1H, d, J=2.7 Hz), 8.20 (1H, d, J=2.7 Hz), 4.34 (2H, d, J=6.9 Hz), 4.28 (2H, d, J=6.9 Hz), 2.85-2.67 (2H, m), 2.18-2.07 (4H, m), 2.01-1.79 (8H, m), MS (ESI) m/z: 354 (M+H)$^+$.

<Step-2>: (5-bromo-2-(cyclobutylmethoxy)pyridin-3-yl)methanol

To a stirred solution of cyclobutylmethyl 5-bromo-2-(cyclobutylmethoxy)nicotinate (Step-1 of Aryl halide-10, 100 mg, 0.28 mmol) in THF (2 mL) is added lithium aluminium hydride (21 mg, 0.57 mmol) at 0° C., and the reaction mixture is stirred at room temperature for 1 hour. The reaction mixture is added 10% aqueous citric acid and extracted with DCM (10 mL×2), and dried over sodium sulfate. Insoluble materials are separated by filtration and the filtrate is concentrated. The residue is purified by column chromatography on silica-gel eluting with n-hexane/EtOAc (1:1 to 1:3) to give 48 mg (63% yield) of the title compound as a pale yellow oil.
$^1$H-NMR (400 MHz, CDCl$_3$) delta 8.10 (1H, d, J=2.7 Hz), 7.71 (1H, d, J=2.7 Hz), 4.63 (2H, d, J=6.4 Hz), 4.30 (2H, d, J=6.9 Hz), 2.83-2.70 (1H, m), 2.23-2.17 (1H, m), 2.17-2.07 (2H, m), 2.01-1.79 (4H, m), MS (ESI) m/z: 272 (M+H)$^+$.

Aryl Halide-11: (3-bromo-6-(cyclobutylmethoxy)pyridin-2-yl)methanol

<Step-1>: 3-bromo-6-(cyclobutylmethoxy)picolinic acid

The title compound is prepared in quantitative yield (216 mg, a pale yellow gum) by the similar manner to Step-1 of Acid-1 using ethyl 3-bromo-6-chloropicolinate (200 mg, 0.76 mmol). In this condition, hydrolysis product is obtained.
MS (ESI) m/z: 286 (M+H)$^+$.

<Step-2>: (3-bromo-6-(cyclobutylmethoxy)pyridin-2-yl)methanol

The title compound is prepared in 15% yield (31 mg, a pale yellow oil) by the similar manner to Step-2 of Aryl halide-10 using 3-bromo-6-(cyclobutylmethoxy)picolinic acid (216 mg, 0.76 mmol).
$^1$H-NMR (400 MHz, CDCl$_3$) delta 7.67 (1H, d, J=8.7 Hz), 6.59 (1H, dt, J=8.7, 0.9 Hz), 4.67 (2H, dd, J=4.6, 0.9 Hz), 4.28 (2H, d, J=6.9 Hz), 4.03 (1H, t, J=6.9 Hz), 2.85-2.71 (1H, m), 2.19-2.08 (2H, m), 2.03-1.79 (4H, m), MS (ESI) m/z: 272 (M+H)$^+$.

Aryl Halide-12: 2-chloro-5-(cyclobutylmethoxy)-3-methylpyridine

<Step-1>: 2-chloro-5-(cyclobutylmethoxy)-3-methylpyridine

The title compound is prepared in 94% yield (160 mg, a colorless liquid) by the similar manner to Step-1 of Acid-46 using 6-chloro-5-methylpyridin-3-ol (200 mg, 1.4 mmol) and (bromomethyl)cyclobutane (249 mg, 1.7 mmol).
$^1$H-NMR (400 MHz, CDCl$_3$) delta 7.89 (1H, d, J=3.0 Hz), 7.10 (1H, d, J=2.4 Hz), 3.94 (2H, d, J=6.1 Hz), 2.80-2.72 (1H, m), 2.34 (3H, s), 2.18-2.10 (2H, m), 2.00-1.83 (4H, m), MS (ESI) m/z: 212 (M+H)$^+$.

Aryl Halide-13: 2-chloro-4-(cyclopropylmethoxy)-3-methylpyridine

<Step-1>: 2-chloro-4-(cyclopropylmethoxy)-3-methylpyridine

The title compound is prepared in 77% yield (208 mg, a white solid) by the similar manner to Step-1 of Acid-1 using 2-chloro-4-fluoro-3-methylpyridine (200 mg, 1.4 mmol).
$^1$H-NMR (400 MHz, CDCl$_3$) delta 8.09 (1H, d, J=5.8 Hz), 6.66 (1H, d, J=5.8 Hz), 3.87 (2H, d, J=6.7 Hz), 2.28 (3H, s), 1.34-1.22 (1H, m), 0.71-0.61 (2H, m), 0.43-0.32 (2H, m), MS (ESI) m/z: 198 (M+H)$^+$.

Aryl Halide-14: 2-chloro-4-(cyclopropylmethoxy)pyridine

<Step-1>: 2-chloro-4-(cyclopropylmethoxy)pyridine

The title compound is prepared in 88% yield (1.3 g, a pale brown oil) by the similar manner to Step-1 of Acid-46 using 2-chloropyridin-4-ol (1.0 g, 7.7 mmol).
$^1$H-NMR (400 MHz, CDCl$_3$) delta 8.17 (1H, d, J=5.5 Hz), 6.82 (1H, d, J=2.4 Hz), 6.74 (1H, dd, J=6.1, 2.4 Hz), 3.85

(2H, d, J=7.3 Hz), 1.32-1.22 (1H, m), 0.75-0.66 (2H, m), 0.42-0.36 (2H, m), MS (ESI) m/z: 184 (M+H)$^+$.

Aryl Halide-15:
4-bromo-2-(cyclopropylmethoxy)-3-methylpyridine

<Step-1>:
4-bromo-2-(cyclopropylmethoxy)-3-methylpyridine

The title compound is prepared in 78% yield (199 mg, a colorless oil) by the similar manner to Step-1 of Acid-1 using 4-bromo-2-fluoro-3-methylpyridine (200 mg, 1.1 mmol).
$^1$H-NMR (400 MHz, CDCl$_3$) delta 7.75 (1H, d, J=5.3 Hz), 7.03 (1H, d, J=5.3 Hz), 4.14 (2H, d, J=7.0 Hz), 2.31 (3H, s), 1.35-1.21 (1H, m), 0.63-0.54 (2H, m), 0.40-0.30 (2H, m), MS (ESI) m/z: 242, 244 (M+H)$^+$.

Aryl Halide-16: 4-bromo-N-(cyclopropylmethyl)-N-methylpyridin-2-amine

<Step-1>: 4-bromo-N-(cyclopropylmethyl)-N-methylpyridin-2-amine

A mixture of 4-bromo-2-fluoropyridine (362 mg, 2.1 mmol), 1-cyclopropyl-N-methylmethanamine hydrochloride (300 mg, 2.5 mmol), and N,N-diisopropylethylamine (1.1 mL, 6.2 mmol) in DMSO (3 mL) is stirred at 120° C. The reaction mixture is diluted with EtOAc/n-hexane (4:1, 50 mL), washed with water (20 mL×3), and dried over sodium sulfate. Insoluble materials are separated by filtration and the filtrate is concentrated. The residue is purified by column chromatography on silica-gel eluting with n-hexane/EtOAc (15:1) to give 289 mg (58% yield) of the title compound as a colorless oil.
$^1$H-NMR (400 MHz, CDCl$_3$) delta 7.96 (1H, d, J=5.0 Hz), 6.68-6.66 (2H, m), 3.43 (2H, d, J=6.4 Hz), 3.07 (3H, s), 1.08-0.98 (1H, m), 0.54-0.48 (2H, m), 0.29-0.23 (2H, m), MS (ESI) m/z: 241 (M+H)$^+$.

Aryl Halide-17:
2-chloro-5-(cyclobutylmethoxy)pyrazine

<Step-1>: 2-chloro-5-(cyclobutylmethoxy)pyrazine

The title compound is prepared in 85% yield (1.1 g, a pale yellow liquid) by the similar manner to Step-1 of Acid-1 using 2,5-dichloropyrazine (1.0 g, 6.7 mmol) and cyclobutylmethanol (0.64 g, 7.4 mmol).
$^1$H-NMR (400 MHz, CDCl$_3$) delta 8.07 (1H, d, J=1.2 Hz), 8.00 (1H, d, J=1.2 Hz), 4.27 (2H, d, J=6.7 Hz), 2.82-2.73 (1H, m), 2.17-2.09 (2H, m), 2.02-1.82 (4H, m).

Aryl Halide-18:
2-chloro-6-(cyclopropylmethoxy)pyrazine

<Step-1>: 2-chloro-6-(cyclopropylmethoxy)pyrazine

The title compound is prepared in 83% yield (1.0 g, a brown liquid) by the similar manner to Step-1 of Acid-1 using 2,6-dichloropyrazine (1.0 g, 6.7 mmol).
$^1$H-NMR (400 MHz, CDCl$_3$) delta 8.17 (1H, s), 8.15 (1H, s), 4.19 (2H, d, J=7.4 Hz), 1.37-1.25 (1H, m), 0.70-0.65 (2H, m), 0.42-0.38 (2H, m).

Aryl Halide-19:
4-chloro-6-(cyclopropylmethoxy)-5-methylpyrimidine

<Step-1>:
4-chloro-6-(cyclopropylmethoxy)-5-methylpyrimidine

To a stirred solution of 4,6-dichloro-5-methylpyrimidine (1.0 g, 6.1 mmol), cyclopropylmethanol (0.49 g, 6.8 mmol) in THF (25 mL) is added potassium tert-butoxide (0.83 g, 7.4 mmol) at 0° C., and the reaction mixture is stirred at 0° C. for 2 hours. The reaction mixture is added saturated aqueous NH$_4$Cl (20 mL) and water (80 mL), and extracted with EtOAc (80 mL). The organic layer is washed with water (80 mL×2), and dried over sodium sulfate. Insoluble materials are separated by filtration and the filtrate is concentrated. The residue is purified by column chromatography on silica-gel eluting with n-hexane/EtOAc (99:1 to 95:5) to give 1.2 g (98% yield) of the title compound as a white solid.
$^1$H-NMR (400 MHz, CDCl$_3$) delta 8.38 (1H, s), 4.27-4.18 (2H, d, J=7.4 Hz), 2.25 (3H, s), 1.34-1.24 (1H, m), 0.65-0.59 (2H, m), 0.38-0.34 (2H, m), MS (ESI) m/z: 199 (M+H)$^+$.

Aryl Halide-20:
5-bromo-2-(cyclopropylmethoxy)-4-methylpyrimidine

<Step-1>:
5-bromo-2-(cyclopropylmethoxy)-4-methylpyrimidine

The title compound is prepared in 50% yield (117 mg, an orange colored oil) by the similar manner to Step-1 of Acid-1 using 5-bromo-2-chloro-4-methylpyrimidine (200 mg, 0.96 mmol).
$^1$H-NMR (400 MHz, CDCl$_3$) delta 8.41 (1H, s), 4.16 (2H, d, J=7.0 Hz), 2.55 (3H, s), 1.38-1.23 (1H, m), 0.68-0.55 (2H, m), 0.43-0.32 (2H, m), MS (ESI) m/z: 243 (M+H)$^+$.

Aryl Halide-21: 5-bromo-N-(cyclopropylmethyl)-N-methylpyrimidin-2-amine

<Step-1>: 5-bromo-N-(cyclopropylmethyl)-N-methylpyrimidin-2-amine

The title compound is prepared in 82% yield (258 mg, a colorless oil) by the similar manner to Step-1 of Aryl halide-16 using 5-bromo-2-chloropyrimidine (250 mg, 1.3 mmol).
$^1$H-NMR (400 MHz, CDCl$_3$) delta 8.27 (2H, s), 3.49 (2H, d, J=6.4 Hz), 3.17 (3H, s), 1.11-1.01 (1H, m), 0.53-0.47 (2H, m), 0.29-0.24 (2H, m), MS (ESI) m/z: 242 (M+H)$^+$.

Aryl Halide-22: tert-butyl (2-(3-bromo-5-(cyclopropylmethoxy)phenoxy)ethyl)carbamate <Step-1>: 3-bromo-5-(cyclopropylmethoxy)phenol The title compound is prepared in 63% yield (451 mg, a colorless oil) by the similar manner to Step-1 of Acid-46 using 5-bromobenzene-1,3-diol (1.7 g, 8.9 mmol).
$^1$H-NMR (400 MHz, CDCl$_3$) delta 6.65-6.63 (1H, m), 6.60-6.58 (1H, m), 6.34-6.32 (1H, m), 4.88 (1H, s), 3.75

(2H, d, J=7.3 Hz), 1.29-1.20 (1H, m), 0.67-0.61 (2H, m), 0.36-0.31 (2H, m), MS (ESI) m/z: 241 (M–H)⁻.

<Step-2>: tert-butyl (2-(3-bromo-5-(cyclopropyl-methoxy)phenoxy)ethyl)carbamate

To a stirred solution of 3-bromo-5-(cyclopropylmethoxy) phenol (Step-1 of Aryl halide-22, 220 mg, 0.91 mmol), tert-butyl (2-bromoethyl)carbamate (406 mg, 1.8 mmol), and potassium iodide in DMF (6 mL) is added cesium carbonate (885 mg, 2.7 mmol), and stirred at 90° C. for 3 hours. The reaction mixture is diluted with EtOAc (50 mL) and washed with water (20 mL×3), and dried over sodium sulfate. Insoluble materials are separated by filtration and the filtrate is concentrated. The residue is purified by column chromatography on silica-gel eluting with n-hexane/EtOAc (10:1) to give 348 mg (100% yield) of the title compound as a colorless oil.
$^1$H-NMR (400 MHz, CDCl$_3$) delta 6.67-6.63 (2H, m), 6.39-6.37 (1H, m), 4.93 (1H, br.s), 3.99-3.95 (2H, m), 3.75 (2H, d, J=7.3 Hz), 3.53-3.47 (2H, m), 1.45 (9H, s), 1.29-1.20 (1H, m), 0.67-0.62 (2H, m), 0.36-0.31 (2H, m).

Aryl Halide-23:
2-(3-bromo-5-(cyclopropylmethoxy)phenoxy)acetamide

<Step-1>:
2-(3-bromo-5-(cyclopropylmethoxy)phenoxy)acetamide

The title compound is prepared in 84% yield (227 mg, a white solid) by the similar manner to Step-2 of Aryl halide-22 using 2-chloroacetamide (169 mg, 1.8 mmol).
$^1$H-NMR (400 MHz, CDCl$_3$) delta 6.73-6.72 (1H, m), 6.69-6.68 (1H, m), 6.43 (1H, br.s), 6.42-6.40 (1H, m), 5.68 (1H, br.s), 4.45 (2H, s), 3.76 (2H, d, J=6.9 Hz), 1.30-1.21 (1H, m), 0.68-0.63 (2H, m), 0.36-0.32 (2H, m), MS (ESI) m/z: 300 (M+H)⁺.

Aryl Halide-24: 1-bromo-3-(cyclopropylmethoxy)-5-(2-methoxyethoxy)benzene

<Step-1>: 1-bromo-3-(cyclopropylmethoxy)-5-(2-methoxyethoxy)benzene

The title compound is prepared in 85% yield (317 mg, a colorless oil) by the similar manner to Step-2 of Aryl halide-22 using 1-bromo-2-methoxyethane (257 mg, 1.9 mmol).
$^1$H-NMR (400 MHz, CDCl$_3$) delta 6.68-6.65 (2H, m), 6.43-6.41 (1H, m), 4.08-4.05 (2H, m), 3.75-3.71 (4H, m), 3.44 (3H, s), 1.30-1.20 (1H, m), 0.66-0.61 (2H, m), 0.35-0.30 (2H, m), MS (ESI) m/z: 301 (M+H)⁺.

Aryl Halide-25:
2-(3-bromo-5-(cyclopropylmethoxy)phenoxy)ethanol

<Step-1>:
2-(3-bromo-5-(cyclopropylmethoxy)phenoxy)ethanol

To a stirred solution of 3-bromo-5-(cyclopropylmethoxy) phenol (Step-1 of Aryl halide-22, 300 mg, 1.2 mmol), (2-bromoethoxy)(tert-butyl)dimethylsilane (443 mg, 1.9 mmol), and potassium iodide in DMF (8 mL) is added cesium carbonate (1.2 g, 3.7 mmol), and stirred at 70° C. for 2 hours. After removal of the solvents, the residue is purified by column chromatography on silica-gel eluting with n-hexane/EtOAc (30:1) to give TBS-protected compound. The residue is dissolved in THF (6 mL) and 1M TBAF in THF (2.5 mL, 2.5 mmol) is added at room temperature with stirring, and the reaction mixture is stirred at room temperature for 1 hour. The reaction mixture is diluted with EtOAc (50 mL), washed with water (30 mL×3), and dried over sodium sulfate. Insoluble materials are separated by filtration and the filtrate is concentrated. The residue is purified by column chromatography on silica-gel eluting with n-hexane/EtOAc (2:1) to give 318 mg (90% yield) of the title compound as a colorless oil.
$^1$H-NMR (400 MHz, CDCl$_3$) delta 6.68-6.66 (2H, m), 6.42-6.40 (1H, m), 4.05-4.02 (2H, m), 3.96-3.92 (2H, m), 3.76 (2H, d, J=6.9 Hz), 1.96 (1H, t, J=6.4 Hz), 1.30-1.20 (1H, m), 0.68-0.62 (2H, m), 0.36-0.31 (2H, m), MS (ESI) m/z: 287 (M+H)⁺.

Aryl Halide-26: (3-bromo-5-(cyclopropylmethoxy) phenyl)(morpholino)methanone

<Step-1>: (3-bromo-5-(cyclopropylmethoxy)phenyl)(morpholino)methanone

To a stirred solution of 3-bromo-5-(cyclopropylmethoxy) benzoic acid (100 mg, 0.37 mmol), morpholine (64 mg, 0.74 mmol), and N,N-diisopropylethylamine (0.19 mL, 1.1 mmol) in DMF (1.5 mL) is added HBTU at room temperature, and the reaction mixture is stirred at 50° C. for 1 hour. The reaction mixture is diluted with EtOAc (10 mL) and washed with water (5 mL×2), and dried over sodium sulfate. Insoluble materials are separated by filtration and the filtrate is concentrated. The residue is purified by column chromatography on NH-gel eluting with EtOAc only to give 125 mg (100% yield) of the title compound as a colorless oil.
MS (ESI) m/z: 340 (M+H)⁺.

Aryl Halide-27:
3-bromo-5-(cyclopropylmethoxy)-N-methylbenzamide

<Step-1>:
3-bromo-5-(cyclopropylmethoxy)-N-methylbenzamide

The title compound is prepared in 92% yield (144 mg, a pale yellow solid) by the similar manner to Step-1 of Aryl halide-26 using methylamine hydrochloride (374 mg, 5.5 mmol).
MS (ESI) m/z: 284 (M+H)⁺.

Aryl Halide-28: 3-bromo-5-(cyclopropylmethoxy)-N,N-dimethylbenzamide

<Step-1>: 3-bromo-5-(cyclopropylmethoxy)-N,N-dimethylbenzamide

The title compound is prepared in 92% yield (152 mg, a pale yellow oil) by the similar manner to Step-1 of Aryl halide-26 using dimethylamine hydrochloride (451 mg, 5.5 mmol).
MS (ESI) m/z: 298 (M+H)⁺.

Aryl Halide-29: 2-(3-bromo-5-(cyclopropyl-methoxy)phenoxy)-N,N-dimethylacetamide <Step-1>: 2-(3-bromo-5-(cyclopropylmethoxy)phenoxy)-N,N-dimethylacetamide The title compound is prepared in 87% yield (236 mg, a colorless oil) by the similar manner to Step-2 of Aryl halide-22 using 2-chloro-N,N-dimethylacetamide (200 mg, 1.6 mmol).

$^1$H-NMR (400 MHz, CDCl$_3$) delta 6.69-6.68 (2H, m), 6.46-6.45 (1H, m), 4.64 (2H, s), 3.75 (2H, d, J=6.9 Hz), 3.06 (3H, s), 2.99 (3H, s), 1.30-1.20 (1H, m), 0.67-0.61 (2H, m), 0.36-0.31 (2H, m), MS (ESI) m/z: 328 (M+H)$^+$.

Aryl Halide-30: (3-bromo-5-(cyclopropylmethoxy) phenyl)(3-methoxyazetidin-1-yl)methanone <Step-1>: (3-bromo-5-(cyclopropylmethoxy)phenyl) (3-methoxyazetidin-1-yl)methanone The title compound is prepared in 36% yield (45 mg, a colorless oil) by the similar manner to Step-1 of Aryl halide-26 using 3-methoxyazetidine hydrochloride (91 mg, 0.74 mmol).
MS (ESI) m/z: 340 (M+H)$^+$.

Aryl Halide-31: 2-((3-bromo-5-(cyclopropyl-methoxy)benzyl)(methyl)amino)ethanol

<Step-1>: 3-bromo-5-(cyclopropylmethoxy)benzaldehyde

The title compound is prepared in 95% yield (969 mg, a colorless oil) by the similar manner to Step-1 of Acid-46 using 3-bromo-5-hydroxybenzaldehyde (800 mg, 4.0 mmol).
$^1$H-NMR (400 MHz, CDCl$_3$) delta 9.89 (1H, s), 7.57-7.56 (1H, m), 7.33-7.30 (2H, m), 3.85 (2H, d, J=6.9 Hz), 1.31-1.22 (1H, m), 0.70-0.65 (2H, m), 0.39-0.34 (2H, m).

<Step-2>: 2-((3-bromo-5-(cyclopropylmethoxy) benzyl)(methyl)amino)ethanol

To a stirred mixture of 3-bromo-5-(cyclopropylmethoxy) benzaldehyde (Step-1 of Aryl halide-31, 200 mg, 0.78 mmol), 2-(methylamino)ethanol (177 mg, 2.4 mmol), acetic acid (0.14 mL, 2.4 mmol) in DCM (5 mL) is added sodium triacetoxyborohydride at room temperature, and the reaction mixture is stirred for 5 hours at room temperature. The reaction mixture is added saturated aqueous NaHCO$_3$ to make the mixture to pH=9. Then, extracted with EtOAc (30 mL), and dried over sodium sulfate. Insoluble materials are separated by filtration and the filtrate is concentrated. The residue is purified by column chromatography on NH-gel eluting with n-hexane/EtOAc (2:1) to give 239 mg (97% yield) of the title compound as a colorless oil.
$^1$H-NMR (400 MHz, CDCl$_3$) delta 7.02 (1H, s), 6.94-6.93 (1H, m), 6.80 (1H, s), 3.77 (2H, d, J=6.9 Hz), 3.63 (2H, t, J=5.3 Hz), 3.48 (2H, s), 2.59 (2H, t, J=5.3 Hz), 2.22 (3H, s), 1.30-1.20 (1H, m), 0.67-0.62 (2H, m), 0.37-0.32 (2H, m), OH is not observed, MS (ESI) m/z: 314, 316 (M+H)$^+$.

Aryl Halide-32: 2-((3-bromo-5-(cyclopropyl-methoxy)benzyl)(methyl)amino)acetamide <Step-1>: 2-((3-bromo-5-(cyclopropylmethoxy) benzyl)(methyl)amino)acetamide The title compound is prepared in 53% yield (257 mg, a white solid) by the similar manner to Step-2 of Aryl halide-31 using 2-(methylamino)acetamide hydrochloride (293 mg, 2.4 mmol).
$^1$H-NMR (400 MHz, CDCl$_3$) delta 7.02 (1H, d, J=1.4 Hz), 6.97 (1H, br.s), 6.95-6.93 (1H, m), 6.78 (1H, d, J=2.3 Hz), 5.75 (1H, br.s), 3.77 (2H, d, J=6.9 Hz), 3.50 (2H, s), 3.03 (2H, s), 2.29 (3H, s), 1.30-1.20 (1H, m), 0.67-0.62 (2H, m), 0.37-0.32 (2H, m), MS (ESI) m/z: 327, 329 (M+H)$^+$.

Amine-1: N-(methylsulfonyl)-4-((3-(6-(piperidin-4-ylmethoxy)pyridin-3-yl)phenoxy)methyl)benzamide dihydrochloride <Step-1>: N-(methylsulfonyl)-4-((3-(6-(piperidin-4-ylmethoxy)pyridin-3-yl)phenoxy)methyl)benzamide dihydrochloride To a stirred mixture of tert-butyl 4-(((5-(3-((4-((methyl-sulfonyl)carbamoyl)benzyl)oxy)phenyl)pyridin-2-yl)oxy) methyl) piperidine-1-carboxylate (Example 11, 179 mg, 0.30 mmol) in EtOAc (1 mL) is added 4M hydrochloric acid in EtOAc (10 mL) at room temperature, and the reaction mixture is stirred for 1 hour at room temperature. The reaction mixture is concentrated to give 140 mg (82% yield) of the title compound as a yellow gum.
MS (ESI) m/z: 496 (M+H)$^+$.

TABLE 3

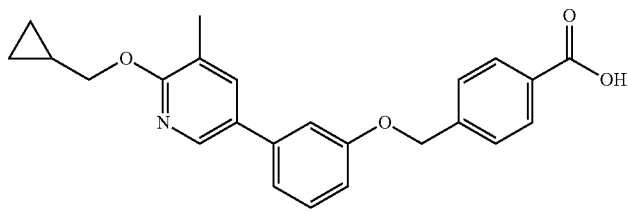

Acid-1

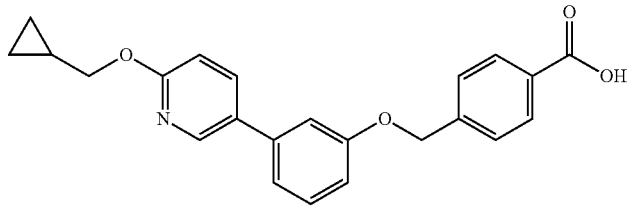 [SMILES: O=C(O)c1ccc(COc2cccc(-c3ccc(OCC4CC4)nc3)c2)cc1]

Acid-2

TABLE 3-continued
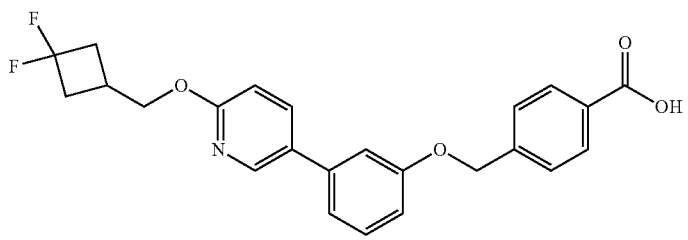 [SMILES: O=C(O)c1ccc(COc2cccc(-c3ccc(OCC4CC(F)(F)C4)nc3)c2)cc1]
Acid-3
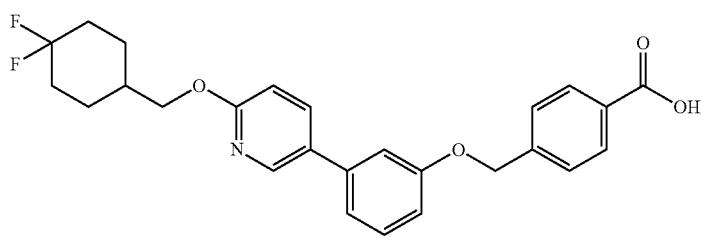 [SMILES: O=C(O)c1ccc(COc2cccc(-c3ccc(OCC4CCC(F)(F)CC4)nc3)c2)cc1]
Acid-4
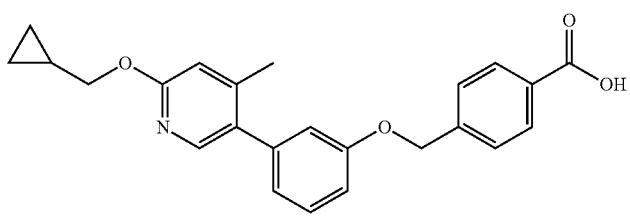 [SMILES: Cc1cc(OCC2CC2)ncc1-c1cccc(OCc2ccc(C(=O)O)cc2)c1]
Acid-5
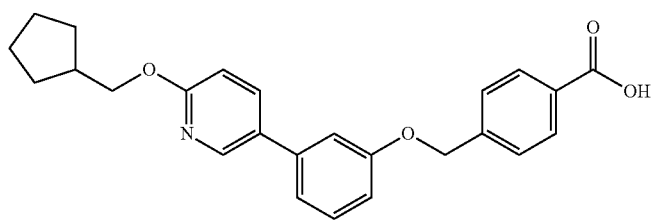 [SMILES: O=C(O)c1ccc(COc2cccc(-c3ccc(OCC4CCCC4)nc3)c2)cc1]
Acid-6
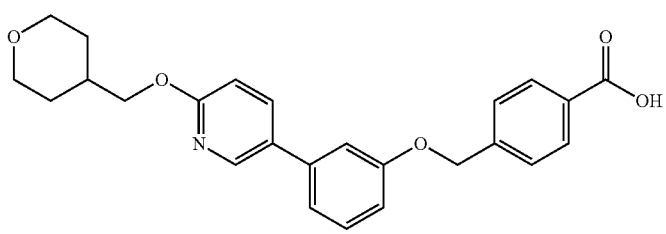 [SMILES: O=C(O)c1ccc(COc2cccc(-c3ccc(OCC4CCOCC4)nc3)c2)cc1]
Acid-7
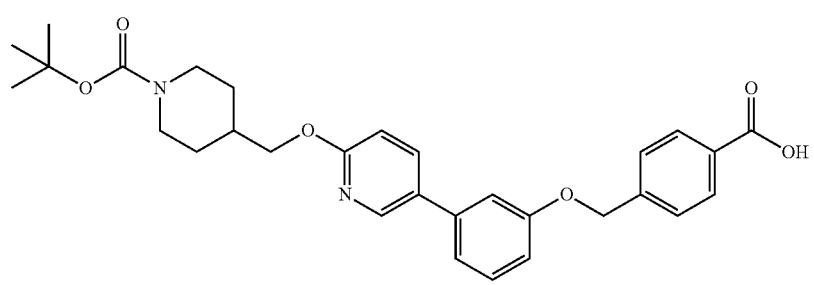 [SMILES: CC(C)(C)OC(=O)N1CCC(COc2ccc(-c3cccc(OCc4ccc(C(=O)O)cc4)c3)cn2)CC1]
Acid-8

TABLE 3-continued
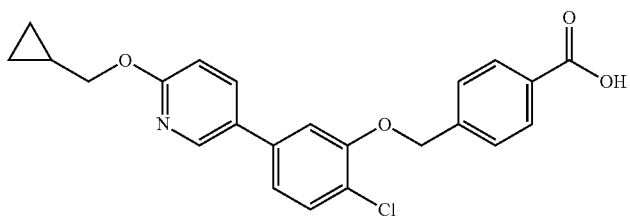 [SMILES: O=C(O)c1ccc(COc2cc(-c3ccc(OCC4CC4)nc3)ccc2Cl)cc1]
Acid-9
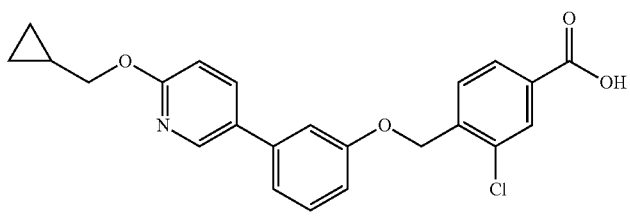 [SMILES: O=C(O)c1ccc(COc2cccc(-c3ccc(OCC4CC4)nc3)c2)c(Cl)c1]
Acid-10
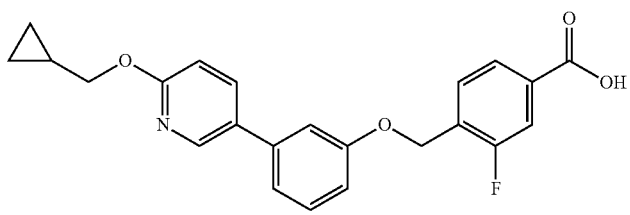 [SMILES: O=C(O)c1ccc(COc2cccc(-c3ccc(OCC4CC4)nc3)c2)c(F)c1]
Acid-11
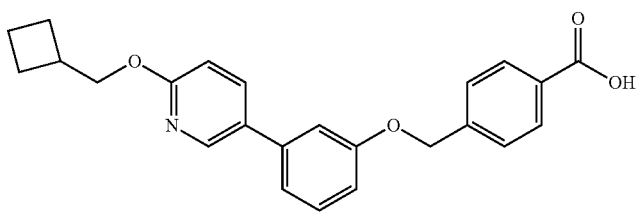 [SMILES: O=C(O)c1ccc(COc2cccc(-c3ccc(OCC4CCC4)nc3)c2)cc1]
Acid-12
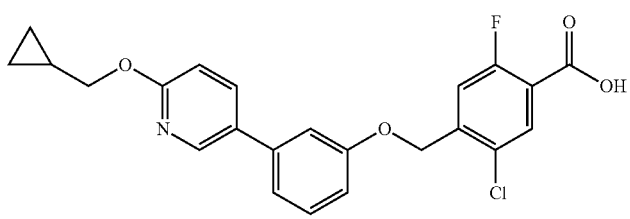 [SMILES: O=C(O)c1cc(Cl)c(COc2cccc(-c3ccc(OCC4CC4)nc3)c2)cc1F]
Acid-13
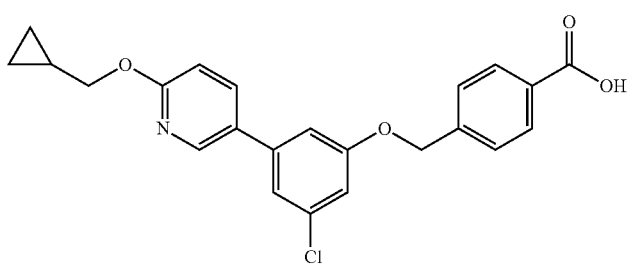
Acid-14
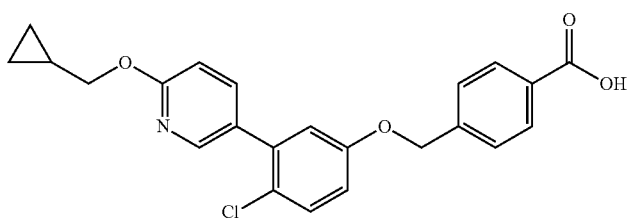 [SMILES: O=C(O)c1ccc(COc2ccc(Cl)c(-c3ccc(OCC4CC4)nc3)c2)cc1]
Acid-15

TABLE 3-continued
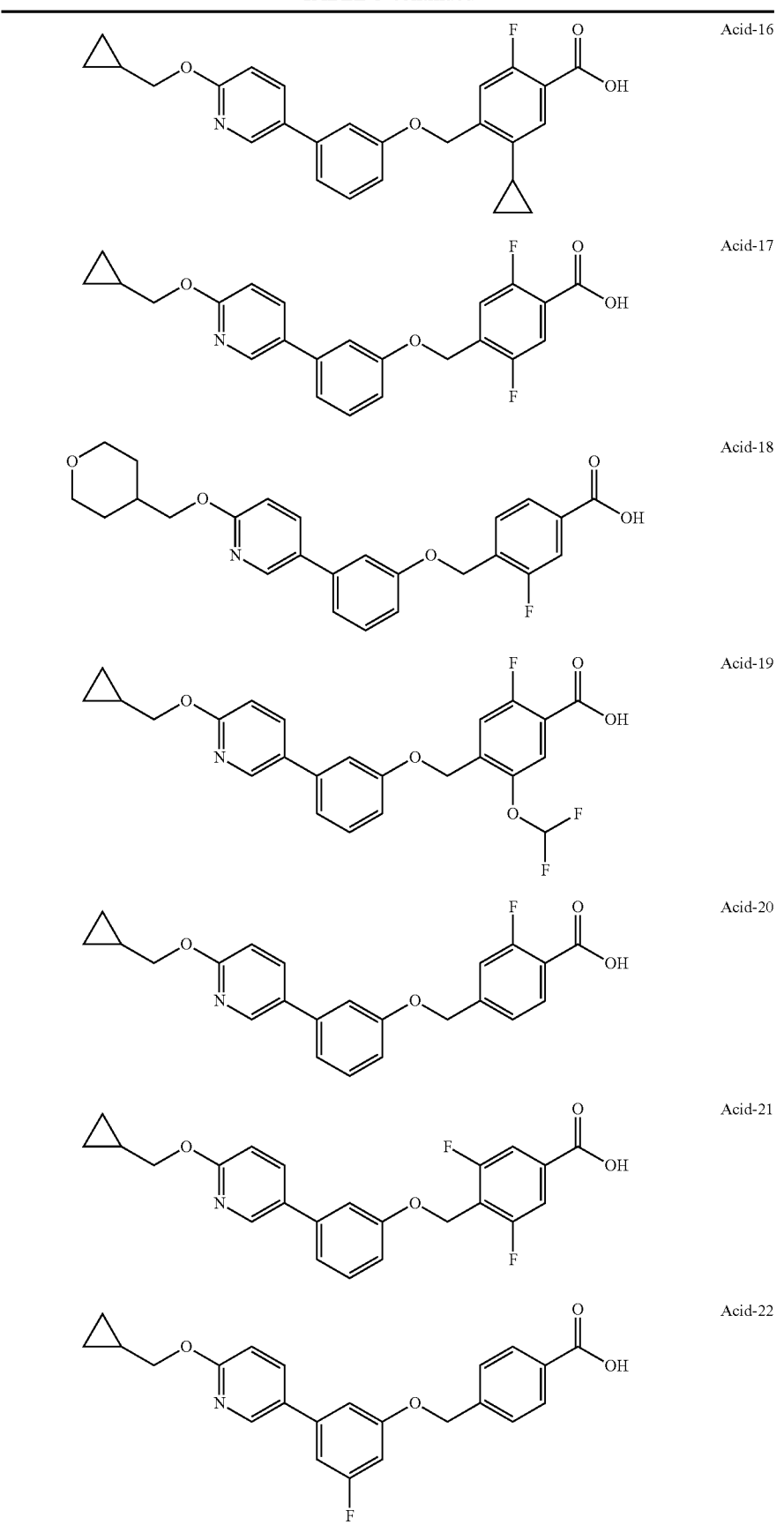

TABLE 3-continued
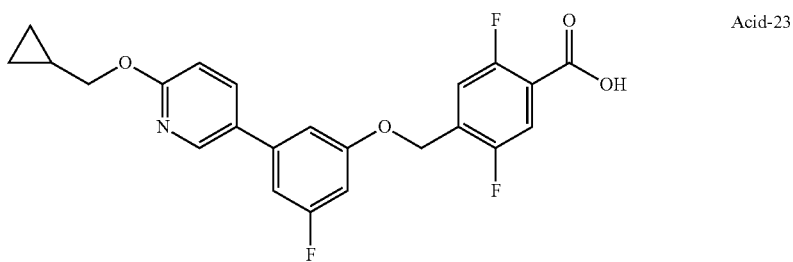
Acid-23
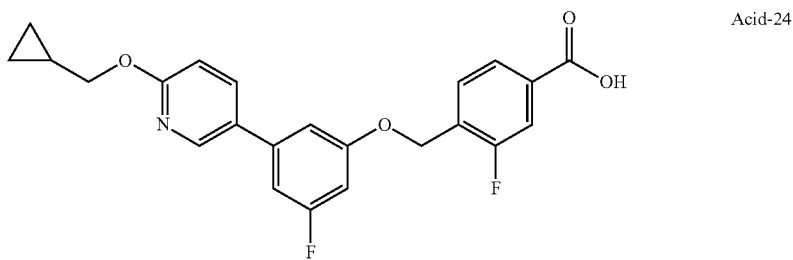
Acid-24
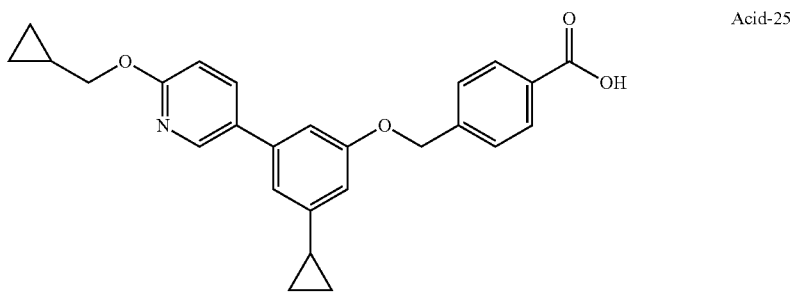
Acid-25
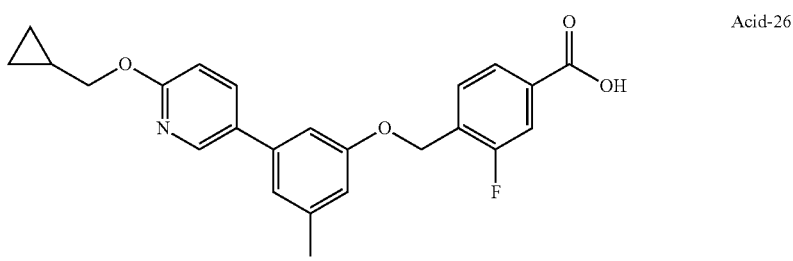
Acid-26
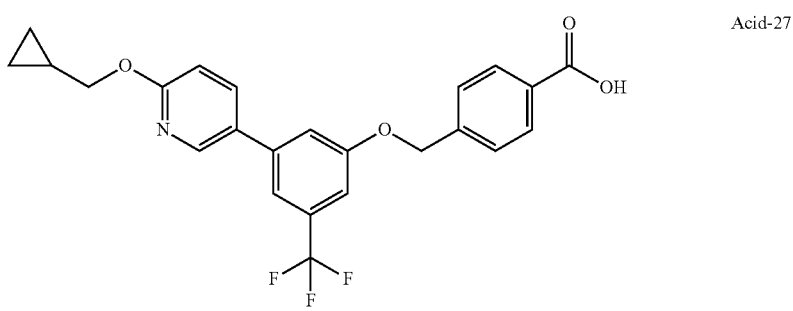
Acid-27
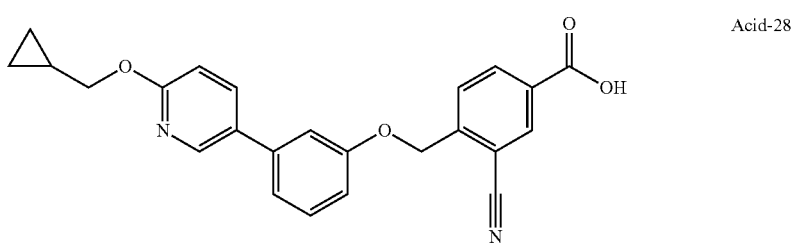
Acid-28

TABLE 3-continued
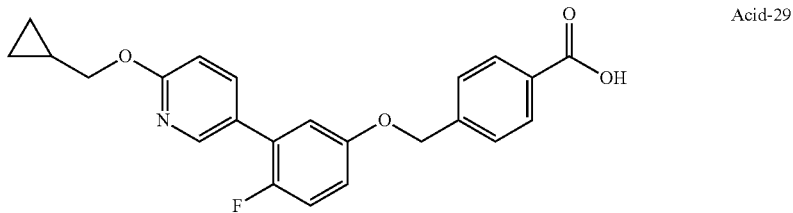 Acid-29
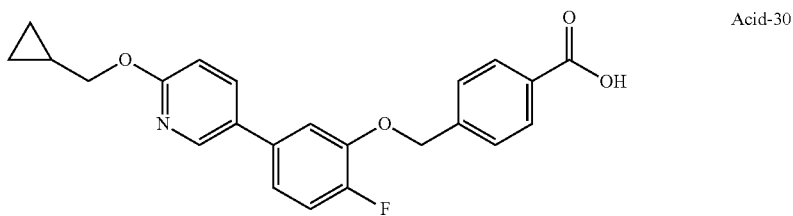 Acid-30
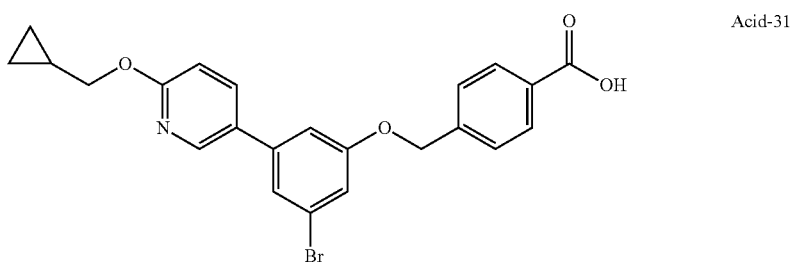 Acid-31
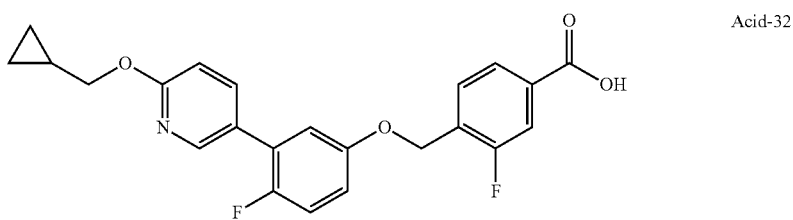 Acid-32
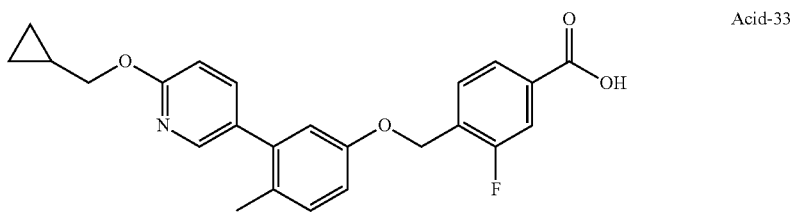 Acid-33
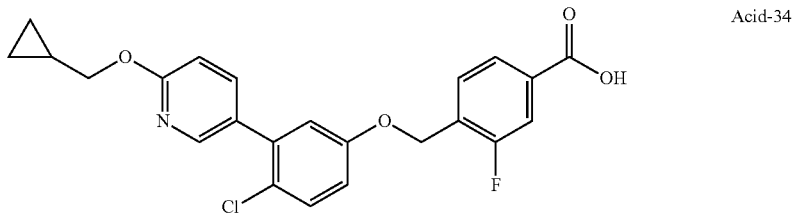 Acid-34
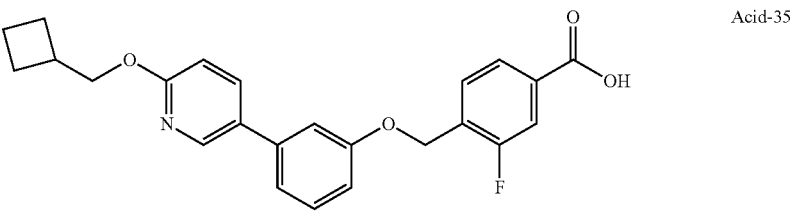 Acid-35

TABLE 3-continued
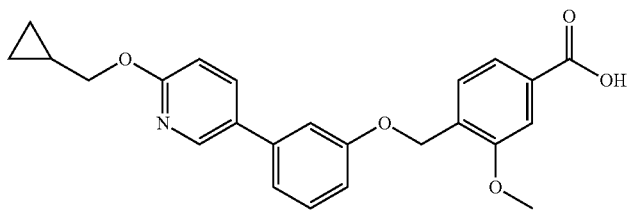 [SMILES: COc1cc(C(=O)O)ccc1COc1cccc(-c2ccc(OCC3CC3)nc2)c1] Acid-36
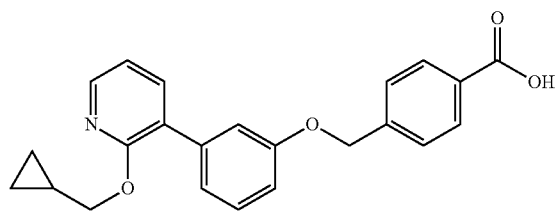 [SMILES: O=C(O)c1ccc(COc2cccc(-c3cccnc3OCC3CC3)c2)cc1] Acid-37
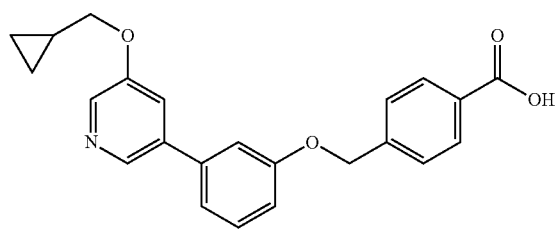 [SMILES: O=C(O)c1ccc(COc2cccc(-c3cncc(OCC4CC4)c3)c2)cc1] Acid-38
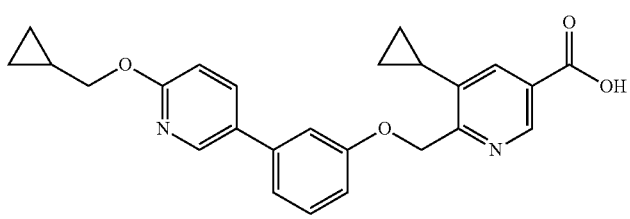 [SMILES: O=C(O)c1cnc(COc2cccc(-c3ccc(OCC4CC4)nc3)c2)c(C2CC2)c1] Acid-39
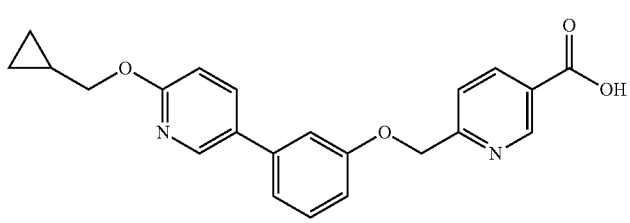 [SMILES: O=C(O)c1ccc(COc2cccc(-c3ccc(OCC4CC4)nc3)c2)nc1] Acid-40
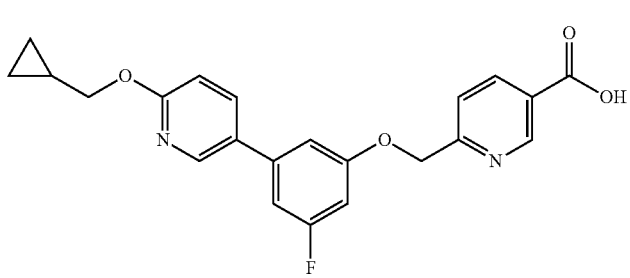 [SMILES: O=C(O)c1ccc(COc2cc(F)cc(-c3ccc(OCC4CC4)nc3)c2)nc1] Acid-41
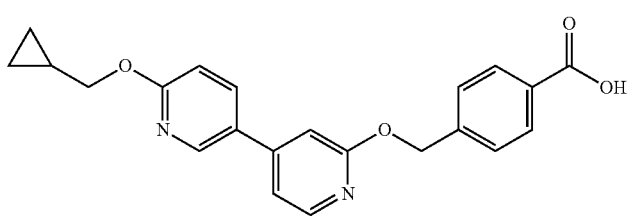 [SMILES: O=C(O)c1ccc(COc2cc(-c3ccc(OCC4CC4)nc3)ccn2)cc1] Acid-42

TABLE 3-continued
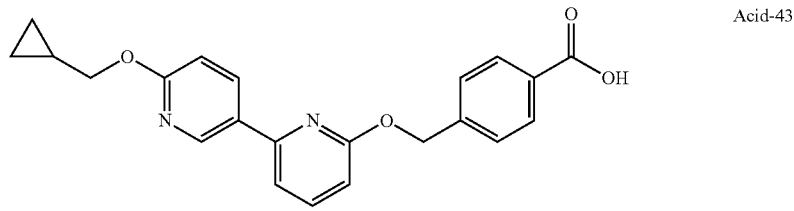
Acid-43
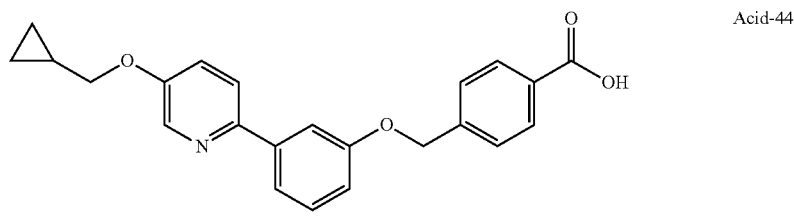
Acid-44
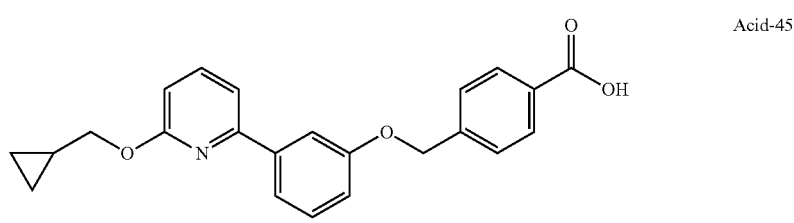
Acid-45
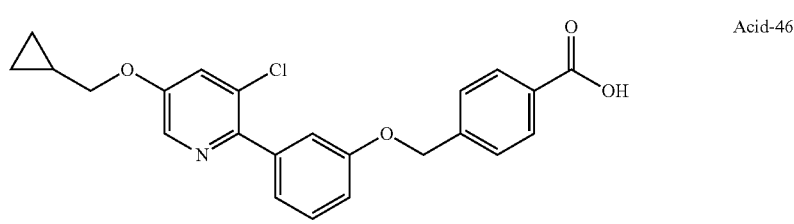
Acid-46
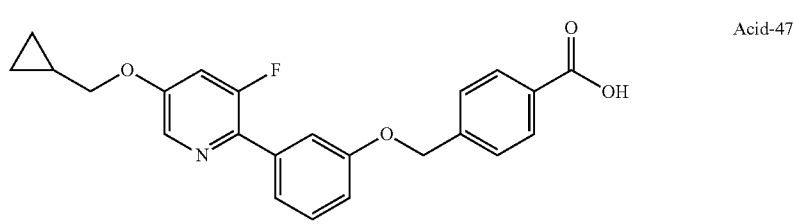
Acid-47
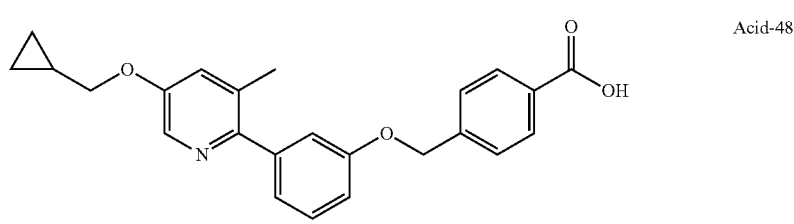
Acid-48
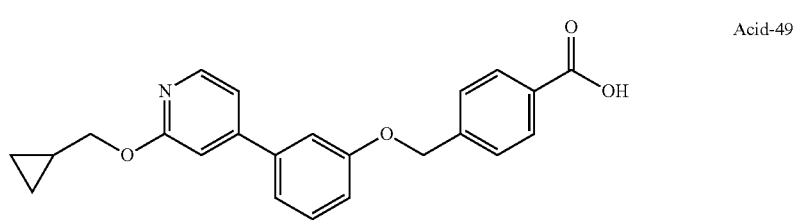
Acid-49

TABLE 3-continued
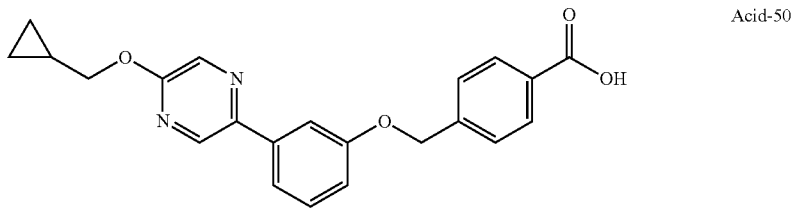 Acid-50
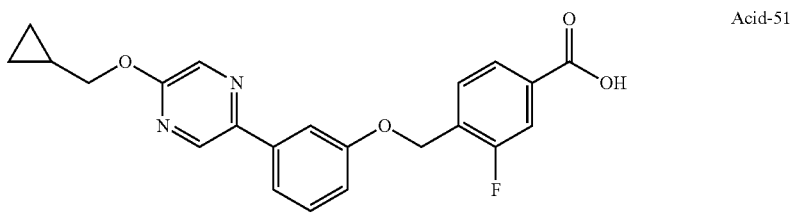 Acid-51
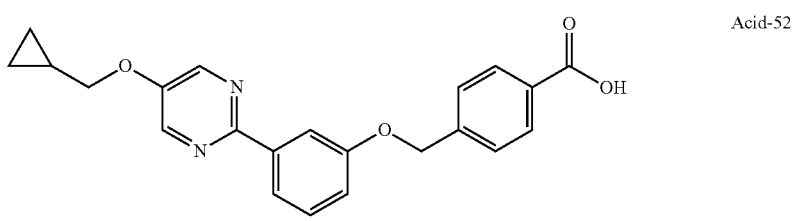 Acid-52
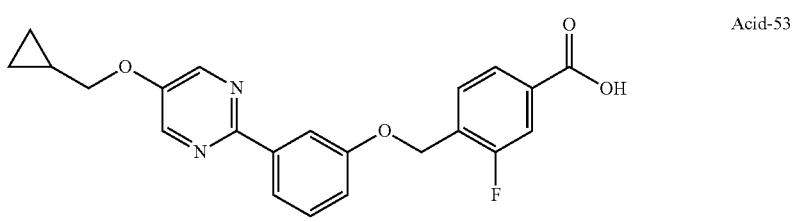 Acid-53
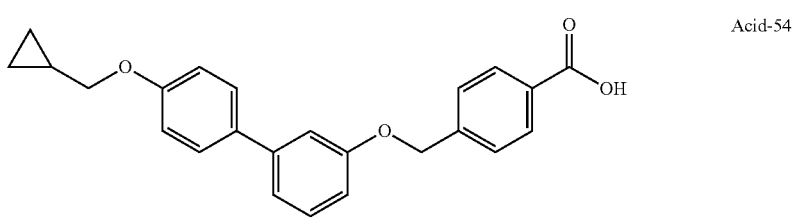 Acid-54
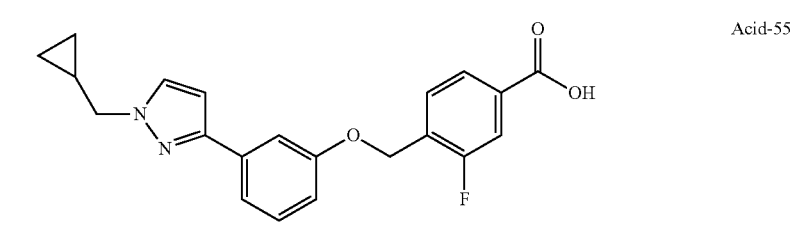 Acid-55
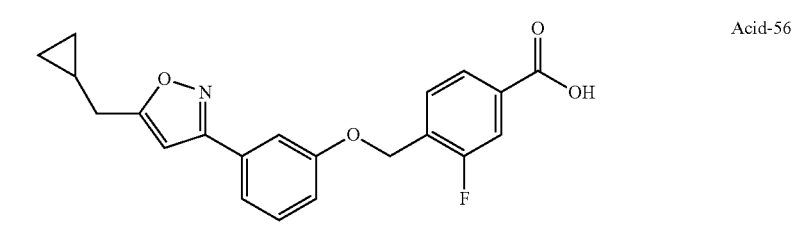 Acid-56

TABLE 3-continued
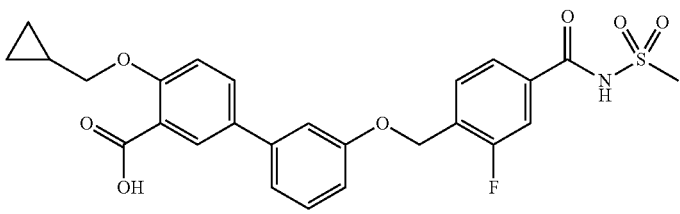 [SMILES: CS(=O)(=O)NC(=O)c1ccc(COc2cccc(-c3ccc(OCC4CC4)c(C(=O)O)c3)c2)c(F)c1]
Acid-57
TABLE 4
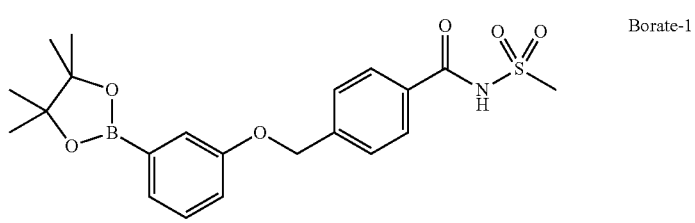
Borate-1
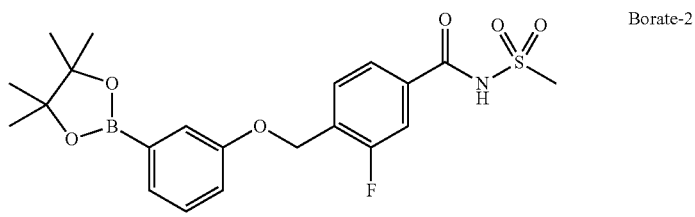
Borate-2
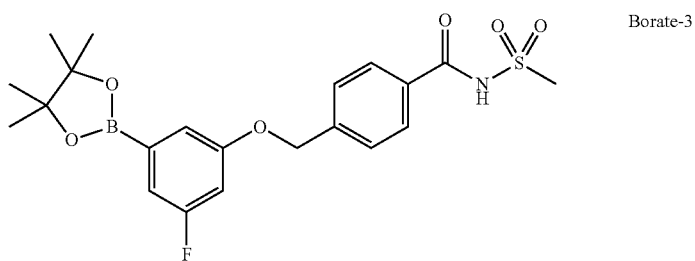
Borate-3
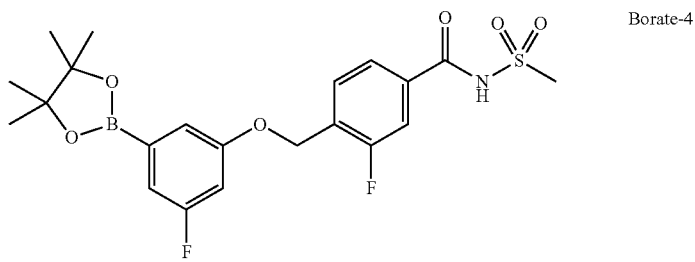
Borate-4
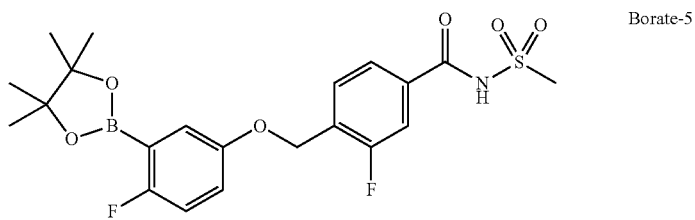
Borate-5

TABLE 4-continued
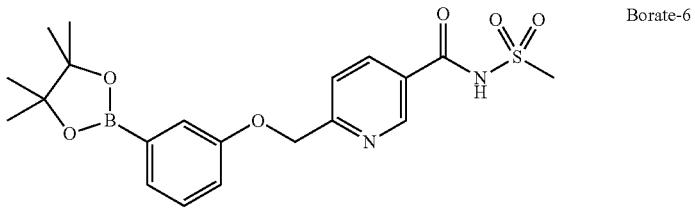
Borate-6
TABLE 5
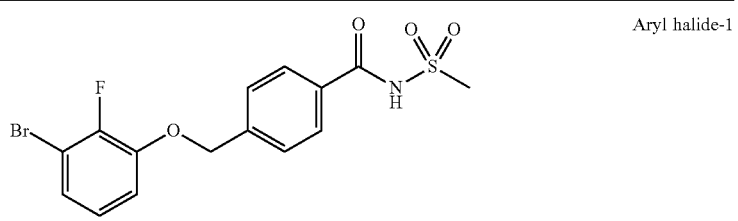
Aryl halide-1
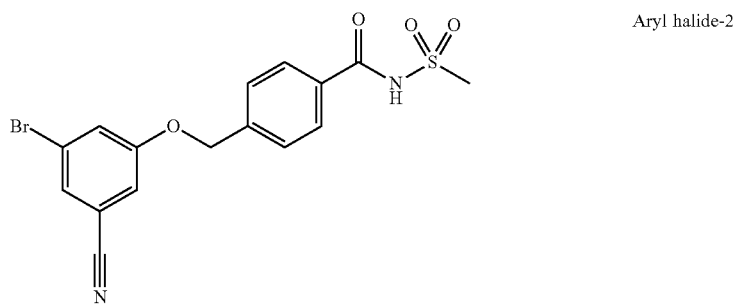
Aryl halide-2
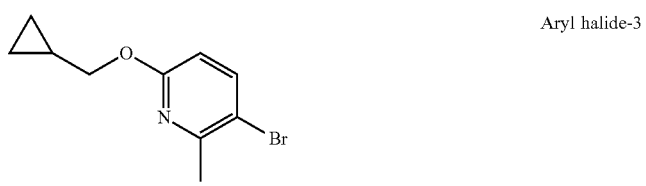
Aryl halide-3
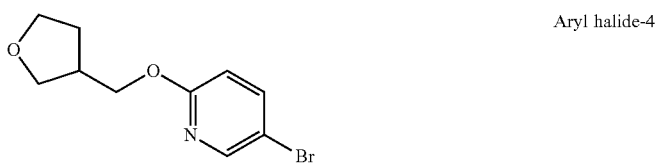
Aryl halide-4
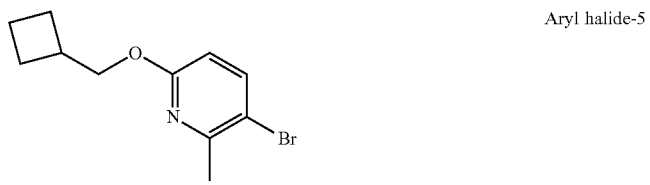
Aryl halide-5
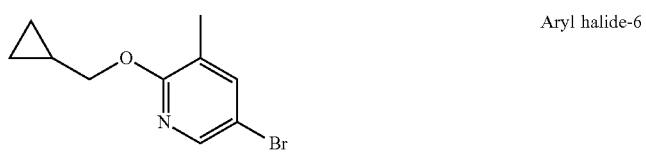
Aryl halide-6

TABLE 5-continued
| | |
|---|---|
| 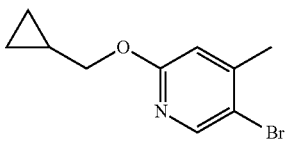 | Aryl halide-7 |
| 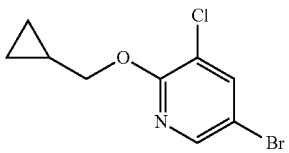 [SMILES: Clc1cc(Br)cnc1OCC1CC1] | Aryl halide-8 |
| 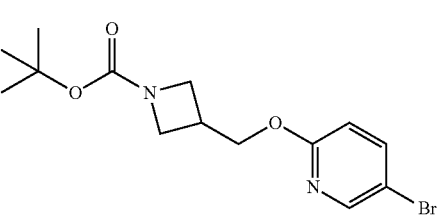 [SMILES: CC(C)(C)OC(=O)N1CC(COc2ccc(Br)cn2)C1] | Aryl halide-9 |
| 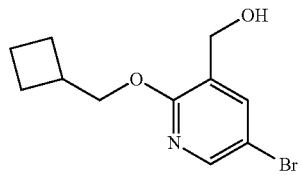 [SMILES: OCc1cc(Br)cnc1OCC1CCC1] | Aryl halide-10 |
| 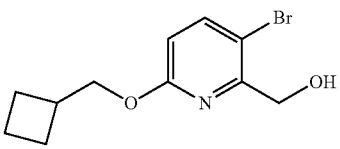 [SMILES: OCc1nc(OCC2CCC2)ccc1Br] | Aryl halide-11 |
| 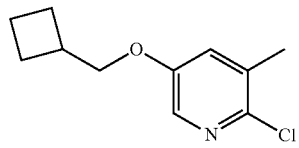 | Aryl halide-12 |
| 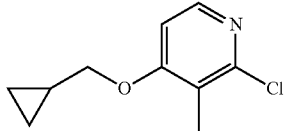 | Aryl halide-13 |
|  | Aryl halide-14 |
| 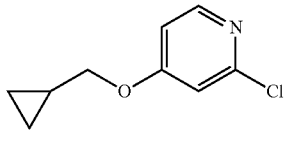 | Aryl halide-15 |
| 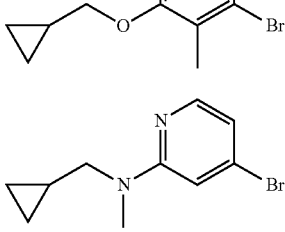 | Aryl halide-16 |

TABLE 5-continued
| | |
|---|---|
| 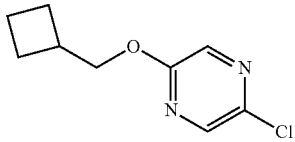 [SMILES: Clc1cnc(OCC2CCC2)cn1] | Aryl halide-17 |
| 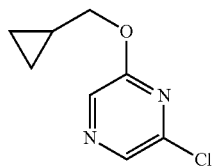 [SMILES: Clc1cncc(OCC2CC2)n1] | Aryl halide-18 |
| 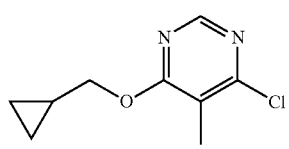 | Aryl halide-19 |
| 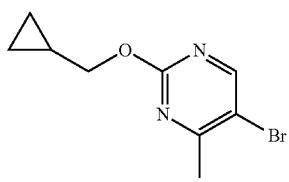 | Aryl halide-20 |
| 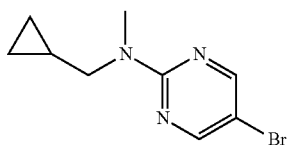 | Aryl halide-21 |
| 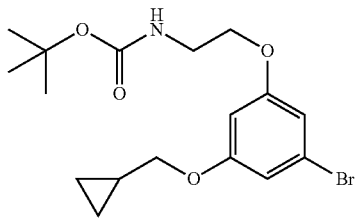 [SMILES: CC(C)(C)OC(=O)NCCOc1cc(Br)cc(OCC2CC2)c1] | Aryl halide-22 |
| 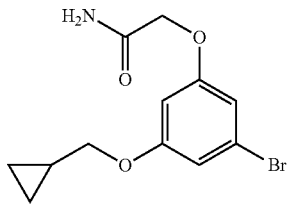 [SMILES: NC(=O)COc1cc(Br)cc(OCC2CC2)c1] | Aryl halide-23 |
| 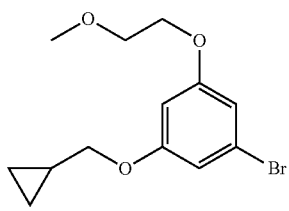 [SMILES: COCCOc1cc(Br)cc(OCC2CC2)c1] | Aryl halide-24 |

TABLE 5-continued
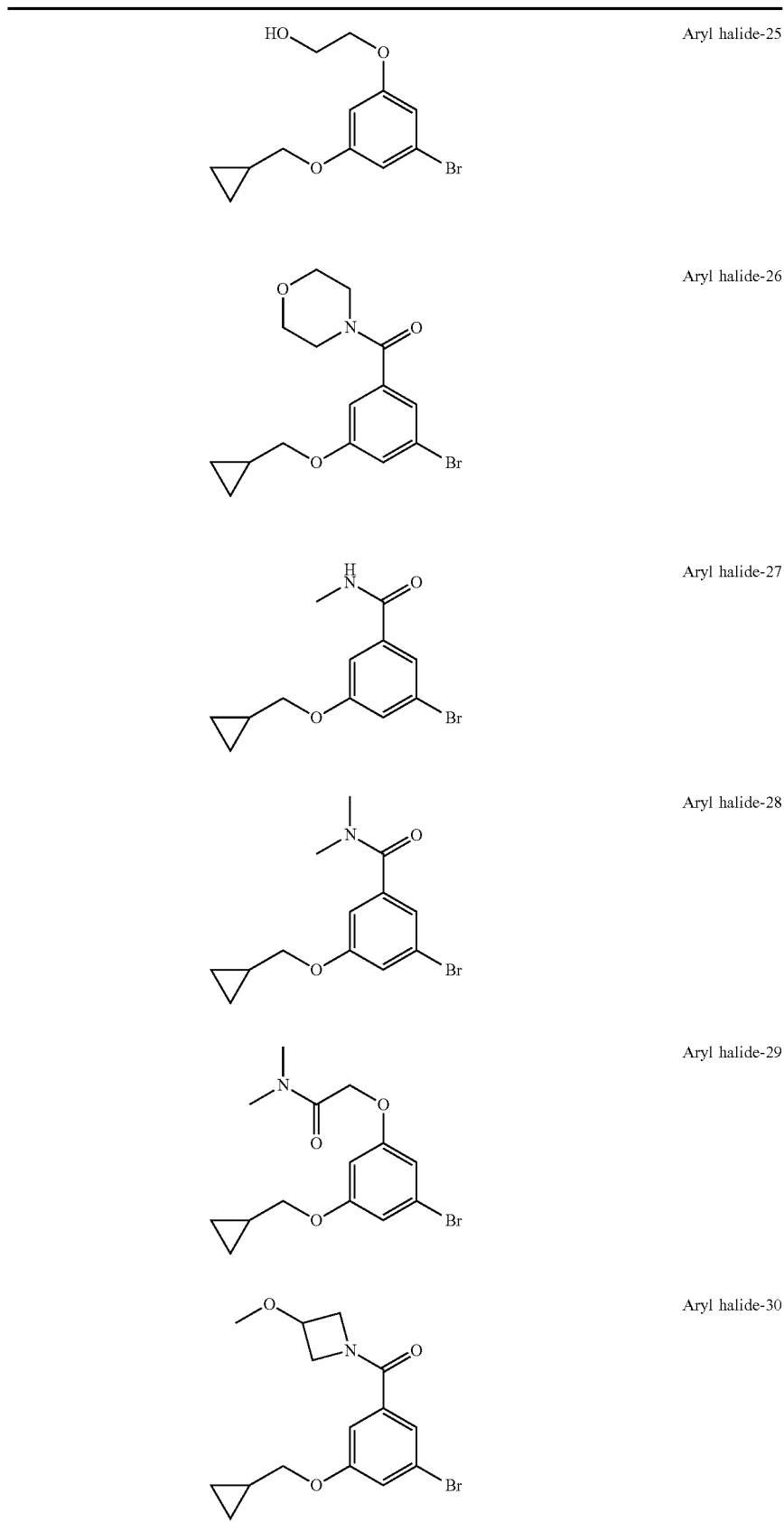
Aryl halide-25
Aryl halide-26
Aryl halide-27
Aryl halide-28
Aryl halide-29
Aryl halide-30

TABLE 5-continued

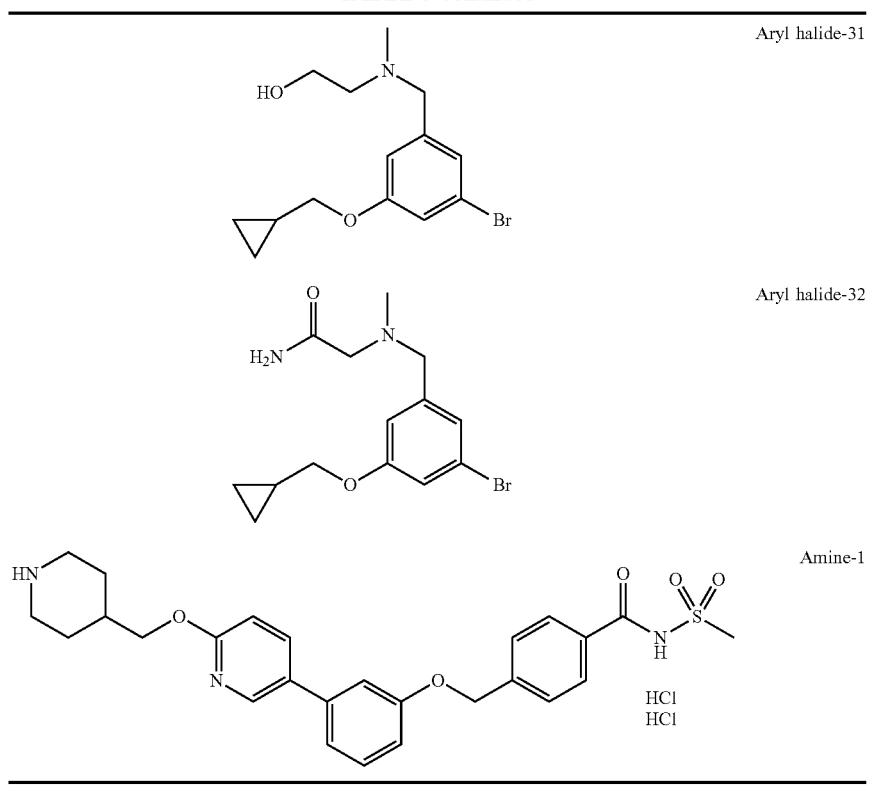

Aryl halide-31

Aryl halide-32

Amine-1

Example Synthesis Part

Example compounds (Example 1 to Example 177) are prepared according to the following representative procedures (Method D, Method E, and Method F).

Representative Procedure for the Method D

The following preparation of Example 1 represents the Method D.

Example 1: N-(methylsulfonyl)-4-((3-(6-((tetrahydro-2H-pyran-4-yl)methoxy)pyridin-3-yl)phenoxy)methyl)benzamide To a stirred solution of 4-((3-(6-((tetrahydro-2H-pyran-4-yl)methoxy)pyridin-3-yl)phenoxy)methyl)benzoic acid (Acid-7, 30 mg, 0.072 mmol), methanesulfonamide (20 mg, 0.22 mmol), and DMAP (26 mg, 0.22 mmol) in DMF (2 mL) is added EDC (41 mg, 0.22 mmol) at room temperature, and the reaction mixture is stirred at room temperature overnight. The reaction mixture is added 10% aqueous citric acid (1 mL) and extracted with EtOAc (3 mL×2), and combined organic layer is washed with water (2 mL×2), and dried over sodium sulfate. Insoluble materials are separated by filtration and the filtrate is concentrated. The residue is purified by a strong cation exchange cartridge (ISOLUTE (registered trademark) SCX, 1 g/6 mL, SPE Columns, Biotage) and then by preparative LC-MS to give 9.3 mg (26% yield) of the title compound.

Representative procedure for Method E

The following preparation of Example 85 represents the Method E.

Example 85: 4-((3-(6-(cyclopropylmethoxy)-2-methylpyridin-3-yl)phenoxy)methyl)-N-(methylsulfonyl)benzamide A mixture of N-(methylsulfonyl)-4-((3-(4,4,5,5-tetramethyl-1,3,2-dioxaborolan-2-yl)phenoxy)methyl)benzamide (Step-4 of Borate-1, 30 mg, 0.070 mmol), 3-bromo-6-(cyclopropylmethoxy)-2-methylpyridine (Aryl halide-3, 20 mg, 0.083 mmol), tetrakis(triphenylphosphine)palladium(0) (4.0 mg, 0.0035 mmol), and potassium carbonate in dioxane/water (2 mL/0.7 mL) is stirred at 100° C. for 2 hours. The reaction mixture is diluted with water (4 mL) and saturated aqueous citric acid to make the mixture to pH=4. The mixture is extracted with EtOAc (3 mL×2), and dried over sodium sulfate. Insoluble materials are separated by filtration and the filtrate is concentrated. The residue is purified by a strong anion exchange cartridge (ISOLUTE (registered trademark) PE-AX, 1 g/6 mL, SPE Columns, Biotage) and then by preparative LC-MS to give 10.9 mg (34% yield) of the title compound.

In any case of the Examples for the Method E, bis(di-tert-butyl(4-dimethylaminophenyl)phosphine)dichloropalladium(II), or palladium (II) etc. are applicable instead of tetrakis(triphenylphosphine)palladium(0).

Representative Procedure for the Method F

The following preparation of Example 171 represents the Method F.

Example 171: ethyl 4-(((5-(3-((4-((methylsulfonyl)carbamoyl)benzyl)oxy)phenyl)pyridin-2-yl)oxy)methyl) piperidine-1-carboxylate To a stirred solution of N-(methylsulfonyl)-4-((3-(6-(piperidin-4-ylmethoxy)pyridin-3-yl)phenoxy)methyl)benzamide dihydrochloride (Step-1 of Amine-1, 25 mg, 0.050 mmol) and diisopropylethylamine (0.035 mL, 0.20 mmol) in DMF (1 mL) is added ethyl carbonochloridate (10 mg, 0.090 mmol) at room temperature, and stirred at room temperature for 1 hour. The reaction mixture is diluted with 10% aqueous citric acid (1 mL) and extracted with EtOAc (2 mL×3), and dried over sodium sulfate. Insoluble materials are separated by filtration and the filtrate is concentrated. The residue is purified by preparative LC-MS to give 2.5 mg (9% yield) of the title compound.

Example 157: 4-(((3'-(2-aminoethoxy)-5'-(cyclopropylmethoxy)-5-fluoro-[1,1'-biphenyl]-3-yl)oxy)methyl)-3-fluoro-N-(methylsulfonyl)benzamide The N-protected compound is prepared by the similar manner to Method E using 3-fluoro-4-((3-fluoro-5-(4,4,5,5-tetramethyl-1,3,2-dioxaborolan-2-yl)phenoxy)methyl)-N-(methylsulfonyl)benzamide (Step 4 of Borate-4, 40 mg, 0.086 mmol) and tert-butyl (2-(3-bromo-5-(cyclopropylmethoxy)phenoxy)ethyl)carbamate (Step 2 of Aryl halide-22, 50 mg, 0.13 mmol). Then, the N-protected compound is dissolved in DCM (2 mL) and TFA (1 mL) is added to the mixture and stirred at room temperature for 20 min. The mixture is concentrated in vacuo and the residue is purified by a strong cation exchange cartridge (ISOLUTE (registered trademark) SCX, 1 g/6 mL, SPE Columns, Biotage) and then by preparative LC-MS to give 8.6 mg (18% yield) of the title compound.

Other examples are prepared according to the procedure descried in the Method D, Method E, or Method F using reactant-1 and reactant-2 shown in Table 6. The reactant-1 and reactant-2 are commercially available materials or obtained by conventional methods known to those skilled in the art, unless otherwise noted in the synthesis part.

The observed MS (positive or negative mode) and retention time by LC-MS of all examples are described in Table 7. $^1$H-NMR of Examples 2, 14, 30, 32, 46, 54, 63, 96, and 139 are described in Table 8.

TABLE 6

| Ex. | Structure | Name | Reactant-1 | Reactant-2 | Method |
|---|---|---|---|---|---|
| 1 | 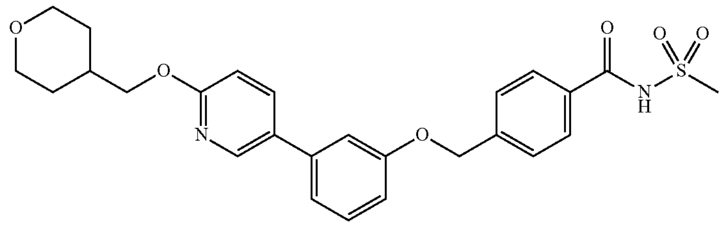 [SMILES: CS(=O)(=O)NC(=O)c1ccc(COc2cccc(-c3ccc(OCC4CCOCC4)nc3)c2)cc1] | N-(methylsulfonyl)-4-((3-(6-((tetrahydro-2H-pyran-4-yl)methoxy)pyridin-3-yl)phenoxy)methyl)benzamide | Acid-7 | | D |
| 2 | 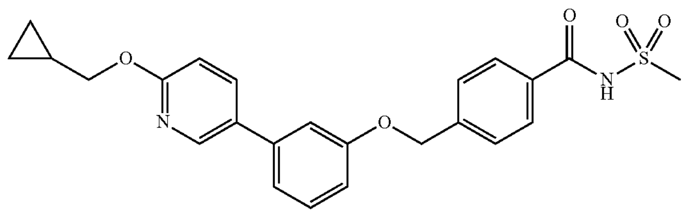 [SMILES: CS(=O)(=O)NC(=O)c1ccc(COc2cccc(-c3ccc(OCC4CC4)nc3)c2)cc1] | 4-((3-(6-(cyclopropylmethoxy)pyridin-3-yl)phenoxy)methyl)-N-(methylsulfonyl)benzamide | Acid-2 | | D |
| 3 | 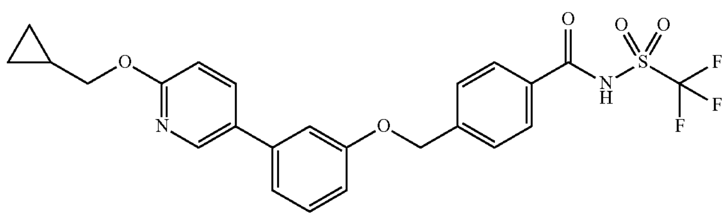 [SMILES: O=C(NS(=O)(=O)C(F)(F)F)c1ccc(COc2cccc(-c3ccc(OCC4CC4)nc3)c2)cc1] | 4-((3-(6-(cyclopropylmethoxy)pyridin-3-yl)phenoxy)methyl)-N-((trifluoromethyl)sulfonyl)benzamide | Acid-2 | | D |
| 4 | 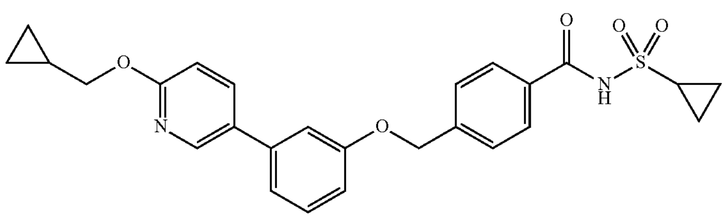 | 4-((3-(6-(cyclopropylmethoxy)pyridin-3-yl)phenoxy)methyl)-N-(cyclopropylsulfonyl)benzamide | Acid-2 | | D |

TABLE 6-continued

| Ex. | Structure | Name | Reactant-1 | Reactant-2 | Method |
|---|---|---|---|---|---|
| 5 | 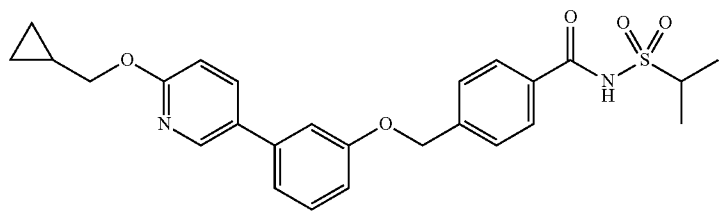 [SMILES: CC(C)S(=O)(=O)NC(=O)c1ccc(COc2cccc(-c3ccc(OCC4CC4)nc3)c2)cc1] | 4-((3-(6-(cyclopropylmethoxy)pyridin-3-yl)phenoxy)methyl)-N-(isopropylsulfonyl)benzamide | Acid-2 | | D |
| 6 | 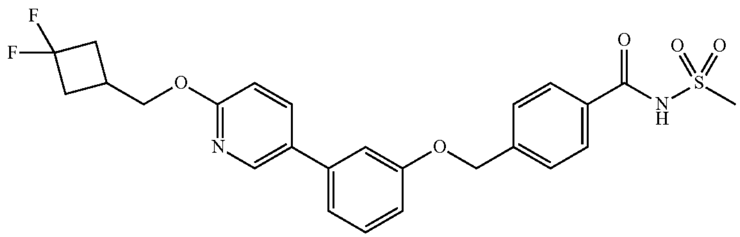 [SMILES: CS(=O)(=O)NC(=O)c1ccc(COc2cccc(-c3ccc(OCC4CC(F)(F)C4)nc3)c2)cc1] | 4-((3-(6-((3,3-difluorocyclobutyl)methoxy)pyridin-3-yl)phenoxy)methyl)-N-(methylsulfonyl)benzamide | Acid-3 | | D |
| 7 | 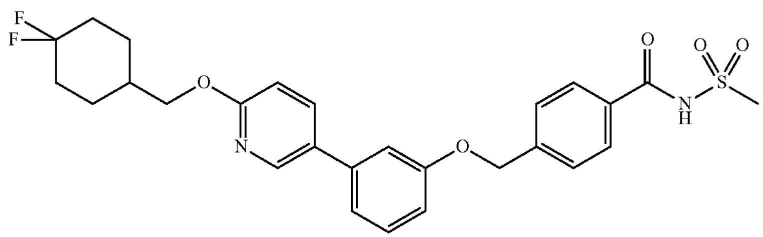 [SMILES: CS(=O)(=O)NC(=O)c1ccc(COc2cccc(-c3ccc(OCC4CCC(F)(F)CC4)nc3)c2)cc1] | 4-((3-(6-((4,4-difluorocyclohexyl)methoxy)pyridin-3-yl)phenoxy)methyl)-N-(methylsulfonyl)benzamide | Acid-4 | | D |
| 8 | 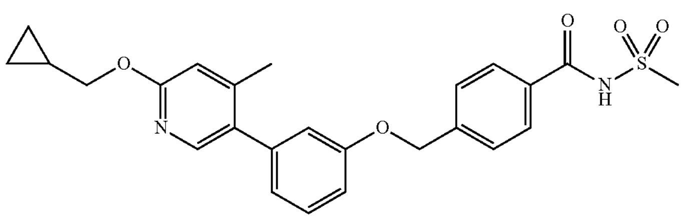 [SMILES: Cc1cc(OCC2CC2)ncc1-c1cccc(OCc2ccc(C(=O)NS(C)(=O)=O)cc2)c1] | 4-((3-(6-(cyclopropylmethoxy)-4-methylpyridin-3-yl)phenoxy)methyl)-N-(methylsulfanyl)benzamide | Acid-5 | | D |

TABLE 6-continued

| Ex. | Structure | Name | Reactant-1 | Reactant-2 | Method |
|---|---|---|---|---|---|
| 9 | 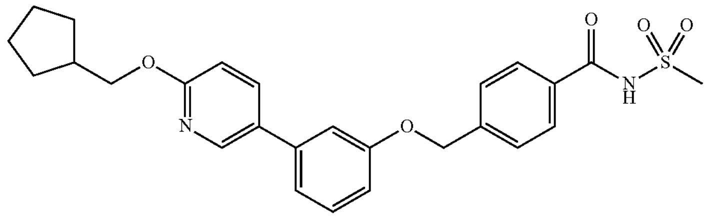 [SMILES: CS(=O)(=O)NC(=O)c1ccc(COc2cccc(-c3ccc(OCC4CCCC4)nc3)c2)cc1] | 4-((3-(6-(cyclopentylmethoxy)pyridin-3-yl)phenoxy)methyl)-N-(methylsulfonyl)benzamide | Acid-6 | | D |
| 10 | 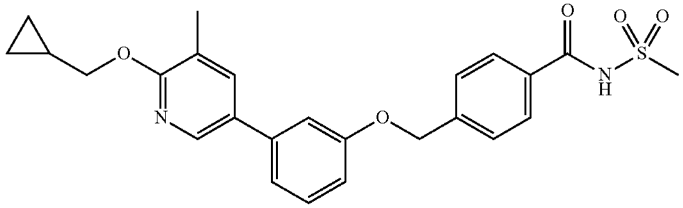 [SMILES: Cc1cc(-c2cccc(OCc3ccc(C(=O)NS(C)(=O)=O)cc3)c2)cnc1OCC1CC1] | 4-((3-(6-(cyclopropylmethoxy)-5-methylpyridin-3-yl)phenoxy)methyl)-N-(methylsulfonyl)benzamide | Acid-1 | | D |
| 11 | 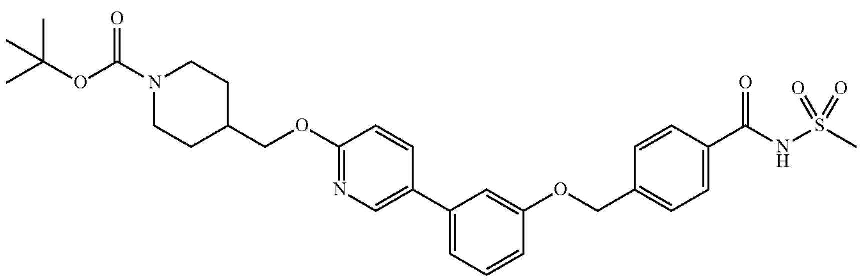 [SMILES: CC(C)(C)OC(=O)N1CCC(COc2ccc(-c3cccc(OCc4ccc(C(=O)NS(C)(=O)=O)cc4)c3)cn2)CC1] | tert-butyl 4-(((5-(3-((4-((methylsulfonyl)carbamoyl)benzyl)oxy)phenyl)pyridin-2-yl)oxy)methyl)piperidine-1-carboxylate | Acid-8 | | D |
| 12 | 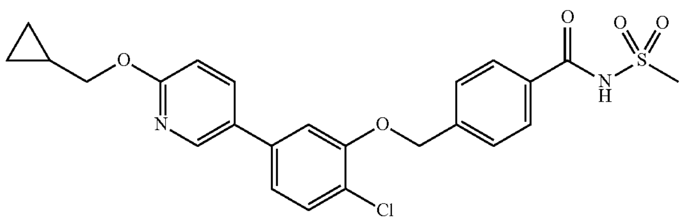 [SMILES: CS(=O)(=O)NC(=O)c1ccc(COc2cc(-c3ccc(OCC4CC4)nc3)ccc2Cl)cc1] | 4-((2-chloro-5-(6-(cyclopropylmethoxy)pyridin-3-yl)phenoxy)methyl)-N-(methylsulfonyl)benzamide | Acid-9 | | D |

TABLE 6-continued

| Ex. | Structure | Name | Reactant-1 | Reactant-2 | Method |
|---|---|---|---|---|---|
| 13 | 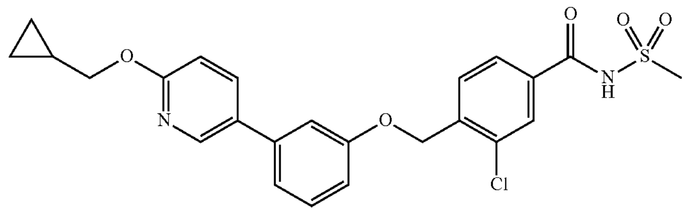 | 3-chloro-4-((3-(6-(cyclopropylmethoxy)pyridin-3-yl)phenoxy)methyl)-N-(methylsulfonyl)benzamide | Acid-10 | methanesulfonamide | D |
| 14 | 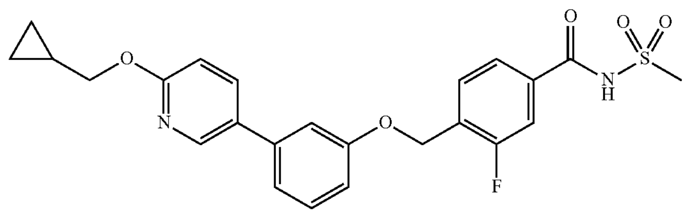 [SMILES: CS(=O)(=O)NC(=O)c1ccc(COc2cccc(-c3ccc(OCC4CC4)nc3)c2)c(F)c1] | 4-((3-(6-(cyclopropylmethoxy)pyridin-3-yl)phenoxy)methyl)-3-fluoro-N-(methylsulfonyl)benzamide | Acid-11 | methanesulfonamide | D |
| 15 | 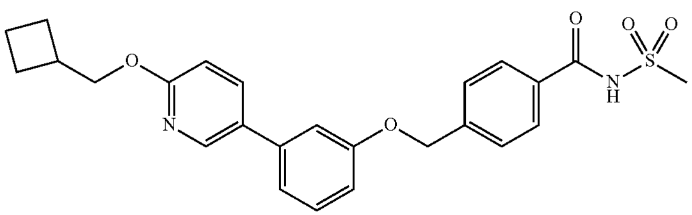 [SMILES: CS(=O)(=O)NC(=O)c1ccc(COc2cccc(-c3ccc(OCC4CCC4)nc3)c2)cc1] | 4-((3-(6-(cyclobutylmethoxy)pyridin-3-yl)phenoxy)methyl)-N-(methylsulfonyl)benzamide | Acid-12 | methanesulfonamide | D |
| 16 | 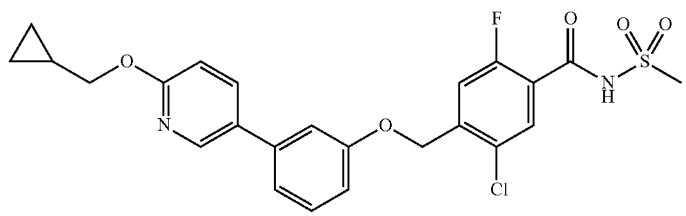 [SMILES: CS(=O)(=O)NC(=O)c1cc(Cl)c(COc2cccc(-c3ccc(OCC4CC4)nc3)c2)cc1F] | 5-chloro-4-((3-(6-(cyclopropylmethoxy)pyridin-3-yl)phenoxy)methyl)-2-fluoro-N-(methylsulfonyl)benzamide | Acid-13 | methanesulfonamide | D |

TABLE 6-continued

| Ex. | Structure | Name | Reactant-1 | Reactant-2 | Method |
|---|---|---|---|---|---|
| 17 | 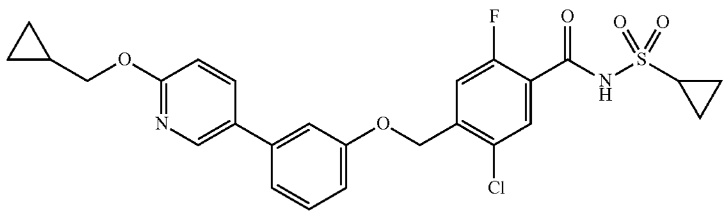 [SMILES: O=C(NS(=O)(=O)C1CC1)c1cc(Cl)c(COc2cccc(-c3ccc(OCC4CC4)nc3)c2)cc1F] | 5-chloro-4-((3-(6-(cyclopropylmethoxy)pyridin-3-yl)phenoxy)methyl)-N-(cyclopropylsulfonyl)-2-fluorobenzamide | Acid-13 | | D |
| 18 | 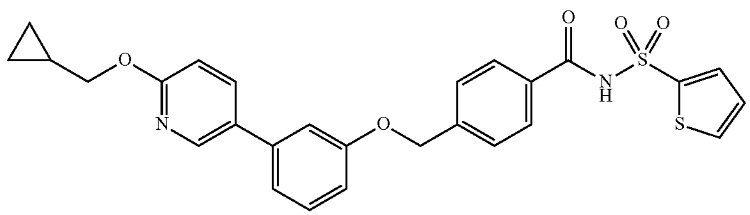 [SMILES: O=C(NS(=O)(=O)c1cccs1)c1ccc(COc2cccc(-c3ccc(OCC4CC4)nc3)c2)cc1] | 4-((3-(6-(cyclopropylmethoxy)pyridin-3-yl)phenoxy)methyl)-N-(thiophen-2-ylsulfonyl)benzamide | Acid-2 | | D |
| 19 | 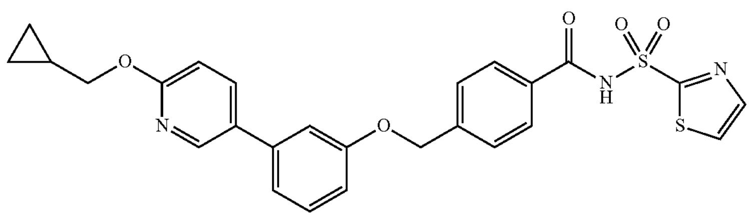 [SMILES: O=C(NS(=O)(=O)c1nccs1)c1ccc(COc2cccc(-c3ccc(OCC4CC4)nc3)c2)cc1] | 4-((3-(6-(cyclopropylmethoxy)pyridin-3-yl)phenoxy)methyl)-N-(thiazol-2-ylsulfonyl)benzamide | Acid-2 | | D |
| 20 | 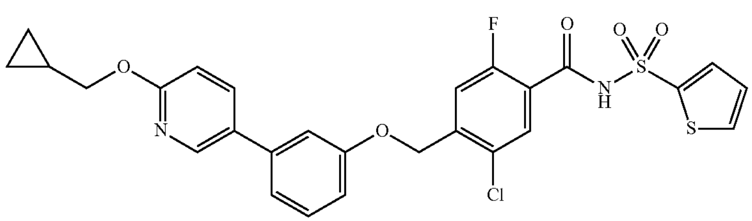 [SMILES: O=C(NS(=O)(=O)c1cccs1)c1cc(Cl)c(COc2cccc(-c3ccc(OCC4CC4)nc3)c2)cc1F] | 5-chloro-4-((3-(6-(cyclopropylmethoxy)pyridin-3-yl)phenoxy)methyl)-2-fluoro-N-(thiophen-2-ylsulfonyl)benzamide | Acid-13 | | D |

TABLE 6-continued

| Ex. | Structure | Name | Reactant-1 | Reactant-2 | Method |
|---|---|---|---|---|---|
| 21 | 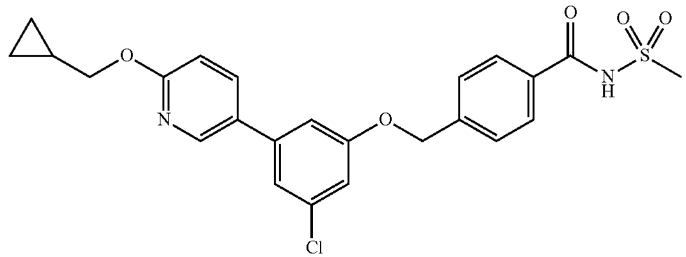 [SMILES: CS(=O)(=O)NC(=O)c1ccc(COc2cc(Cl)cc(-c3ccc(OCC4CC4)nc3)c2)cc1] | 4-((3-chloro-5-(6-(cyclopropylmethoxy)pyridin-3-yl)phenoxy)methyl)-N-(methylsulfonyl)benzamide | Acid-14 | | D |
| 22 | 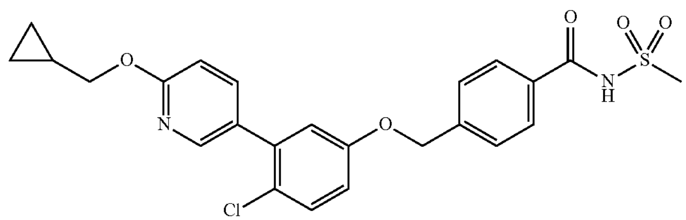 [SMILES: CS(=O)(=O)NC(=O)c1ccc(COc2ccc(Cl)c(-c3ccc(OCC4CC4)nc3)c2)cc1] | 4-((4-chloro-3-(6-(cyclopropylmethoxy)pyridin-3-yl)phenoxy)methyl)-N-(methylsulfonyl)benzamide | Acid-15 | | D |
| 23 | 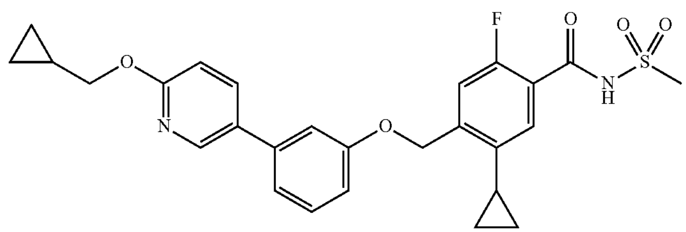 [SMILES: CS(=O)(=O)NC(=O)c1cc(C2CC2)c(COc2cccc(-c3ccc(OCC4CC4)nc3)c2)cc1F] | 5-cyclopropyl-4-((3-(6-(cyclopropylmethoxy)pyridin-3-yl)phenoxy)methyl)-2-fluoro-N-(methylsulfonyl)benzamide | Acid-16 | | D |
| 24 | 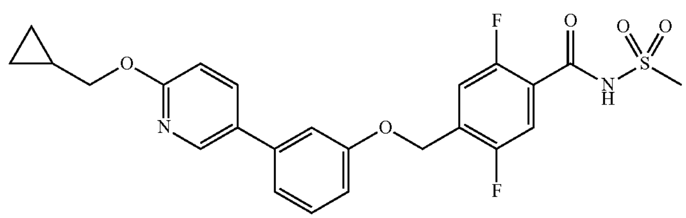 [SMILES: CS(=O)(=O)NC(=O)c1cc(F)c(COc2cccc(-c3ccc(OCC4CC4)nc3)c2)cc1F] | 4-((3-(6-(cyclopropylmethoxy)pyridin-3-yl)phenoxy)methyl)-2,5-difluoro-N-(methylsulfonyl)benzamide | Acid-17 | | D |

TABLE 6-continued

| Ex. | Structure | Name | Reactant-1 | Reactant-2 | Method |
|---|---|---|---|---|---|
| 25 | 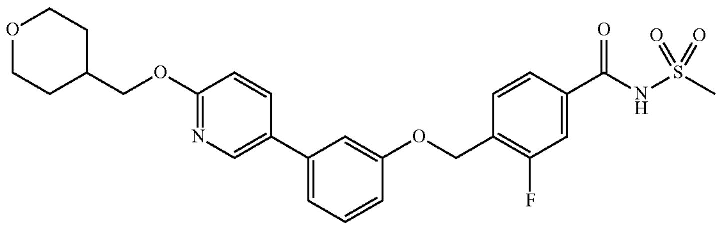 [SMILES: CS(=O)(=O)NC(=O)c1ccc(COc2cccc(-c3ccc(OCC4CCOCC4)nc3)c2)c(F)c1] | 3-fluoro-N-(methylsulfonyl)-4-((3-(6-((tetrahydro-2H-pyran-4-yl)methoxy)pyridin-3-yl)phenoxy)methyl)benzamide | Acid-18 | methanesulfonamide | D |
| 26 | 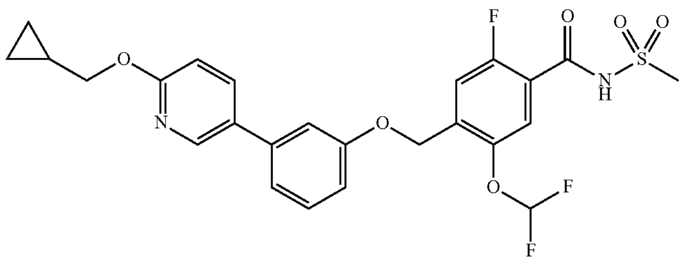 [SMILES: CS(=O)(=O)NC(=O)c1cc(OC(F)F)c(COc2cccc(-c3ccc(OCC4CC4)nc3)c2)cc1F] | 4-((3-(6-(cyclopropylmethoxy)pyridin-3-yl)phenoxy)methyl)-5-(difluoromethoxy)-2-fluoro-N-(methylsulfonyl)benzamide | Acid-19 | methanesulfonamide | D |
| 27 | 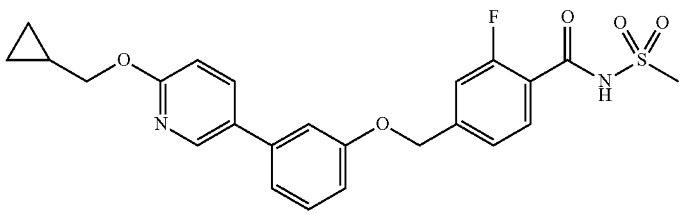 [SMILES: CS(=O)(=O)NC(=O)c1ccc(COc2cccc(-c3ccc(OCC4CC4)nc3)c2)cc1F] | 4-((3-(6-(cyclopropylmethoxy)pyridin-3-yl)phenoxy)methyl)-2-fluoro-N-(methylsulfonyl)benzamide | Acid-20 | methanesulfonamide | D |
| 28 | 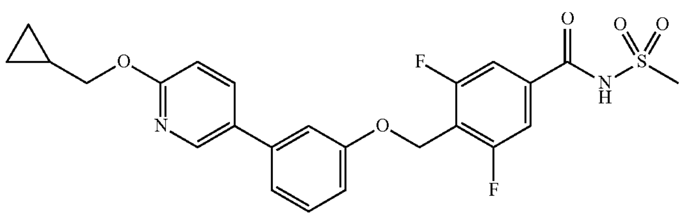 [SMILES: CS(=O)(=O)NC(=O)c1cc(F)c(COc2cccc(-c3ccc(OCC4CC4)nc3)c2)c(F)c1] | 4-((3-(6-(cyclopropylmethoxy)pyridin-3-yl)phenoxy)methyl)-3,5-difluoro-N-(methylsulfonyl)benzamide | Acid-21 | methanesulfonamide | D |

TABLE 6-continued

| Ex. | Structure | Name | Reactant-1 | Reactant-2 | Method |
|---|---|---|---|---|---|
| 29 | 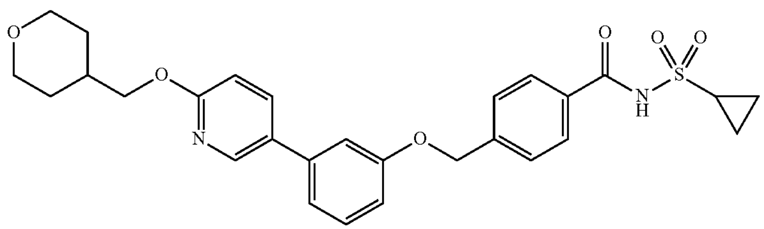 [SMILES: O=C(NS(=O)(=O)C1CC1)c1ccc(COc2cccc(-c3ccc(OCC4CCOCC4)nc3)c2)cc1] | N-(cyclopropylsulfonyl)-4-((3-(6-((tetrahydro-2H-pyran-4-yl)methoxy)pyridin-3-yl)phenoxy)methyl)benzamide | Acid-7 | | D |
| 30 | 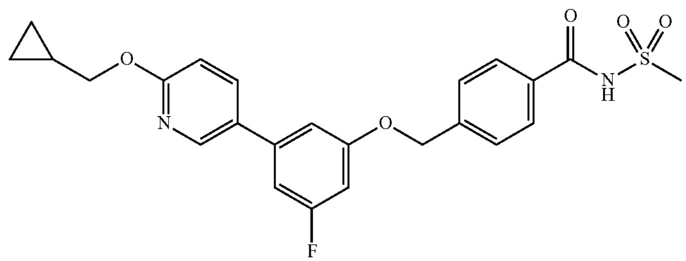 [SMILES: CS(=O)(=O)NC(=O)c1ccc(COc2cc(F)cc(-c3ccc(OCC4CC4)nc3)c2)cc1] | 4-((3-(6-(cyclopropylmethoxy)pyridin-3-yl)-5-fluorophenoxy)methyl)-N-(methylsulfonyl)benzamide | Acid-22 | | D |
| 31 | 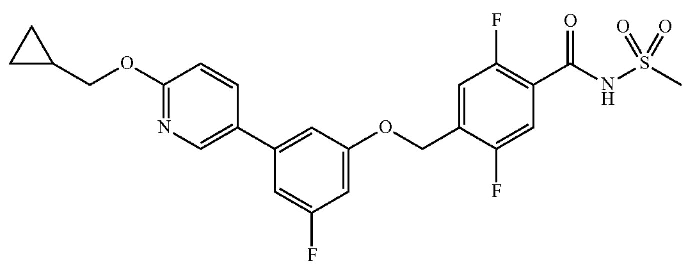 [SMILES: CS(=O)(=O)NC(=O)c1cc(F)c(COc2cc(F)cc(-c3ccc(OCC4CC4)nc3)c2)cc1F] | 4-((3-(6-(cyclopropylmethoxy)pyridin-3-yl)-5-fluorophenoxy)methyl)-2,5-difluoro-N-(methylsulfonyl)benzamide | Acid-23 | | D |
| 32 | 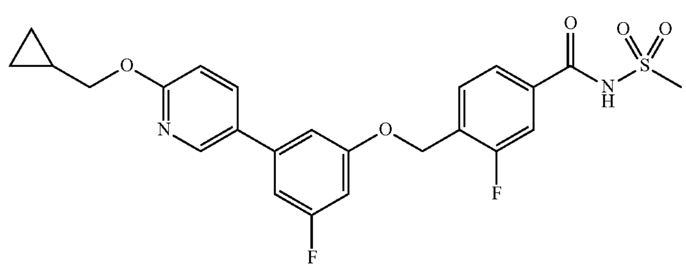 [SMILES: CS(=O)(=O)NC(=O)c1ccc(COc2cc(F)cc(-c3ccc(OCC4CC4)nc3)c2)c(F)c1] | 4-((3-(6-(cyclopropylmethoxy)pyridin-3-yl)-5-fluorophenoxy)methyl)-3-fluoro-N-(methylsulfonyl)benzamide | Acid-24 | | D |

TABLE 6-continued

| Ex. | Structure | Name | Reactant-1 | Reactant-2 | Method |
|---|---|---|---|---|---|
| 33 | 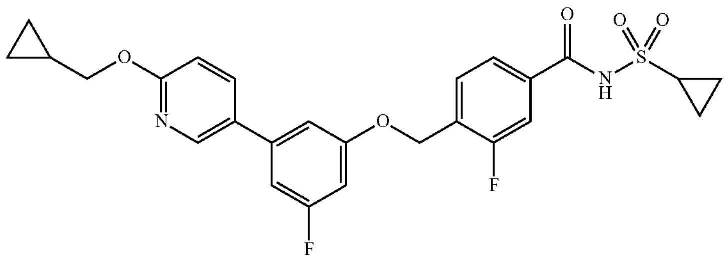 [SMILES: O=C(NS(=O)(=O)C1CC1)c1ccc(COc2cc(F)cc(-c3ccc(OCC4CC4)nc3)c2)c(F)c1] | 4-((3-(6-(cyclopropylmethoxy)pyridin-3-yl)-5-fluorophenoxy)methyl)-N-(cyclopropylsulfonyl)-3-fluorobenzamide | Acid-24 | | D |
| 34 | 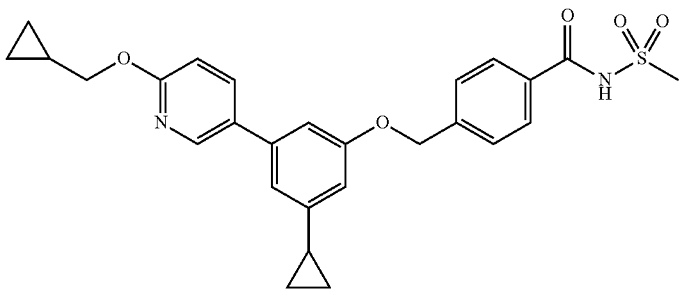 [SMILES: CS(=O)(=O)NC(=O)c1ccc(COc2cc(-c3ccc(OCC4CC4)nc3)cc(C3CC3)c2)cc1] | 4-((3-cyclopropyl-5-(6-(cyclopropylmethoxy)pyridin-3-yl)phenoxy)methyl)-N-(methylsulfonyl)benzamide | Acid-25 | | D |
| 35 | 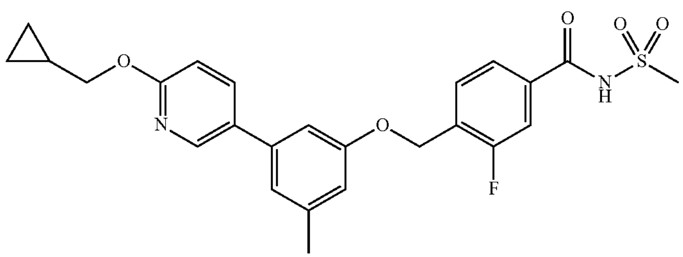 [SMILES: Cc1cc(OCc2ccc(C(=O)NS(C)(=O)=O)cc2F)cc(-c2ccc(OCC3CC3)nc2)c1] | 4-((3-(6-(cyclopropylmethoxy)pyridin-3-yl)-5-methylphenoxy)methyl)-3-fluoro-N-(methylsulfonyl)benzamide | Acid-26 | | D |

TABLE 6-continued

| Ex. | Structure | Name | Reactant-1 | Reactant-2 | Method |
|---|---|---|---|---|---|
| 36 | 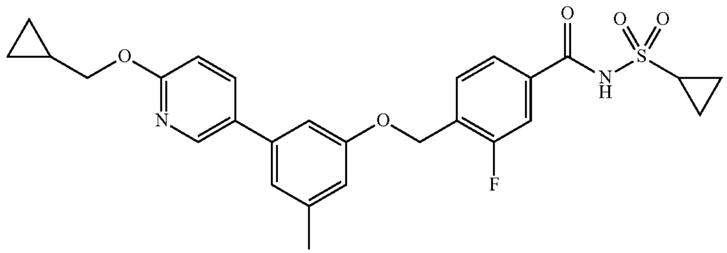 [SMILES: Cc1cc(OCc2ccc(C(=O)NS(=O)(=O)C3CC3)cc2F)cc(-c2ccc(OCC3CC3)nc2)c1] | 4-((3-(6-(cyclopropylmethoxy)pyridin-3-yl)-5-methylphenoxy)methyl)-N-(cyclopropylsulfonyl)-3-fluorobenzamide | Acid-26 | | D |
| 37 | 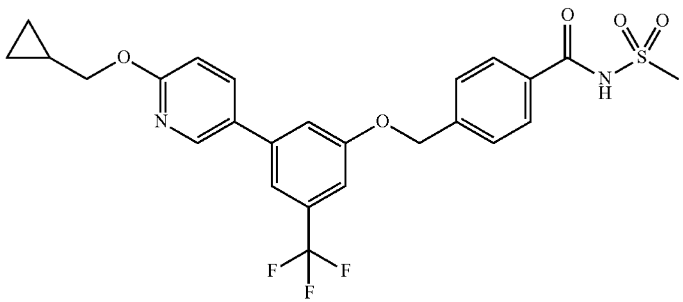 [SMILES: CS(=O)(=O)NC(=O)c1ccc(COc2cc(-c3ccc(OCC4CC4)nc3)cc(C(F)(F)F)c2)cc1] | 4-((3-(6-(cyclopropylmethoxy)pyridin-3-yl)-5-(trifluoromethyl)phenoxy)methyl)-N-(methylsulfonyl)benzamide | Acid-27 | | D |
| 38 | 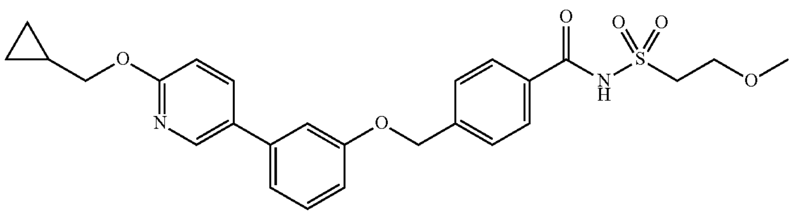 [SMILES: COCCS(=O)(=O)NC(=O)c1ccc(COc2cccc(-c3ccc(OCC4CC4)nc3)c2)cc1] | 4-((3-(6-(cyclopropylmethoxy)pyridin-3-yl)phenoxy)methyl)-N-((2-methoxyethyl)sulfonyl)benzamide | Acid-2 | | D |
| 39 | 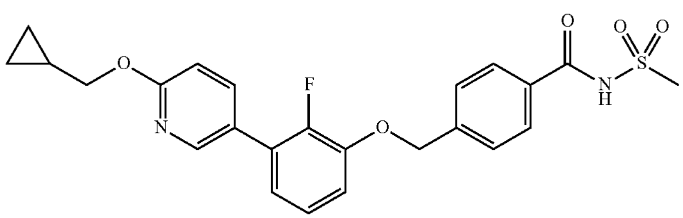 [SMILES: CS(=O)(=O)NC(=O)c1ccc(COc2cccc(-c3ccc(OCC4CC4)nc3)c2F)cc1] | 4-((3-(6-(cyclopropylmethoxy)pyridin-3-yl)-2-fluorophenoxy)methyl)-N-(methylsulfonyl)benzamide | Aryl halide-1 | | E |

TABLE 6-continued

| Ex. | Structure | Name | Reactant-1 | Reactant-2 | Method |
|---|---|---|---|---|---|
| 40 | 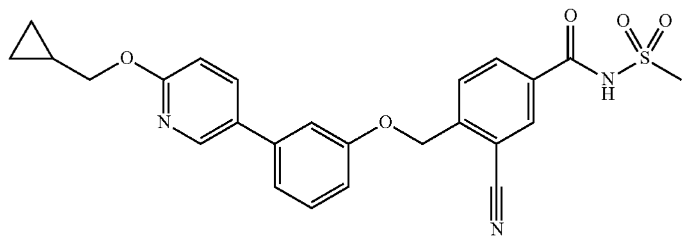 [SMILES: CS(=O)(=O)NC(=O)c1ccc(COc2cccc(-c3ccc(OCC4CC4)nc3)c2)c(C#N)c1] | 3-cyano-4-((3-(6-(cyclopropylmethoxy)pyridin-3-yl)phenoxy)methyl)-N-(methylsulfonyl)benzamide | Acid-28 | | D |
| 41 | 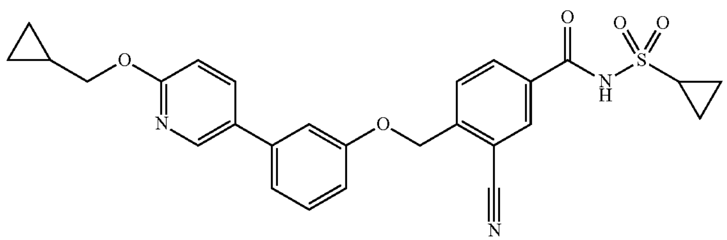 [SMILES: N#Cc1cc(C(=O)NS(=O)(=O)C2CC2)ccc1COc1cccc(-c2ccc(OCC3CC3)nc2)c1] | 3-cyano-4-((3-(6-(cyclopropylmethoxy)pyridin-3-yl)phenoxy)methyl)-N-(cyclopropylsulfonyl)benzamide | Acid-28 | | D |
| 42 | 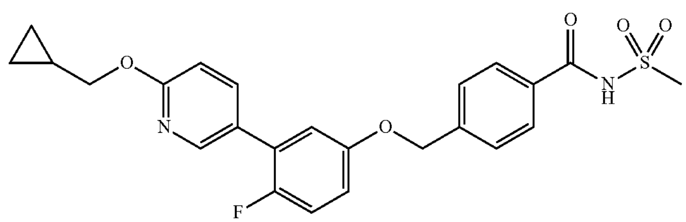 [SMILES: CS(=O)(=O)NC(=O)c1ccc(COc2ccc(F)c(-c3ccc(OCC4CC4)nc3)c2)cc1] | 4-((3-(6-(cyclopropylmethoxy)pyridin-3-yl)-4-fluorophenoxy)methyl)-N-(methylsulfonyl)benzamide | Acid-29 | | D |
| 43 | 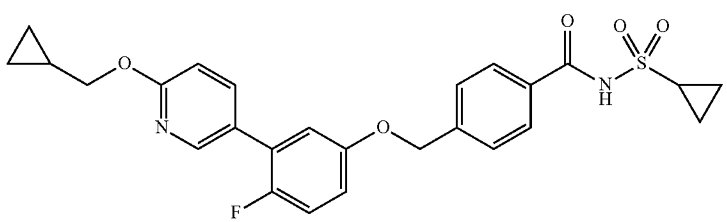 [SMILES: O=C(NS(=O)(=O)C1CC1)c1ccc(COc2ccc(F)c(-c3ccc(OCC4CC4)nc3)c2)cc1] | 4-((3-(6-(cyclopropylmethoxy)pyridin-3-yl)-4-fluorophenoxy)methyl)-N-(cyclopropylsulfonyl)benzamide | Acid-29 | | D |

TABLE 6-continued

| Ex. | Structure | Name | Reactant-1 | Reactant-2 | Method |
|---|---|---|---|---|---|
| 44 | 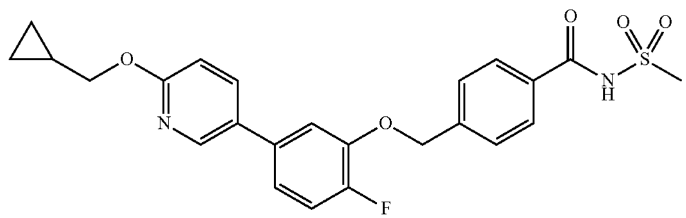 [SMILES: CS(=O)(=O)NC(=O)c1ccc(COc2cc(-c3ccc(OCC4CC4)nc3)ccc2F)cc1] | 4-((5-(6-(cyclopropylmethoxy)pyridin-3-yl)-2-fluorophenoxy)methyl)-N-(methylsulfonyl)benzamide | Acid-30 | | D |
| 45 | 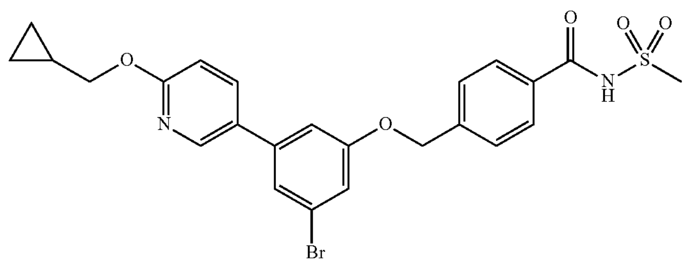 [SMILES: CS(=O)(=O)NC(=O)c1ccc(COc2cc(Br)cc(-c3ccc(OCC4CC4)nc3)c2)cc1] | 4-((3-bromo-5-(6-(cyclopropylmethoxy)pyridin-3-yl)phenoxy)methyl)-N-(methylsulfonyl)benzamide | Acid-31 | | D |
| 46 | 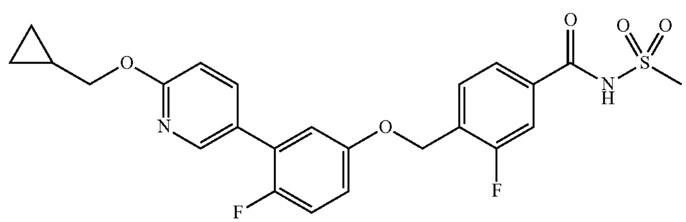 [SMILES: CS(=O)(=O)NC(=O)c1ccc(COc2ccc(F)c(-c3ccc(OCC4CC4)nc3)c2)c(F)c1] | 4-((3-(6-(cyclopropylmethoxy)pyridin-3-yl)-4-fluorophenoxy)methyl)-3-fluoro-N-(methylsulfonyl)benzamide | Acid-32 | | D |
| 47 | 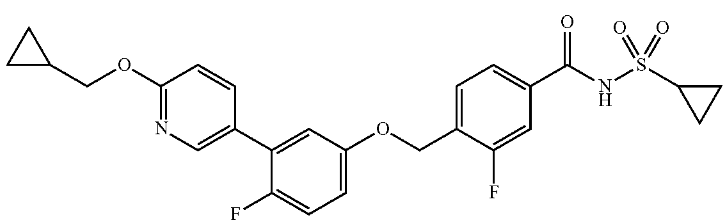 [SMILES: O=C(NS(=O)(=O)C1CC1)c1ccc(COc2ccc(F)c(-c3ccc(OCC4CC4)nc3)c2)c(F)c1] | 4-((3-(6-(cyclopropylmethoxy)pyridin-3-yl)-4-fluorophenoxy)methyl)-N-(cyclopropylsulfonyl)-3-fluorobenzamide | Acid-32 | | D |

TABLE 6-continued

| Ex. | Structure | Name | Reactant-1 | Reactant-2 | Method |
|---|---|---|---|---|---|
| 48 | 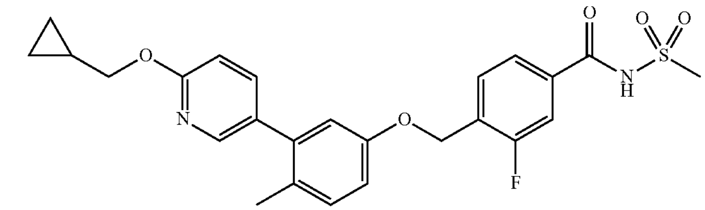 [SMILES: Cc1ccc(OCc2ccc(C(=O)NS(C)(=O)=O)cc2F)cc1-c1ccc(OCC2CC2)nc1] | 4-((3-(6-(cyclopropylmethoxy)pyridin-3-yl)-4-methylphenoxy)methyl)-3-fluoro-N-(methylsulfonyl)benzamide | Acid-33 | | D |
| 49 | 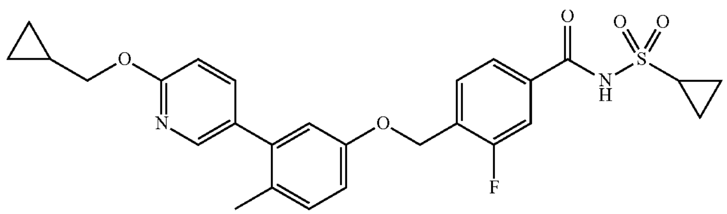 [SMILES: Cc1ccc(OCc2ccc(C(=O)NS(=O)(=O)C3CC3)cc2F)cc1-c1ccc(OCC2CC2)nc1] | 4-((3-(6-(cyclopropylmethoxy)pyridin-3-yl)-4-methylphenoxy)methyl)-N-(cyclopropylsulfonyl)-3-fluorobenzamide | Acid-33 | | D |
| 50 | 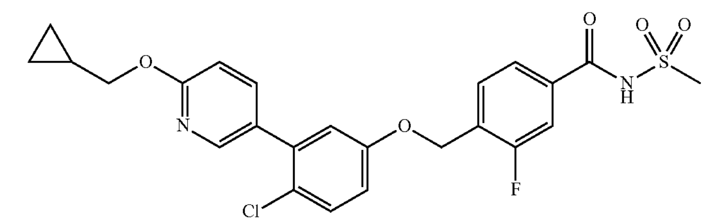 | 4-((4-chloro-3-(6-(cyclopropylmethoxy)pyridin-3-yl)phenoxy)methyl)-3-fluoro-N-(methylsulfonyl)benzamide | Acid-34 | | D |
| 51 | 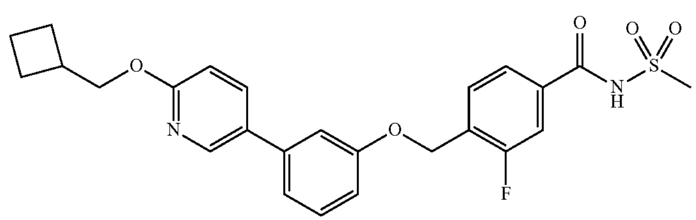 [SMILES: CS(=O)(=O)NC(=O)c1ccc(COc2cccc(-c3ccc(OCC4CCC4)nc3)c2)c(F)c1] | 4-((3-(6-(cyclopropylmethoxy)pyridin-3-yl)phenoxy)methyl)-3-fluoro-N-(methylsulfonyl)benzamide | Acid-35 | | D |

TABLE 6-continued

| Ex. | Structure | Name | Reactant-1 | Reactant-2 | Method |
|---|---|---|---|---|---|
| 52 | 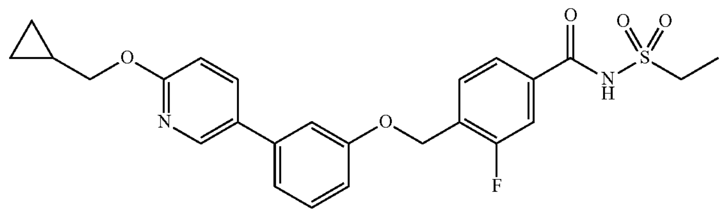 [SMILES: CCS(=O)(=O)NC(=O)c1ccc(COc2cccc(-c3ccc(OCC4CC4)nc3)c2)c(F)c1] | 4-((3-(6-(cyclopropylmethoxy)pyridin-3-yl)phenoxy)methyl)-N-(ethylsulfonyl)-3-fluorobenzamide | Acid-11 | | D |
| 53 | 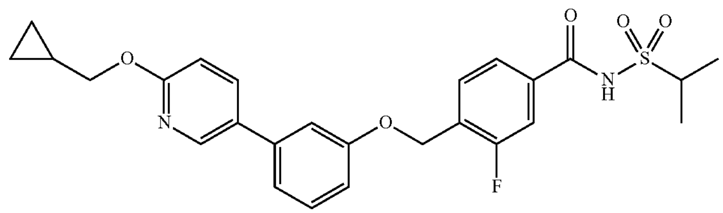 [SMILES: CC(C)S(=O)(=O)NC(=O)c1ccc(COc2cccc(-c3ccc(OCC4CC4)nc3)c2)c(F)c1] | 4-((3-(6-(cyclopropylmethoxy)pyridin-3-yl)phenoxy)methyl)-3-fluoro-N-(isopropylsulfonyl)benzamide | Acid-11 | | D |
| 54 | 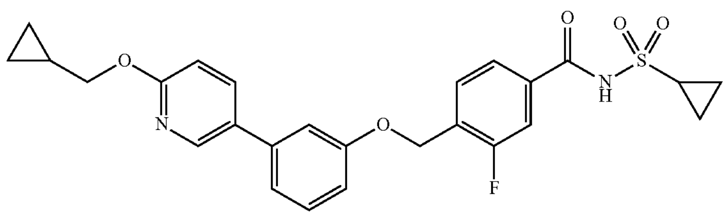 [SMILES: O=C(NS(=O)(=O)C1CC1)c1ccc(COc2cccc(-c3ccc(OCC4CC4)nc3)c2)c(F)c1] | 4-((3-(6-(cyclopropylmethoxy)pyridin-3-yl)phenoxy)methyl)-N-(cyclopropylsulfonyl)-3-fluorobenzamide | Acid-11 | | D |
| 55 | 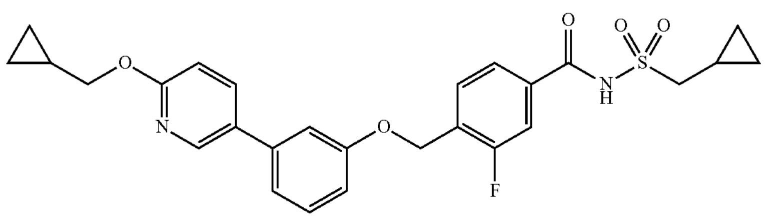 [SMILES: O=C(NS(=O)(=O)CC1CC1)c1ccc(COc2cccc(-c3ccc(OCC4CC4)nc3)c2)c(F)c1] | 4-((3-(6-(cyclopropylmethoxy)pyridin-3-yl)phenoxy)methyl)-N-((cyclopropylmethyl)sulfonyl)-3-fluorobenzamide | Acid-11 | | D |

TABLE 6-continued

| Ex. | Structure | Name | Reactant-1 | Reactant-2 | Method |
|---|---|---|---|---|---|
| 56 | 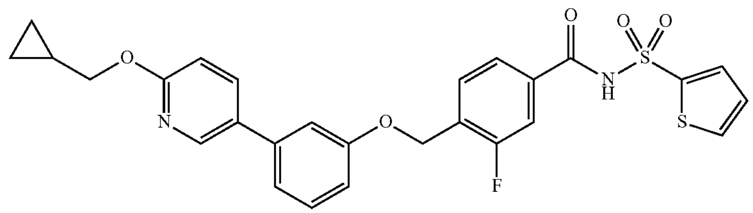 [SMILES: O=C(NS(=O)(=O)c1cccs1)c1ccc(COc2cccc(-c3ccc(OCC4CC4)nc3)c2)c(F)c1] | 4-((3-(6-(cyclopropylmethoxy)pyridin-3-yl)phenoxy)methyl)-3-fluoro-N-(thiophen-2-ylsulfonyl)benzamide | Acid-11 | | D |
| 57 | 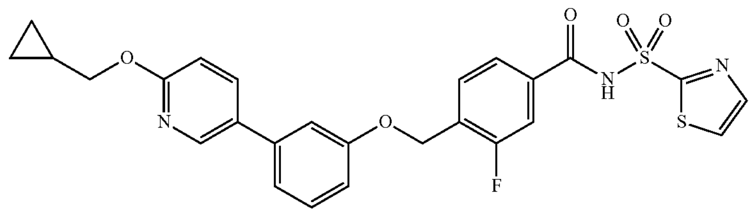 [SMILES: O=C(NS(=O)(=O)c1nccs1)c1ccc(COc2cccc(-c3ccc(OCC4CC4)nc3)c2)c(F)c1] | 4-((3-(6-(cyclopropylmethoxy)pyridin-3-yl)phenoxy)methyl)-3-fluoro-N-(thiazol-2-ylsulfonyl)benzamide | Acid-11 | | D |
| 58 | 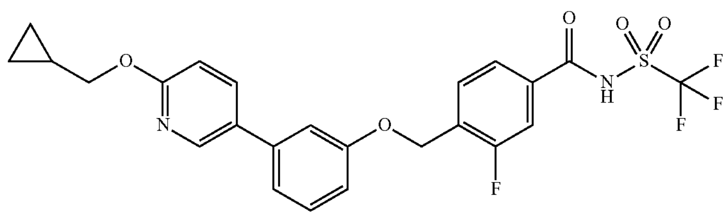 [SMILES: O=C(NS(=O)(=O)C(F)(F)F)c1ccc(COc2cccc(-c3ccc(OCC4CC4)nc3)c2)c(F)c1] | 4-((3-(6-(cyclopropylmethoxy)pyridin-3-yl)phenoxy)methyl)-3-fluoro-N-((trifluoromethyl)sulfonyl)benzamide | Acid-11 | | D |
| 59 | 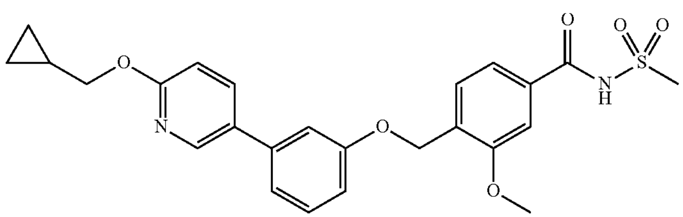 [SMILES: COc1cc(C(=O)NS(C)(=O)=O)ccc1COc1cccc(-c2ccc(OCC3CC3)nc2)c1] | 4-((3-(6-(cyclopropylmethoxy)pyridin-3-yl)phenoxy)methyl)-3-methoxy-N-(methylsulfonyl)benzamide | Acid-36 | | D |

TABLE 6-continued

| Ex. | Structure | Name | Reactant-1 | Reactant-2 | Method |
|---|---|---|---|---|---|
| 60 | 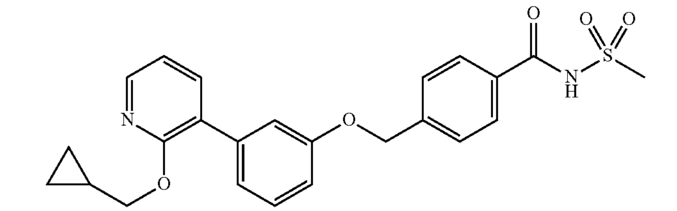 [SMILES: CS(=O)(=O)NC(=O)c1ccc(COc2cccc(-c3cccnc3OCC3CC3)c2)cc1] | 4-((3-(2-(cyclopropylmethoxy)pyridin-3-yl)phenoxy)methyl)-N-(methylsulfonyl)benzamide | Acid-37 |  | D |
| 61 | 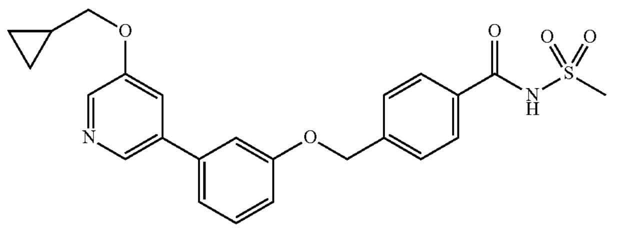 [SMILES: CS(=O)(=O)NC(=O)c1ccc(COc2cccc(-c3cncc(OCC4CC4)c3)c2)cc1] | 4-((3-(5-(cyclopropylmethoxy)pyridin-3-yl)phenoxy)methyl)-N-(methylsulfonyl)benzamide | Acid-38 |  | D |
| 62 | 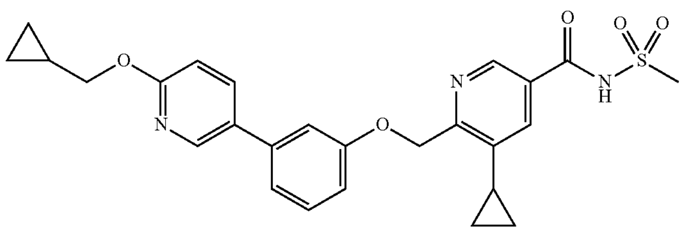 [SMILES: CS(=O)(=O)NC(=O)c1cnc(COc2cccc(-c3ccc(OCC4CC4)nc3)c2)c(C2CC2)c1] | 5-cyclopropyl-6-((3-(6-(cyclopropylmethoxy)pyridin-3-yl)phenoxy)methyl)-N-(methylsulfonyl)nicotinamide | Acid-39 |  | D |
| 63 | 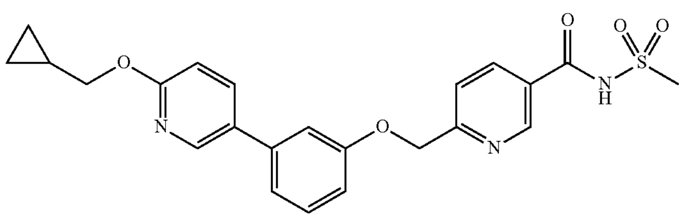 | 6-((3-(6-(cyclopropylmethoxy)pyridin-3-yl)phenoxy)methyl)-N-(methylsulfonyl)nicotinamide | Acid-40 |  | D |

TABLE 6-continued

| Ex. | Structure | Name | Reactant-1 | Reactant-2 | Method |
|---|---|---|---|---|---|
| 64 | 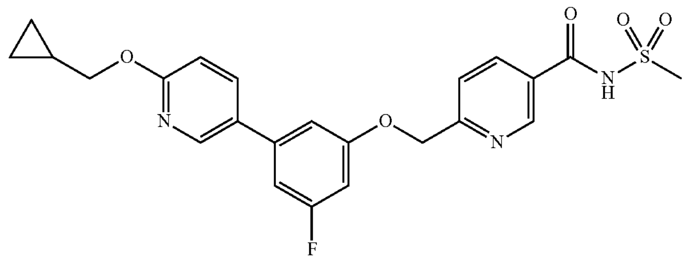 | 6-((3-(6-(cyclopropylmethoxy)pyridin-3-yl)-5-fluorophenoxy)methyl)-N-(methylsulfonyl)nicotinamide | Acid-41 | | D |
| 65 | 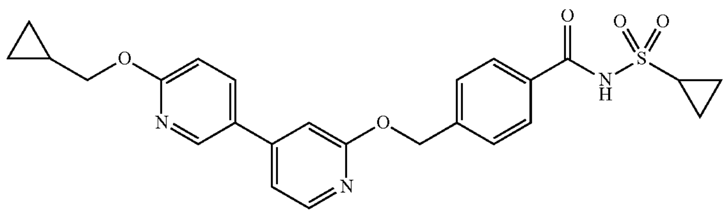 [SMILES: O=C(NS(=O)(=O)C1CC1)c1ccc(COc2cc(-c3ccc(OCC4CC4)nc3)ccn2)cc1] | 4-(((6-(cyclopropylmethoxy)-[3,4'-bipyridin]-2'-yl)oxy)methyl)-N-(cyclopropylsulfonyl)benzamide | Acid-42 | | D |
| 66 | 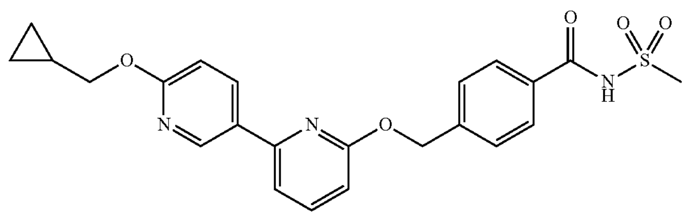 [SMILES: CS(=O)(=O)NC(=O)c1ccc(COc2cccc(-c3ccc(OCC4CC4)nc3)n2)cc1] | 4-(((6-(cyclopropylmethoxy)-[2,3'-bipyridin]-6-yl)oxy)methyl)-N-(methylsulfonyl)benzamide | Acid-43 | | D |
| 67 | 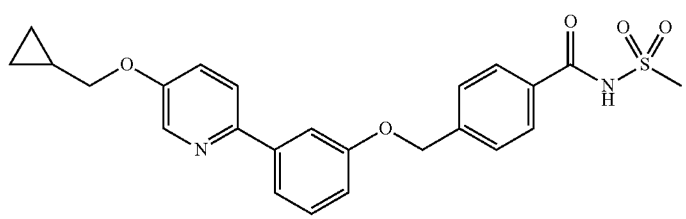 [SMILES: CS(=O)(=O)NC(=O)c1ccc(COc2cccc(-c3ccc(OCC4CC4)cn3)c2)cc1] | 4-((3-(5-(cyclopropylmethoxy)pyridin-2-yl)phenoxy)methyl)-N-(methylsulfonyl)benzamide | Acid-44 | | D |

TABLE 6-continued

| Ex. | Structure | Name | Reactant-1 | Reactant-2 | Method |
|---|---|---|---|---|---|
| 68 | 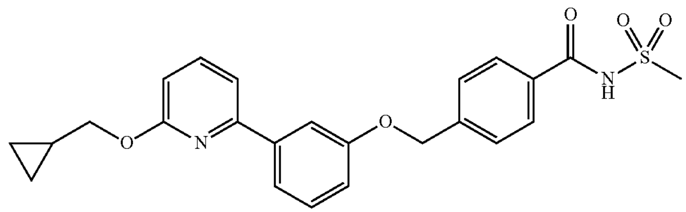 [SMILES: CS(=O)(=O)NC(=O)c1ccc(COc2cccc(-c3cccc(OCC4CC4)n3)c2)cc1] | 4-((3-(6-(cyclopropylmethoxy)pyridin-2-yl)phenoxy)methyl)-N-(methylsulfonyl)benzamide | Acid-45 | | D |
| 69 | 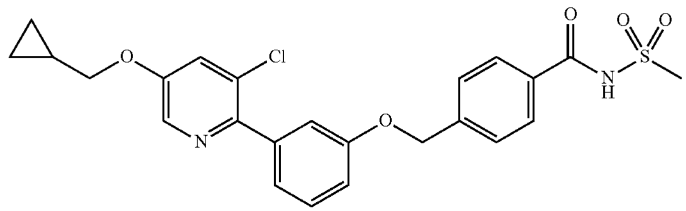 | 4-((3-(3-chloro-5-(cyclopropylmethoxy)pyridin-2-yl)phenoxy)methyl)-N-(methylsulfonyl)benzamide | Acid-46 | | D |
| 70 | 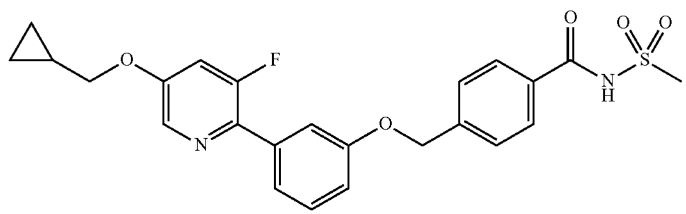 [SMILES: CS(=O)(=O)NC(=O)c1ccc(COc2cccc(-c3ncc(OCC4CC4)cc3F)c2)cc1] | 4-((3-(5-(cyclopropylmethoxy)-3-fluoropyridin-2-yl)phenoxy)methyl)-N-(methylsulfonyl)benzamide | Acid-47 | | D |
| 71 | 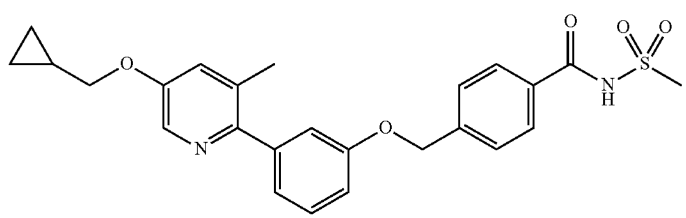 [SMILES: Cc1cc(OCC2CC2)cnc1-c1cccc(OCc2ccc(C(=O)NS(C)(=O)=O)cc2)c1] | 4-((3-(5-(cyclopropylmethoxy)-3-methylpyridin-2-yl)phenoxy)methyl)-N-(methylsulfonyl)benzamide | Acid-48 | | D |

TABLE 6-continued

| Ex. | Structure | Name | Reactant-1 | Reactant-2 | Method |
|---|---|---|---|---|---|
| 72 | 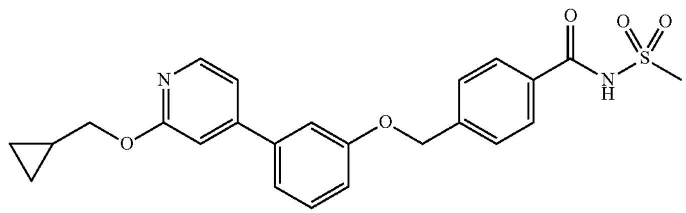 [SMILES: CS(=O)(=O)NC(=O)c1ccc(COc2cccc(-c3ccnc(OCC4CC4)c3)c2)cc1] | 4-((3-(2-(cyclopropylmethoxy)pyridin-4-yl)phenoxy)methyl)-N-(methylsulfonyl)benzamide | Acid-49 | | D |
| 73 | 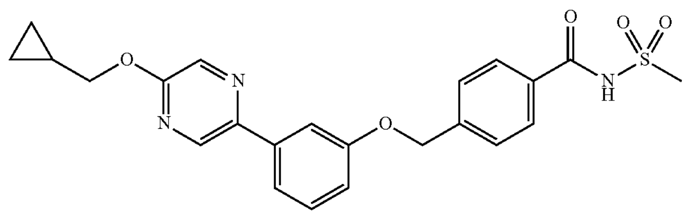 [SMILES: CS(=O)(=O)NC(=O)c1ccc(COc2cccc(-c3cnc(OCC4CC4)cn3)c2)cc1] | 4-((3-(5-(cyclopropylmethoxy)pyrazin-2-yl)phenoxy)methyl)-N-(methylsulfonyl)benzamide | Acid-50 | | D |
| 74 | 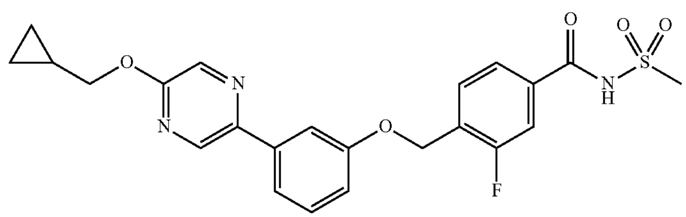 | 4-((3-(5-(cyclopropylmethoxy)pyrazin-2-yl)phenoxy)methyl)-3-fluoro-N-(methylsulfonyl)benzamide | Acid-51 | | D |
| 75 | 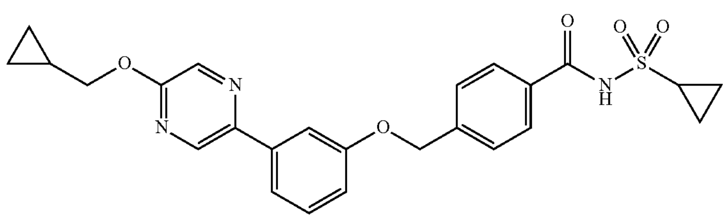 [SMILES: O=C(NS(=O)(=O)C1CC1)c1ccc(COc2cccc(-c3cnc(OCC4CC4)cn3)c2)cc1] | 4-((3-(5-(cyclopropylmethoxy)pyrazin-2-yl)phenoxy)methyl)-N-(cyclopropylsulfonyl)benzamide | Acid-50 | | D |

TABLE 6-continued

| Ex. | Structure | Name | Reactant-1 | Reactant-2 | Method |
|---|---|---|---|---|---|
| 76 | 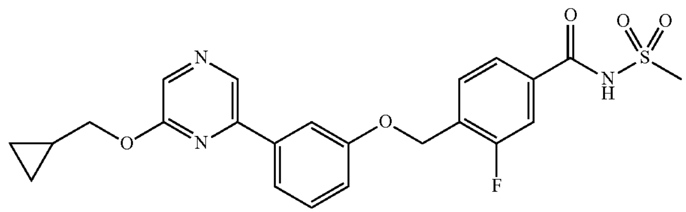 [SMILES: CS(=O)(=O)NC(=O)c1ccc(COc2cccc(-c3cncc(OCC4CC4)n3)c2)c(F)c1] | 4-((3-(6-(cyclopropylmethoxy)pyrazin-2-yl)phenoxy)methyl)-3-fluoro-N-(methylsulfonyl)benzamide | Borate-2 | Aryl halide-18 | E |
| 77 | 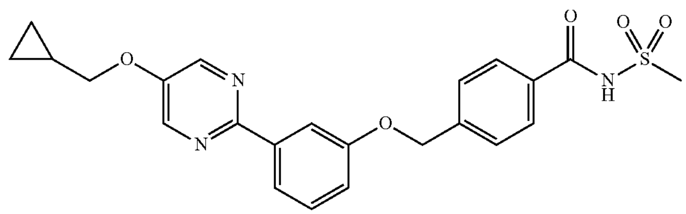 [SMILES: CS(=O)(=O)NC(=O)c1ccc(COc2cccc(-c3ncc(OCC4CC4)cn3)c2)cc1] | 4-((3-(5-(cyclopropylmethoxy)pyrimidin-2-yl)phenoxy)methyl)-N-(methylsulfonyl)benzamide | Acid-52 | | D |
| 78 | 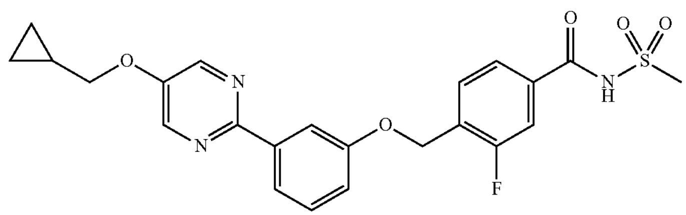 [SMILES: CS(=O)(=O)NC(=O)c1ccc(COc2cccc(-c3ncc(OCC4CC4)cn3)c2)c(F)c1] | 4-((3-(5-(cyclopropylmethoxy)pyrimidin-2-yl)phenoxy)methyl)-3-fluoro-N-(methylsulfonyl)benzamide | Acid-53 | | D |
| 79 | 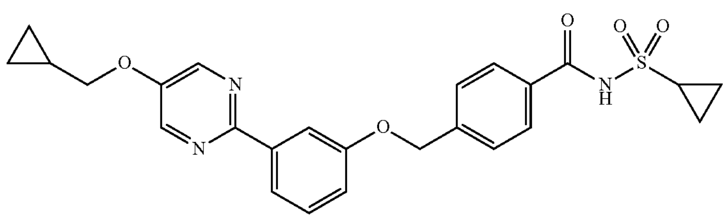 [SMILES: O=C(NS(=O)(=O)C1CC1)c1ccc(COc2cccc(-c3ncc(OCC4CC4)cn3)c2)cc1] | 4-((3-(5-(cyclopropylmethoxy)pyrimidin-2-yl)phenoxy)methyl)-N-(cyclopropylsulfonyl)benzamide | Acid-52 | | D |

TABLE 6-continued

| Ex. | Structure | Name | Reactant-1 | Reactant-2 | Method |
|---|---|---|---|---|---|
| 80 | 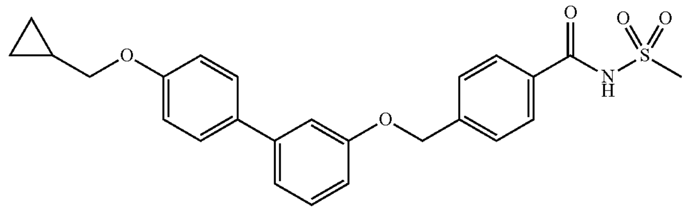 [SMILES: CS(=O)(=O)NC(=O)c1ccc(COc2cccc(-c3ccc(OCC4CC4)cc3)c2)cc1] | 4-((4'-(cyclopropylmethoxy)-[1,1'-biphenyl]-3-yl)oxy)methyl)-N-(methylsulfonyl)benzamide | Acid-54 | H₂N-S(=O)(=O)-CH₃ | D |
| 81 | 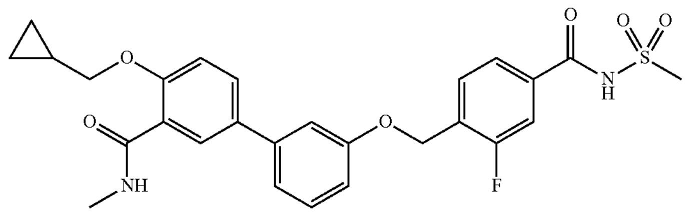 [SMILES: CNC(=O)c1cc(-c2cccc(OCc3ccc(C(=O)NS(C)(=O)=O)cc3F)c2)ccc1OCC1CC1] | 4-(cyclopropylmethoxy)-3'-((2-fluoro-4-((methylsulfonyl)carbamoyl)benzyl)oxy)-N-methyl-[1,1'-biphenyl]-3-carboxamide | Acid-57 | —NH₂ HCl | D |
| 82 | 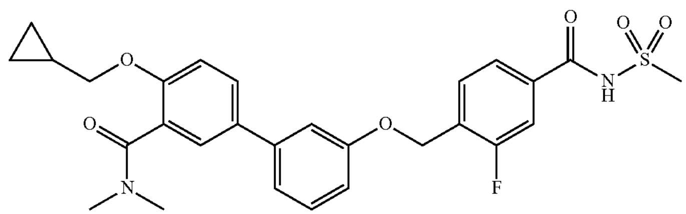 [SMILES: CN(C)C(=O)c1cc(-c2cccc(OCc3ccc(C(=O)NS(C)(=O)=O)cc3F)c2)ccc1OCC1CC1] | 4-(cyclopropylmethoxy)-3'-((2-fluoro-4-((methylsulfonyl)carbamoyl)benzyl)oxy)-N,N-methyl-[1,1'-biphenyl]-3-carboxamide | Acid-57 | —NH(CH₃) HCl | D |
| 83 | 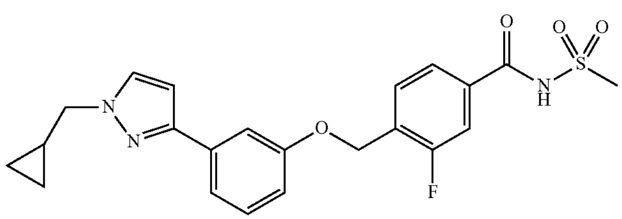 [SMILES: CS(=O)(=O)NC(=O)c1ccc(COc2cccc(-c3ccn(CC4CC4)n3)c2)c(F)c1] | 4-((3-(1-(cyclopropylmethyl)-1H-pyrazol-3-yl)phenoxy)methyl)-3-fluoro-N-(methylsulfonyl)benzamide | Acid-55 | H₂N-S(=O)(=O)-CH₃ | D |

TABLE 6-continued

| Ex. | Structure | Name | Reactant-1 | Reactant-2 | Method |
|---|---|---|---|---|---|
| 84 | 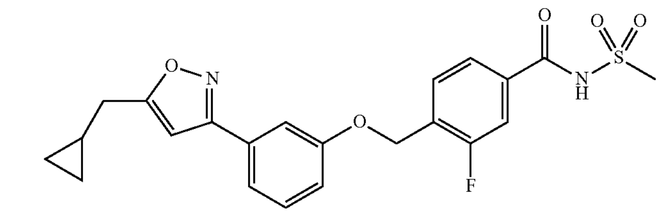 [SMILES: CS(=O)(=O)NC(=O)c1ccc(COc2cccc(-c3cc(CC4CC4)on3)c2)c(F)c1] | 4-((3-(5-(cyclopropylmethyl)isoxazol-3-yl)phenoxy)methyl)-3-fluoro-N-(methylsulfonyl)benzamide | Acid-56 | | D |
| 85 | 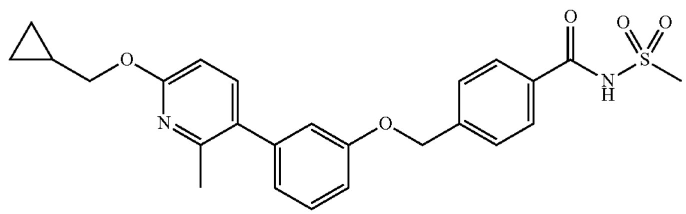 [SMILES: Cc1nc(OCC2CC2)ccc1-c1cccc(OCc2ccc(C(=O)NS(C)(=O)=O)cc2)c1] | 4-((3-(6-(cyclopropylmethoxy)-2-methylpyridin-3-yl)phenoxy)methyl)-N-(methylsulfonyl)benzamide | Borate-1 | Aryl halide-3 | E |
| 86 | 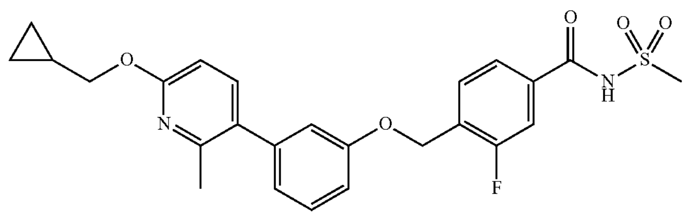 [SMILES: Cc1nc(OCC2CC2)ccc1-c1cccc(OCc2ccc(C(=O)NS(C)(=O)=O)cc2F)c1] | 4-((3-(6-(cyclopropylmethoxy)-2-methylpyridin-3-yl)phenoxy)methyl)-3-fluoro-N-(methylsulfonyl)benzamide | Borate-2 | Aryl halide-3 | E |
| 87 | 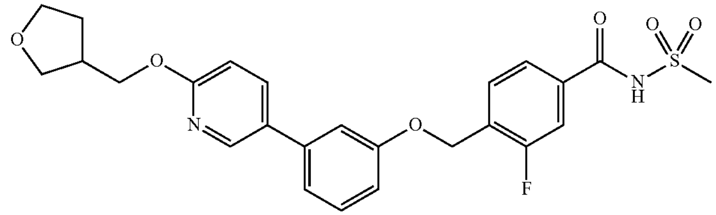 [SMILES: CS(=O)(=O)NC(=O)c1ccc(COc2cccc(-c3ccc(OCC4CCOC4)nc3)c2)c(F)c1] | 3-fluoro-N-(methylsulfonyl)-4-((3-(6-((tetrahydrofuran-3-yl)methoxy)pyridin-3-yl)phenoxy)methyl)benzamide | Borate-2 | Aryl halide-4 | E |

| Ex. | Structure | Name | Reactant-1 | Reactant-2 | Method |
|---|---|---|---|---|---|
| 88 | 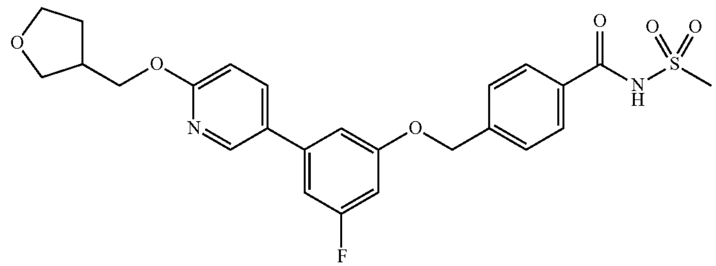 [SMILES: CS(=O)(=O)NC(=O)c1ccc(COc2cc(F)cc(-c3ccc(OCC4CCOC4)nc3)c2)cc1] | 4-((3-fluoro-5-(6-((tetrahydrofuran-3-yl)methoxy)pyridin-3-yl)phenoxy)methyl)-N-(methylsulfonyl)benzamide | Borate-3 | Aryl halide-4 | E |
| 89 | 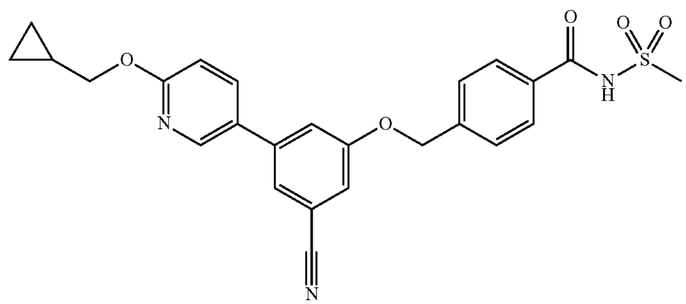 [SMILES: CS(=O)(=O)NC(=O)c1ccc(COc2cc(C#N)cc(-c3ccc(OCC4CC4)nc3)c2)cc1] | 4-((3-cyano-5-(6-(cyclopropylmethoxy)pyridin-3-yl)phenoxy)methyl)-N-(methylsulfonyl)benzamide | Aryl halide-2 | 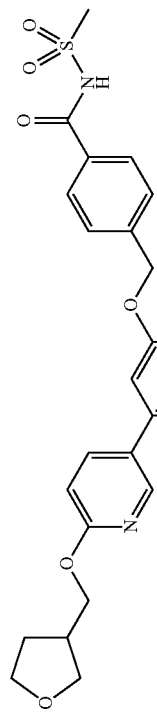 | E |
| 90 | 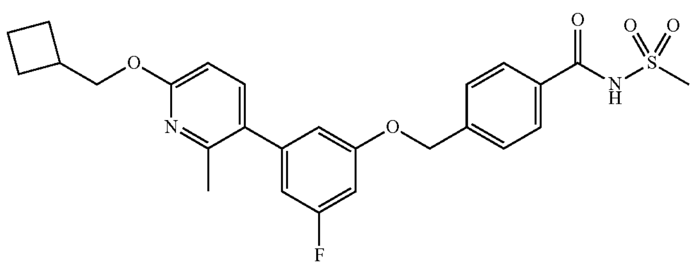 [SMILES: Cc1nc(OCC2CCC2)ccc1-c1cc(F)cc(OCc2ccc(C(=O)NS(C)(=O)=O)cc2)c1] | 4-((3-(6-(cyclobutylmethoxy)-2-methylpyridin-3-yl)-5-fluorophenoxy)methyl)-N-(methylsulfonyl)benzamide | Borate-3 | Aryl halide-5 | E |

TABLE 6-continued

| Ex. | Structure | Name | Reactant-1 | Reactant-2 | Method |
|---|---|---|---|---|---|
| 91 | 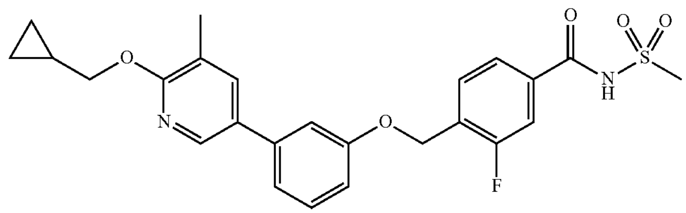 [SMILES: Cc1cc(-c2cccc(OCc3ccc(C(=O)NS(C)(=O)=O)cc3F)c2)cnc1OCC1CC1] | 4-((3-(6-(cyclopropylmethoxy)-5-methylpyridin-3-yl)phenoxy)methyl)-3-fluoro-N-(methylsulfonyl)benzamide | Borate-2 | Aryl halide-6 | E |
| 92 | 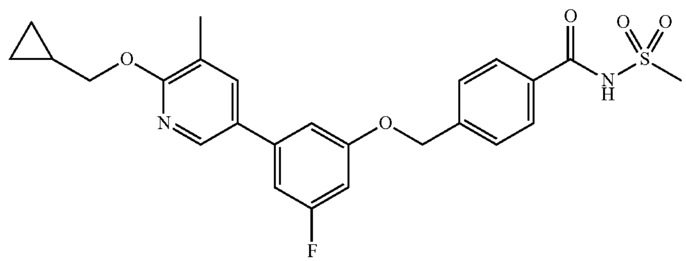 [SMILES: Cc1cc(-c2cc(F)cc(OCc3ccc(C(=O)NS(C)(=O)=O)cc3)c2)cnc1OCC1CC1] | 4-((3-(6-(cyclopropylmethoxy)-5-methylpyridin-3-yl)-6-fluorophenoxy)methyl)-N-(methylsulfonyl)benzamide | Borate-3 | Aryl halide-6 | E |
| 93 | 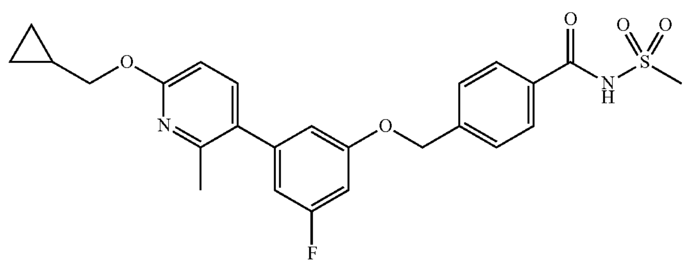 [SMILES: Cc1nc(OCC2CC2)ccc1-c1cc(F)cc(OCc2ccc(C(=O)NS(C)(=O)=O)cc2)c1] | 4-((3-(6-(cyclopropylmethoxy)-2-methylpyridin-3-yl)-5-fluorophenoxy)methyl)-N-(methylsulfonyl)benzamide | Borate-3 | Aryl halide-3 | E |
| 94 | 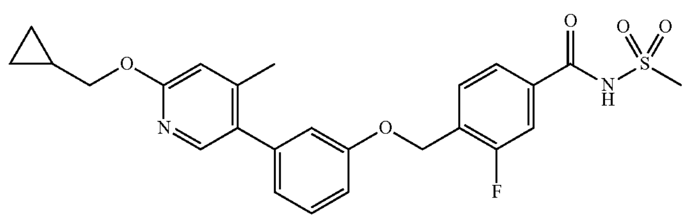 [SMILES: Cc1cc(OCC2CC2)ncc1-c1cccc(OCc2ccc(C(=O)NS(C)(=O)=O)cc2F)c1] | 4-((3-(6-(cyclopropylmethoxy)-4-methylpyridin-3-yl)phenoxy)methyl)-3-fluoro-N-(methylsulfonyl)benzamide | Borate-2 | Aryl halide-7 | E |

TABLE 6-continued

| Ex. | Structure | Name | Reactant-1 | Reactant-2 | Method |
|---|---|---|---|---|---|
| 95 | 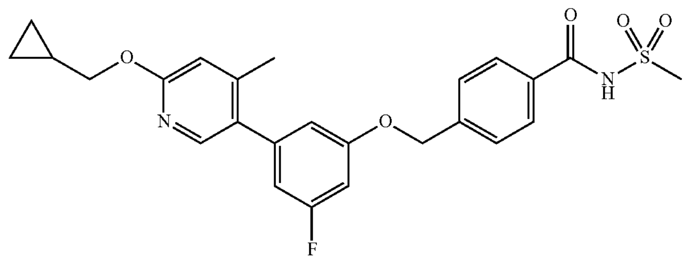 [SMILES: Cc1cc(OCC2CC2)ncc1-c1cc(F)cc(OCc2ccc(C(=O)NS(C)(=O)=O)cc2)c1] | 4-((3-(6-(cyclopropylmethoxy)-4-methylpyridin-3-yl)-5-fluorophenoxy)methyl)-N-(methylsulfonyl)benzamide | Borate-3 | Aryl halide-7 | E |
| 96 | 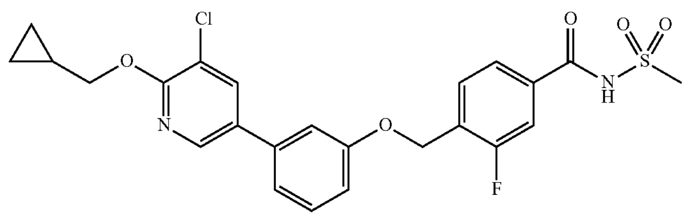 [SMILES: CS(=O)(=O)NC(=O)c1ccc(COc2cccc(-c3cnc(OCC4CC4)c(Cl)c3)c2)c(F)c1] | 4-(3-(5-chloro-6-(cyclopropylmethoxy)pyridin-3-yl)phenoxy)methyl)-3-fluoro-N-(methylsulfonyl)benzamide | Borate-2 | Aryl halide-8 | E |
| 97 | 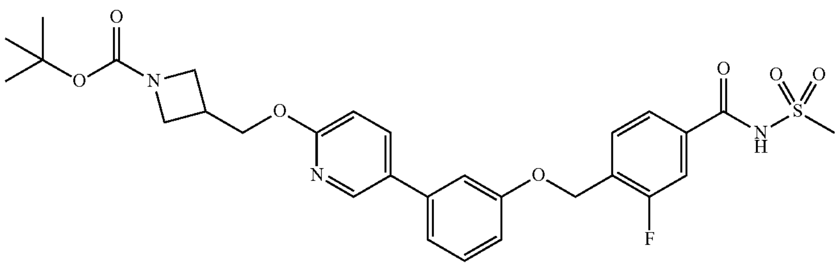 [SMILES: CC(C)(C)OC(=O)N1CC(COc2ccc(-c3cccc(OCc4ccc(C(=O)NS(C)(=O)=O)cc4F)c3)cn2)C1] | tert-butyl 3-((5-(3-((2-fluoro-4-((methylsulfonyl)carbamoyl)benzyl)oxy)phenyl)pyridin-2-yl)oxy)methyl)azetidine-1-carboxylate | Borate-2 | Aryl halide-9 | E |
| 98 | 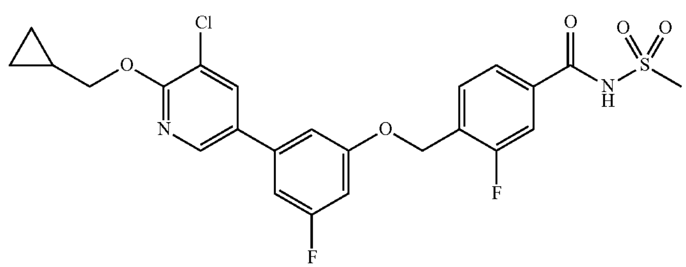 [SMILES: CS(=O)(=O)NC(=O)c1ccc(COc2cc(F)cc(-c3cnc(OCC4CC4)c(Cl)c3)c2)c(F)c1] | 4-((3-(5-chloro-6-(cyclopropylmethoxy)pyridin-3-yl)-5-fluorophenoxy)methyl)-3-fluoro-N-(methylsulfonyl)benzamide | Borate-4 | Aryl halide-8 | E |

TABLE 6-continued

| Ex. | Structure | Name | Reactant-1 | Reactant-2 | Method |
|---|---|---|---|---|---|
| 99 | 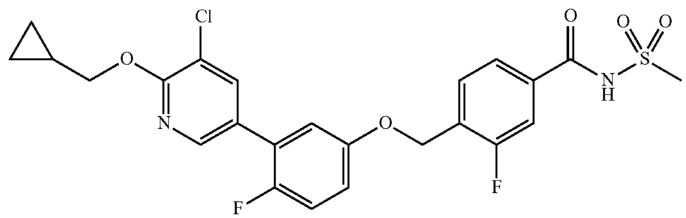 [SMILES: CS(=O)(=O)NC(=O)c1ccc(COc2ccc(F)c(-c3cnc(OCC4CC4)c(Cl)c3)c2)c(F)c1] | 4-((3-(5-chloro-6-(cyclopropylmethoxy)pyridin-3-yl)-4-fluorophenoxy)methyl)-3-fluoro-N-(methylsulfonyl)benzamide | Borate-5 | Aryl halide-8 | E |
| 100 | 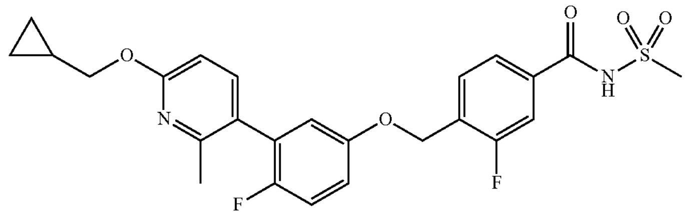 [SMILES: Cc1nc(OCC2CC2)ccc1-c1cc(OCc2ccc(C(=O)NS(C)(=O)=O)cc2F)ccc1F] | 4-((3-(6-(cyclopropylmethoxy)-2-methylpyridin-3-yl)-4-fluorophenoxy)methyl)-3-fluoro-N-(methylsulfonyl)benzamide | Borate-5 | Aryl halide-3 | E |
| 101 | 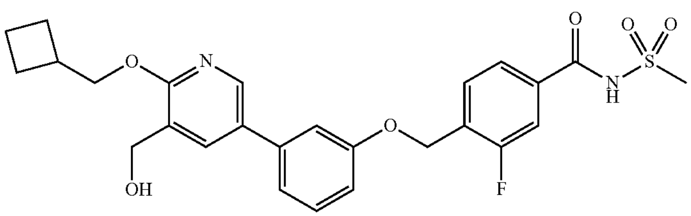 [SMILES: CS(=O)(=O)NC(=O)c1ccc(COc2cccc(-c3cnc(OCC4CCC4)c(CO)c3)c2)c(F)c1] | 4-((3-(6-(cyclobutylmethoxy)-5-(hydroxymethyl)pyridin-3-yl)phenoxy)methyl)-3-fluoro-N-(methylsulfonyl)benzamide | Borate-2 | Aryl halide-10 | E |
| 102 | 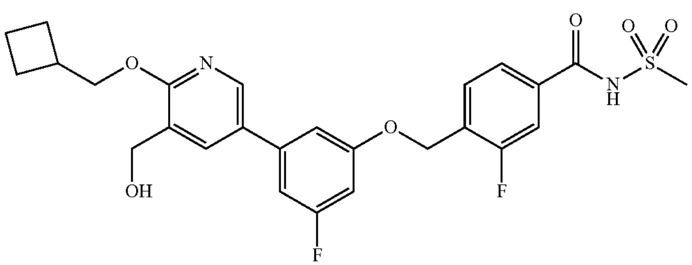 [SMILES: CS(=O)(=O)NC(=O)c1ccc(COc2cc(F)cc(-c3cnc(OCC4CCC4)c(CO)c3)c2)c(F)c1] | 4-((3-(6-(cyclobutylmethoxy)-5-(hydroxymethyl)pyridin-3-yl)-5-fluorophenoxy)methyl)-3-fluoro-N-(methylsulfonyl)benzamide | Borate-4 | Aryl halide-10 | E |

TABLE 6-continued

| Ex. | Structure | Name | Reactant-1 | Reactant-2 | Method |
|---|---|---|---|---|---|
| 103 | 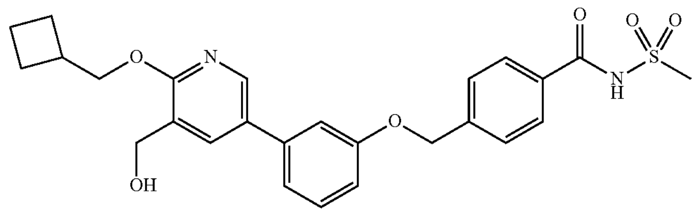 [SMILES: CS(=O)(=O)NC(=O)c1ccc(COc2cccc(-c3cnc(OCC4CCC4)c(CO)c3)c2)cc1] | 4-((3-(6-(cyclobutylmethoxy)-5-(hydroxymethyl)pyridin-3-yl)phenoxy)methyl)-N-(methylsulfonyl)benzamide | Borate-1 | Aryl halide-10 | E |
| 104 | 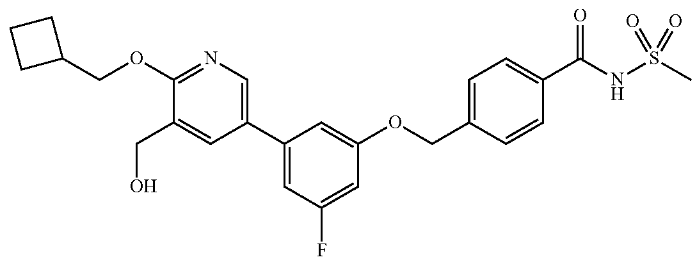 [SMILES: CS(=O)(=O)NC(=O)c1ccc(COc2cc(F)cc(-c3cnc(OCC4CCC4)c(CO)c3)c2)cc1] | 4-((3-(6-(cyclobutylmethoxy)-5-(hydroxymethyl)pyridin-3-yl)-5-fluorophenoxy)methyl)-N-(methylsulfonyl)benzamide | Borate-3 | Aryl halide-10 | E |
| 105 | 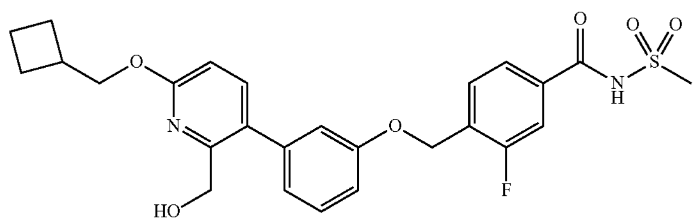 [SMILES: CS(=O)(=O)NC(=O)c1ccc(COc2cccc(-c3ccc(OCC4CCC4)nc3CO)c2)c(F)c1] | 4-((3-(6-(cyclobutylmethoxy)-2-(hydroxymethyl)pyridin-3-yl)phenoxy)methyl)-3-fluoro-N-(methylsulfonyl)benzamide | Borate-2 | Aryl halide-11 | E |
| 106 | 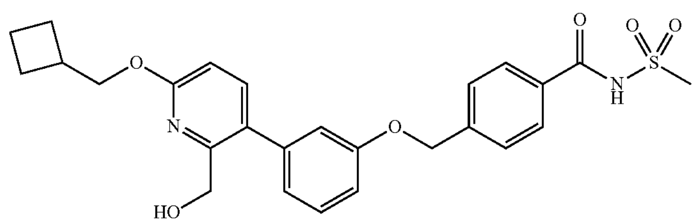 [SMILES: CS(=O)(=O)NC(=O)c1ccc(COc2cccc(-c3ccc(OCC4CCC4)nc3CO)c2)cc1] | 4-((3-(6-(cyclobutylmethoxy)-2-(hydroxymethyl)pyridin-3-yl)phenoxy)methyl)-N-(methylsulfonyl)benzamide | Borate-1 | Aryl halide-11 | E |

TABLE 6-continued

| Ex. | Structure | Name | Reactant-1 | Reactant-2 | Method |
|---|---|---|---|---|---|
| 107 | 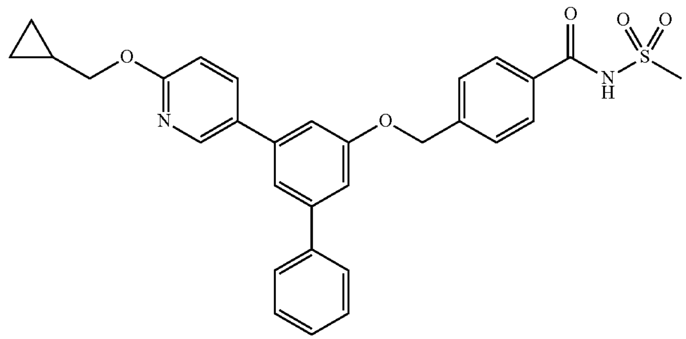 [SMILES: CS(=O)(=O)NC(=O)c1ccc(COc2cc(-c3ccccc3)cc(-c3ccc(OCC4CC4)nc3)c2)cc1] | 4-((5-(6-(cyclopropylmethoxy)pyridin-3-yl)-[1,1'-biphenyl]-3-yl)oxy)methyl)-N-(methylsulfonyl)benzamide | Example 45 | phenylboronic acid | E |
| 108 | 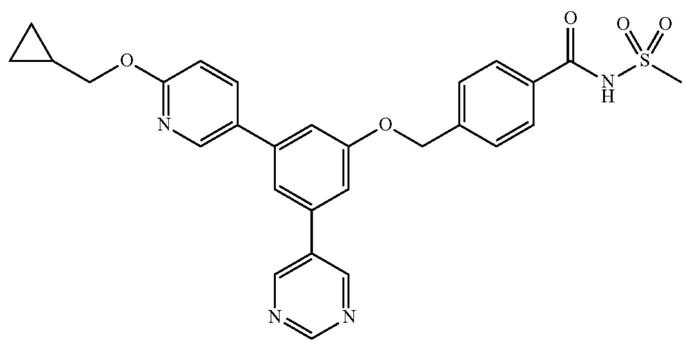 | 4-((3-(6-(cyclopropylmethoxy)pyridin-3-yl)-5-(pyrimidin-5-yl)phenoxy)methyl)-N-(methylsulfonyl)benzamide | Example 45 | pyrimidin-5-yl pinacol boronate | E |
| 109 | 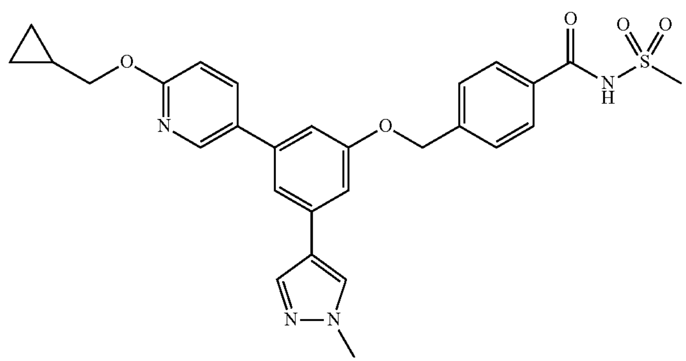 [SMILES: Cn1cc(-c2cc(OCc3ccc(C(=O)NS(C)(=O)=O)cc3)cc(-c3ccc(OCC4CC4)nc3)c2)cn1] | 4-((3-(6-(cyclopropylmethoxy)pyridin-3-yl)-5-(1-methyl-1H-pyrazol-4-yl)phenoxy)methyl)-N-(methylsulfonyl)benzamide | Example 45 | 1-methyl-1H-pyrazol-4-yl pinacol boronate | E |

TABLE 6-continued

| Ex. | Structure | Name | Reactant-1 | Reactant-2 | Method |
|---|---|---|---|---|---|
| 110 | 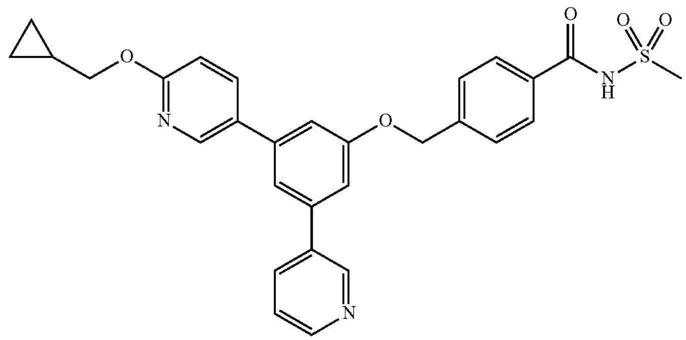 [SMILES: CS(=O)(=O)NC(=O)c1ccc(COc2cc(-c3cccnc3)cc(-c3ccc(OCC4CC4)nc3)c2)cc1] | 4-((3-(6-(cyclopropylmethoxy)pyridin-3-yl)-5-(pyridin-3-yl)phenoxy)methyl)-N-(methylsulfonyl)benzamide | Example 45 | | E |
| 111 | 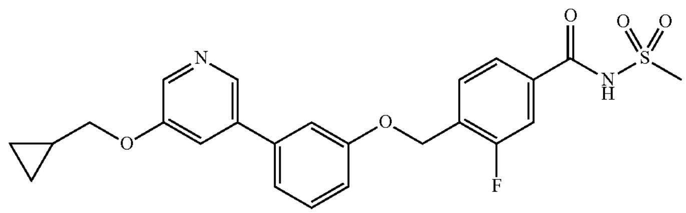 [SMILES: CS(=O)(=O)NC(=O)c1ccc(COc2cccc(-c3cncc(OCC4CC4)c3)c2)c(F)c1] | 4-((3-(5-(cyclopropylmethoxy)pyridin-3-yl)phenoxy)methyl)-3-fluoro-N-(methylsulfonyl)benzamide | Borate-2 | | E |
| 112 | 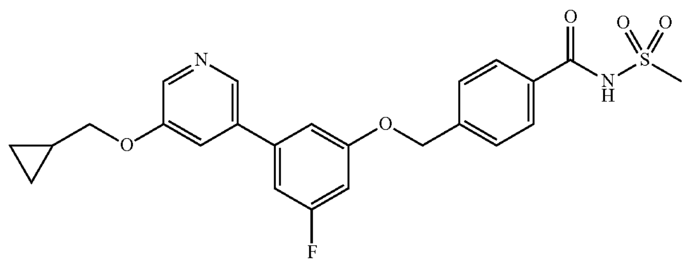 | 4-((3-(5-(cyclopropylmethoxy)pyridin-3-yl)-5-fluorophenoxy)methyl)-N-(methylsulfonyl)benzamide | Borate-3 | | E |

TABLE 6-continued

| Ex. | Structure | Name | Reactant-1 | Reactant-2 | Method |
|---|---|---|---|---|---|
| 113 | 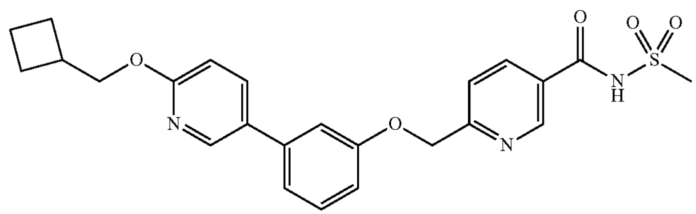 [SMILES: CS(=O)(=O)NC(=O)c1ccc(COc2cccc(-c3ccc(OCC4CCC4)nc3)c2)nc1] | 6-((3-(6-(cyclobutylmethoxy)pyridin-3-yl)phenoxy)methyl)-N-(methylsulfonyl)nicotinamide | Borate-6 | Step-1 of Acid-12 | E |
| 114 | 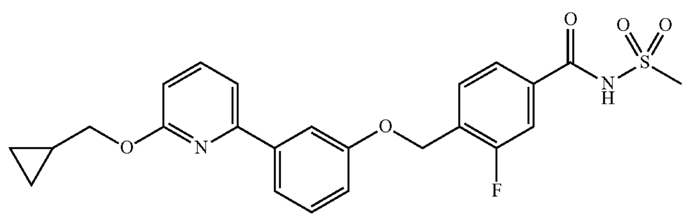 [SMILES: CS(=O)(=O)NC(=O)c1ccc(COc2cccc(-c3cccc(OCC4CC4)n3)c2)c(F)c1] | 4-((3-(6-(cyclopropylmethoxy)pyridin-2-yl)phenoxy)methyl)-3-fluoro-N-(methylsulfonyl)benzamide | Borate-2 | | E |
| 115 | 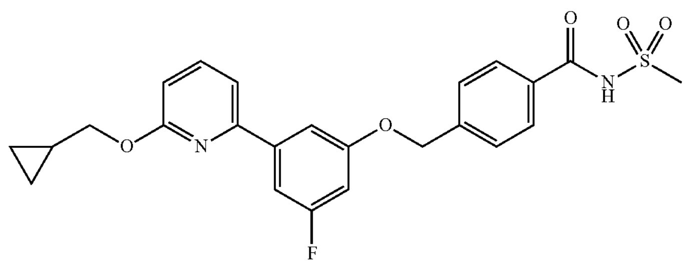 [SMILES: CS(=O)(=O)NC(=O)c1ccc(COc2cc(F)cc(-c3cccc(OCC4CC4)n3)c2)cc1] | 4-((3-(6-(cyclopropylmethoxy)pyridin-2-yl)-5-fluorophenoxy)methyl)-N-(methylsulfonyl)benzamide | Borate-3 | | E |
| 116 | 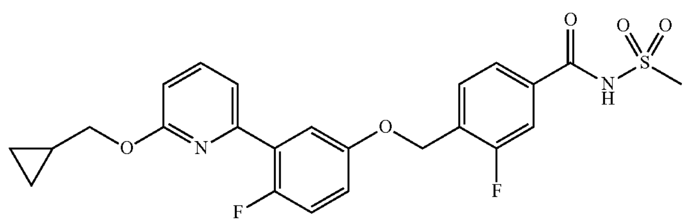 [SMILES: CS(=O)(=O)NC(=O)c1ccc(COc2ccc(F)c(-c3cccc(OCC4CC4)n3)c2)c(F)c1] | 4-((3-(6-(cyclopropylmethoxy)pyridin-2-yl)-4-fluorophenoxy)methyl)-3-fluoro-N-(methylsulfonyl)benzamide | Borate-5 | | E |

TABLE 6-continued

| Ex. | Structure | Name | Reactant-1 | Reactant-2 | Method |
|---|---|---|---|---|---|
| 117 | 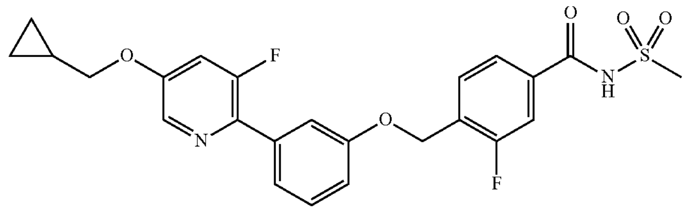 [SMILES: CS(=O)(=O)NC(=O)c1ccc(COc2cccc(-c3ncc(OCC4CC4)cc3F)c2)c(F)c1] | 4-((3-(5-(cyclopropylmethoxy)-3-fluoropyridin-2-yl)phenoxy)methyl)-3-fluoro-N-(methylsulfonyl)benzamide | Borate-2 | | E |
| 118 | 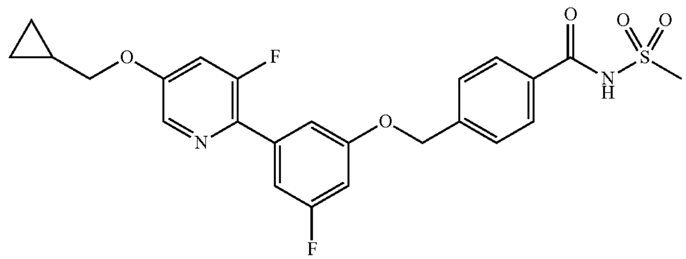 [SMILES: CS(=O)(=O)NC(=O)c1ccc(COc2cc(F)cc(-c3ncc(OCC4CC4)cc3F)c2)cc1] | 4-((3-(5-(cyclopropylmethoxy)-3-fluoropyridin-2-yl)-5-fluorophenoxy)methyl)-N-(methylsulfonyl)benzamide | Borate-3 | | E |
| 119 | 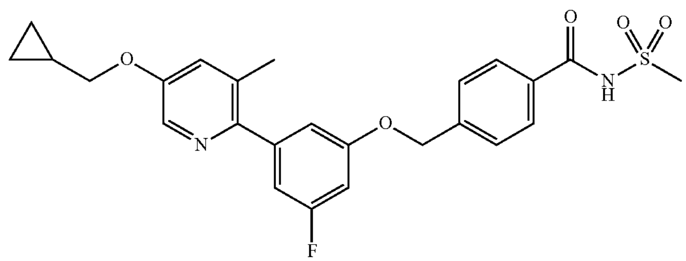 [SMILES: Cc1cc(OCC2CC2)cnc1-c1cc(F)cc(OCc2ccc(C(=O)NS(C)(=O)=O)cc2)c1] | 4-((3-(5-(cyclopropylmethoxy)-3-fluoropyridin-2-yl)-5-fluorophenoxy)methyl)-N-(methylsulfonyl)benzamide | Borate-3 | Step-1 of Acid-48 | E |
| 120 | 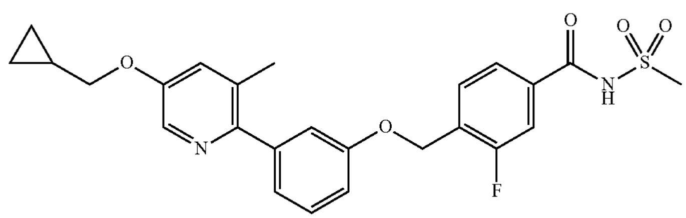 [SMILES: Cc1cc(OCC2CC2)cnc1-c1cccc(OCc2ccc(C(=O)NS(C)(=O)=O)cc2F)c1] | 4-((3-(5-(cyclopropylmethoxy)-3-methylpyridin-2-yl)phenoxy)methyl)-3-fluoro-N-(methylsulfonyl)benzamide | Borate-2 | Step-1 of Acid-48 | E |

TABLE 6-continued

| Ex. | Structure | Name | Reactant-1 | Reactant-2 | Method |
|---|---|---|---|---|---|
| 121 | 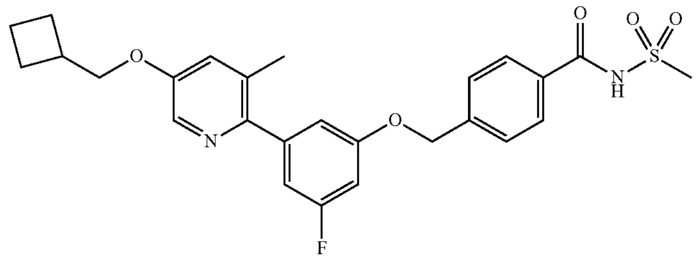 [SMILES: Cc1cc(OCC2CCC2)cnc1-c1cc(F)cc(OCc2ccc(C(=O)NS(C)(=O)=O)cc2)c1] | 4-((3-(5-(cyclobutylmethoxy)-3-methylpyridin-2-yl)-5-fluorophenoxy)methyl)-N-(methylsulfonyl)benzamide | Borate-3 | Aryl halide-12 | E |
| 122 | 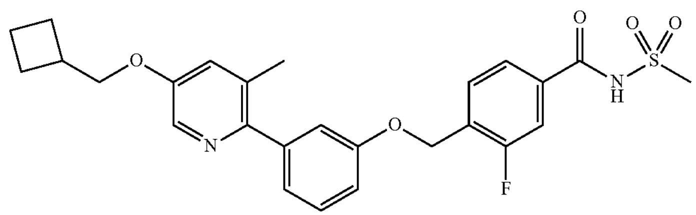 [SMILES: Cc1cc(OCC2CCC2)cnc1-c1cccc(OCc2ccc(C(=O)NS(C)(=O)=O)cc2F)c1] | 4-((3-(5-(cyclopropylmethoxy)-3-methylpyridin-2-yl)phenoxy)methyl)-3-fluoro-N-(methylsulfonyl)benzamide | Borate-2 | Aryl halide-12 | E |
| 123 | 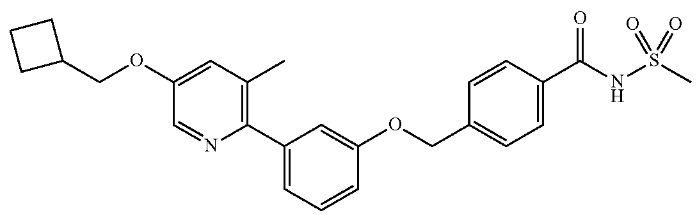 [SMILES: Cc1cc(OCC2CCC2)cnc1-c1cccc(OCc2ccc(C(=O)NS(C)(=O)=O)cc2)c1] | 4-((3-(5-(cyclobutylmethoxy)-3-methylpyridin-2-yl)phenoxy)methyl)-N-(methylsulfonyl)benzamide | Borate-1 | Aryl halide-12 | E |
| 124 | 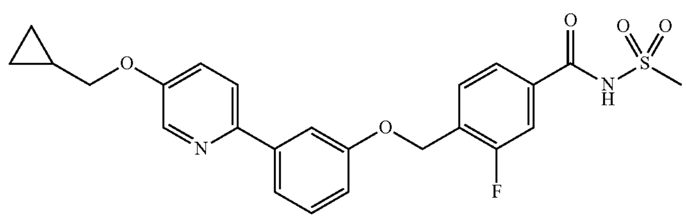 [SMILES: CS(=O)(=O)NC(=O)c1ccc(COc2cccc(-c3ccc(OCC4CC4)cn3)c2)c(F)c1] | 4-((3-(5-(cyclopropylmethoxy)pyridin-2-yl)phenoxy)methyl)-3-fluoro-N-(methylsulfonyl)benzamide | Borate-2 | | E |

TABLE 6-continued

| Ex. | Structure | Name | Reactant-1 | Reactant-2 | Method |
|---|---|---|---|---|---|
| 125 | 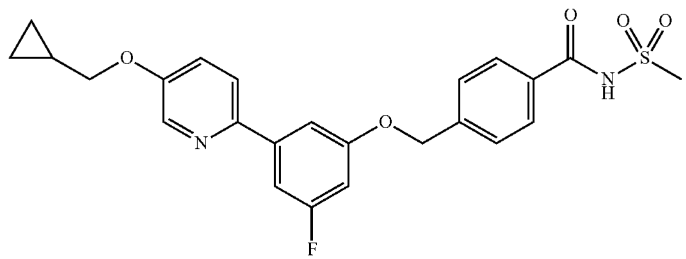 [SMILES: CS(=O)(=O)NC(=O)c1ccc(COc2cc(F)cc(-c3ccc(OCC4CC4)cn3)c2)cc1] | 4-((3-(5-(cyclopropylmethoxy)pyridin-2-yl)-5-fluorophenoxy)methyl)-N-(methylsulfonyl)benzamide | Borate-3 | (2-bromo-5-(cyclopropylmethoxy)pyridine) | E |
| 126 | 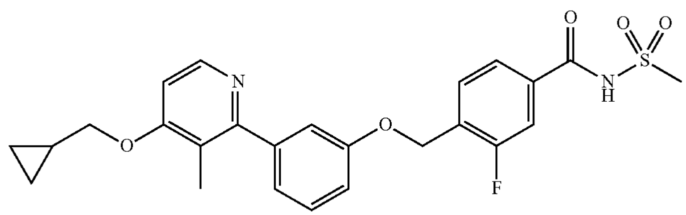 [SMILES: Cc1c(OCC2CC2)ccnc1-c1cccc(OCc2ccc(C(=O)NS(C)(=O)=O)cc2F)c1] | 4-((3-(4-(cyclopropylmethoxy)-3-methylpyridin-2-yl)phenoxy)methyl)-3-fluoro-N-(methylsulfonyl)benzamide | Borate-2 | Aryl halide-13 | E |
| 127 | 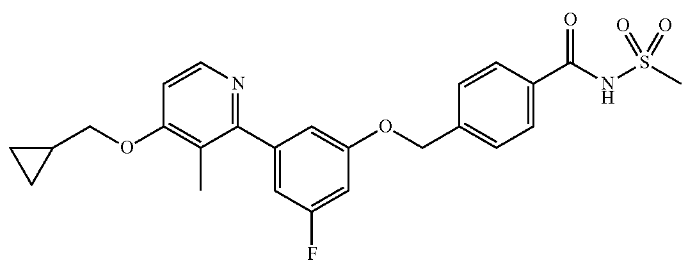 | 4-((3-(4-(cyclopropylmethoxy)-3-methylpyridin-2-yl)-5-fluorophenoxy)methyl)-N-(methylsulfonyl)benzamide | Borate-3 | Aryl halide-13 | E |
| 128 | 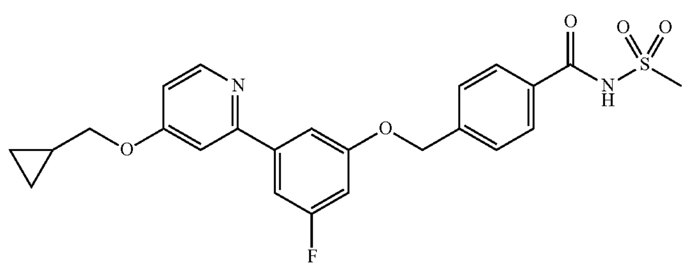 [SMILES: CS(=O)(=O)NC(=O)c1ccc(COc2cc(F)cc(-c3cc(OCC4CC4)ccn3)c2)cc1] | 4-((3-(4-(cyclopropylmethoxy)pyridin-2-yl)-5-fluorophenoxy)methyl)-N-(methylsulfonyl)benzamide | Borate-3 | Aryl halide-14 | E |

TABLE 6-continued

| Ex. | Structure | Name | Reactant-1 | Reactant-2 | Method |
|---|---|---|---|---|---|
| 129 | 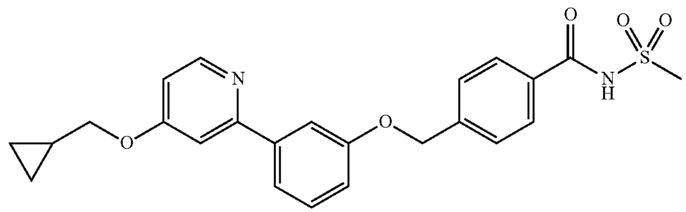 [SMILES: CS(=O)(=O)NC(=O)c1ccc(COc2cccc(-c3cc(OCC4CC4)ccn3)c2)cc1] | 4-((3-(4-(cyclopropylmethoxy)pyridin-2-yl)phenoxy)methyl)-N-(methylsulfonyl)benzamide | Borate-1 | Aryl halide-14 | E |
| 130 | 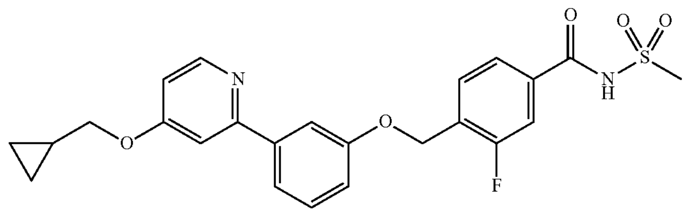 [SMILES: CS(=O)(=O)NC(=O)c1ccc(COc2cccc(-c3cc(OCC4CC4)ccn3)c2)c(F)c1] | 4-((3-(4-(cyclopropylmethoxy)pyridin-2-yl)phenoxy)methyl)-3-fluoro-N-(methylsulfonyl)benzamide | Borate-2 | Aryl halide-14 | E |
| 131 | 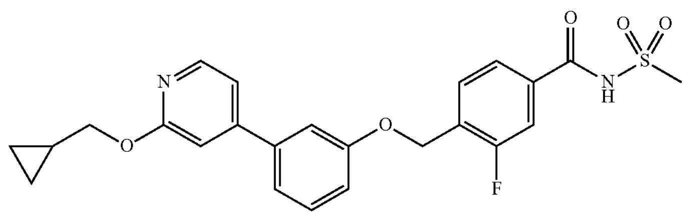 [SMILES: CS(=O)(=O)NC(=O)c1ccc(COc2cccc(-c3ccnc(OCC4CC4)c3)c2)c(F)c1] | 4-((3-(2-(cyclopropylmethoxy)pyridin-4-yl)phenoxy)methyl)-3-fluoro-N-(methylsulfonyl)benzamide | Borate-2 | | E |
| 132 | 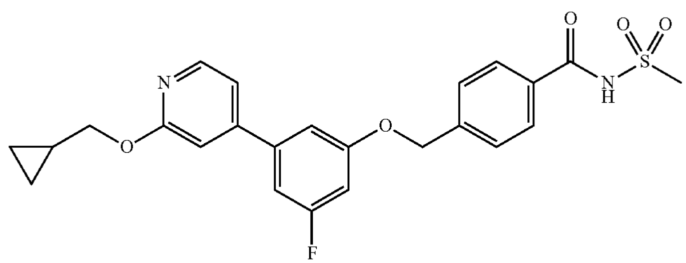 | 4-((3-(2-(cyclopropylmethoxy)pyridin-4-yl)-5-fluorophenoxy)methyl)-N-(methylsulfonyl)benzamide | Borate-3 | | E |

TABLE 6-continued

| Ex. | Structure | Name | Reactant-1 | Reactant-2 | Method |
|---|---|---|---|---|---|
| 133 | 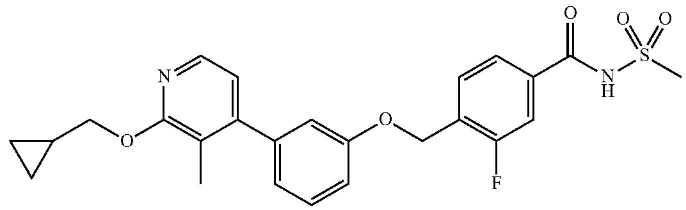 [SMILES: Cc1c(-c2cccc(OCc3ccc(C(=O)NS(C)(=O)=O)cc3F)c2)ccnc1OCC1CC1] | 4-((3-(2-(cyclopropylmethoxy)-3-methylpyridin-4-yl)phenoxy)methyl)-3-fluoro-N-(methylsulfonyl)benzamide | Borate-2 | Aryl halide-15 | E |
| 134 | 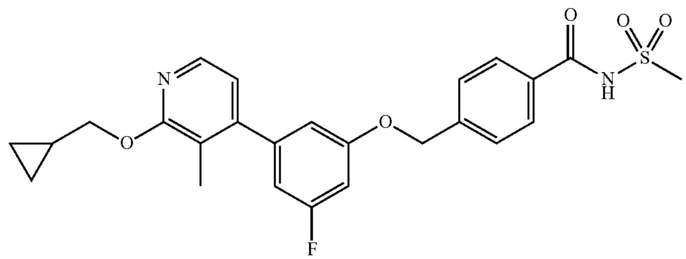 [SMILES: Cc1c(-c2cc(F)cc(OCc3ccc(C(=O)NS(C)(=O)=O)cc3)c2)ccnc1OCC1CC1] | 4-((3-(2-(cyclopropylmethoxy)-3-methylpyridin-4-yl)-5-fluorophenoxy)methyl)-N-(methylsulfonyl)benzamide | Borate-3 | Aryl halide-15 | E |
| 135 | 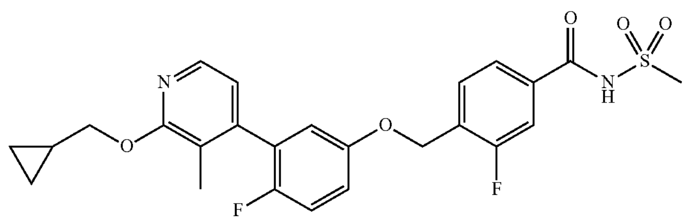 [SMILES: Cc1c(-c2cc(OCc3ccc(C(=O)NS(C)(=O)=O)cc3F)ccc2F)ccnc1OCC1CC1] | 4-((3-(2-(cyclopropylmethoxy)-3-methylpyridin-4-yl)-4-fluorophenoxy)methyl)-3-fluoro-N-(methylsulfonyl)benzamide | Borate-5 | Aryl halide-15 | E |
| 136 | 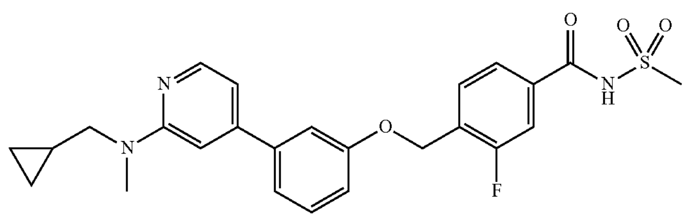 [SMILES: CN(CC1CC1)c1cc(-c2cccc(OCc3ccc(C(=O)NS(C)(=O)=O)cc3F)c2)ccn1] | 4-((3-(2-((cyclopropylmethyl)(methyl)amino)pyridin-4-yl)phenoxy)methyl)-3-fluoro-N-(methylsulfonyl)benzamide | Borate-2 | Aryl halide-16 | E |

TABLE 6-continued

| Ex. | Structure | Name | Reactant-1 | Reactant-2 | Method |
|---|---|---|---|---|---|
| 137 | 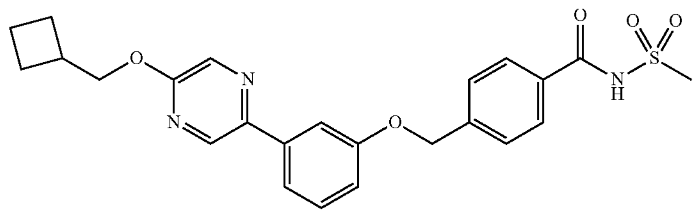 [SMILES: CS(=O)(=O)NC(=O)c1ccc(COc2cccc(-c3cnc(OCC4CCC4)cn3)c2)cc1] | 4-((3-(5-(cyclobutylmethoxy)pyrazin-2-yl)phenoxy)methyl)-N-(methylsulfonyl)benzamide | Borate-1 | Aryl halide-17 | E |
| 138 | 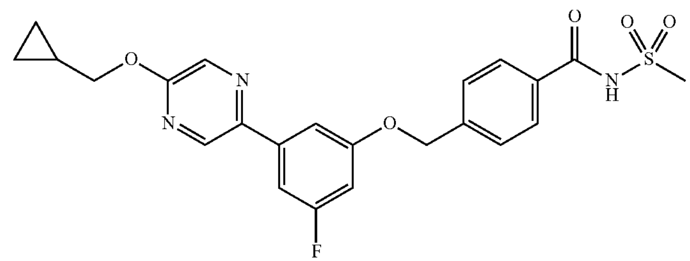 [SMILES: CS(=O)(=O)NC(=O)c1ccc(COc2cc(F)cc(-c3cnc(OCC4CC4)cn3)c2)cc1] | 4-((3-(5-(cyclopropylmethoxy)pyrazin-2-yl)-5-fluorophenoxy)methyl)-N-(methylsulfonyl)benzamide | Borate-3 | Step-1 of Acid-50 | E |
| 139 | 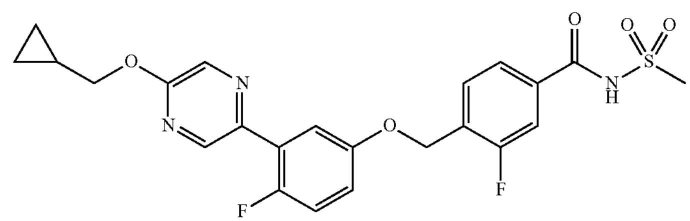 [SMILES: CS(=O)(=O)NC(=O)c1ccc(COc2ccc(F)c(-c3cnc(OCC4CC4)cn3)c2)c(F)c1] | 4-((3-(5-(cyclopropylmethoxy)pyrazin-2-yl)-4-fluorophenoxy)methyl)-3-fluoro-N-(methylsulfonyl)benzamide | Borate-5 | Step-1 of Acid-50 | E |
| 140 | 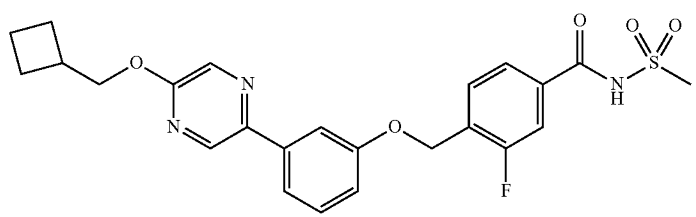 [SMILES: CS(=O)(=O)NC(=O)c1ccc(COc2cccc(-c3cnc(OCC4CCC4)cn3)c2)c(F)c1] | 4-((3-(5-(cyclobutylmethoxy)pyrazin-2-yl)phenoxy)methyl)-3-fluoro-N-(methylsulfonyl)benzamide | Borate-2 | Step-1 of Acid-50 | E |

TABLE 6-continued

| Ex. | Structure | Name | Reactant-1 | Reactant-2 | Method |
|---|---|---|---|---|---|
| 141 | 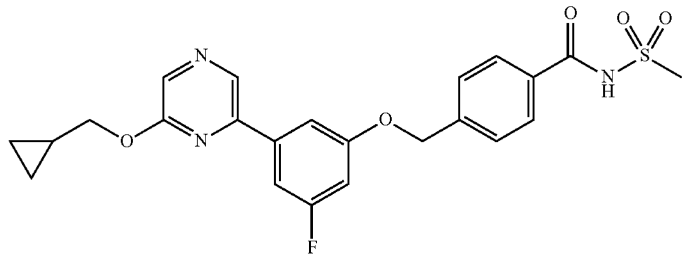 [SMILES: CS(=O)(=O)NC(=O)c1ccc(COc2cc(F)cc(-c3cncc(OCC4CC4)n3)c2)cc1] | 4-((3-(6-(cyclopropylmethoxy)pyrazin-2-yl)-5-fluorophenoxy)methyl)-N-(methylsulfonyl)benzamide | Borate-3 | Aryl halide-18 | E |
| 142 | 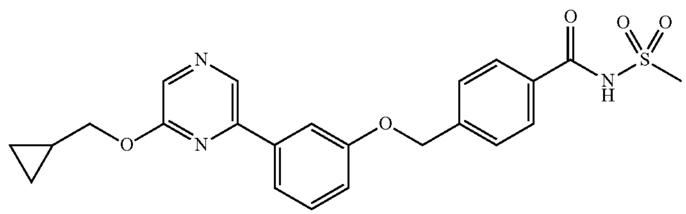 [SMILES: CS(=O)(=O)NC(=O)c1ccc(COc2cccc(-c3cncc(OCC4CC4)n3)c2)cc1] | 4-((3-(6-(cyclopropylmethoxy)pyrazin-2-yl)phenoxy)methyl)-N-(methylsulfonyl)benzamide | Borate-1 | Aryl halide-18 | E |
| 143 | 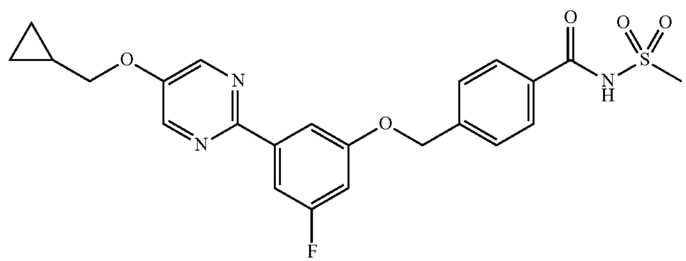 | 4-((3-(5-(cyclopropylmethoxy)pyrimidin-2-yl)-5-fluorophenoxy)methyl)-N-(methylsulfonyl)benzamide | Borate-3 | | E |
| 144 | 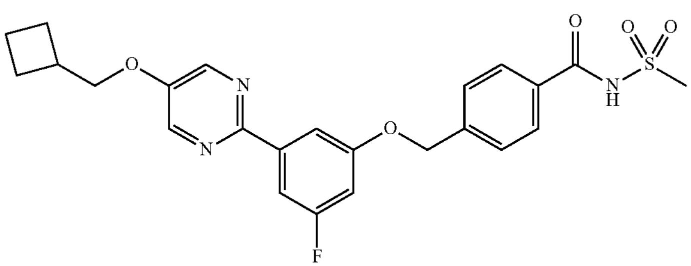 [SMILES: CS(=O)(=O)NC(=O)c1ccc(COc2cc(F)cc(-c3ncc(OCC4CCC4)cn3)c2)cc1] | 4-((3-(5-(cyclobutylmethoxy)pyrimidin-2-yl)-5-fluorophenoxy)methyl)-N-(methylsulfonyl)benzamide | Borate-3 | | E |

TABLE 6-continued

| Ex. | Structure | Name | Reactant-1 | Reactant-2 | Method |
|---|---|---|---|---|---|
| 145 | 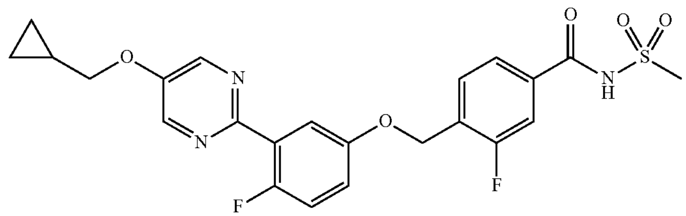 [SMILES: CS(=O)(=O)NC(=O)c1ccc(COc2ccc(F)c(-c3ncc(OCC4CC4)cn3)c2)c(F)c1] | 4-((3-(5-(cyclopropylmethoxy)pyrimidin-2-yl)-4-fluorophenoxy)methyl)-3-fluoro-N-(methylsulfonyl)benzamide | Borate-5 | | E |
| 146 | 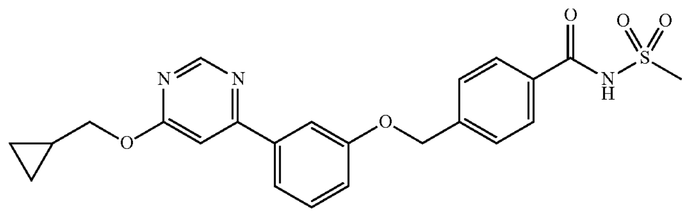 [SMILES: CS(=O)(=O)NC(=O)c1ccc(COc2cccc(-c3cc(OCC4CC4)ncn3)c2)cc1] | 4-((3-(5-(cyclopropylmethoxy)pyrimidin-4-yl)phenoxy)methyl)-N-(methylsulfonyl)benzamide | Borate-1 | | E |
| 147 | 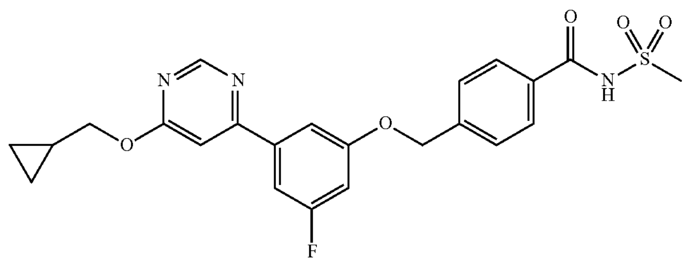 | 4-((3-(6-(cyclopropylmethoxy)pyrimidin-4-yl)-5-fluorophenoxy)methyl)-N-(methylsulfonyl)benzamide | Borate-3 | | E |
| 148 | 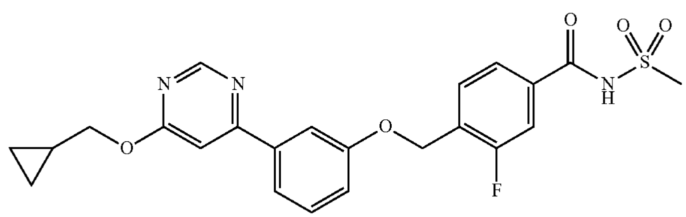 [SMILES: CS(=O)(=O)NC(=O)c1ccc(COc2cccc(-c3cc(OCC4CC4)ncn3)c2)c(F)c1] | 4-((3-(6-(cyclopropylmethoxy)pyrimidin-4-yl)phenoxy)methyl)-3-fluoro-N-(methylsulfonyl)benzamide | Borate-2 | | E |

TABLE 6-continued

| Ex. | Structure | Name | Reactant-1 | Reactant-2 | Method |
|---|---|---|---|---|---|
| 149 | 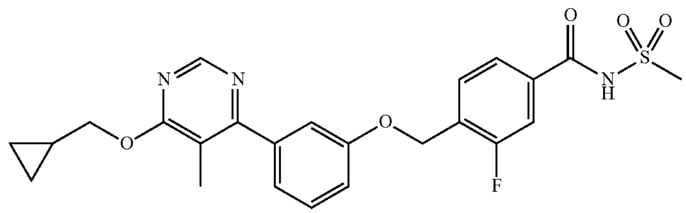 [SMILES: Cc1c(OCC2CC2)ncnc1-c1cccc(OCc2ccc(C(=O)NS(C)(=O)=O)cc2F)c1] | 4-((3-(6-(cyclopropylmethoxy)-5-methylpyrimidin-4-yl)phenoxy)methyl)-3-fluoro-N-(methylsulfonyl)benzamide | Borate-2 | Aryl halide-19 | E |
| 150 | 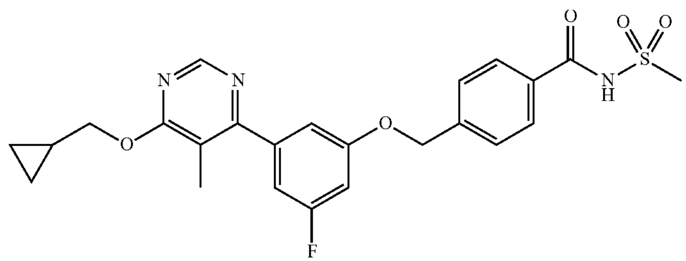 [SMILES: Cc1c(OCC2CC2)ncnc1-c1cc(F)cc(OCc2ccc(C(=O)NS(C)(=O)=O)cc2)c1] | 4-((3-(6-(cyclopropylmethoxy)-5-methylpyrimidin-4-yl)-5-fluorophenoxy)methyl)-N-(methylsulfonyl)benzamide | Borate-3 | Aryl halide-19 | E |
| 151 | 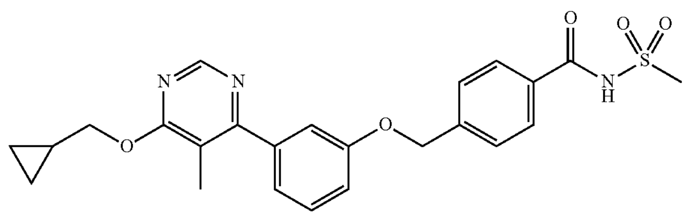 [SMILES: Cc1c(OCC2CC2)ncnc1-c1cccc(OCc2ccc(C(=O)NS(C)(=O)=O)cc2)c1] | 4-((3-(6-(cyclopropylmethoxy)-5-methylpyrimidin-4-yl)phenoxy)methyl)-N-(methylsulfonyl)benzamide | Borate-1 | Aryl halide-19 | E |
| 152 | 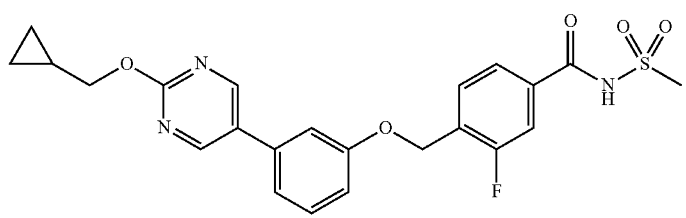 [SMILES: CS(=O)(=O)NC(=O)c1ccc(COc2cccc(-c3cnc(OCC4CC4)nc3)c2)c(F)c1] | 4-((3-(2-(cyclopropylmethoxy)pyrimidin-5-yl)phenoxy)methyl)-3-fluoro-N-(methylsulfonyl)benzamide | Borate-2 | | E |

TABLE 6-continued

| Ex. | Structure | Name | Reactant-1 | Reactant-2 | Method |
|---|---|---|---|---|---|
| 153 | 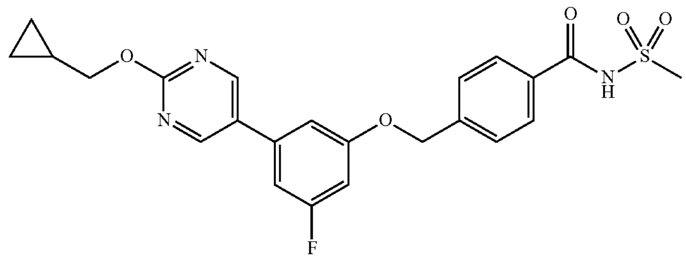 [SMILES: CS(=O)(=O)NC(=O)c1ccc(COc2cc(F)cc(-c3cnc(OCC4CC4)nc3)c2)cc1] | 4-((3-(2-(cyclopropylmethoxy)pyrimidin-5-yl)-5-fluorophenoxy)methyl)-N-(methylsulfonyl)benzamide | Borate-3 | | E |
| 154 | 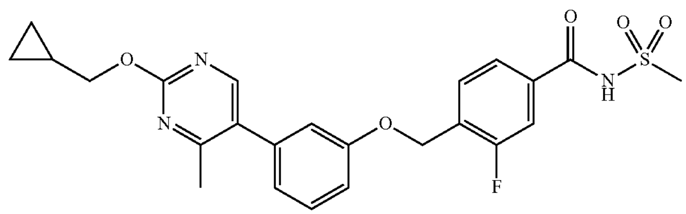 [SMILES: Cc1nc(OCC2CC2)ncc1-c1cccc(OCc2ccc(C(=O)NS(C)(=O)=O)cc2F)c1] | 4-((3-(2-(cyclopropylmethoxy)-4-methylpyrimidin-5-yl)phenoxy)methyl)-3-fluoro-N-(methylsulfonyl)benzamide | Borate-2 | Aryl halide-20 | E |
| 155 | 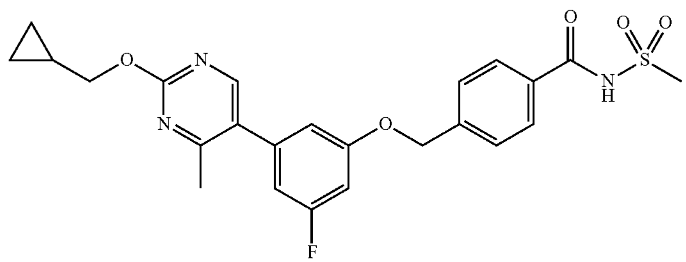 | 4-((3-(2-(cyclopropylmethoxy)-4-methylpyrimidin-5-yl)-5-fluorophenoxy)methyl)-N-(methylsulfonyl)benzamide | Borate-3 | Aryl halide-20 | E |
| 156 | 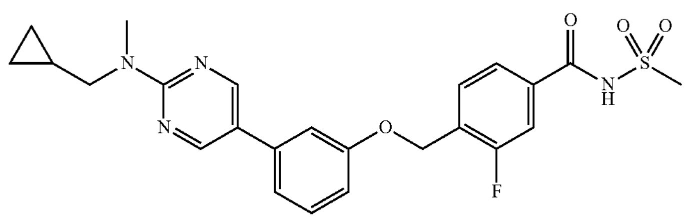 | 4-((3-(2-((cyclopropylmethyl)(methyl)amino)pyrimidin-5-yl)phenoxy)methyl)-3-fluoro-N-(methylsulfonyl)benzamide | Borate-2 | Aryl halide-21 | E |

TABLE 6-continued

| Ex. | Structure | Name | Reactant-1 | Reactant-2 | Method |
|---|---|---|---|---|---|
| 157 | 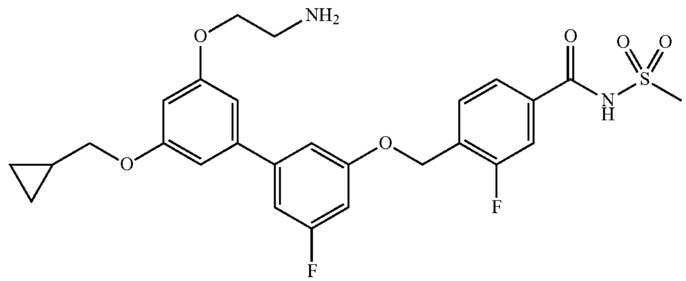 | 4-(((3'-(2-aminoethoxy)-5'-(cyclopropylmethoxy)-5-fluoro-[1,1'-biphenyl]-3-yl)oxy)methyl)-3-fluoro-N-(methylsulfonyl)benzamide | Borate-4 | Aryl halide-22 | E |
| 158 | 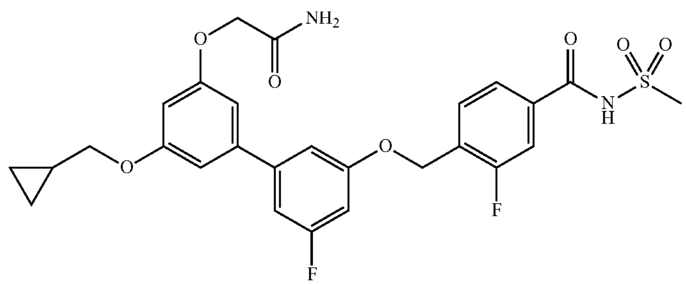 [SMILES: CS(=O)(=O)NC(=O)c1ccc(COc2cc(F)cc(-c3cc(OCC(N)=O)cc(OCC4CC4)c3)c2)c(F)c1] | 4-(((3'-(2-amino-2-oxoethoxy)-5'-(cyclopropylmethoxy)-5-fluoro-[1,1'-biphenyl]-3-yl)oxy)methyl)-3-fluoro-N-(methylsulfonyl)benzamide | Borate-4 | Aryl halide-23 | E |
| 159 | 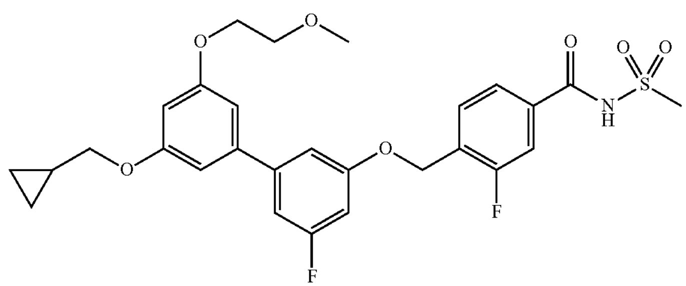 [SMILES: COCCOc1cc(OCC2CC2)cc(-c2cc(F)cc(OCc3ccc(C(=O)NS(C)(=O)=O)cc3F)c2)c1] | 4-(((3'-(cyclopropylmethoxy)-5-fluoro-5'-(2-methoxyethoxy)-[1,1'-biphenyl]-3-yl)oxy)methyl)-3-fluoro-N-(methylsulfonyl)benzamide | Borate-4 | Aryl halide-24 | E |

TABLE 6-continued

| Ex. | Structure | Name | Reactant-1 | Reactant-2 | Method |
|---|---|---|---|---|---|
| 160 | 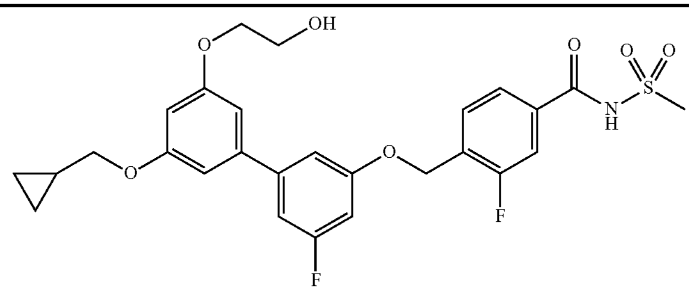 | 4-(((3'-(cyclopropylmethoxy)-5-fluoro-5'-(2-hydroxyethoxy)-[1,1'-biphenyl]-3-yl)oxy)methyl)-3-fluoro-N-(methylsulfonyl)benzamide | Borate-4 | Aryl halide-25 | E |
| 161 | 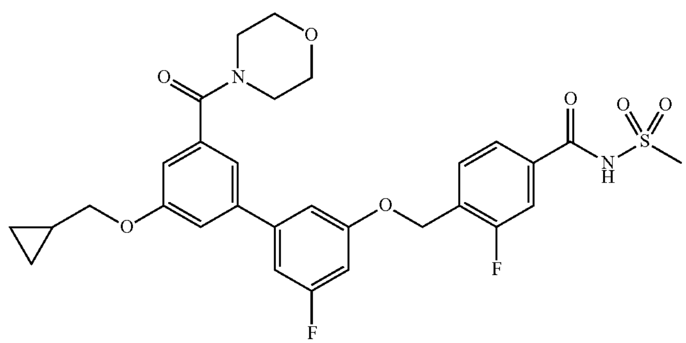 [SMILES: CS(=O)(=O)NC(=O)c1ccc(COc2cc(F)cc(-c3cc(OCC4CC4)cc(C(=O)N4CCOCC4)c3)c2)c(F)c1] | 4-(((3'-(cyclopropylmethoxy)-5-fluoro-5'-(morpholine-4-carbonyl)-[1,1'-biphenyl]-3-yl)oxy)methyl)-3-fluoro-N-(methylsulfonyl)benzamide | Borate-4 | Aryl halide-26 | E |
| 162 | 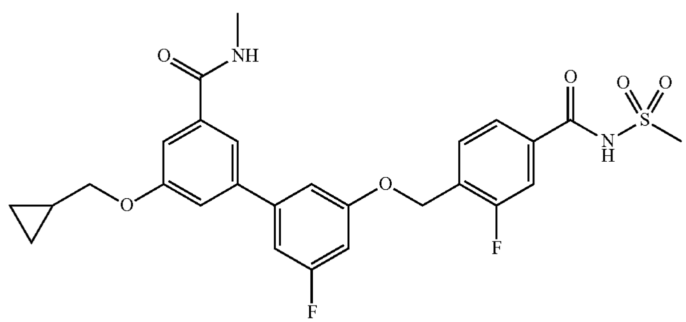 [SMILES: CNC(=O)c1cc(OCC2CC2)cc(-c2cc(F)cc(OCc3ccc(C(=O)NS(C)(=O)=O)cc3F)c2)c1] | 5-(cyclopropylmethoxy)-3'-fluoro-5'-((2-fluoro-4-((methylsulfonyl)carbamoyl)benzyl)oxy)-N-methyl-[1,1'-biphenyl]-3-carboxamide | Borate-4 | Aryl halide-27 | E |

TABLE 6-continued

| Ex. | Structure | Name | Reactant-1 | Reactant-2 | Method |
|---|---|---|---|---|---|
| 163 | 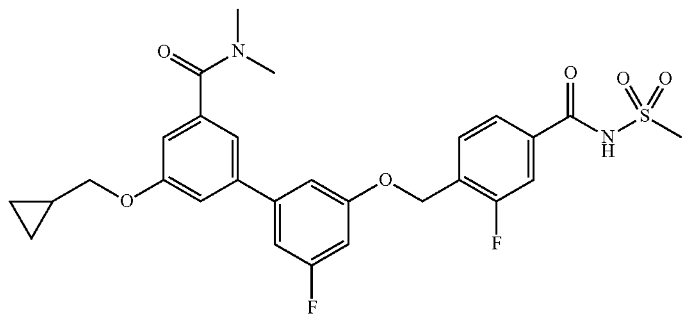 [SMILES: CN(C)C(=O)c1cc(OCC2CC2)cc(-c2cc(F)cc(OCc3ccc(C(=O)NS(C)(=O)=O)cc3F)c2)c1] | 5-(cyclopropylmethoxy)-3-fluoro-5'-((2-fluoro-4-((methylsulfonyl)carbamoyl)benzyl)oxy)-N,N-dimethyl-[1,1'-biphenyl]-3-carboxamide | Borate-4 | Aryl halide-28 | E |
| 164 | 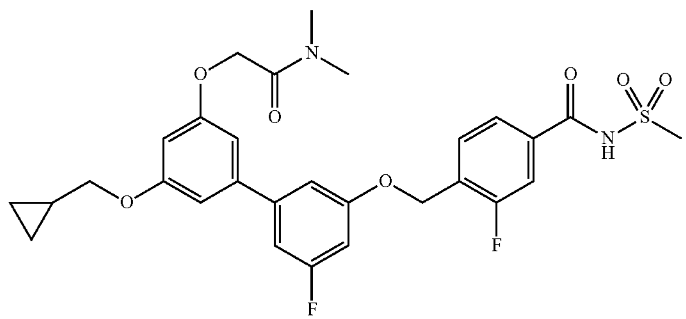 [SMILES: CN(C)C(=O)COc1cc(OCC2CC2)cc(-c2cc(F)cc(OCc3ccc(C(=O)NS(C)(=O)=O)cc3F)c2)c1] | 4-((3'-(cyclopropylmethoxy)-5'-(2-(dimethylamino)-2-oxoethoxy)-5-fluoro-[1,1'-biphenyl]-3-yl)oxy)methyl)-3-fluoro-N-(methylsulfonyl)benzamide | Borate-4 | Aryl halide-29 | E |
| 165 | 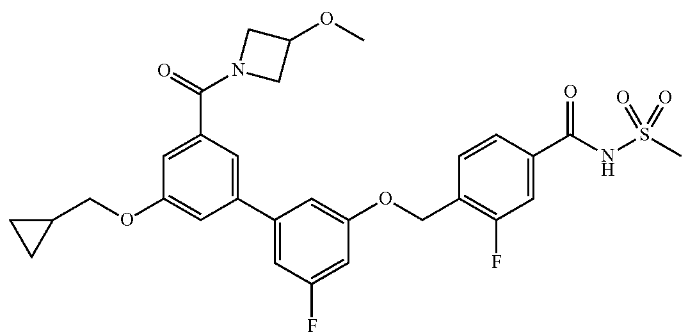 [SMILES: COC1CN(C(=O)c2cc(OCC3CC3)cc(-c3cc(F)cc(OCc4ccc(C(=O)NS(C)(=O)=O)cc4F)c3)c2)C1] | 4-((3'-(cyclopropylmethoxy)-5-fluoro-5'-(3-methoxyazetidine-1-carbonyl)-[1,1'-biphenyl]-3-yl)oxy)methyl)-3-fluoro-N-(methylsulfonyl)benzamide | Borate-4 | Aryl halide-30 | E |

TABLE 6-continued

| Ex. | Structure | Name | Reactant-1 | Reactant-2 | Method |
|---|---|---|---|---|---|
| 166 | 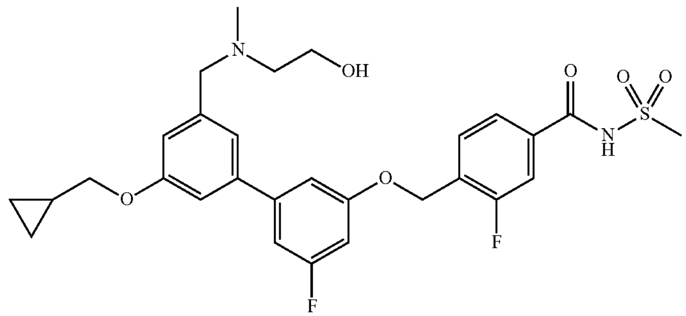 [SMILES: CN(CCO)Cc1cc(OCC2CC2)cc(-c2cc(F)cc(OCc3ccc(C(=O)NS(C)(=O)=O)cc3F)c2)c1] | 4-(((3'-(cyclopropylmethoxy)-5-fluoro-5'-(((2-hydroxyethyl)(methyl)amino)methyl)-[1,1'-biphenyl]-3-yl)oxy)methyl)-3-fluoro-N-(methylsulfonyl)benzamide | Borate-4 | Aryl halide-31 | E |
| 167 | 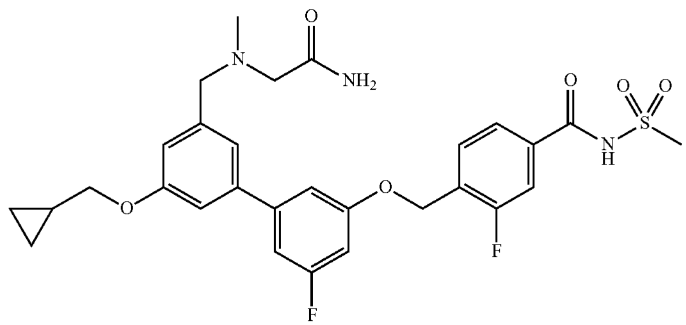 [SMILES: CN(CC(N)=O)Cc1cc(OCC2CC2)cc(-c2cc(F)cc(OCc3ccc(C(=O)NS(C)(=O)=O)cc3F)c2)c1] | 4-(((3'-(((2-amino-2-oxoethyl)(methyl)amino)methyl)-5'-(cyclopropylmethoxy)-5-fluoro-[1,1'-biphenyl]-3-yl)oxy)methyl)-3-fluoro-N-(methylsulfonyl)benzamide | Borate-4 | Aryl halide-32 | E |
| 168 | 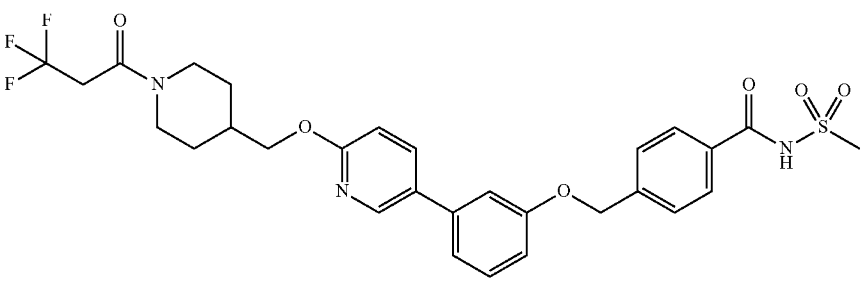 [SMILES: CS(=O)(=O)NC(=O)c1ccc(COc2cccc(-c3ccc(OCC4CCN(C(=O)CC(F)(F)F)CC4)nc3)c2)cc1] | N-(methylsulfonyl)-4-((3-(6-((1-(3,3,3-trifluoropropanoyl)piperidin-4-yl)methoxy)pyridin-3-yl)phenoxy)methyl)benzamide | Amine-1 | | F |

TABLE 6-continued

| Ex. | Structure | Name | Reactant-1 | Reactant-2 | Method |
|---|---|---|---|---|---|
| 169 | 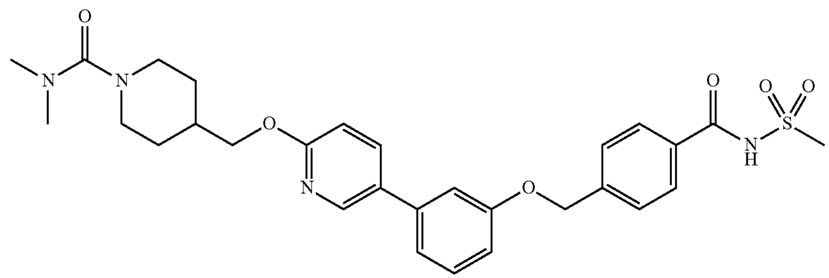 | N,N-dimethyl-4-(((5-(3-((4-((methylsulfonyl)carbamoyl)benzyl)oxy)phenyl)pyridin-2-yl)oxy)methyl)piperidine-1-carboxamide | Amine-1 | dimethylcarbamoyl chloride | F |
| 170 | 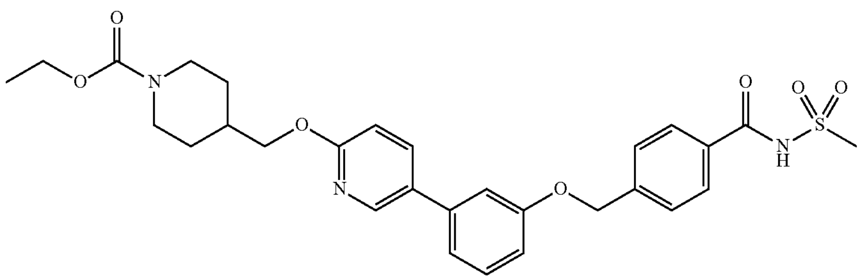 [SMILES: CCOC(=O)N1CCC(COc2ccc(-c3cccc(OCc4ccc(C(=O)NS(C)(=O)=O)cc4)c3)cn2)CC1] | ethyl 4-((5-(3-((4-((methylsulfonyl)carbamoyl)benzyl)oxy)phenyl)pyridin-2-yl)oxy)methyl)piperidine-1-carboxamide | Amine-1 | ethyl chloroformate | F |
| 171 | 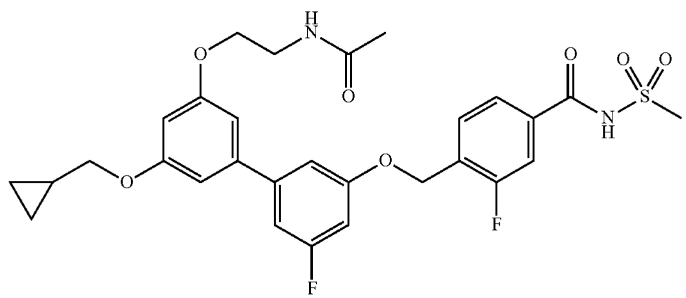 [SMILES: CC(=O)NCCOc1cc(OCC2CC2)cc(-c2cc(F)cc(OCc3ccc(C(=O)NS(C)(=O)=O)cc3F)c2)c1] | 4-(((3'-(2-acetamidoethoxy)-5'-(cyclopropylmethoxy)-5-fluoro-[1,1'-biphenyl]-3-yl)oxy)methyl)-3-fluoro-N-(methylsulfonyl)benzamide | Example 157 | acetyl chloride | F |

TABLE 6-continued

| Ex. | Structure | Name | Reactant-1 | Reactant-2 | Method |
|---|---|---|---|---|---|
| 172 | 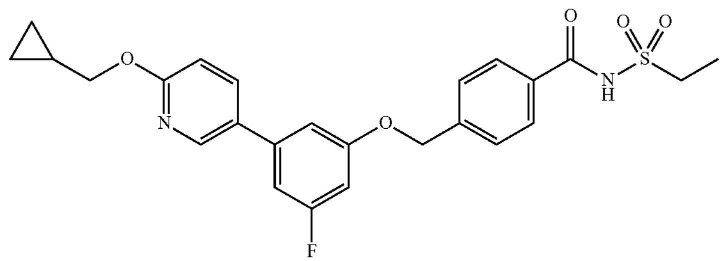 [SMILES: CCS(=O)(=O)NC(=O)c1ccc(COc2cc(F)cc(-c3ccc(OCC4CC4)nc3)c2)cc1] | 4-((3-(6-(cyclopropyl-methoxy)pyridin-3-yl)-5-fluorophenoxy)methyl)-N-(ethylsulfonyl)benzamide | Acid-22 | | D |
| 173 | 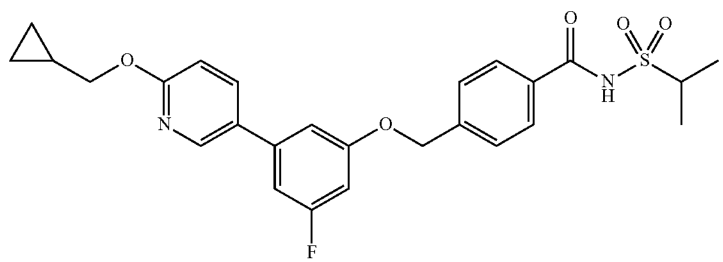 [SMILES: CC(C)S(=O)(=O)NC(=O)c1ccc(COc2cc(F)cc(-c3ccc(OCC4CC4)nc3)c2)cc1] | 4-((3-(6-(cyclopropyl-methoxy)pyridin-3-yl)-5-fluorophenoxy)methyl)-N-(isopropylsulfonyl)benzamide | Acid-22 | | D |
| 174 | 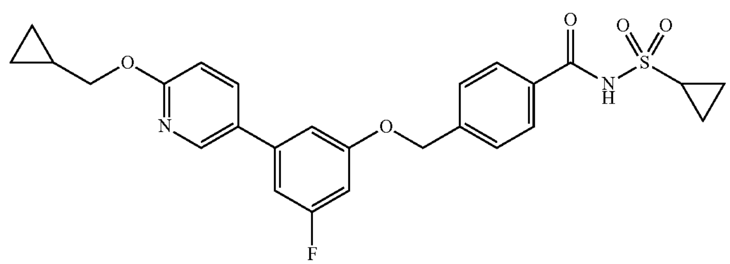 [SMILES: O=C(NS(=O)(=O)C1CC1)c1ccc(COc2cc(F)cc(-c3ccc(OCC4CC4)nc3)c2)cc1] | 4-((3-(6-(cyclopropyl-methoxy)pyridin-3-yl)-5-fluorophenoxy)methyl)-N-(cyclopropylsulfonyl)benzamide | Acid-22 | | D |

TABLE 6-continued

| Ex. | Structure | Name | Reactant-1 | Reactant-2 | Method |
|---|---|---|---|---|---|
| 175 | 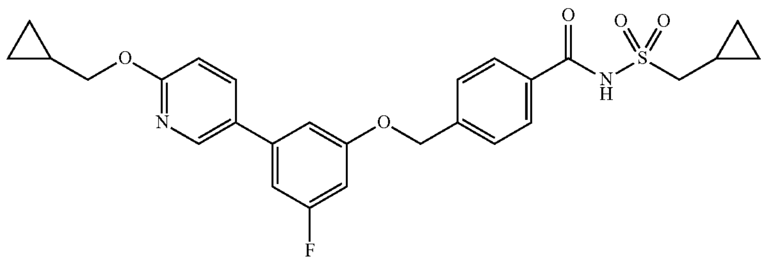 [SMILES: O=C(NS(=O)(=O)CC1CC1)c1ccc(COc2cc(F)cc(-c3ccc(OCC4CC4)nc3)c2)cc1] | 4-((3-(6-(cyclopropyl-methoxy)pyridin-3-yl)-5-fluorophenoxy)methyl)-N-((cyclopropylmethyl)sulfonyl)benzamide | Acid-22 | | D |
| 176 | 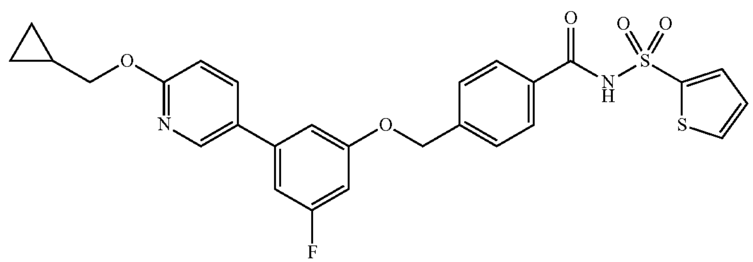 [SMILES: O=C(NS(=O)(=O)c1cccs1)c1ccc(COc2cc(F)cc(-c3ccc(OCC4CC4)nc3)c2)cc1] | 4-((3-(6-(cyclopropyl-methoxy)pyridin-3-yl)-5-fluorophenoxy)methyl)-N-(thiophen-2-ylsulfonyl)benzamide | Acid-22 | | D |
| 177 | 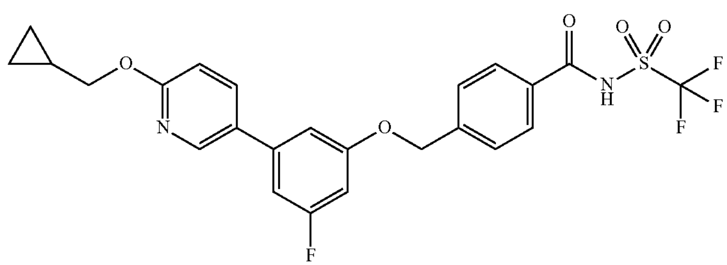 [SMILES: O=C(NS(=O)(=O)C(F)(F)F)c1ccc(COc2cc(F)cc(-c3ccc(OCC4CC4)nc3)c2)cc1] | 4-((3-(6-(cyclopropyl-methoxy)pyridin-3-yl)-5-fluorophenoxy)methyl)-N-(((trifluoromethyl)sulfonyl)benzamide | Acid-22 | | D |

TABLE 7

| Ex | tR (min) | m/z | HPLC-method |
|---|---|---|---|
| 1 | 1.38 | 497.0 | B |
| 2 | 1.48 | 453.2 | A |
| 3 | 1.70 | 506.9 | A |
| 4 | 1.51 | 479.0 | A |
| 5 | 1.54 | 481.0 | A |
| 6 | 1.51 | 503.0 | A |
| 7 | 1.62 | 531.0 | B |
| 8 | 1.53 | 466.9 | B |
| 9 | 1.74 | 481.0 | B |
| 10 | 1.59 | 467.2 | A |
| 11 | 1.70 | 596.1 | B |
| 12 | 1.54 | 486.9 | C |
| 13 | 1.55 | 486.9 | C |
| 14 | 1.50 | 470.9 | C |
| 15 | 1.59 | 466.9 | C |
| 16 | 1.55 | 504.9 | C |
| 17 | 1.59 | 530.9 | C |
| 18 | 1.65 | 520.9 | B |
| 19 | 1.62 | 521.9 | B |
| 20 | 1.66 | 573.0 | C |
| 21 | 1.59 | 486.9 | C |
| 22 | 1.51 | 486.9 | C |
| 23 | 1.57 | 510.9 | C |
| 24 | 1.50 | 488.9 | C |
| 25 | 1.41 | 514.9 | C |
| 26 | 1.56 | 537.0 | C |
| 27 | 1.48 | 470.9 | C |
| 28 | 1.55 | 488.9 | C |
| 29 | 1.42 | 523.0 | C |
| 30 | 1.51 | 471.0 | C |
| 31 | 1.55 | 507.1 | C |
| 32 | 1.54 | 489.0 | C |
| 33 | 1.58 | 515.0 | C |
| 34 | 1.59 | 493.1 | C |
| 35 | 1.59 | 485.1 | C |
| 36 | 1.62 | 511.1 | C |
| 37 | 1.63 | 521.1 | C |
| 38 | 1.58 | 497.1 | D |
| 39 | 1.54 | 471.1 | D |
| 40 | 156 | 478.1 | D |
| 41 | 1.60 | 504.1 | D |
| 42 | 1.56 | 471.1 | D |
| 43 | 1.61 | 497.0 | D |
| 44 | 1.54 | 471.1 | D |
| 45 | 1.68 | 531.1 | D |
| 48 | 1.59 | 489.1 | D |
| 47 | 1.63 | 515.2 | D |
| 48 | 1.60 | 485.1 | D |
| 49 | 1.64 | 511.2 | D |
| 50 | 1.63 | 505.1 | D |
| 51 | 1.65 | 485.1 | D |
| 52 | 1.55 | 485.0 | D |
| 53 | 1.58 | 499.0 | D |
| 54 | 1.56 | 497.0 | D |
| 55 | 1.60 | 511.0 | D |
| 56 | 1.60 | 539.0 | D |
| 57 | 1.61 | 540.0 | D |
| 58 | 1.78 | 525.0 | D |
| 59 | 1.54 | 483.1 | D |
| 60 | 1.44 | 453.0 | C |
| 61 | 1.33 | 453.0 | B |
| 62 | 1.46 | 493.9 | C |
| 63 | 1.37 | 453.9 | B |
| 64 | 1.42 | 471.9 | C |
| 65 | 151 | 480.1 | D |
| 66 | 1.51 | 454.0 | D |
| 67 | 1.4 | 453.2 | A |
| 68 | 1.52 | 453.2 | A |
| 69 | 1.47 | 487.2 | A |
| 70 | 1.45 | 470.9 | C |
| 71 | 1.39 | 467 0 | C |
| 72 | 1.48 | 453.0 | B |
| 73 | 1.46 | 454.0 | B |
| 74 | 1.48 | 471.9 | C |
| 75 | 1.49 | 480.0 | C |
| 76 | 1.48 | 472.1 | D |
| 77 | 1.38 | 453.9 | B |
| 78 | 1.41 | 471.8 | C |
| 79 | 1.41 | 479.9 | C |
| 80 | 1.54 | 452.2 | A |
| 81 | 1.43 | 527.2 | D |
| 82 | 1.41 | 541 2 | D |
| 83 | 1.35 | 444.1 | D |
| 84 | 1.46 | 445.2 | D |
| 85 | 1.54 | 467.1 | C |
| 86 | 1.58 | 485.1 | C |
| 87 | 1.42 | 501.1 | D |
| 88 | 1.43 | 501.1 | D |
| 89 | 1.52 | 478.1 | D |
| 90 | 1.79 | 499.1 | D |
| 91 | 1.68 | 485.1 | D |
| 92 | 1.69 | 485.1 | D |
| 93 | 1.63 | 485.1 | D |
| 94 | 1.58 | 485.1 | D |
| 95 | 1.59 | 485.1 | D |
| 96 | 1.69 | 505.1 | D |
| 97 | 1.58 | 586.3 | D |
| 98 | 1.72 | 523.1 | D |
| 99 | 1.71 | 523.1 | D |
| 100 | 1.62 | 503.1 | D |
| 101 | 1.50 | 515.2 | D |
| 102 | 1.56 | 533.1 | D |
| 103 | 1.46 | 497.1 | D |
| 104 | 1.51 | 515.1 | D |
| 105 | 1.55 | 515.0 | D |
| 106 | 1.51 | 497.0 | D |
| 107 | 1.75 | 529.2 | D |
| 108 | 1.41 | 531.2 | D |
| 109 | 1.44 | 533.2 | D |
| 110 | 1.48 | 530.2 | D |
| 111 | 1.40 | 471.1 | D |
| 112 | 1.41 | 471.1 | D |
| 113 | 1.50 | 468.1 | C |
| 114 | 1.55 | 471.1 | C |
| 115 | 1.61 | 471.1 | D |
| 116 | 1.62 | 489.0 | D |
| 117 | 1.56 | 489.0 | D |
| 118 | 1.59 | 489.0 | D |
| 119 | 1.48 | 485.1 | D |
| 120 | 1.46 | 485.1 | D |
| 121 | 1.62 | 499.1 | D |
| 122 | 1.61 | 499.1 | D |
| 123 | 1.56 | 481.2 | D |
| 124 | 147 | 471.1 | D |
| 125 | 1.49 | 471.1 | D |
| 126 | 1.45 | 485.2 | D |
| 127 | 1.46 | 485.2 | D |
| 128 | 1.47 | 471.1 | D |
| 129 | 1.36 | 453.0 | B |
| 130 | 1.43 | 471.1 | D |
| 131 | 1.53 | 471.1 | D |
| 132 | 1.54 | 471.1 | D |
| 133 | 1.64 | 485.1 | D |
| 134 | 1.64 | 485.1 | D |
| 135 | 1.62 | 503.1 | D |
| 136 | 1.48 | 484.0 | C |
| 137 | 1.58 | 468.1 | C |
| 138 | 1.59 | 472.1 | D |
| 139 | 1.57 | 490.0 | D |
| 140 | 1.61 | 486.1 | C |
| 141 | 1.50 | 472.1 | D |
| 142 | 1.43 | 454.1 | D |
| 143 | 1.52 | 472.1 | D |
| 144 | 1.65 | 486.1 | D |
| 145 | 1.37 | 490.0 | D |
| 146 | 1.39 | 454.0 | C |
| 147 | 1.52 | 472.1 | D |
| 148 | 1.49 | 472.1 | D |
| 149 | 1.50 | 486.1 | D |
| 150 | 1.51 | 486.1 | D |
| 151 | 1.45 | 468.1 | D |
| 152 | 1.43 | 472.0 | D |
| 153 | 1.44 | 472.0 | D |
| 154 | 1.45 | 486.1 | D |

TABLE 7-continued

| Ex | tR (min) | m/z | HPLC-method |
|---|---|---|---|
| 155 | 1.45 | 486.1 | D |
| 156 | 1.50 | 485.1 | C |
| 157 | 1.40 | 547.1 | D |
| 158 | 1.40 | 561.1 | D |
| 159 | 1.63 | 562.0 | D |
| 160 | 1.47 | 548.0 | D |
| 161 | 1.44 | 601.2 | D |
| 162 | 1.43 | 545.1 | D |
| 163 | 1.45 | 559.2 | D |
| 164 | 1.45 | 589.3 | D |
| 165 | 1.46 | 601.2 | D |
| 166 | 1.39 | 575.2 | D |
| 167 | 1.43 | 588.2 | D |
| 168 | 1.41 | 606.1 | C |
| 169 | 1.37 | 567.1 | C |
| 170 | 1.50 | 568 1 | C |
| 171 | 1.44 | 589.2 | D |
| 172 | 1.63 | 485.0 | D |
| 173 | 1.68 | 499.0 | D |
| 174 | 1.65 | 497.0 | D |
| 175 | 1.70 | 511.0 | D |
| 176 | 1.74 | 539.0 | D |
| 177 | 1.90 | 524.9 | D |

TABLE 8

Example data

| | |
|---|---|
| 2 | $^1$H-NMR (400 MHz, CDCl$_3$) delta 8.32 (1H, d, J = 2.4 Hz), 7.88 (2H, d, J = 8.6 Hz), 7.76 (1H, dd, J = 8.6, 2.4 Hz), 7.59 (2H, d, J = 8.6 Hz), 7.36 (1H, t, J = 7.9 Hz), 7.14 (1H, d, J = 7.9 Hz), 7.11-7.09 (1H, m), 6.93 (1H, dd, J = 7.9, 2.4 Hz), 6.84 (1H, d, J = 8.6 Hz), 5.20 (2H, s), 4.17 (2H, d, J = 7.3 Hz), 3.45 (3H, s), 1.36-1.25 (1H, m), 0.67-0.59 (2H, m), 0.40-0.32 (2H, m), NH is not observed. |
| 14 | $^1$H-NMR (400 MHz, DMSO-d$_6$) delta 8.47 (1H, d, J = 2.4 Hz), 8.03 (1H, dd, J = 8.6, 2.4 Hz), 7.84-7.77 (2H, m), 7.71 (1H, t, J = 7.3 Hz), 7.39 (1H, t, J = 7.9 Hz), 7.33 (1H, d, J = 1.8 Hz), 7.26 (1H, d, J = 7.9 Hz), 7.04 (1H, dd, J = 7.9, 1.8 Hz), 6.90 (1H, d, J = 8.6 Hz), 5.30 (2H, s), 4.14 (2H, d, J = 6.7 Hz), 3.78 (3H, s), 1.31-1.23 (1H, m), 0.60-0.54 (2H, m), 0.38-0.32 (2H, m), NH is not observed. |
| 30 | $^1$H-NMR (400 MHz, CDCl$_3$) delta 8.29 (1H, d, J = 2.4 Hz), 7.88 (2H, d, J = 8.6 Hz), 7.73 (1H, dd, J = 8.6, 2.4 Hz), 7.59 (2H, d, J = 8.6 Hz), 6.90-6.32 (3H, m), 6.67-6.63 (1H, m), 5.19 (2H, s), 4.17 (2H, d, J = 6.7 Hz), 3.45 (3H, s), 1.37-1.27 (1H, m), 0.67-0.63 (2H, m), 0.39-0.35 (2H, m), NH is not observed. |
| 32 | $^1$H-NMR (400 MHz, DMSO-d$_6$) delta 8.52 (1H, d, J = 2.4 Hz), 8.07 (1H, d, J = 8.6, 2.4 Hz), 7.86-7.80 (2H, m), 7.74 (1H, t, J = 7.9 Hz), 7.22 (1H, d, J = 1.8 Hz), 7.18 (1H, dd, J = 9.8, 1.8 Hz), 6.97 (1H, dd, J = 11.0, 2.4 Hz), 6.91 (1H, d, J = 8.6 Hz), 5.33 (2H, s), 4.14 (2H, d, J = 7.3 Hz), 3.36 (3H, s), 1.31-1.21 (1H, m), 0.61-0.53 (2H, m), 0.39-0.31 (2H, m), NH is not observed. |
| 46 | $^1$H-NMR (400 MHz, CDCl$_3$) delta 8.25 (1H, s), 7.78-7.74 (1H, m), 7.70-7,63 (3H, m), 7.09 (1H, t, J = 9.7 Hz), 6.98-6.95 (1H, m), 6.92-6.87 (1H, m), 6.84 (1H, d, J = 8.6 Hz), 5.19 (2H, s), 4.17 (2H, d, J = 7.3 Hz), 3.42 (3H, s), 1.37-1.25 (1H, m), 0.67-0.59 (2H, m), 0.40-0.35 (2H, m), NH is not observed. |
| 54 | $^1$H-NMR (400 MHz, CDCl$_3$) delta 8.33 (1H, d, J = 2.7 Hz), 7.78 (1H, dd. J = 8.7, 2.7 Hz), 7.72 (1H, t, J = 7.8 Hz), 7.66-7.61 (2H, m), 7.38 (1H, t, J = 7.8 Hz), 7.18-7.11 (2H, m), 6.96 (1H, dd, J = 8.2, 2.7 Hz), 6.84 (1H, d, J = 8.7 Hz), 5.26 (2H, s), 4.17 (2H, d, J = 6.9 Hz), 3.18-3.10 (1H, m), 1.50-1.44 (2H, m), 1.38-1.16 (3H, m), 0.69-0.61 (2H, m), 0.43-0.35 (2H, m), NH is not observed. |
| 63 | $^1$H-NMR (400 MHz, CDCl$_3$) delta 9.06 (1H, s), 8.30 (1H, d, J = 1.8 Hz), 8.20 (1H, dd, J = 8.0, 2.4 Hz), 7.77 (1H, dd, J = 8.6, 3.1 Hz), 7.73 (1H, d, J = 8.0 Hz), 7.37 (1H, t, J = 8.0 Hz), 7.16 (1H, d, J = 7.9 Hz), 7.12 (1H, s), 6.94 (1H, dd, J = 7.3, 2.4 Hz), 6.84 (1H, d, J = 8.6 Hz), 5.33 (2H, s), 4.16 (2H, d, J = 6.7 Hz), 3.46 (3H, s), 1.36-1.26 (1H, m), 0.66-0.62 (2H, m), 0.39-0 35 (2H, m), NH is not observed. |
| 96 | $^1$H-NMR (400 MHz, CDCl$_3$) delta 8.17 (1H, d, J = 2.4 Hz), 7.79 (1H, d, J = 2.4 Hz), 7.69-757 (3H, m), 7.32 (1H, t, J = 7.9 Hz), 7.13-7.05 (2H, m), 6.96-6.88 (1H, m), 5.16 (2H, s), 4.25 (2H, d, J = 7.3 Hz), 3.32 (3H, s), 1.39-1.28 (1H, m), 0.67-0.57 (2H, m), 0.46-0.36 (2H, m), NH is not observed. |
| 139 | $^1$H-NMR (400 MHz, CDCl$_3$) delta 8.61-8.59 (1H, m), 8.33 (1H, d, J = 1.8 Hz), 7.72 (1H, t, J = 7.3 Hz), 7.65-7.58 (3H, m), 7.11 (1H, t, J = 9.2 Hz), 6.97-6.92 (1H, m), 5.23 (2H, s), 4.22 (2H, d, J = 6.7 Hz), 3.40 (3H, s), 1.38-1.27 (1H, m), 0.69-0.64 (2H, m), 0.43-0.37 (2H, m), NH is not observed. |

Pharmacological Assays

In Vitro Activities Against Human Voltage Gated Sodium Channels

The inhibitory activities of compounds against voltage gated sodium channels are determined by methodology well known in the art.

The ability of the biaryloxy derivatives of formula (I) to inhibit the Nav$_{1.7}$ and Nav$_{1.5}$ channels is measured by Fluorescence Resonance Energy Transfer (FRET) assay and electrophysiology assay described below.

EFS-FRET Assay

This screen is used to determine the effects of compounds on human Nav$_{1.7}$ channels, utilizing electrical field stimulation (EFS) system in 96-well plate format on FDSS (Hamamatsu Photonics) platform. The changes of membrane potential are monitored with FRET dye pair, DiSBAC2(3) and PTS 18.

Cell Maintenance:

CHO (Chinese hamster ovary) cells expressing human Nav$_{1.7}$ channels are grown in T225 flasks, in a 5% CO$_2$ humidified incubator to about 80% confluence. Media composition consists of HAM/F12 with Glutamax I, 10% FCS, 100 units/mL penicillin and 100 microgram/mL hygromycin.

Protocol:

Seed each cell lines (1×10⁵ cells/well) into 96-well plates prior to experimentation.

Incubate at 37° C. in 5% $CO_2$ for 24 hours.

Wash each well with assay buffer (140 mM NaCl, 4.5 mM KCl, 10 mM D-Glucose, 2 mM $CaCl_2$, 1 mM $MgCl_2$, 10 mM HEPES, pH 7.4 adjusted with NaOH) twice.

Add 1st loading solution containing 10 microM PTS 18 and 0.06% Pluronic F-127 in assay buffer.

Incubate the plate at rt in dark for 1 hour.

Remove 1st loading solution and add 2nd loading solution containing 12.5 microM DiSBAC2(3), 1.25 mM Xylene Fast Yellow and 0.0075% Pluronic F-127 in assay buffer.

Place the plate under the dark at rt for 25 minutes.

Add compound solutions into the assay plate.

Set the assay plate in FDSS and place an EFS device on the plate.

Measure EFS-induced fluorescent response by FDSS.

The data are analyzed and reported as normalized ratios of intensities measured at 440 nm. The process of calculating these ratios is performed as follows:

$$\% \text{ Inhibition} = \left\{ 1 - \frac{(FIR \text{ of each well}) - (\text{median } FIR \text{ in 100\% inhibition})}{(\text{median } FIR \text{ in 0\% inhibition}) - (\text{median } FIR \text{ in 100\% inhibition})} \right\} \times 100 \quad [\text{Math. 1}]$$

$FIR$ = Fluorescence integration Ratio = the integral of the ratio normalized by baseline (before EFS)

This analysis is performed using a computerized specific program designed for FDSS generated data. Fluorescence ratio values are plotted using XLfit to determine an $IC_{50}$ value for each compound.

FRET Assay

This screen is used to determine the effects of compounds on human $Nav_{1.5}$ channels, utilizing the cell imaging technology by Hamamatsu Photonics's Functional Drug Screening System (FDSS). The changes of membrane potential are monitored with fluorescent membrane potential dye pair, DiSBAC2(3) and CC2-DMPE, using FRET technology.

Cell Maintenance:

HEK293 cells expressing human $Nav_{1.5}$ channels are grown in T225 flasks, in a 5% $CO_2$ humidified incubator to about 80% confluence. HEK293 cells expressing human $Nav_{1.5}$ channels are maintained in Dulbecco's Modified Eagle Medium (high glucose) supplemented with 10% fetal calf serum (FCS), 100 units/mL Penicillin, 100 microgram/mL Streptomycin and 500 microgram/mL Geneticine.

Protocol:

Seed each cell lines (1.5×10⁴ cells/well) into 384-well plates prior to experimentation.

Incubate at 37° C. in 5% $CO_2$ for 24 hours.

Wash each well with buffer #1 (140 mM NaCl, 4.5 mM KCl, 10 mM D-Glucose, 2 mM $CaCl_2$, 1 mM $MgCl_2$, 10 mM HEPES, pH 7.4 adjusted with NaOH) twice using plate washer.

Add 1st loading solution containing 7.5 microM CC2-DMPE and 0.06% Pluronic F-127 in buffer #1.

Incubate the plate at rt in dark for 0.5 hours.

Wash each well with buffer #2 (160 mM Choline, 10 mM D-Glucose, 0.1 mM $CaCl_2$, 1 mM $MgCl_2$, 10 mM HEPES, pH 7.4 adjusted with KOH) twice using plate washer.

Add 2nd loading solution containing 75 microM DiS-BAC2(3), 2.5 mM Xylene Fast Yellow, 10 microM Deltamethrin or 100 microM veratridine and 0.02% Pluronic F-127 in buffer #2.

Add compound solutions into the assay plate and leave the plate for 30 minutes under the dark at rt.

Monitor the fluorescent membrane potentials before and after the addition of buffer #2 by FDSS.

The data is analyzed and reported as normalized ratios of intensities measured in the 465 nm and 575 nm channels. The process of calculating these ratios is performed as follows:

$$FR = (FI465Max/FI575Min) - (FI465B/FI575B) \quad [\text{Math. 2}]$$

"FR"=fluorescence ratio

"FI465B"=the mean of fluorescence intensity as baseline (before $Na^+$ ligand addition) at 465 nm "FI575B"=the mean of fluorescence intensity as baseline (before $Na^+$ ligand addition) at 575 nm "FI465Max" maximum fluorescence intensity at 465 nm after $Na^+$ stimulation "FI575Min"=minimum fluorescence intensity at 575 nm after $Na^+$ stimulation $$\text{Inhibition (\%)} = 100 - \frac{(FR \text{ of each well}) - (\text{median } FR \text{ in positive controls})}{(\text{median } FR \text{ in negative controls}) - (\text{median } FR \text{ in positive controls})} \times 100 \quad [\text{Math. 3}]$$

This analysis is performed using a computerized specific program designed for FDSS generated data. Fluorescence ratio values are plotted using XLfit to determine an $IC_{50}$ value for each compound.

All tested compounds show less than about 3 microM of $IC_{50}$ against $Nav_{1.7}$ in the above assays. Preferable compounds show less than about 1 microM of $IC_{50}$ against $Nav_{1.7}$ in the above assays.

Compounds with $IC_{50}$ against $Nav_{1.7}$<0.50 microM are: Examples 1, 2, 3, 4, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 59, 60, 61, 63, 64, 65, 66, 68, 69, 70, 72, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 146, 147, 148, 149, 150, 151, 152, 153, 154, 156, 158, 159, 160, 161, 163, 164, 165, 166, 170, 172, 173, 174, 175, 176, and 177.

Regarding all tested compounds, the ratio of activities against $Nav_{1.5}$ vs. $Nav_{1.7}$ is more than three times. For example, the activities of Example 2 against $Nav_{1.5}$ and $Nav_{1.7}$, are more than 30 microM and 0.084 microM, respectively.

Automated Electrophysiology Assay

Automated patch clamp recordings are conducted for evaluation of inhibitory effect against $Nav_{1.5}$ with the Qpatch HTX system according the manufacturer's specifications (Sophion).

The extracellular and intercellular solutions consist of the following composition:

Extracellular recording solution (mM): 137 NaCl, 4 KCl, 1.8 $CaCl_2$, 1 $MgCl_2$, 10 HEPES, and 10 Glucose, pH 7.4 adjusted with NaOH Intercellular solution (mM): 135 CsF, 10 NaCl, 5 EGTA, and 10 HEPES, pH 7.3 adjusted with CsOH.

To evaluate of inhibitory effects of test compounds against $Nav_{1.5}$, the cells are clamped at −110 mV. First test pulse to −10 mV (Test 1 pulse) is applied following conditioning pulse for 8 sec at −70 mV, at which approximately 50% channels are inactivated, followed by 20 msec recovery period at −110 mV and second pulse to −10 mV (Test 2 pulse). Command pulses are delivered at interval of 30 sec. Test compound solutions are consecutively applied.

Peak currents evoked by Test1 and Test 2 pulses are sampled with Qpatch assay software (Sophion). Averaged peak currents under vehicle or test compounds are calculated from 3 data points at end of each condition. Inhibitory effect (% inhibition) of test compound is calculated as bellow;

$$\% \text{ inhibition} = [1-\text{Averaged peak current (Compound)/Averaged peak current (Vehicle)}] \times 100 \quad [\text{Math.4}]$$

Inhibitory effects (% inhibition) of each concentration are measured from at least 2 cells. Averaged inhibitory effects are plotted against test concentration and $IC_{50}$ values at Test 1 (Closed $IC_{50}$) or Test 2 (Inactivated $IC_{50}$) are calculated with Hill equation, respectively. Data analyses are performed using XLfit (Version 5.2.0.0.).

All tested compounds of the invention show weak inhibitory effect against $Na_{V1.5}$ in this model. For example, Inactivated $IC_{50}$ of Example 30 is more than 30 microM.

Manual Patch Clamp Assay

Manual patch clamp recordings are conducted at RT using the voltage-clamp amplifier (Axon Instruments or HEKA electronik). Electrodes are pulled with P-97 electrode puller (Sutter Instrument). The electrode resistances are 1-3 MOhm when intercellular solution is filled. Currents are lowpass filtered between 2-5 kHz and digitally sampled at 10 kHz.

The extracellular and intercellular solutions for human $Nav_{1.7}$ and $Na_{V1.5}$ consist of the following composition:

Extracellular recording solution (mM): 135 NaCl, 5 KCl, 2 $CaCl_2$, 1 $MgCl_2$, 10 HEPES, and 10 Glucose, pH 7.4 adjusted with NaOH; and Intercellular solution (mM): 120 CsF, 15 NaCl, 10 EGTA, and 10 HEPES, pH 7.2 adjusted with CsOH.

Two Pulse Protocol

After whole-cell configuration is achieved, cell is monitored at least 10 minutes to allow cell dialysis with pipette solution. To evaluate of inhibitory effects of test compounds, the cells are clamped at −120 or −130 mV. First test pulse to 0 mV (Test 1 pulse) is applied following conditioning pulse for 8 sec, at which approximately 50% channels are inactivated, followed by 10 or 20 msec recovery period at −120 or −130 mV and second pulse to 0 mV (Test 2 pulse). Command pulses are delivered at interval of 30 sec. Test compound solutions are consecutively applied.

Peak currents evoked by Test 1 and Test 2 pulses are sampled with Clampex (Axon Instruments) or Pulse+Pulse Fit (HEKA). Averaged peak currents under vehicle or test compounds are calculated from 3 data points at end of each condition. Inhibitory effect (% inhibition) of test compound is calculated as bellow;

$$\% \text{ inhibition} = [1-\text{Averaged peak current (Compound)/Averaged peak current (Vehicle)}] \times 100 \quad [\text{Math.5}]$$

Inhibitory effects (% inhibition) on peak currents at Test 1 or Test 2 pulse are plotted against test concentration and $IC_{50}$ values at Test 1 (Closed $IC_{50}$) or Test 2 (Inactivated $IC_{50}$) are calculated with Hill equation, respectively. Data analyses are performed using XLfit (Version 5.2.0.0.).

All tested compounds of the invention show selective $Nav_{1.7}$ inhibitory effects as compared to with $Nav_{1.5}$ in this model. For example, Example 2 shows 75-fold selective for $Nav_{1.7}$ over $Nav_{1.5}$.

Affinity to Resting State ($K_r$) and Inactivated State ($K_i$) of Test Compound The normalized steady-state inactivation curve is constructed using 2 sec (for vehicle) or 60 sec (for drugs) conditioning pulse to different potentials followed immediately by the test pulse to −10 mV. Peak currents are plotted as fraction of the maximum current at the conditioning potentials ranging from −120 mV to 0 mV for $Nav_{1.7}$. V1/2 and k values are estimated from Boltzmann fits. The affinity of test compound to resting state of Na channels ($K_{resting}$ or $K_r$) is assessed by depolarizing test pulse from a negative holding potential of −130 mV, where virtually all channels are in the resting state. $K_r$ value is calculated by a conventional 1:1 binding model:

$$K_{resting}(K_r) = \{[\text{drug}]I_{max},\text{drug}/(I_{max},\text{control}-I_{max},\text{drug})\} \quad [\text{Math.6}]$$

where $K_{resting}$ (=$K_r$) is a dissociation constant for the resting state and [drug] is compound concentration. $I_{max}$,control and $I_{max}$,drug are peak currents in the absence and presence of compound, respectively.

The affinity of test compound to inactivated state of Na channels ($K_{inact}$ or $K_i$) is estimated from the compound induced leftward shift of the steady-state inactivation curve. Interaction of the compound with the channel on inactivated state is evaluated by the following equation:

$$K_{inact}(K_i) = \{[\text{drug}]/((1+[\text{drug}]/Kr)^*\exp(-\Delta V/k)-1)\} \quad [\text{Math.7}]$$

where $K_{inact}$ (=$K_i$) is a dissociation constant for the inactivated state. $\Delta V$ is the compound-induced voltage shift of half maximal voltage of Boltzmann curve and k is the slop factor on presense of compound.

All tested compounds of the invention show potent activities in this model. For example, the activities (Ki) of example 2 against $Nav_{1.7}$ is 0.022 microM.

In Vivo Assay

The efficacy of the compounds of the invention for the treatment of a condition or disorder in which TTX-S channel blockers are involved can be determined using an appropriate model known to those skilled in the art. For example, models for the treatment of pain includes, not limited to, neuropathic pain model, chronic constriction injury (CCI)-induced static allodynia, CCI-induced thermal hyperalgesia, partial sciatic nerve ligation (PSNL)-induced static allodynia, spinal nerve ligation (SNL)-induced static allodynia, spared nerve injury (SNI)-induced mechanical allodynia, complete Freund's Adjuvant (CFA)-induced thermal hyperalgesia, Paclitaxel-induced static allodynia, formalin-induced nociceptive behaviors, CFA-induced weight bearing deficit, and paw incision-induced static allodynia. Some of the models for the treatment of pain are disclosed in Fundam. Clin. Pharmacol., 2011, 25, 1-28.

Human Dofetilide Binding Assay

Human HERG transfected HEK293S cells are prepared and grown in-house. The collected cells are suspended in 50 mM Tris-HCl (pH 7.4 at 4° C.) and homogenized using a hand held Polytron PT 1200 homogenizer set at full power for 20 sec on ice. The homogenates are centrifuged at 48,000×g at 4° C. for 20 min. The pellets are then resuspended, homogenized, and centrifuged once more in the same manner. The final pellets are resuspended in an appropriate volume of 50 mM Tris-HCl, 10 mM KCl, 1 mM MgCl$_2$ (pH 7.4 at 4° C.), homogenized, aliquoted and stored at −80° C. until use. An aliquot of membrane fractions is used for protein concentration determination using BCA protein assay kit (PIERCE) and ARVOsx plate reader (Wallac). Binding assays are conducted in a total volume of 30 microL in 384-well plates. The activity is measured by PHERAstar (BMG LABTECH) using fluorescence polarization technology. Ten microL of test compounds are incubated with 10 microL of fluorescence ligand (6 nM Cy3B tagged dofetilide derivative) and 10 microL of membrane homogenate (6 microgram protein) for 120 minutes at room temperature. Nonspecific binding is determined by 10 microM E4031 at the final concentration.

All tested compounds of the invention show higher IC$_{50}$ values in human dofetilide binding than IC$_{50}$ values in Na$_{v1.7}$ FRET Assay. The high IC$_{50}$ values in human dofetilide binding activities lead to reducing the risk of cardiovascular adverse events.

Metabolic Stability Assay:

Half-Life in Human Liver Microsomes (HLM)

Test compounds (1 microM) are incubated with 3.3 mM MgCl$_2$ and 0.78 mg/mL HLM (HL101) or 0.74 mg/mL HLM (Gentest UltraPool 150) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. (NADPH generation system is also used instead of NADPH.) An aliquot of samples of P450 group is collected at 0, 10, 30, and 60 min time point, where 0 min time point indicated the time when NADPH is added into the reaction mixture of P450 group. An aliquot of samples of non-P450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system.

The half-life value is obtained by plotting the natural logarithm of the peak area ratio of compounds/internal standard versus time. The slope of the line of best fit through the points yield the rate of metabolism (k). This is converted to a half-life value using following equations.

Half-life=ln 2/$k$  [Math.8]

The compounds of this invention show preferable stability, which show the above-mentioned practical use.

Drug-Drug Interaction Assay

This method essentially involves determining the percent inhibition of metabolites formation from probes (Tacrine (Sigma A3773-1G) 2 microM, Dextromethorphan (Sigma D-9684) 5 microM, Diclofenac (Sigma D-6899-10G) 5 microM, and Midazolam (ULTRAFINE UC-429) 2 microM) at 3 microM of the each compound.

More specifically, the assay is carried out as follows. The compounds (60 microM, 10 microL) are pre-incubated in 170 microL of mixture including 0.1 mg protein/mL human liver microsomes, 100 mM potassium phosphate buffer (pH 7.4), 1 mM MgCl$_2$ and probes as substrate for 5 min. Reaction is started by adding a 20 microL of 10 mM NADPH (20 microL of NADPH generating system, which consist of 10 mM NADP$^+$, 50 mM DL-isocitric acid and 10 U/mL Isocitric Dehydrogenase, is also used). The assay plate is incubated at 37° C. Acetonitrile is added to the incubate solution at appropriate time (e.g. 8 min).

The metabolites' concentration in the supernatant is measured by LC/MS/MS system.

The degree of drug-drug interaction is interpreted based on generation % of metabolites in the presence or absence of test compound.

The compounds of this invention show preferable results, which show the above-mentioned practical use.

Plasma Protein Binding Assay

Plasma protein binding of the test compound (1 microM) is measured by the method of equilibrium dialysis using 96-well plate type equipment. HTD96a (registered trademark), regenerated cellulose membranes (molecular weight cut-off 12,000-14,000, 22 mm×120 mm) are soaked for overnight in distilled water, then for 15 minutes in 30% ethanol, and finally for 20 minutes in dialysis buffer (Dulbecco's phosphate buffered saline, pH7.4). Frozen plasma of human, Sprague-Dawley rats, and Beagle dogs are used. The dialysis equipment is assembled and added 150 microL of compound-fortified plasma to one side of each well and 150 microL of dialysis buffer to the other side of each well. After 4 hours incubation at 37° C. for 150 r.p.m, aliquots of plasma and buffer are sampled. The compound in plasma and buffer are extracted with 300 microL of acetonitrile containing internal standard compounds for analysis. The concentration of the compound is determined with LC/MS/MS analysis.

The fraction of the compound unbound is calculated by the following equation (A) or (B):

[Math.9]

$$fu = 1 - \{([plasma]_{eq} - [buffer]_{eq})/([plasma]_{eq})\} \quad (A)$$

wherein [plasma]$_{eq}$ and [buffer]$_{eq}$ are the concentrations of the compound in plasma and buffer, respectively.

$$(B) \quad fu(\%) = \frac{Cb/Cis, b \times 4}{Cp/Cis, p \times 4/3} \times 100 \quad [Math. 10]$$

wherein Cp is the peak area of the compound in plasma sample;

Cis,p is the peak area of the internal standard in plasma sample;

Cb is the peak area of the compound in buffer sample;

Cis,b is the peak area of the internal standard in buffer sample;

4 and 4/3 is the reciprocal of the dilution rate in plasma and buffer, respectively The compounds of this invention show preferable plasma protein binding, which show the above-mentioned practical use.

Equilibrium Aqueous Solubility Study

The DMSO solution (2 microL, 30 mM) of each compound is dispensed into each well of a 96-well glass bottom plate. Potassium phosphate buffer solution (50 mM, 198 microL, pH 6.5) is added to each well, and the mixture is incubated at 37° C. with rotate shaking for 24 hours. After centrifugation at 2000 g for 5 minutes, the supernatant is filtered through the polycarbonate iso-pore membrane. The concentration of samples is determined by a general gradient HPLC method (J. Pharm. Sci. 2006, 95, 2115-2122).

The compounds of this invention show preferable aqueous solubility, which show the above-mentioned practical use.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

INDUSTRIAL APPLICABILITY

The biaryloxy derivatives of the present invention are useful in the treatment of a wide range of disorders, particularly pain, such as acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back pain, orofacial pain and chemo-induced pain.

The invention claimed is:
1. A compound of the following formula (I):

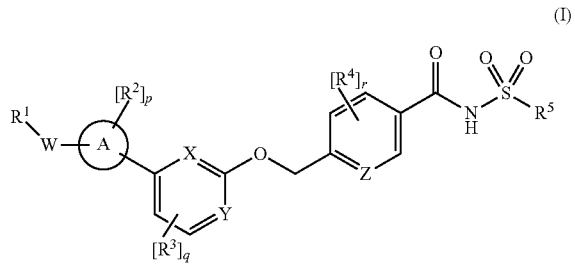

wherein:
A is aryl or heteroaryl;
W is selected from the group consisting of a chemical bond, —NR$^a$—, —O—, and —S—;
R$^a$ is hydrogen or C$_{1-6}$ alkyl;
R$^1$ is independently selected from the group consisting of:
(1) C$_{3-7}$ cycloalkyl, (2) heterocyclyl, (3) C$_{3-7}$ cycloalkylC$_{1-6}$ alkyl, and (4) heterocyclylC$_{1-6}$ alkyl;
wherein the C$_{3-7}$ cycloalkyl, the heterocyclyl, the C$_{3-7}$ cycloalkylC$_{1-6}$ alkyl, or the heterocyclylC$_{1-6}$ alkyl is unsubstituted or substituted with one or more substituents independently selected from the group consisting of: halogen, hydroxyl, C$_{1-6}$ alkyl, —O—C$_{1-6}$ alkyl, hydroxylC$_{1-6}$ alkyl, hydroxylC$_{1-6}$ alkoxy, —NR$^6$R$^7$, —(C=O)—R$^6$, —(C=O)—OR$^6$, —(C=O)—NR$^6$R$^7$, and —NR$^6$—(C=O)—R$^7$;
R$^2$ is independently selected from the group consisting of:
(1) hydrogen, (2) halogen, (3) hydroxyl, (4) C$_{1-6}$ alkyl, (5) —O—C$_{1-6}$ alkyl, (6) C$_{3-7}$ cycloalkyl-, (7) —O—C$_{3-7}$ cycloalkyl, (8) —(C=O)—NR$^6$R$^7$, (9) —NR$^6$(C=O)R$^7$, (10) —NR$^6$(C=O)NR$^7$R$^8$, (11) —NR$^6$R$^7$, (12) —CN, and (13) —NO$_2$; wherein the C$_{1-6}$ alkyl, the —O—C$_{1-6}$ alkyl, the C$_{3-7}$ cycloalkyl, or the —O—C$_{3-7}$ cycloalkyl is unsubstituted or substituted with one or more substituents independently selected from the group consisting of: halogen, hydroxyl, C$_{1-6}$ alkoxyl, —NR$^6$R$^7$, —(C=O)—NR$^6$R$^7$, —NR$^6$—(C=O)—R$^7$, and —NR$^6$CH$_2$—(C=O)—NH$_2$;
p is 0, 1, 2, 3, or 4; when p is two or more, each R$^2$ is the same or different;

R$^3$ is independently selected from the group consisting of:
(1) hydrogen, (2) halogen, (3) hydroxyl, (4) C$_{1-6}$ alkyl, (5) —O—C$_{1-6}$ alkyl, wherein the C$_{1-6}$alkyl or the —O—C$_{1-6}$ alkyl is unsubstituted or substituted with one or more substituents independently selected form the group consisting of: halogen, hydroxyl, C$_{1-6}$ alkoxyl, and C$_{3-7}$ cycloalkyl, (6) C$_{3-7}$ cycloalkyl, (7) —O—C$_{3-7}$ cycloalkyl, (8) aryl, (9) heteroaryl, (10) heterocyclyl, (11) —NR$^6$R$^7$, and (12) —CN; wherein the C$_{3-7}$ cycloalkyl, the —O—C$_{3-7}$ cycloalkyl, the aryl, the heteroaryl, or the heterocyclyl is unsubstituted or substituted with one or more substituents independently selected form the group consisting of: halogen, hydroxyl, and C$_{1-6}$ alkyl;
q is 0, 1, 2, 3, or 4; when q is two or more, each R$^3$ is the same or different;
X is CR$^3$ or N;
Y is CR$^3$ or N;
R$^4$ is independently selected from the group consisting of:
(1) hydrogen, (2) halogen, (3) hydroxyl, (4) C$_{1-6}$ alkyl, (5) —O—C$_{1-6}$ alkyl, (6) C$_{3-7}$ cycloalkyl, (7) —O—C$_{3-7}$ cycloalkyl, and (8) —CN; wherein the C$_{1-6}$ alkyl, the —O—C$_{1-6}$ alkyl, the C$_{3-7}$ cycloalkyl, or the —O—C$_{3-7}$ cycloalkyl is unsubstituted or substituted with one or more substituents independently selected form the group consisting of: halogen and hydroxyl;
r is 0, 1, 2, 3, or 4; when r is two or more, each R$^4$ is the same or different;
Z is CR$^4$ or N;
R$^5$ is selected from the group consisting of:
(1) C$_{1-6}$ alkyl, (2) —O—C$_{1-6}$ alkyl, (3) C$_{3-7}$ cycloalkyl, (4) C$_{3-7}$ cycloalkylC$_{1-6}$ alkyl, wherein the C$_{1-6}$ alkyl, the —O—C$_{1-6}$ alkyl, the C$_{3-7}$ cycloalkyl, or the C$_{3-7}$ cycloalkylC$_{1-6}$ alkyl is unsubstituted or substituted with one or more substituents independently selected form the group consisting of: halogen, hydroxyl, and C$_{1-6}$ alkoxyl, (5) aryl, (6) heteroaryl, wherein the aryl or the heteroaryl is unsubstituted or substituted with one or more substituents independently selected form the group consisting of: halogen, hydroxyl, C$_{1-6}$ alkyl and C$_{1-6}$ alkoxyl, and (7) —NR$^6$R$^7$;
R$^6$ and R$^7$ are independently selected from the group consisting of:
(1) hydrogen, (2) C$_{1-6}$ alkyl, and (3) C$_{1-6}$ alkoxyC$_{1-6}$ alkyl, wherein the C$_{1-6}$ alkyl or the C$_{1-6}$ alkoxyC$_{1-6}$ alkyl is unsubstituted or substituted with one or more substituents independently selected from the group consisting of: halogen and hydroxyl; R$^6$ may form a 4 to 7 membered ring with R$^7$ which may contain a nitrogen atom, an oxygen atom, a sulfur atom, carbonyl, or a double bond; wherein the 4 to 7 membered ring is unsubstituted or substituted with one or more substituents independently selected from the group consisting of: halogen, hydroxyl, and C$_{1-6}$ alkoxyl;
or a pharmaceutically acceptable salt thereof.
2. The compound according to claim 1, wherein:
A is phenyl or 5-6 membered heteroaryl;
W is a chemical bond, —NR$^a$—, or —O—; and
R$^a$ is hydrogen or C$_{1-6}$ alkyl;
or a pharmaceutically acceptable salt thereof.
3. The compound according to claim 1, wherein:
A is phenyl or 5-6 membered N-containing heteroaryl;
or a pharmaceutically acceptable salt thereof.
4. The compound according to claim 1, wherein:
A is phenyl, pyridyl, pyrazyl, pyrimidyl, pyrazolyl, or isoxazolyl;
or a pharmaceutically acceptable salt thereof.

5. The compound according to claim 1, wherein:

A is phenyl, pyridyl, pyrazyl, or pyrimidyl;

W is selected from the group consisting of —NR$^a$— and —O—;

R$^a$ is hydrogen or C$_{1-6}$ alkyl;

R$^1$ is independently selected from the group consisting of:
(1) C$_{3-7}$ cycloalkyl, (2) heterocyclyl, (3) C$_{3-7}$ cycloalkylC$_{1-6}$ alkyl, and (4) heterocyclylC$_{1-6}$ alkyl;
wherein the C$_{3-7}$ cycloalkyl or the C$_{3-7}$ cycloalkylC$_{1-6}$ alkyl is unsubstituted or substituted with one or more substituents independently selected from the group consisting of: halogen, hydroxyl, and C$_{1-6}$ alkyl; wherein the heterocyclyl or the heterocyclylC$_{1-6}$ alkyl is unsubstituted or substituted with one or more substituents independently selected from the group consisting of halogen, hydroxyl, C$_{1-6}$ alkyl, —(C=O)—R$^6$, —(C=O)—OR$^6$, —(C=O)—NR$^6$R$^7$, and —NR$^6$—(C=O)—R$^7$;

R$^2$ is independently selected from the group consisting of:
(1) hydrogen, (2) halogen, (4) C$_{1-6}$ alkyl, (5) —O—C$_{1-6}$ alkyl, (6) C$_{3-7}$ cycloalkyl, (7) —O—C$_{3-7}$ cycloalkyl, (8) —(C=O)—NR$^6$R$^7$, and (9) —NR$^6$(C=O)R$^7$, wherein the C$_{1-6}$ alkyl, the —O—C$_{1-6}$ alkyl, the C$_{3-7}$ cycloalkyl, or the —O—C$_{3-7}$ cycloalkyl is unsubstituted or substituted with one or more substituents independently selected from the group consisting of: halogen, hydroxyl, C$_{1-6}$ alkoxyl, —NR$^6$R$^7$, —(C=O)—NR$^6$R$^7$, —NR$^6$—(C=O)—R$^7$ and —NR$^6$CH$_2$—(C=O)—NH$_2$;

p is 0, 1, or 2; when p is two or more, each R$^2$ is the same or different;

R$^3$ is independently selected from the group consisting of:
(1) hydrogen, (2) halogen, (4) C$_{1-6}$ alkyl, (5) —O—C$_{1-6}$ alkyl, wherein the C$_{1-6}$ alkyl or the —O—C$_{1-6}$ alkyl is unsubstituted or substituted with one or more substituents independently selected form the group consisting of: halogen, hydroxyl, C$_{1-6}$ alkoxyl, and C$_{3-7}$ cycloalkyl, (6) C$_{3-7}$ cycloalkyl, (7) —O—C$_{3-7}$ cycloalkyl, (8) aryl, (9) heteroaryl, (11) —NR$^6$R$^7$, and (12) —CN; wherein the C$_{3-7}$ cycloalkyl, the —O—C$_{3-7}$ cycloalkyl, the aryl, or the heteroaryl is unsubstituted or substituted with one or more substituents independently selected form the group consisting of: halogen, hydroxyl, and C$_{1-6}$ alkyl;

q is 0, 1, or 2; when q is two or more, each R$^3$ is the same or different;

X is CR$^3$ or N;

Y is CR$^3$ or N;

R$^4$ is independently selected from the group consisting of:
(1) hydrogen, (2) halogen, (4) C$_{1-6}$ alkyl, (5) —O—C$_{1-6}$ alkyl, (6) C$_{3-7}$ cycloalkyl, (7) —O—C$_{3-7}$ cycloalkyl, and (8) —CN; wherein the C$_{1-6}$ alkyl, the —O—C$_{1-6}$ alkyl, the C$_{3-7}$ cycloalkyl, or the —O—C$_{3-7}$ cycloalkyl is unsubstituted or substituted with one or more substituents independently selected form the group consisting of: halogen and hydroxyl:

r is 0, 1, 2, or 3; when r is two or more, each R$^4$ is the same or different;

Z is CR$^4$ or N;

R$^5$ is selected from the group consisting of:
(1) C$_{1-6}$ alkyl, (3) C$_{3-7}$ cycloalkyl, (4) C$_{3-7}$ cycloalkylC$_{1-6}$ alkyl, wherein the C$_{1-6}$ alkyl, the C$_{3-7}$ cycloalkyl, or the C$_{3-7}$ cycloalkylC$_{1-6}$ alkyl is unsubstituted or substituted with one or more substituents independently selected form the group consisting of: halogen, hydroxyl, and C$_{1-6}$ alkoxyl, (5) aryl, and (6) heteroaryl, wherein the aryl or the heteroaryl is unsubstituted or substituted with one or more substituents independently selected form the group consisting of:
halogen, hydroxyl, C$_{1-6}$ alkyl, and C$_{1-6}$ alkoxyl;

R$^6$ and R$^7$ are independently selected from the group consisting of:
(1) hydrogen, (2) C$_{1-6}$ alkyl, and (3) C$_{1-6}$ alkoxyC$_{1-6}$ alkyl, wherein the C$_{1-6}$ alkyl or the C$_{1-6}$ alkoxyC$_{1-6}$ alkyl is unsubstituted or substituted with one or more substituents independently selected from the group consisting of: halogen and hydroxyl; R$^6$ may form a 4 to 7 membered ring with R$^7$ which may contain a nitrogen atom, an oxygen atom, a sulfur atom, carbonyl, or a double bond; wherein the 4 to 7 membered ring is unsubstituted or substituted with one or more substituents independently selected from the group consisting of: halogen, hydroxyl, and C$_{1-6}$ alkoxyl;

or a pharmaceutically acceptable salt thereof.

6. The compound according to claim 1, wherein:

A is phenyl, pyridyl, pyrazyl, or pyrimidyl;

W is selected from the group consisting of —NR$^a$— and —O—;

R$^a$ is hydrogen or C$_{1-4}$ alkyl;

R$^1$ is independently selected from the group consisting of:
(1) C$_{3-7}$ cycloalkyl, (2) 3-7 membered heterocyclyl, (3) C$_{3-7}$ cycloalkylC$_{1-4}$ alkyl, and (4) 3-7 membered heterocyclylC$_{1-4}$ alkyl; wherein the C$_{3-7}$ cycloalkyl or the C$_{3-7}$ cycloalkylC$_{1-4}$ alkyl is unsubstituted or substituted with one or more substituents independently selected from the group consisting of: halogen, hydroxyl, and C$_{1-4}$ alkyl; wherein the 3-7 membered heterocyclyl or the 3-7 membered heterocyclylC$_{1-4}$ alkyl is unsubstituted or substituted with one or more substituents independently selected from the group consisting of halogen, hydroxyl, C$_{1-4}$ alkyl, —(C=O)—R$^6$, —(C=O)—OR$^6$, —(C=O)—NR$^6$R$^7$, and —NR$^6$—(C=O)—R$^7$;

R$^2$ is independently selected from the group consisting of:
(1) hydrogen, (2) halogen, (4) C$_{1-4}$ alkyl, (5) —O—C$_{1-4}$ alkyl, (6) C$_{3-7}$ cycloalkyl, (7) —O—C$_{3-7}$ cycloalkyl, (8) —(C=O)—NR$^6$R$^7$, and (9) —NR$^6$(C=O)R$^7$, wherein the C$_{1-4}$ alkyl, the —O—C$_{1-4}$ alkyl, the C$_{3-7}$ cycloalkyl, or the —O—C$_{3-7}$ cycloalkyl is unsubstituted or substituted with one or more substituents independently selected from the group consisting of: halogen, hydroxyl, C$_{1-4}$ alkoxyl, —NR$^6$R$^7$, —(C=O)—NR$^6$R$^7$, —NR$^6$—(C=O)—R$^7$ and —NR$^6$CH$_2$—(C=O)—NH$_2$;

p is 0, 1, or 2; when p is two or more, each R$^2$ is the same or different;

R$^3$ is independently selected from the group consisting of:
(1) hydrogen, (2) halogen, (4) C$_{1-4}$ alkyl, (5) —O—C$_{1-4}$ alkyl, wherein the C$_{1-4}$ alkyl or the —O—C$_{1-4}$ alkyl is unsubstituted or substituted with one or more substituents independently selected form the group consisting of: halogen, hydroxyl, C$_{1-4}$ alkoxyl, and C$_{3-7}$ cycloalkyl, (6) C$_{3-7}$ cycloalkyl, (7) —O—C$_{3-7}$ cycloalkyl, (8) aryl, (9) 5-6 membered heteroaryl, (11) —NR$^6$R$^7$, and (12) —CN;
wherein the C$_{3-7}$ cycloalkyl, the —O—C$_{3-7}$ cycloalkyl, the aryl, or the 5-6 membered heteroaryl is unsubstituted or substituted with one or more substituents independently selected form the group consisting of: halogen, hydroxyl, and C$_{1-4}$ alkyl;

q is 0, 1, or 2; when q is two or more, each R$^3$ is the same or different;

X is CR$^3$ or N;

Y is CR$^3$ or N;

241

$R^4$ is independently selected from the group consisting of: (1) hydrogen, (2) halogen, (4) $C_{1-4}$ alkyl, (5) —O—$C_{1-4}$ alkyl, (6) $C_{3-7}$ cycloalkyl, (7) —O—$C_{3-7}$ cycloalkyl, and (8) —CN; wherein the $C_{1-4}$ alkyl, the —O—$C_{1-4}$ alkyl, the $C_{3-7}$ cycloalkyl, or the —O—$C_{3-7}$ cycloalkyl is unsubstituted or substituted with one or more substituents independently selected form the group consisting of: halogen and hydroxyl;

r is 0, 1, 2, or 3; when r is two or more, each $R^4$ is the same or different;

Z is $CR^4$ or N;

$R^5$ is selected from the group consisting of:
(1) $C_{1-4}$ alkyl, (3) $C_{3-7}$ cycloalkyl, (4) $C_{3-7}$ cycloalkyl$C_{1-4}$ alkyl, wherein the $C_{1-4}$ alkyl, the $C_{3-7}$ cycloalkyl, or the $C_{3-7}$ cycloalkyl$C_{1-4}$ alkyl is unsubstituted or substituted with one or more substituents independently selected form the group consisting of: halogen, hydroxyl, and $C_{1-4}$ alkoxyl, (5) aryl, and (6) 5-6 membered heteroaryl, wherein the aryl or the 5-6 membered heteroaryl is unsubstituted or substituted with one or more substituents independently selected form the group consisting of: halogen, hydroxyl, $C_{1-4}$ alkyl, and $C_{1-4}$ alkoxyl;

$R^6$ and $R^7$ are independently selected from the group consisting of:
(1) hydrogen, (2) $C_{1-4}$ alkyl, and (3) $C_{1-4}$ alkoxy$C_{1-4}$ alkyl, wherein the $C_{1-4}$ alkyl or the $C_{1-4}$ alkoxy$C_{1-4}$ alkyl is unsubstituted or substituted with one or more substituents independently selected from the group consisting of: halogen and hydroxyl; $R^6$ may form a 4 to 7 membered ring with $R^7$ which may contain a nitrogen atom, an oxygen atom, a sulfur atom, carbonyl, or a double bond; wherein the 4 to 7 membered ring is unsubstituted or substituted with one or more substituents independently selected from the group consisting of: halogen, hydroxyl, and $C_{1-4}$ alkoxyl;

or a pharmaceutically acceptable salt thereof.

7. The compound according to claim 1, wherein:
A is pyridyl or pyrazyl;
W is —O—;
$R^1$ is independently selected from the group consisting of: (1) $C_{3-7}$ cycloalkyl and (3) $C_{3-7}$ cycloalkyl$C_{1-6}$ alkyl, wherein the $C_{3-7}$ cycloalkyl or the $C_{3-7}$ cycloalkyl$C_{1-6}$ alkyl is unsubstituted or substituted with one or more halogens;
$R^2$ is independently selected from the group consisting of: (2) halogen and (4) $C_{1-6}$ alkyl;
p is 0 or 1;
$R^3$ is independently selected from the group consisting of: (1) hydrogen, (2) halogen, and (4) $C_{1-6}$ alkyl;
q is 0 or 1;
X is $CR^3$;
Y is $CR^3$;
$R^4$ is independently selected from the group consisting of: (1) hydrogen, (2) halogen, and (4) $C_{1-6}$ alkyl;
r is 0 or 1;
Z is $CR^4$;
$R^5$ is selected from the group consisting of: (1) $C_{1-4}$ alkyl, (3) $C_{3-7}$ cycloalkyl, (4) $C_{3-7}$ cycloalkyl$C_{1-4}$ alkyl, wherein the $C_{1-4}$ alkyl, the $C_{3-7}$ cycloalkyl, or the $C_{3-7}$ cycloalkyl$C_{1-4}$ alkyl is unsubstituted or substituted with one or more halogens;
or a pharmaceutically acceptable salt thereof.

8. The compound according to claim 1, wherein:
A is pyridyl or pyrazyl;
W is —O—;
$R^1$ is independently selected from the group consisting of: (1) $C_{3-6}$ cycloalkyl and (3) $C_{3-6}$ cycloalkyl$C_{1-4}$ alkyl,

242 wherein the $C_{3-6}$ cycloalkyl or the $C_{3-6}$ cycloalkyl$C_{1-4}$ alkyl is unsubstituted or substituted with one or more halogens;
$R^2$ is independently selected from the group consisting of: (2) halogen and (4) $C_{1-4}$ alkyl;
p is 0 or 1;
$R^3$ is independently selected from the group consisting of: (1) hydrogen, (2) halogen, and (4) $C_{1-4}$ alkyl;
q is 0 or 1;
X is $CR^3$;
Y is $CR^3$;
$R^4$ is independently selected from the group consisting of: (1) hydrogen, (2) halogen, and (4) $C_{1-4}$ alkyl;
r is 0 or 1;
Z is $CR^4$;
$R^5$ is selected from the group consisting of: (1) $C_{1-4}$ alkyl, (3) $C_{3-7}$ cycloalkyl, (4) $C_{3-7}$ cycloalkyl$C_{1-4}$ alkyl, wherein the $C_{1-4}$ alkyl, the $C_{3-7}$ cycloalkyl, or the $C_{3-7}$ cycloalkyl$C_{1-4}$ alkyl is unsubstituted or substituted with one or more halogens;
or a pharmaceutically acceptable salt thereof.

9. The compound according to claim 1, which is selected from the group consisting of:
N-(methylsulfonyl)-4-((3-(6-((tetrahydro-2H-pyran-4-yl)methoxy)pyridin-3-yl)phenoxy)methyl)benzamide;
4-((3-(6-(cyclopropylmethoxy)pyridin-3-yl)phenoxy)methyl)-N-(methylsulfonyl)benzamide;
4-((3-(6-(cyclopropylmethoxy)pyridin-3-yl)phenoxy)methyl)-N-((trifluoromethyl)sulfonyl)benzamide;
4-((3-(6-(cyclopropylmethoxy)pyridin-3-yl)phenoxy)methyl)-N-(cyclopropylsulfonyl)benzamide;
4-((3-(6-(cyclopropylmethoxy)pyridin-3-yl)phenoxy)methyl)-N-(isopropylsulfonyl)benzamide;
4-((3-(6-((3,3-difluorocyclobutyl)methoxy)pyridin-3-yl)phenoxy)methyl)-N-(methylsulfonyl)benzamide;
4-((3-(6-((4,4-difluorocyclohexyl)methoxy)pyridin-3-yl)phenoxy)methyl)-N-(methylsulfonyl)benzamide;
4-((3-(6-(cyclopropylmethoxy)-4-methylpyridin-3-yl)phenoxy)methyl)-N-(methylsulfonyl)benzamide;
4-((3-(6-(cyclopentylmethoxy)pyridin-3-yl)phenoxy)methyl)-N-(methylsulfonyl)benzamide;
4-((3-(6-(cyclopropylmethoxy)-5-methylpyridin-3-yl)phenoxy)methyl)-N-(methylsulfonyl)benzamide;
tert-butyl 4-(((5-(3-((4-((methylsulfonyl)carbamoyl)benzyl)oxy)phenyl)pyridin-2-yl)oxy)methyl)piperidine-1-carboxylate;
4-((2-chloro-5-(6-(cyclopropylmethoxy)pyridin-3-yl)phenoxy)methyl)-N-(methylsulfonyl)benzamide;
3-chloro-4-((3-(6-(cyclopropylmethoxy)pyridin-3-yl)phenoxy)methyl)-N-(methylsulfonyl)benzamide;
4-((3-(6-(cyclopropylmethoxy)pyridin-3-yl)phenoxy)methyl)-3-fluoro-N-(methylsulfonyl)benzamide;
4-((3-(6-(cyclobutyl methoxy)pyridin-3-yl)phenoxy)methyl)-N-(methylsulfonyl)benzamide;
5-chloro-4-((3-(6-(cyclopropylmethoxy)pyridin-3-yl)phenoxy)methyl)-2-fluoro-N-(methylsulfonyl)benzamide;
5-chloro-4-((3-(6-(cyclopropylmethoxy)pyridin-3-yl)phenoxy)methyl)-N-(cyclopropylsulfonyl)-2-fluorobenzamide;
4-((3-(6-(cyclopropylmethoxy)pyridin-3-yl)phenoxy)methyl)-N-(thiophen-2-ylsulfonyl)benzamide;
4-((3-(6-(cyclopropylmethoxy)pyridin-3-yl)phenoxy)methyl)-N-(thiazol-2-ylsulfonyl)benzamide;
5-chloro-4-((3-(6-(cyclopropylmethoxy)pyridin-3-yl)phenoxy)methyl)-2-fluoro-N-(thiophen-2-ylsulfonyl)benzamide;

4-((3-chloro-5-(6-(cyclopropylmethoxy)pyridin-3-yl)phenoxy)methyl)-N-(methylsulfonyl)benzamide;
4-((4-chloro-3-(6-(cyclopropylmethoxy)pyridin-3-yl)phenoxy)methyl)-N-(methylsulfonyl)benzamide;
5-cyclopropyl-4-((3-(6-(cyclopropylmethoxy)pyridin-3-yl)phenoxy)methyl)-2-fluoro-N-(methylsulfonyl)benzamide;
4-((3-(6-(cyclopropylmethoxy)pyridin-3-yl)phenoxy)methyl)-2,5-difluoro-N-(methylsulfonyl)benzamide;
3-fluoro-N-(methylsulfonyl)-4-((3-(6-((tetrahydro-2H-pyran-4-yl)methoxy)pyridin-3-yl)phenoxy)methyl)benzamide;
4-((3-(6-(cyclopropylmethoxy)pyridin-3-yl)phenoxy)methyl)-5-(difluoromethoxy)-2-fluoro-N-(methylsulfonyl)benzamide;
4-((3-(6-(cyclopropylmethoxy)pyridin-3-yl)phenoxy)methyl)-2-fluoro-N-(methylsulfonyl)benzamide;
4-((3-(6-(cyclopropylmethoxy)pyridin-3-yl)phenoxy)methyl)-3,5-difluoro-N-(methylsulfonyl)benzamide;
N-(cyclopropylsulfonyl)-4-((3-(6-((tetrahydro-2H-pyran-4-yl)methoxy)pyridin-3-yl)phenoxy)methyl)benzamide;
4-((3-(6-(cyclopropylmethoxy)pyridin-3-yl)-5-fluorophenoxy)methyl)-N-(methylsulfonyl)benzamide;
4-((3-(6-(cyclopropylmethoxy)pyridin-3-yl)-5-fluorophenoxy)methyl)-2,5-difluoro-N-(methylsulfonyl)benzamide;
4-((3-(6-(cyclopropylmethoxy)pyridin-3-yl)-5-fluorophenoxy)methyl)-3-fluoro-N-(methylsulfonyl)benzamide;
4-((3-(6-(cyclopropylmethoxy)pyridin-3-yl)-5-fluorophenoxy)methyl)-N-(cyclopropylsulfonyl)-3-fluorobenzamide;
4-((3-cyclopropyl-5-(6-(cyclopropylmethoxy)pyridin-3-yl)phenoxy)methyl)-N-(methylsulfonyl)benzamide;
4-((3-(6-(cyclopropylmethoxy)pyridin-3-yl)-5-methylphenoxy)methyl)-3-fluoro-N-(methylsulfonyl)benzamide;
4-((3-(6-(cyclopropylmethoxy)pyridin-3-yl)-5-methylphenoxy)methyl)-N-(cyclopropylsulfonyl)-3-fluorobenzamide;
4-((3-(6-(cyclopropylmethoxy)pyridin-3-yl)-5-(trifluoromethyl)phenoxy)methyl)-N-(methylsulfonyl)benzamide;
4-((3-(6-(cyclopropylmethoxy)pyridin-3-yl)phenoxy)methyl)-N-((2-methoxyethyl)sulfonyl)benzamide;
4-((3-(6-(cyclopropylmethoxy)pyridin-3-yl)-2-fluorophenoxy)methyl)-N-(methylsulfonyl)benzamide;
3-cyano-4-((3-(6-(cyclopropylmethoxy)pyridin-3-yl)phenoxy)methyl)-N-(methylsulfonyl)benzamide;
3-cyano-4-((3-(6-(cyclopropylmethoxy)pyridin-3-yl)phenoxy)methyl)-N-(cyclopropylsulfonyl)benzamide;
4-((3-(6-(cyclopropylmethoxy)pyridin-3-yl)-4-fluorophenoxy)methyl)-N-(methylsulfonyl)benzamide;
4-((3-(6-(cyclopropylmethoxy)pyridin-3-yl)-4-fluorophenoxy)methyl)-N-(cyclopropylsulfonyl)benzamide;
4-((5-(6-(cyclopropylmethoxy)pyridin-3-yl)-2-fluorophenoxy)methyl)-N-(methylsulfonyl)benzamide;
4-((3-bromo-5-(6-(cyclopropylmethoxy)pyridin-3-yl)phenoxy)methyl)-N-(methylsulfonyl)benzamide;
4-((3-(6-(cyclopropylmethoxy)pyridin-3-yl)-4-fluorophenoxy)methyl)-3-fluoro-N-(methylsulfonyl)benzamide;
4-((3-(6-(cyclopropylmethoxy)pyridin-3-yl)-4-fluorophenoxy)methyl)-N-(cyclopropylsulfonyl)-3-fluorobenzamide;
4-((3-(6-(cyclopropylmethoxy)pyridin-3-yl)-4-methylphenoxy)methyl)-3-fluoro-N-(methylsulfonyl)benzamide;
4-((3-(6-(cyclopropylmethoxy)pyridin-3-yl)-4-methylphenoxy)methyl)-N-(cyclopropylsulfonyl)-3-fluorobenzamide;
4-((4-chloro-3-(6-(cyclopropylmethoxy)pyridin-3-yl)phenoxy)methyl)-3-fluoro-N-(methylsulfonyl)benzamide;
4-((3-(6-(cyclobutylmethoxy)pyridin-3-yl)phenoxy)methyl)-3-fluoro-N-(methylsulfonyl)benzamide;
4-((3-(6-(cyclopropylmethoxy)pyridin-3-yl)phenoxy)methyl)-N-(ethylsulfonyl)-3-fluorobenzamide;
4-((3-(6-(cyclopropylmethoxy)pyridin-3-yl)phenoxy)methyl)-3-fluoro-N-(isopropylsulfonyl)benzamide;
4-((3-(6-(cyclopropylmethoxy)pyridin-3-yl)phenoxy)methyl)-N-(cyclopropylsulfonyl)-3-fluorobenzamide;
4-((3-(6-(cyclopropylmethoxy)pyridin-3-yl)phenoxy)methyl)-N-((cyclopropylmethyl)sulfonyl)-3-fluorobenzamide;
4-((3-(6-(cyclopropylmethoxy)pyridin-3-yl)phenoxy)methyl)-3-fluoro-N-(thiophen-2-ylsulfonyl)benzamide;
4-((3-(6-(cyclopropylmethoxy)pyridin-3-yl)phenoxy)methyl)-3-fluoro-N-(thiazol-2-ylsulfonyl)benzamide;
4-((3-(6-(cyclopropylmethoxy)pyridin-3-yl)phenoxy)methyl)-3-fluoro-N-((trifluoromethyl)sulfonyl)benzamide;
4-((3-(6-(cyclopropylmethoxy)pyridin-3-yl)phenoxy)methyl)-3-methoxy-N-(methylsulfonyl)benzamide;
4-((3-(2-(cyclopropylmethoxy)pyridin-3-yl)phenoxy)methyl)-N-(methylsulfonyl)benzamide;
4-((3-(5-(cyclopropylmethoxy)pyridin-3-yl)phenoxy)methyl)-N-(methylsulfonyl)benzamide;
5-cyclopropyl-6-((3-(6-(cyclopropylmethoxy)pyridin-3-yl)phenoxy)methyl)-N-(methylsulfonyl)nicotinamide;
6-((3-(6-(cyclopropylmethoxy)pyridin-3-yl)phenoxy)methyl)-N-(methylsulfonyl)nicotinamide;
6-((3-(6-(cyclopropylmethoxy)pyridin-3-yl)-5-fluorophenoxy)methyl)-N-(methylsulfonyl)nicotinamide;
4-(((6-(cyclopropylmethoxy)-[3,4'-bipyridin]-2'-yl)oxy)methyl)-N-(cyclopropylsulfonyl)benzamide;
4-(((6'-(cyclopropylmethoxy)-[2,3'-bipyridin]-6-yl)oxy)methyl)-N-(methylsulfonyl)benzamide;
4-((3-(5-(cyclopropylmethoxy)pyridin-2-yl)phenoxy)methyl)-N-(methylsulfonyl)benzamide;
4-((3-(6-(cyclopropylmethoxy)pyridin-2-yl)phenoxy)methyl)-N-(methylsulfonyl)benzamide;
4-((3-(3-chloro-5-(cyclopropylmethoxy)pyridin-2-yl)phenoxy)methyl)-N-(methylsulfonyl)benzamide;
4-((3-(5-(cyclopropylmethoxy)-3-fluoropyridin-2-yl)phenoxy)methyl)-N-(methylsulfonyl)benzamide;
4-((3-(5-(cyclopropylmethoxy)-3-methylpyridin-2-yl)phenoxy)methyl)-N-(methylsulfonyl)benzamide;
4-((3-(2-(cyclopropylmethoxy)pyridin-4-yl)phenoxy)methyl)-N-(methylsulfonyl)benzamide;
4-((3-(5-(cyclopropylmethoxy)pyrazin-2-yl)phenoxy)methyl)-N-(methylsulfonyl)benzamide;
4-((3-(5-(cyclopropylmethoxy)pyrazin-2-yl)phenoxy)methyl)-3-fluoro-N-(methylsulfonyl)benzamide;
4-((3-(5-(cyclopropylmethoxy)pyrazin-2-yl)phenoxy)methyl)-N-(cyclopropylsulfonyl)benzamide;
4-((3-(6-(cyclopropylmethoxy)pyrazin-2-yl)phenoxy)methyl)-3-fluoro-N-(methylsulfonyl)benzamide;
4-((3-(5-(cyclopropylmethoxy)pyrimidin-2-yl)phenoxy)methyl)-N-(methylsulfonyl)benzamide;
4-((3-(5-(cyclopropylmethoxy)pyrimidin-2-yl)phenoxy)methyl)-3-fluoro-N-(methylsulfonyl)benzamide;
4-((3-(5-(cyclopropylmethoxy)pyrimidin-2-yl)phenoxy)methyl)-N-(cyclopropylsulfonyl)benzamide;

4-(((4'-cyclopropylmethoxy)-[1,1'-biphenyl]-3-yl)oxy)methyl)-N-(methylsulfonyl)benzamide;
4-(cyclopropylmethoxy)-3'-((2-fluoro-4-((methylsulfonyl)carbamoyl)benzyl)oxy)-N-methyl-[1,1'-biphenyl]-3-carboxamide;
4-(cyclopropylmethoxy)-3'-((2-fluoro-4-((methylsulfonyl)carbamoyl)benzyl)oxy)-N,N-dimethyl-[1,1'-biphenyl]-3-carboxamide;
4-((3-(1-(cyclopropylmethyl)-1H-pyrazol-3-yl)phenoxy)methyl)-3-fluoro-N-(methylsulfonyl)benzamide;
4-((3-(5-(cyclopropylmethyl)isoxazol-3-yl)phenoxy)methyl)-3-fluoro-N-(methylsulfonyl)benzamide;
4-((3-(6-(cyclopropylmethoxy)-2-methylpyridin-3-yl)phenoxy)methyl)-N-(methylsulfonyl)benzamide;
4-((3-(6-(cyclopropylmethoxy)-2-methylpyridin-3-yl)phenoxy)methyl)-3-fluoro-N-(methylsulfonyl)benzamide;
3-fluoro-N-(methylsulfonyl)-4-((3-(6-((tetrahydrofuran-3-yl)methoxy)pyridin-3-yl)phenoxy)methyl)benzamide;
4-((3-fluoro-5-(6-((tetrahydrofuran-3-yl)methoxy)pyridin-3-yl)phenoxy)methyl)-N-(methylsulfonyl)benzamide;
4-((3-cyano-5-(6-(cyclopropylmethoxy)pyridin-3-yl)phenoxy)methyl)-N-(methylsulfonyl)benzamide;
4-((3-(6-(cyclobutylmethoxy)-2-methylpyridin-3-yl)-5-fluorophenoxy)methyl)-N-(methylsulfonyl)benzamide;
4-((3-(6-(cyclopropylmethoxy)-5-methylpyridin-3-yl)phenoxy)methyl)-3-fluoro-N-(methylsulfonyl)benzamide;
4-((3-(6-(cyclopropylmethoxy)-5-methylpyridin-3-yl)-5-fluorophenoxy)methyl)-N-(methylsulfonyl)benzamide;
4-((3-(6-(cyclopropylmethoxy)-2-methylpyridin-3-yl)-5-fluorophenoxy)methyl)-N-(methylsulfonyl)benzamide;
4-((3-(6-(cyclopropylmethoxy)-4-methylpyridin-3-yl)phenoxy)methyl)-3-fluoro-N-(methylsulfonyl)benzamide;
4-((3-(6-(cyclopropylmethoxy)-4-methylpyridin-3-yl)-5-fluorophenoxy)methyl)-N-(methylsulfonyl)benzamide;
4-((3-(5-chloro-6-(cyclopropylmethoxy)pyridin-3-yl)phenoxy)methyl)-3-fluoro-N-(methylsulfonyl)benzamide;
tert-butyl 3-(((5-(3-((2-fluoro-4-((methylsulfonyl)carbamoyl)benzyl)oxy)phenyl)pyridin-2-yl)oxy)methyl)azetidine-1-carboxylate;
4-((3-(5-chloro-6-(cyclopropylmethoxy)pyridin-3-yl)-5-fluorophenoxy)methyl)-3-fluoro-N-(methylsulfonyl)benzamide;
4-((3-(5-chloro-6-(cyclopropylmethoxy)pyridin-3-yl)-4-fluorophenoxy)methyl)-3-fluoro-N-(methylsulfonyl)benzamide;
4-((3-(6-(cyclopropylmethoxy)-2-methylpyridin-3-yl)-4-fluorophenoxy)methyl)-3-fluoro-N-(methylsulfonyl)benzamide;
4-((3-(6-(cyclobutyl in ethoxy)-5-(hydroxymethyl)pyridin-3-yl)phenoxy)methyl)-3-fluoro-N-(methylsulfonyl)benzamide;
4-((3-(6-(cyclobutylmethoxy)-5-(hydroxymethyl)pyridin-3-yl)-5-fluorophenoxy)methyl)-3-fluoro-N-(methylsulfonyl)benzamide;
4-((3-(6-(cyclobutylmethoxy)-5-(hydroxymethyl)pyridin-3-yl)phenoxy)methyl)-N-(methylsulfonyl)benzamide;
4-((3-(6-(cyclobutylmethoxy)-5-(hydroxymethyl)pyridin-3-yl)-5-fluorophenoxy)methyl)-N-(methylsulfonyl)benzamide;
4-((3-(6-(cyclobutylmethoxy)-2-(hydroxymethyl)pyridin-3-yl)phenoxy)methyl)-3-fluoro-N-(methylsulfonyl)benzamide;
4-((3-(6-(cyclobutylmethoxy)-2-(hydroxymethyl)pyridin-3-yl)phenoxy)methyl)-N-(methylsulfonyl)benzamide;
4-(((5-(6-(cyclopropylmethoxy)pyridin-3-yl)-[1,1'-biphenyl]-3-yl)oxy)methyl)-N-(methylsulfonyl)benzamide;
4-((3-(6-(cyclopropylmethoxy)pyridin-3-yl)-5-(pyrimidin-5-yl)phenoxy)methyl)-N-(methylsulfonyl)benzamide;
4-((3-(6-(cyclopropylmethoxy)pyridin-3-yl)-5-(1-methyl-1H-pyrazol-4-yl)phenoxy)methyl)-N-(methylsulfonyl)benzamide;
4-((3-(6-(cyclopropylmethoxy)pyridin-3-yl)-5-(pyridin-3-yl)phenoxy)methyl)-N-(methylsulfonyl)benzamide;
4-((3-(5-(cyclopropylmethoxy)pyridin-3-yl)phenoxy)methyl)-3-fluoro-N-(methylsulfonyl)benzamide;
4-((3-(5-(cyclopropylmethoxy)pyridin-3-yl)-5-fluorophenoxy)methyl)-N-(methylsulfonyl)benzamide;
6-((3-(6-(cyclobutyl methoxy)pyridin-3-yl)phenoxy)methyl)-N-(methylsulfonyl)nicotinamide;
4-((3-(6-(cyclopropylmethoxy)pyridin-2-yl)phenoxy)methyl)-3-fluoro-N-(methylsulfonyl)benzamide;
4-((3-(6-(cyclopropylmethoxy)pyridin-2-yl)-5-fluorophenoxy)methyl)-N-(methylsulfonyl)benzamide;
4-((3-(6-(cyclopropylmethoxy)pyridin-2-yl)-4-fluorophenoxy)methyl)-3-fluoro-N-(methylsulfonyl)benzamide;
4-((3-(5-(cyclopropylmethoxy)-3-fluoropyridin-2-yl)phenoxy)methyl)-3-fluoro-N-(methylsulfonyl)benzamide;
4-((3-(5-(cyclopropylmethoxy)-3-fluoropyridin-2-yl)-5-fluorophenoxy)methyl)-N-(methylsulfonyl)benzamide;
4-((3-(5-(cyclopropylmethoxy)-3-methylpyridin-2-yl)-5-fluorophenoxy)methyl)-N-(methylsulfonyl)benzamide;
4-((3-(5-(cyclopropylmethoxy)-3-methylpyridin-2-yl)phenoxy)methyl)-3-fluoro-N-(methylsulfonyl)benzamide;
4-((3-(5-(cyclobutylmethoxy)-3-methylpyridin-2-yl)-5-fluorophenoxy)methyl)-N-(methylsulfonyl)benzamide;
4-((3-(5-(cyclobutylmethoxy)-3-methylpyridin-2-yl)phenoxy)methyl)-3-fluoro-N-(methylsulfonyl)benzamide;
4-((3-(5-(cyclobutylmethoxy)-3-methylpyridin-2-yl)phenoxy)methyl)-N-(methylsulfonyl)benzamide;
4-((3-(5-(cyclopropylmethoxy)pyridin-2-yl)phenoxy)methyl)-3-fluoro-N-(methylsulfonyl)benzamide;
4-((3-(5-(cyclopropylmethoxy)pyridin-2-yl)-5-fluorophenoxy)methyl)-N-(methylsulfonyl)benzamide;
4-((3-(4-(cyclopropylmethoxy)-3-methylpyridin-2-yl)phenoxy)methyl)-3-fluoro-N-(methylsulfonyl)benzamide;
4-((3-(4-(cyclopropylmethoxy)-3-methylpyridin-2-yl)-5-fluorophenoxy)methyl)-N-(methylsulfonyl)benzamide;
4-((3-(4-(cyclopropylmethoxy)pyridin-2-yl)-5-fluorophenoxy)methyl)-N-(methylsulfonyl)benzamide;
4-((3-(4-(cyclopropylmethoxy)pyridin-2-yl)phenoxy)methyl)-N-(methylsulfonyl)benzamide;
4-((3-(4-(cyclopropylmethoxy)pyridin-2-yl)phenoxy)methyl)-3-fluoro-N-(methylsulfonyl)benzamide;
4-((3-(2-(cyclopropylmethoxy)pyridin-4-yl)phenoxy)methyl)-3-fluoro-N-(methylsulfonyl)benzamide
4-((3-(2-(cyclopropylmethoxy)pyridin-4-yl)-5-fluorophenoxy)methyl)-N-(methylsulfonyl)benzamide;
4-((3-(2-(cyclopropylmethoxy)-3-methylpyridin-4-yl)phenoxy)methyl)-3-fluoro-N-(methylsulfonyl)benzamide;
4-((3-(2-(cyclopropylmethoxy)-3-methylpyridin-4-yl)-5-fluorophenoxy)methyl)-N-(methylsulfonyl)benzamide;

4-((3-(2-(cyclopropylmethoxy)-3-methylpyridin-4-yl)-4-fluorophenoxy)methyl)-3-fluoro-N-(methylsulfonyl)benzamide;
4-((3-(2-((cyclopropylmethyl)(methyl)amino)pyridin-4-yl)phenoxy)methyl)-3-fluoro-N-(methylsulfonyl)benzamide;
4-((3-(5-(cyclobutylmethoxy)pyrazin-2-yl)phenoxy)methyl)-N-(methylsulfonyl)benzamide;
4-((3-(5-(cyclopropylmethoxy)pyrazin-2-yl)-5-fluorophenoxy)methyl)-N-(methylsulfonyl)benzamide;
4-((3-(5-(cyclopropylmethoxy)pyrazin-2-yl)-4-fluorophenoxy)methyl)-3-fluoro-N-(methylsulfonyl)benzamide;
4-((3-(5-(cyclobutylmethoxy)pyrazin-2-yl)phenoxy)methyl)-3-fluoro-N-(methylsulfonyl)benzamide;
4-((3-(6-(cyclopropylmethoxy)pyrazin-2-yl)-5-fluorophenoxy)methyl)-N-(methylsulfonyl)benzamide;
4-((3-(6-(cyclopropylmethoxy)pyrazin-2-yl)phenoxy)methyl)-N-(methylsulfonyl)benzamide;
4-((3-(5-(cyclopropylmethoxy)pyrimidin-2-yl)-5-fluorophenoxy)methyl)-N-(methylsulfonyl)benzamide;
4-((3-(5-(cyclobutyl in ethoxy)pyri midi n-2-yl)-5-fluorophenoxy)methyl)-N-(methylsulfonyl)benzamide;
4-((3-(5-(cyclopropylmethoxy)pyrimidin-2-yl)-4-fluorophenoxy)methyl)-3-fluoro-N-(methylsulfonyl)benzamide;
4-((3-(6-(cyclopropylmethoxy)pyrimidin-4-yl)phenoxy)methyl)-N-(methylsulfonyl)benzamide;
4-((3-(6-(cyclopropylmethoxy)pyrimidin-4-yl)-5-fluorophenoxy)methyl)-N-(methylsulfonyl)benzamide;
4-((3-(6-(cyclopropylmethoxy)pyrimidin-4-yl)phenoxy)methyl)-3-fluoro-N-(methylsulfonyl)benzamide;
4-((3-(6-(cyclopropylmethoxy)-5-methylpyrimidin-4-yl)phenoxy)methyl)-3-fluoro-N-(methylsulfonyl)benzamide;
4-((3-(6-(cyclopropylmethoxy)-5-methylpyrimidin-4-yl)-5-fluorophenoxy)methyl)-N-(methylsulfonyl)benzamide;
4-((3-(6-(cyclopropylmethoxy)-5-methylpyrimidin-4-yl)phenoxy)methyl)-N-(methylsulfonyl)benzamide;
4-((3-(2-(cyclopropylmethoxy)pyrimidin-5-yl)phenoxy)methyl)-3-fluoro-N-(methylsulfonyl)benzamide;
4-((3-(2-(cyclopropylmethoxy)pyrimidin-5-yl)-5-fluorophenoxy)methyl)-N-(methylsulfonyl)benzamide;
4-((3-(2-(cyclopropylmethoxy)-4-methylpyrimidin-5-yl)phenoxy)methyl)-3-fluoro-N-(methylsulfonyl)benzamide;
4-((3-(2-(cyclopropylmethoxy)-4-methylpyrimidin-5-yl)-5-fluorophenoxy)methyl)-N-(methylsulfonyl)benzamide;
4-((3-(2-((cyclopropylmethyl)(methyl)amino)pyrimidin-5-yl)phenoxy)methyl)-3-fluoro-N-(methylsulfonyl)benzamide;
4-(((3'-(2-aminoethoxy)-5'-(cyclopropylmethoxy)-5-fluoro-[1,1'-biphenyl]-3-yl)oxy)methyl)-3-fluoro-N-(methylsulfonyl)benzamide;
4-(((3'-(2-amino-2-oxoethoxy)-5'-(cyclopropylmethoxy)-5-fluoro-[1,1'-biphenyl]-3-yl)oxy)methyl)-3-fluoro-N-(methylsulfonyl)benzamide;
4-(((3'-(cyclopropylmethoxy)-5-fluoro-5'-(2-methoxyethoxy)-[1,1'-biphenyl]-3-yl)oxy)methyl)-3-fluoro-N-(methylsulfonyl)benzamide;
4-(((3'-(cyclopropylmethoxy)-5-fluoro-5'-(2-hydroxyethoxy)-[1,1'-biphenyl]-3-yl)oxy)methyl)-3-fluoro-N-(methylsulfonyl)benzamide;
4-(((3'-(cyclopropylmethoxy)-5-fluoro-5'-(morpholine-4-carbonyl)-[1,1'-biphenyl]-3-yl)oxy)methyl)-3-fluoro-N-(methylsulfonyl)benzamide;
5-(cyclopropylmethoxy)-3'-fluoro-5'-((2-fluoro-4-((methylsulfonyl)carbamoyl)benzyl)oxy)-N-methyl-[1,1'-biphenyl]-3-carboxamide;
5-(cyclopropylmethoxy)-3'-fluoro-5'-((2-fluoro-4-((methylsulfonyl)carbamoyl)benzyl)oxy)-N,N-dimethyl-[1,1'-biphenyl]-3-carboxamide;
4-(((3'-(cyclopropylmethoxy)-5'-(2-(dimethylamino)-2-oxoethoxy)-5-fluoro-[1,1-'-biphenyl]-3-yl)oxy)methyl)-3-fluoro-N-(methylsulfonyl)benzamide;
4-(((3'-(cyclopropylmethoxy)-5-fluoro-5'-(3-methoxyazetidine-1-carbonyl)-[1,1'-biphenyl]-3-yl)oxy)methyl)-3-fluoro-N-(methylsulfonyl)benzamide;
4-(((3'-(cyclopropylmethoxy)-5-fluoro-5'-(((2-hydroxyethyl)(methyl)amino)methyl)-[1,1'-biphenyl]-3-yl)oxy)methyl)-3-fluoro-N-(methylsulfonyl)benzamide;
4-(((3'-(((2-amino-2-oxoethyl)(methyl)amino)methyl)-5'-(cyclopropylmethoxy)-5-fluoro-[1,1'-biphenyl]-3-yl)oxy)methyl)-3-fluoro-N-(methylsulfonyl)benzamide;
N-(methylsulfonyl)-4-((3-(6-((1-(3,3,3-trifluoropropanoyl)piperidin-4-yl)methoxy)pyridin-3-yl)phenoxy)methyl)benzamide;
N,N-dimethyl-4-(((5-(3-((4-((methylsulfonyl)carbamoyl)benzyl)oxy)phenyl)pyridin-2-yl)oxy)methyl)piperidine-1-carboxamide;
ethyl 4-(((5-(3-((4-((methylsulfonyl)carbamoyl)benzyl)oxy)phenyl)pyridin-2-yl)oxy)methyl)piperidine-1-carboxylate;
4-(((3'-(2-acetamidoethoxy)-5'-(cyclopropylmethoxy)-5-fluoro-[1,1'-biphenyl]-3-yl)oxy)methyl)-3-fluoro-N-(methylsulfonyl)benzamide;
4-((3-(6-(cyclopropylmethoxy)pyridin-3-yl)-5-fluorophenoxy)methyl)-N-(ethylsulfonyl)benzamide;
4-((3-(6-(cyclopropylmethoxy)pyridin-3-yl)-5-fluorophenoxy)methyl)-N-(isopropylsulfonyl)benzamide;
4-((3-(6-(cyclopropylmethoxy)pyridin-3-yl)-5-fluorophenoxy)methyl)-N-(cyclopropylsulfonyl)benzamide;
4-((3-(6-(cyclopropylmethoxy)pyridin-3-yl)-5-fluorophenoxy)methyl)-N-((cyclopropylmethyl)sulfonyl)benzamide;
4-((3-(6-(cyclopropylmethoxy)pyridin-3-yl)-5-fluorophenoxy)methyl)-N-(thiophen-2-ylsulfonyl)benzamide; and
4-((3-(6-(cyclopropylmethoxy)pyridin-3-yl)-5-fluorophenoxy)methyl)-N-((trifluoromethyl)sulfonyl)benzamide,
or a pharmaceutically acceptable salt thereof.

10. The compound according to claim 9, which is selected from the group consisting of:
4-((3-(6-(cyclopropylmethoxy)pyridin-3-yl)phenoxy)methyl)-N-((trifluoromethyl)sulfonyl)benzamide;
4-((3-(6-(cyclopropylmethoxy)pyridin-3-yl)-5-fluorophenoxy)methyl)-3-fluoro-N-(methylsulfonyl)benzamide;
4-((3-(6-(cyclopropylmethoxy)pyridin-3-yl)-5-methylphenoxy)methyl)-3-fluoro-N-(methylsulfonyl)benzamide;
4-((3-bromo-5-(6-(cyclopropylmethoxy)pyridin-3-yl)phenoxy)methyl)-N-(methylsulfonyl)benzamide;
4-((3-(6-(cyclopropylmethoxy)pyridin-3-yl)-4-fluorophenoxy)methyl)-3-fluoro-N-(methylsulfonyl)benzamide;
4-((3-(6-(cyclopropylmethoxy)pyridin-3-yl)-4-methylphenoxy)methyl)-3-fluoro-N-(methylsulfonyl)benzamide;

4-((4-chloro-3-(6-(cyclopropylmethoxy)pyridin-3-yl)phenoxy)methyl)-3-fluoro-N-(methylsulfonyl)benzamide;

4-((3-(6-(cyclopropylmethoxy)pyridin-2-yl)phenoxy)methyl)-N-(in ethylsulfonyl)benzamide;

4-((3-(6-(cyclopropylmethoxy)-2-methylpyridin-3-yl)phenoxy)methyl)-3-fluoro-N-(methylsulfonyl)benzamide;

4-((3-(5-chloro-6-(cyclopropylmethoxy)pyridin-3-yl)phenoxy)methyl)-3-fluoro-N-(methylsulfonyl)benzamide;

4-((3-(5-chloro-6-(cyclopropylmethoxy)pyridin-3-yl)-5-fluorophenoxy)methyl)-3-fluoro-N-(methylsulfonyl)benzamide;

4-((3-(5-chloro-6-(cyclopropylmethoxy)pyridin-3-yl)-4-fluorophenoxy)methyl)-3-fluoro-N-(methylsulfonyl)benzamide;

4-((3-(6-(cyclopropylmethoxy)-2-methylpyridin-3-yl)-4-fluorophenoxy)methyl)-3-fluoro-N-(methylsulfonyl)benzamide;

4-((3-(6-(cyclobutylmethoxy)-5-(hydroxymethyl)pyridin-3-yl)phenoxy)methyl)-3-fluoro-N-(methylsulfonyl)benzamide;

4-((3-(6-(cyclobutylmethoxy)-5-(hydroxymethyl)pyridin-3-yl)-5-fluorophenoxy)methyl)-3-fluoro-N-(methylsulfonyl)benzamide;

4-((3-(6-(cyclobutylmethoxy)-5-(hydroxymethyl)pyridin-3-yl)-5-fluorophenoxy)methyl)-N-(methylsulfonyl)benzamide;

4-((3-(6-(cyclopropylmethoxy)pyridin-2-yl)-4-fluorophenoxy)methyl)-3-fluoro-N-(methylsulfonyl)benzamide;

4-((3-(2-(cyclopropylmethoxy)-3-methylpyridin-4-yl)-4-fluorophenoxy)methyl)-3-fluoro-N-(methylsulfonyl)benzamide;

4-((3-(2-((cyclopropylmethyl)(methyl)amino)pyridin-4-yl)phenoxy)methyl)-3-fluoro-N-(methylsulfonyl)benzamide;

4-((3-(5-(cyclopropylmethoxy)pyrazin-2-yl)-4-fluorophenoxy)methyl)-3-fluoro-N-(methylsulfonyl)benzamide;

4-((3-(5-(cyclobutylmethoxy)pyrazin-2-yl)phenoxy)methyl)-3-fluoro-N-(methylsulfonyl)benzamide;

4-(((3'-(cyclopropylmethoxy)-5-fluoro-5'-(2-methoxyethoxy)-[1,1'-biphenyl]-3-yl)oxy)methyl)-3-fluoro-N-(methylsulfonyl)benzamide;

4-((3-(6-(cyclopropylmethoxy)pyridin-3-yl)phenoxy)methyl)-N-(methylsulfonyl)benzamide;

4-((3-(6-(cyclopropylmethoxy)pyridin-3-yl)phenoxy)methyl)-3-fluoro-N-(methylsulfonyl)benzamide;

4-((3-(6-(cyclopropylmethoxy)pyridin-3-yl)-5-fluorophenoxy)methyl)-N-(methylsulfonyl)benzamide;

4-((3-(6-(cyclopropylmethoxy)pyridin-3-yl)phenoxy)methyl)-N-(cyclopropylsulfonyl)-3-fluorobenzamide;

4-((3-(6-(cyclopropylmethoxy)pyridin-3-yl)-5-fluorophenoxy)methyl)-N-(ethylsulfonyl)benzamide;

4-((3-(6-(cyclopropylmethoxy)pyridin-3-yl)-5-fluorophenoxy)methyl)-N-(cyclopropylsulfonyl)benzamide;

4-((3-(6-(cyclopropylmethoxy)pyridin-3-yl)-5-fluorophenoxy)methyl)-N-((cyclopropylmethyl)sulfonyl)benzamide; and 4-((3-(6-(cyclopropylmethoxy)pyridin-3-yl)-5-fluorophenoxy)methyl)-N-(thiophen-2-ylsulfonyl)benzamide, or a pharmaceutically acceptable salt thereof.

11. A pharmaceutical composition comprising a compound or a pharmaceutically acceptable salt thereof, according to claim 1, and a pharmaceutically acceptable carrier.

12. The pharmaceutical composition according to claim 11, further comprising another pharmacologically active agent.

13. A method for the treatment of a condition or disorder in which TTX-S channel blockers are involved in an animal or a human, which comprises administering to the animal or human in need of such treatment a therapeutically effective amount of a compound or a pharmaceutically acceptable salt thereof, according to claim 1 wherein the condition or disorder is at least one selected from the group consisting of acute pain, chronic pain, neuropathic pain, inflammatory pain, visceral pain, nociceptive pain, pruritus, multiple sclerosis, neurodegenerative disorder, irritable bowel syndrome, osteoarthritis, rheumatoid arthritis, a neuropathological disorder, a functional bowel disorder, inflammatory bowel disease pain, pain associated with dysmenorrhea, pelvic pain, cystitis pain, pancreatitis pain, migraine, a cluster and tension headache, diabetic neuropathy, peripheral neuropathic pain, sciatica, fibromyalgia, Crohn's disease, epilepsy, an epileptic condition, bipolar depression, tachyarrhythmias, mood disorder, bipolar disorder, a psychiatric disorder, myotonia, arrhythmia, a movement disorder, a neuroendocrine disorder, ataxia, incontinence, trigeminal neuralgia, herpetic neuralgia, general neuralgia, postherpetic neuralgia, radicular pain, back pain, head pain, neck pain, severe pain, intractable pain, breakthrough pain, postsurgical pain, stroke pain, cancer pain, seizure disorder, causalgia, and chemo-induced pain; and combinations thereof.

14. A process for preparing a pharmaceutical composition comprising mixing a compound or a pharmaceutically acceptable salt thereof, according to claim 1, and a pharmaceutically acceptable carrier or excipient.

15. The method according to claim 13, wherein the psychiatric disorder is at least one selected from the group consisting of anxiety and depression.

* * * * *